United States Patent
Beutler et al.

(10) Patent No.: US 9,649,373 B2
(45) Date of Patent: May 16, 2017

(54) NEOSEPTINS: SMALL MOLECULE ADJUVANTS

(71) Applicants: THE SCRIPPS RESEARCH INSTITUTE, La Jolla, CA (US); THE BOARD OF REGENTS OF THE UNIVERSITY OF TEXAS SYSTEM, Austin, TX (US)

(72) Inventors: Bruce Beutler, Dallas, TX (US); Dale L. Boger, La Jolla, CA (US)

(73) Assignees: The Scripps Institute, La Jolla, CA (US); Board of Regents of the University of Texas Systems, Austin, TX (US)

( * ) Notice: Subject to any disclaimer, the term of this patent is extended or adjusted under 35 U.S.C. 154(b) by 0 days.

(21) Appl. No.: 14/770,002

(22) PCT Filed: Feb. 25, 2014

(86) PCT No.: PCT/US2014/018380
§ 371 (c)(1),
(2) Date: Aug. 24, 2015

(87) PCT Pub. No.: WO2014/131023
PCT Pub. Date: Aug. 28, 2014

(65) Prior Publication Data
US 2016/0000907 A1    Jan. 7, 2016

Related U.S. Application Data

(60) Provisional application No. 61/768,712, filed on Feb. 25, 2013.

(51) Int. Cl.
*A61K 39/39* (2006.01)
*A61K 31/166* (2006.01)
(Continued)

(52) U.S. Cl.
CPC ............ *A61K 39/39* (2013.01); *A61K 31/166* (2013.01); *A61K 45/06* (2013.01); *C07C 237/20* (2013.01); *C07C 237/36* (2013.01); *C07C 237/44* (2013.01)

(58) Field of Classification Search
CPC .. A61K 31/166; A61K 2300/00; A61K 39/39; A61K 45/06; C07C 237/20; C07C 237/36; C07C 237/44
(Continued)

(56) References Cited

U.S. PATENT DOCUMENTS

| | | | |
|---|---|---|---|
| 4,031,083 | A | 6/1977 | Haviv et al. |
| 4,118,562 | A | 10/1978 | Haviv et al. |

(Continued)

FOREIGN PATENT DOCUMENTS

| | | |
|---|---|---|
| WO | WO 2007/005583 A1 | 1/2007 |
| WO | WO 2007/024707 A2 | 3/2007 |

OTHER PUBLICATIONS

Shaginian Supporting Information, p. S1-S39, 2009.*
(Continued)

*Primary Examiner* — Jafar Parsa
*Assistant Examiner* — Amy C Bonaparte
(74) *Attorney, Agent, or Firm* — Husch Blackwell LLP

(57) ABSTRACT

A MD-2:TLR4 complex agonist compound is disclosed whose structure corresponds to Formula (I), as defined within. Also disclosed are a method of its preparation and use, as well as a pharmaceutical composition containing the same.

(Continued)

(I)

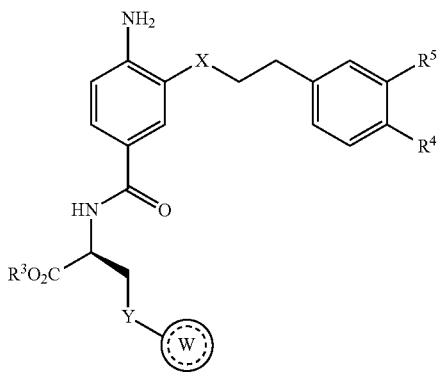

14 Claims, 15 Drawing Sheets

(51) Int. Cl.
 *A61K 45/06* (2006.01)
 *C07C 237/36* (2006.01)
 *C07C 237/44* (2006.01)
 *C07C 237/20* (2006.01)
(58) Field of Classification Search
 USPC .................................... 424/278.1; 562/448
 See application file for complete search history.

(56) References Cited

U.S. PATENT DOCUMENTS

| 2005/0004144 A1 | 1/2005 | Carson et al. |
| 2011/0081365 A1 | 4/2011 | Cortez et al. |
| 2012/0148660 A1 | 6/2012 | Carson et al. |

OTHER PUBLICATIONS

Baldridge ("Taking a Toll on human disease: Toll-like receptor 4 agonists as vaccine adjuvants and monotherapeutic agents" Expert Opinion on Biological Therapy, 4:7, 2004, p. 1129-1138).*
Fox ("Chapter 14: Synthetic and Natural TLR4 Agonists as Safe and Effective Vaccine Adjuvants" Endotoxins: Structure, Function, and Recognition, Subcellular Biochemistry, 53, 2010, p. 303-321.*
Alex Shaginian et a l., "Design, Synthesis, and Evaluation of an re-Helix Mimetic Library Targeting Protein-Protein Interations," J . Am. Chem. Soc . , 2009 , vol. 131.
International Search Report of related international application PCT/US2014/018380, mailed Jun. 8, 2014 (4pgs.).
Wang et al., Proc Natl Acad Sci, USA, 113(7):E884-E893 | PNAS | Published online Feb. 1, 2016.
Morin et al., J. Med. Chem. 2016, 59, 4812-4830
Chemical Book, 2016 2-acetamidoacrylic acid-suppliers.
Look Chem, Suppliers of 3-(phenylamino)-L-alanine 2016.
Noller, *Chemistry of Organic Compounds,* W.B. Saunders Company, Philadelphia, 1951, p. 35.

* cited by examiner

NEOSEPTINS: SMALL MOLECULE ADJUVANTS

CROSS-REFERENCE TO RELATED APPLICATION

This application claims priority from provisional application No. 61/768,712, filed Feb. 25, 2013.

GOVERNMENTAL SUPPORT

The present invention was made with governmental support pursuant to grant AI082657 from the National Institutes of Health/National Institute of Allergy and Infectious Diseases. The government has certain rights in the invention.

TECHNICAL FIELD

The present invention contemplates a small molecule adjuvant compound, and particularly a group of well-defined compounds that induce the secretion of TNF-α in macrophage preparations and thereby mimic some of the properties of LPS without the structural diversity or toxicity exhibited by LPS.

BACKGROUND ART

The innate immune system is the first line of defense against infection and is thought to primarily be mediated by phagocytic immune cells such as macrophages and dendritic cells. These cells recognize microorganisms via a limited number of germline-encoded pattern recognition receptors (PRRs) that recognize microbial components known as pathogen-associated molecular patterns, which are essential for the survival of the microorganism and, therefore, difficult for the microorganism to alter.

Several classes of PRRs, including cell surface-located Toll-like receptors (TLRs) and cytoplasmic receptors, recognize distinct microbial components and directly activate immune cells, triggering intracellular signaling cascades that rapidly induce the expression of a variety of inflammatory cytokines that initiate a variety of overlapping immune responses. One of the best known PRRs is TLR4, which recognizes the major Gram-negative bacterial surface component lipopolysaccharide (LPS) [Akira et al., *Cell* 124:783-801 (2006)]. See also, Beutler, *Blood,* 113:1399-1407 (2009), and Moresco et al., *Curr. Biol.* 21(13):R488-93, (2011) and the citations therein for a historical perspective of the research done in finding TLRs and determining the function of TLRs.

Most of the TLRs are functional multimers. Some are heteromeric. Some appear to be homomeric, and in some cases, non-TLR subunits are part of the signaling complex. For example, TLR4 seems not to detect LPS directly, but only as a complex with MD-2, a small secreted protein that is tightly associated with the TLR4 ectodomain. Crystallographic analysis has shown the nature of the interaction between specific TLR ligands and the Toll-like receptors, including interactions between LPS and the MD-2:TLR4 complex. Beutler, *Blood* 113:1399-1407 (2009).

Studies on TLR4 signaling in monocytes, macrophages, and dendritic cells have revealed that engagement of the MD-2:TLR4 complex (hereinafter just "TLR4", for ease in expression) by LPS triggers a signaling cascade involving several intracytoplasmic and nuclear transcriptional factors. TLR4 activation first engages a set of adaptor family members that link TLR4 to the serine/threonine kinases. These kinases mediate phosphorylation and ubiquitination of various substrates, eventually resulting in the activation of the transcriptional factor NF-κB, which regulates the expression of several immunomodulatory cytokines [Kawai et al., *Cell Death Differ* 13:816-825 (2006)].

Freund's adjuvant (mycobacteria in mineral or vegetable oils), aluminum hydroxide ("alum"), and LPS (lipopolysaccharide) have been used to augment antibody responses to co-administered proteins. In the US, only alum is approved for use in human vaccines.

Of these adjuvants, only LPS and its derived lipid A have a well-defined target—TLR4, but the toxicity of these TLR4 ligands is considerable as is their instability in vivo and they are not easily conjugated to antigens.

In work that provides a powerful paradigm for synthetic "unnatural" adjuvant discovery, we identified a new class of robust small molecule adjuvants that: (1) emerged from screening an α-helix mimetic library, (2) act by a well-defined mechanism (TLR4 agonist), (3) are easy to produce and structurally manipulate, (4) are non-toxic, and (5) elicit improved and qualitatively different responses from LPS even though they share the same receptor. Such adjuvants may be used for co-administration or for covalently-tethered vaccination against any microbe susceptible to antibody-based protective immunization.

BRIEF SUMMARY OF THE INVENTION

The present invention contemplates a TLR4 receptor agonist compound that does not exhibit the toxicity of LPS while exhibiting activation of many similar cellular signaling pathways. A contemplated compound corresponds in structure to Formula I, below, or its pharmaceutically acceptable salt,

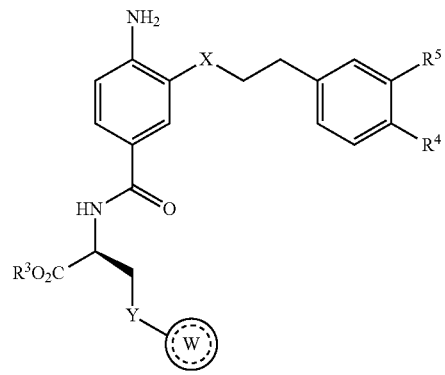

I wherein X is O, S, $NR^1$, $CH_2$, where $R^1$ is H, or $C_1$-$C_4$ hydrocarbyl, or X is absent and two atoms link the depicted phenyl rings. Y is O, S, $NR^2$, $CH_2$, where $R^2$ is H, or a $C_1$-$C_4$ hydrocarbyl group. $R^3$ is a $C_1$-$C_6$ hydrocarbyl group. $R^4$ and $R^5$ are hydrido or hydroxyl, but only one of $R^4$ and $R^5$ is hydrido, or both of $R^4$ and $R^5$ are hydroxyl. W is a ring structure that contains one or two rings and includes 5 to 12 atoms in the ring structure. That ring structure W optionally contains: a) 1, 2, 3 or 4 heteroatoms that are independently oxygen, nitrogen or sulfur, and b) one or more substituent groups bonded to one or more ring atoms, in which the one or more substituents contain a total of up to 8 atoms that are selected from the group consisting of fluorine, chlorine, carbon, nitrogen, oxygen and sulfur, and mixtures thereof. A dotted line (----) represents one or more optional double bonds.

In separate preferences as to a compound of Formula I, a) X is absent or O; b) Y is $CH_2$; c) ring structure W contains up to 10 atoms in the ring structure; and d) W is a single ring structure.

One preferred compound of Formula I is a compound of Formula II, below, its pharmaceutically acceptable salt. In Formula II, A, B, E, G, L and M

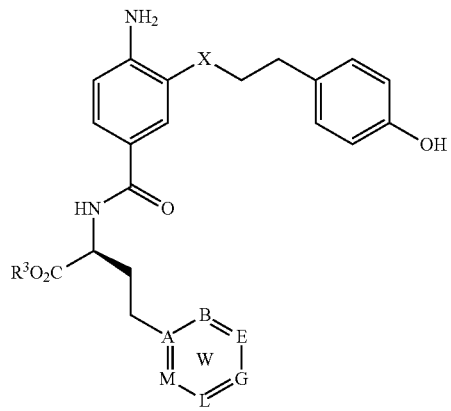

II of ring system W are carbon (C) or nitrogen (N), with no more than three of A, B, E, G, L and M being nitrogen. In addition, ring system W optionally contains one or more substituent groups bonded to one or more ring atoms, in which the one or more substituents contain a total of up to 8 atoms, selected from the group consisting of fluorine, chlorine, carbon, nitrogen, oxygen and sulfur, and mixtures thereof. X is O, S, $NR^1$, $CH_2$, where $R^1$ is H, or $C_1$-$C_4$ hydrocarbyl, or X is absent and two atoms link the depicted phenyl rings. $R^3$ is a $C_1$-$C_6$ hydrocarbyl group.

In further separate preferences as to a compound of Formula II, a) no more than two of A, B, E, G, L and M are nitrogen; X is absent or O; b) $R^3$ is a bulky hydrocarbyl group containing 4-6 carbon atoms; and c) ring structure W contains a substituent selected from the group consisting of azido, fluoro, methyl, methoxy and trifluoromethyl groups, and that substituent is present at 4-position of a 6-membered ring and the 3-position of a 5-membered ring counting from the position of attachment to the remainder of the molecule.

Particularly preferred compounds and salts of Formula II are compounds and pharmaceutically acceptable salts of a compound of Formula III or Formula IV, below, where A, B, E, G, L and M are

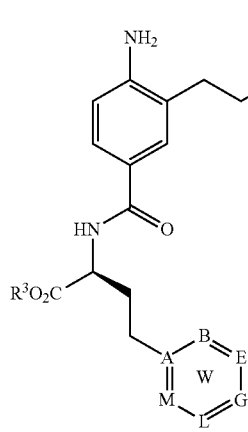

III

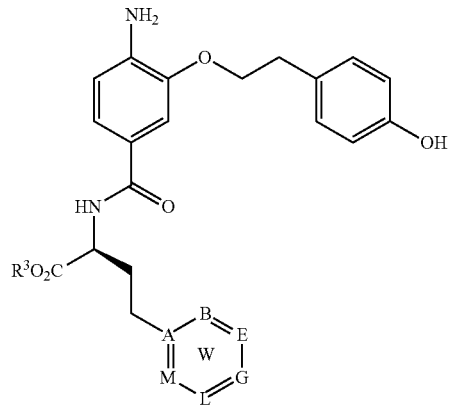

IV are carbon (C) or nitrogen (N) atoms, with no more than two of A, B, E, G, L and M being nitrogen, and $R^3$ is a bulky hydrocarbyl group containing 4-6 carbon atoms. In a compound of Formula III and Formula IV, $R^3$ is preferably a tert-butyl group, a neopentyl group, a cyclopentyl group or cyclohexyl group, and separately, W is preferably phenyl.

Particularly preferred compounds of Formula III and Formula IV are shown below and are named neoseptin-3 and neoseptin-4, respectively.

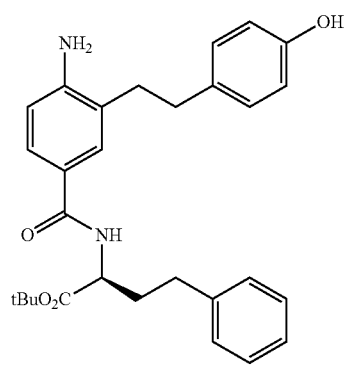

Neoseptin-3

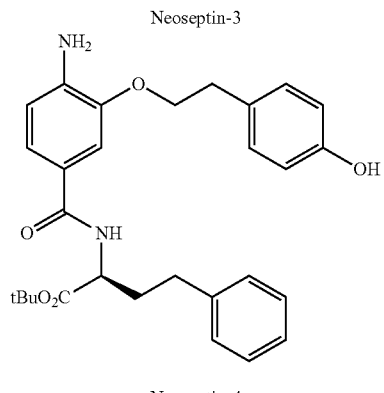

Neoseptin-4

A pharmaceutical composition that contains an effective amount of a compound of Formula I or a pharmaceutically acceptable salt thereof dissolved or dispersed in a physiologically acceptable carrier is also contemplated.

An improved method of vaccination is also contemplated. Here, mammalian cells in need of vaccination are contacted with an immunizing composition that comprises an effective amount of an immunogen and an effective amount of an adjuvant. The improvement in this method comprises use of a compound or a pharmaceutically acceptable compound salt of Formula I as the adjuvant.

BRIEF DESCRIPTION OF THE DRAWINGS

In the drawings forming a portion of this disclosure,

FIG. 11, in three panels as FIGS. 11A, 11-B and 11-C, provides a structural formula for particularly preferred embodiments of the invention in which

Figures 1, 1A:
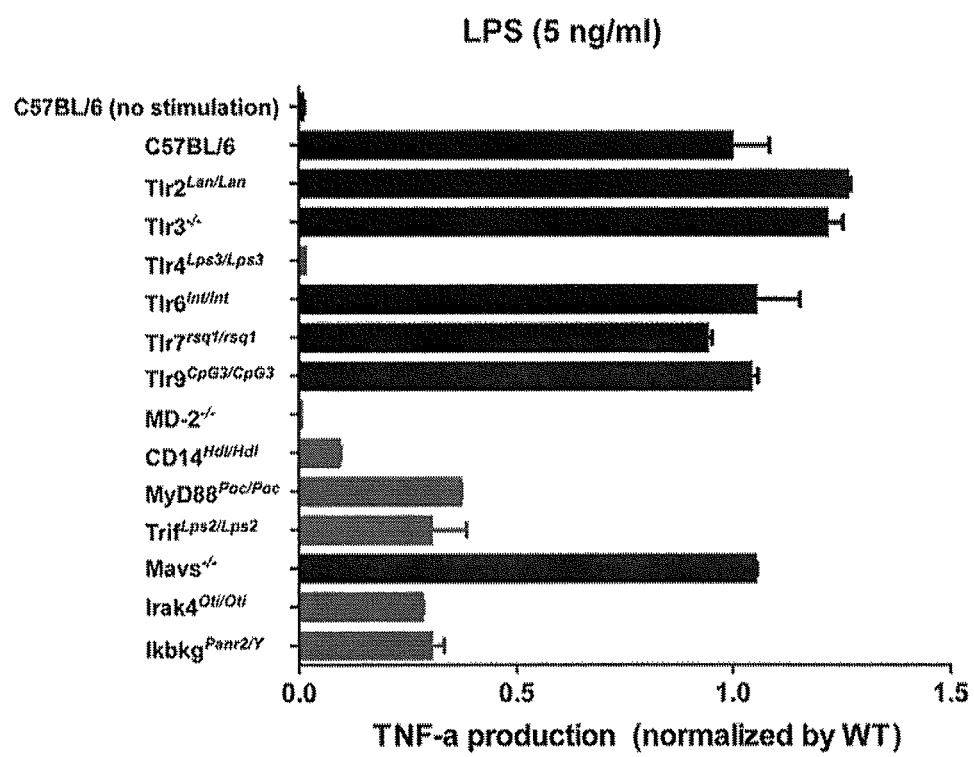
FIG. 1 in two parts as FIG. 1A and FIG. 1B are bar graphs that illustrate an assay of normalized TNF-α production in macrophages from mice containing disabling germline mutations or knockouts of genes encoding TLRs and downstream signaling proteins using 5 ng/ml of LPS or 50 mM neoseptin-3.
Figure 1B:
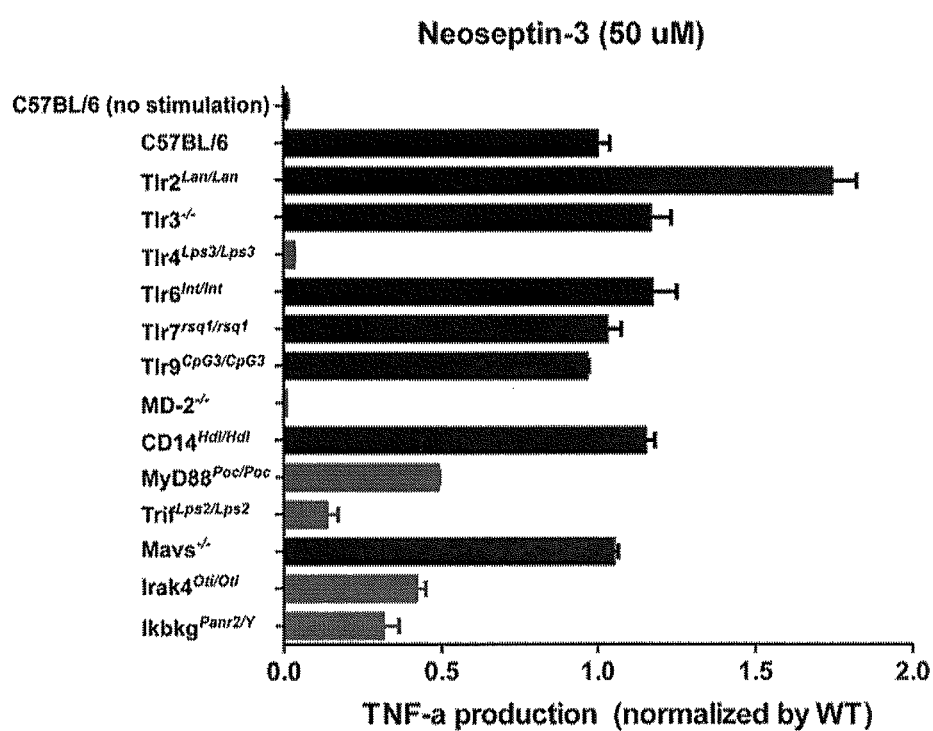

The present invention has several benefits and advantages. One benefit is that discovery of molecularly well defined and easily structurally manipulated adjuvants to replace the ill-defined Freund's adjuvant or alum (aluminum hydroxide) and toxic LPS is a major advance.

An advantage is that an adjuvant developed can be useful in the prevention of premature death by infections. The small molecules disclosed such as neoseptin-3 are more promising adjuvant candidates than the natural ligands (LPS or lipid A), being easier to produce and structurally manipulate, and they are less toxic, eliciting improved and qualitatively different responses than LPS or lipid A even though they share the same receptor (TLR4).

DEFINITIONS

In the context of the present invention and the associated claims, the following terms have the following meanings:

The articles "a" and "an" are used herein to refer to one or to more than one (i.e., to at least one) of the grammatical object of the article. By way of example, "an element" means one element or more than one element.

The word "antigen" has been used historically to designate an entity that is bound by an antibody, and also to designate the entity that induces the production of the antibody. More current usage limits the meaning of antigen to that entity bound by an antibody, whereas the word "immunogen" is used for the entity that induces antibody production. That more current usage will be followed herein.

The words "ortho", "meta" and "para" are used in their usual manner to describe benzenoid compounds that are substituted "1-2", "1-3" and "1-4", respectively. Those same words are also used herein as a convenience to describe those same substitution patterns in aliphatic compounds.

The word "hydrocarbyl" is used herein as a short hand term for a non-aromatic group that includes straight and branched chain aliphatic as well as alicyclic groups or radicals that contain only carbon and hydrogen. Thus, alkyl, alkenyl and alkynyl groups are contemplated, whereas aromatic hydrocarbons such as phenyl and naphthyl groups, which strictly speaking are also hydrocarbyl groups, are referred to herein as aryl groups or radicals; as discussed hereinafter.

Where a specific aliphatic hydrocarbyl substituent group is intended, that group is recited; i.e., $C_1$-$C_4$ alkyl, methyl or tert-butyl. Exemplary hydrocarbyl groups contain a chain of 1 to 4 carbon atoms, and preferably 1 or 2 carbon atoms.

A particularly preferred hydrocarbyl group is an alkyl group. As a consequence, a generalized, but more preferred substituent can be recited by replacing the descriptor "hydrocarbyl" with "alkyl" in any of the substituent groups enumerated herein.

Examples of alkyl radicals include methyl, ethyl, n-propyl, isopropyl, n-butyl, isobutyl, sec-butyl, tert-butyl. Examples of suitable alkenyl radicals include ethenyl (vinyl), 2-propenyl, 3-propenyl, 1,4-butadienyl, 1-butenyl, 2-butenyl, and 3-butenyl. Examples of alkynyl radicals include ethynyl, 2-propynyl, 1-propynyl, 1-butynyl, 2-butynyl, 3-butynyl, and 1-methyl-2-propynyl.

As a skilled worker will understand, a substituent that cannot exist such as a $C_1$ alkenyl group is not intended to be encompassed by the word "hydrocarbyl", although such substituents with two or more carbon atoms are intended.

Usual chemical suffix nomenclature is followed when using the word "hydrocarbyl" except that the usual practice of removing the terminal "yl" and adding an appropriate suffix is not always followed because of the possible similarity of a resulting name to one or more substituents. Thus, a hydrocarbyl ether is referred to as a "hydrocarbyloxy" group rather than a "hydrocarboxy" group as may possibly be more proper when following the usual rules of chemical nomenclature. Illustrative hydrocarbyloxy groups include methoxy, ethoxy, n-propoxy, isopropoxy, allyloxy, n-butoxy, iso-butoxy, sec-butoxy, and tert-butoxy groups.

The term "ring structure" is used herein to mean a cyclic substituent that can contain a single ring such as an imidazolyl or phenyl group, or two fused rings as are present in a naphthyl, purinyl, or decalinyl group, or two linked rings as are present in a biphenyl group.

The term "cyclohydrocarbyl" or "carbocyclic", alone or in combination, means a cyclic hydrocarbyl radical (or ring) that contains 5 to about 12 carbon atoms, preferably about 5 to about 10 carbon atoms. Examples of such cyclohydrocarbyl radicals include cyclopropyl, cyclobutyl, cyclopentenyl, cyclohexyl, cycloheptynyl, 1- and 2-decalinyl and the like.

The term "aryl", alone or in combination, means an aromatic ring system. Such a ring system includes a phenyl, naphthyl and biphenyl ring system.

The heterocyclyl (heterocyclo) is a single 5- or 6-membered ring or a fused or linked 5,5-5,6-6,6-ring system that contains 1 to 4 hetero atoms (non-carbons) in the ring that independently are nitrogen, oxygen or sulfur atoms in a saturated or partially unsaturated ring. Examples of such heterocyclyl groups are pyrrolidinyl, piperidinyl, piperazinyl, morpholinyl, thiamorpholinyl, oxathiazolyl, 1,2,3-triazolyl, 1,2,4-triazolyl, pyrazolyl, 1,2,4-oxadiazinyl and azepinyl groups and a bipiperidinyl group.

A "heteroaryl" group is an aromatic heterocyclic ring that preferably contains one, or two, or three or four atoms in the ring other than carbon. Those heteroatoms can independently be nitrogen, sulfur or oxygen. A heteroaryl group can contain a single 5- or 6-membered ring or a fused ring system having two 6-membered rings or a 5- and a 6-membered ring, or a linked 5,5-, 5,6- or 6,6-membered rings as in a bipyridinyl group. Exemplary additional heteroaryl groups include 6-membered ring substituents such as pyridyl, pyrazyl, pyrimidinyl, and pyridazinyl; 5-membered ring substituents such as 1,3,5-, 1,2,4- or 1,2,3-triazinyl, imidazyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl groups; 6-/5-membered fused ring substituents such as benzothiofuranyl, isobenzothiofuranyl, benzisoxazolyl, benzoxazolyl, purinyl and anthranilyl groups; and 6-/6-membered fused rings such as 1,2-, 1,4-, 2,3- and 2,1-benzopyronyl, quinolinyl, isoquinolinyl, cinnolinyl, quinazolinyl, and 1,4-benzoxazinyl groups.

Each of the four ring systems discussed above is encompassed by the ring system W. Each of those ring systems can optionally carry one or more substituent groups that contain a total of up to 8 atoms selected from the group consisting of fluorine, chlorine, carbon, nitrogen, oxygen and sulfur, and mixtures thereof. Hydrogens are not counted in the total number of atoms present in the one or more substituents.

DETAILED DESCRIPTION OF THE INVENTION

The present invention contemplates a Compound of Formula I or a pharmaceutically acceptable salt thereof, a pharmaceutical composition containing an effective amount of such a compound or its salt, and a method of using a compound or its pharmaceutically acceptable salt. More particularly, a contemplated compound is sometimes referred to herein as a neoseptin and corresponds in structure to Formula I, below.

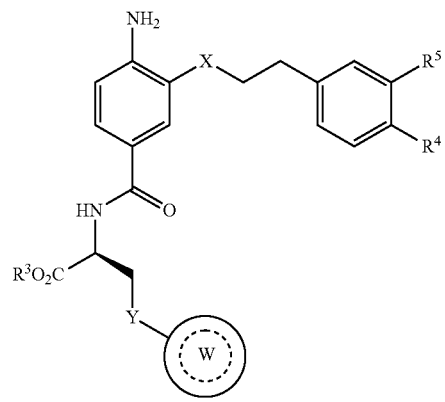

In a Compound of Formula I, X is O, S, $NR^1$, $CH_2$, where $R^1$ is H, or $C_1$-$C_4$ hydrocarbyl, or X is absent and two atoms link the depicted phenyl rings. Preferably, X is absent or O.

Y is O, S, $NR^2$, $CH_2$, where $R^2$ is H, or a $C_1$-$C_4$ hydrocarbyl group. Preferably, Y is preferably $CH_2$. $R^3$ is a $C_1$-$C_6$ hydrocarbyl group. $R^4$ and $R^5$ are hydrido or hydroxyl but at least one of $R^4$ and $R^5$ is hydroxyl, or both of $R^4$ and $R^5$ are hydroxyl.

W is a ring structure that contains one or two rings and includes 5 to 12 atoms in the ring structure, and preferably 5 to 10 atoms. W can optionally contain: a) 1, 2, 3 or 4 heteroatoms in the ring structure that are independently oxygen, nitrogen or sulfur, and b) one or more substituent groups bonded to one or more ring atoms, in which the one or more substituents contain a total of up to 8 atoms, and preferably up to 6 atoms, selected from the group consisting of fluorine, chlorine, carbon, nitrogen, oxygen and sulfur, and mixtures thereof. Preferred substituents include azido, fluoro, methyl, methoxy and trifluoromethyl groups. Where W is a single ring structure, it is preferred that a substituent be in the 4-position of a 6-membered ring and the 3-position of a 5-membered ring counting from the position of attachment to the remainder of the molecule. For example, counting from Y in Formula I.

A dotted line (----) represents one or more optional double bonds.

A ring system W is preferably aromatic or heteroaromatic, as compared to being cyclohydrocarbyl or heterocyclo, so that the optional double bonds are present. It is also preferred that up to three hetero atoms are present and that those heteroatoms are each nitrogen. It is more preferred that there are one or two nitrogen atoms in ring system W.

Looking broadly, illustrative W ring systems include cyclopentenyl, cyclohexyl, cycloheptynyl, cyclooctyl, 1- and 2-decalinyl, phenyl, naphthyl biphenyl, pyrrolidinyl, piperidinyl, piperazinyl, morpholinyl, thiamorpholinyl, oxathiazolyl, 1,2,3-triazolyl, 1,2,4-triazolyl, pyrazolyl, 1,2,4-oxadiazinyl, azepinyl, bipyridinyl, pyridyl, pyrazyl, pyrimidinyl, pyridazinyl, 1,3,5-, 1,2,4- or 1,2,3-triazinyl, imidazyl, furanyl, thiophenyl, pyrazolyl, oxazolyl, isoxazolyl, thiazolyl, 1,2,3-, 1,2,4-, 1,2,5-, or 1,3,4-oxadiazolyl, isothiazolyl, benzothiofuranyl, isobenzothiofuranyl, benzisoxazolyl, benzoxazolyl, purinyl, anthraniloyl, 1,2-, 1,4-, 2,3- and 2,1-benzopyronyl, quinolinyl, isoquinolinyl, cinnolinyl, quinazolinyl, and 1,4-benzoxazinyl groups.

Single ring-containing 6- or 5-membered ring W ring systems are preferred and include phenyl, pyridyl, pyrazyl, pyrimidinyl, pyridazinyl, imidazyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl groups. Phenyl, pyridyl, pyrazyl, pyrimidinyl, imidazyl and furanyl groups are more preferred, with phenyl being presently particularly preferred.

An $R^3$ is a $C_1$-$C_6$ hydrocarbyl group. Preferably, $R^3$ is a bulky hydrocarbyl group containing 4-6 carbon atoms such as a tert-butyl (t-Bu) group, a neopentyl group or a cyclopentyl or cyclohexyl group. $R^3$ is more preferably a tert-butyl group.

Following the above-described preferences, one preferred Compound of Formula I is a Compound of Formula II, below

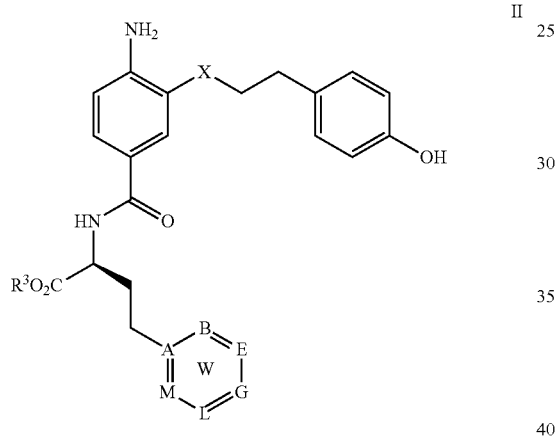

II wherein A, B, E, G, L and M are carbon (C) or nitrogen (N), with no more than three being nitrogen. As noted above, it is preferred that all of A, B, E, G, L and M are carbon so that W is a phenyl group. In a Compound of Formula II, X and $R^3$ are as previously defined, with $R^3$ preferably being a bulky hydrocarbyl group containing up 4-6 carbon atoms.

Particularly preferred Compounds of Formula II are those of Formula III and Formula IV, below.

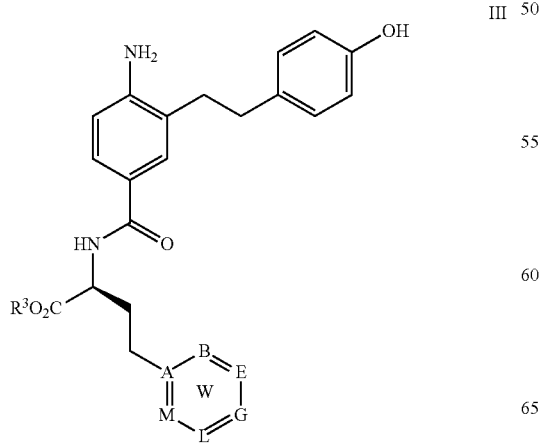

III

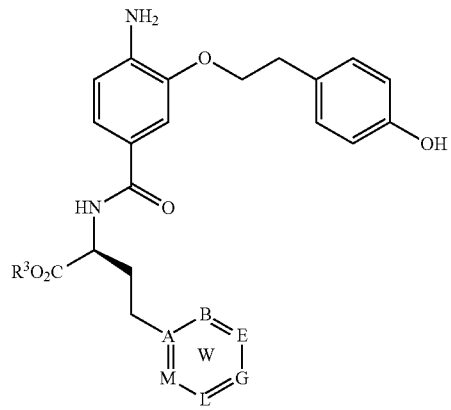

IV

In a Compound of Formula III and Formula IV, A, B, E, G, L and M are carbon (C) or nitrogen (N), with no more than two being nitrogen, and $R^3$ is as previously defined.

Neoseptin-3 and neoseptin-4 are particularly preferred Compounds of Formula III and Formula IV, respectively.

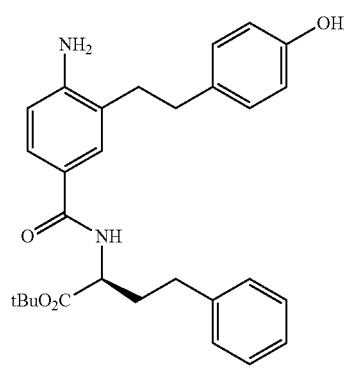

Neoseptin-3

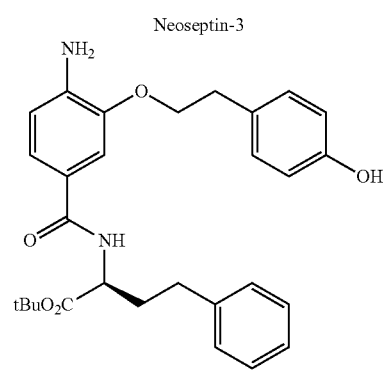

Neoseptin-4

Pharmaceutical Composition and Methods

A contemplated Compound of Formula I, a neoseptin, can also be used in the manufacture of a medicament (pharmaceutical composition). When so used, a contemplated compound of Formula I is present in a TLR4 agonist-effective amount dissolved or dispersed in a pharmaceutically acceptable diluent (or carrier).

One use for such a composition is as an adjuvant for a vaccine. As such, an improved method of vaccination is contemplated in which a mammal in need of vaccination is administered an effective amount of an immunogen and an effective amount of an adjuvant. Here, the improvement comprises using a Compound of Formula I or its pharmaceutically acceptable salt as the adjuvant.

For example, studies illustrated elsewhere herein, neoseptin-3 acts as a robust in vivo adjuvant or TLR4 agonist that evoked a more sustained immune response of equal or greater efficacy than LPS when co-injected with ovalbumin as immunogen by an intramuscular route. In addition, at the maximum doses capable of administration, neoseptin-3 did not display the overt toxicity that is characteristic of LPS administration when used as an adjuvant. Thus, a contemplated Compound of Formula I acts as an agonist at the TLR4 receptor in that it binds to the TLR4 receptor of a cell and triggers a response by that cell, thereby mimicking the action of LPS, without the toxic result from using LPS as an adjuvant.

A contemplated composition also typically contains pharmaceutically acceptable salts, buffers and the like excipients that collectively are referred to as pharmaceutically (or physiologically) acceptable diluents or carriers as compared to those that can be present in a composition that is not intended for pharmaceutical use, as in an in vitro assay.

A compound of the invention can be provided for use by itself, or as a pharmaceutically acceptable salt. A contemplated Compound of Formula I, an aniline, is a weak base. Parental anilinium ion has a reported pKa value of 4.6. A carboxyl group is also present in the molecule that is preferably esterified, but can be present as a salt.

Exemplary salts useful for a contemplated compound include but are not limited to the following: sulfate, hydrochloride, hydro bromides, acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenyl-propionate, picrate, pivalate, propionate, succinate, tartrate, thiocyanate, tosylate, mesylate and undecanoate. Salts of the carboxylate group include sodium, potassium, magnesium, calcium, aluminum, ammonium, and the many substituted ammonium salts.

The reader is directed to Berge, *J. Pharm. Sci.* 1977 68(1):1-19 for lists of commonly used pharmaceutically acceptable acids and bases that form pharmaceutically acceptable salts with pharmaceutical compounds.

In some cases, the salts can also be used as an aid in the isolation, purification or resolution of the compounds of this invention. In such uses, the acid used and the salt prepared need not be pharmaceutically acceptable.

As is seen from the data that follow, a contemplated compound is active in in vivo and in in vitro assay studies at micromolar amounts. When used in an assay such as an in vitro assay, a contemplated compound is present in the composition in an amount that is sufficient to provide a concentration of about 10 µM to about 100 µM to contact cells to be assayed.

A contemplated pharmaceutical composition contains an effective amount of a Compound of Formula I or a pharmaceutically acceptable salt thereof dissolved or dispersed in a physiologically (pharmaceutically) acceptable carrier. In some embodiments, an adjuvant effective (TLR4 agonist effective) amount is utilized. Such a composition can be administered to mammalian cells in vitro as in a cell culture to contact those cells, or the cells can be contacted in vivo as in a living, host mammal in need.

When used as a vaccine adjuvant, a Compound of Formula I is preferably administered together with the selected immunogen. Both components are preferably present together in a single composition. However, the two ingredients can be present in separately administered compositions, and those separate compositions can be administered up to about one to about two hours apart. It is preferred when two separate compositions are administered, that they be administered as close together in time as possible.

A Compound of Formula I was illustratively administered in vivo in a weight of adjuvant per kilogram of subject animal at about 250 mg/kg. Usually, a Compound of Formula I contemplated here is administered parenterally in vivo in a weight amount per square meter of the recipient's body surface area (bsa). For adults, this amount is typically about 1 to about 20 $mg/m^2$ bsa, and about one-half those amounts for children A contemplated composition is typically administered in vivo to a subject in need thereof a plurality of times within one month, such as daily or weekly, and can be administered over a period of several months to several years. More usually, a contemplated composition is administered a plurality of times over a course of treatment.

A contemplated pharmaceutical composition can be administered orally (perorally) or parenterally, which is preferred, in a formulation containing conventional nontoxic pharmaceutically acceptable carriers, adjuvants, and vehicles as desired. The term parenteral as used herein includes subcutaneous injections, intravenous, intramuscular (which is most preferred), intrasternal injection, or infusion techniques. Formulation of drugs is discussed in, for example, Hoover, John E., *Remington's Pharmaceutical Sciences*, Mack Publishing Co., Easton, Pa.; 1975 and Liberman, H. A. and Lachman, L., Eds., *Pharmaceutical Dosage Forms*, Marcel Decker, New York, N.Y., 1980.

A contemplated pharmaceutical composition is preferably adapted for parenteral administration. Thus, a pharmaceutical composition is preferably in liquid form when administered, and most preferably, the liquid is an aqueous liquid, although other liquids are contemplated as discussed below, and a presently most preferred composition is an injectable preparation.

Thus, injectable preparations, for example, sterile injectable aqueous or oleaginous solutions or suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution, phosphate-buffered saline.

Other liquid pharmaceutical compositions include, for example, solutions suitable for parenteral administration. Sterile water solutions of a Compound of Formula I or sterile solution of a Compound of Formula I in solvents comprising water, ethanol, or propylene glycol are examples of liquid compositions suitable for parenteral administration. In some aspects, a contemplated Compound of Formula I is provided as a dry powder that is to be dissolved in an appropriate liquid medium such as sodium chloride for injection prior to use.

In addition, sterile, fixed oils are conventionally employed as a solvent or suspending medium. For this purpose any bland fixed oil can be employed including synthetic monoor diglycerides. In addition, fatty acids such as oleic acid find use in the preparation of an injectable composition. Dimethyl acetamide, surfactants including ionic and nonionic detergents, polyethylene glycols can be used. Mixtures of solvents and wetting agents such as those discussed above are also useful. Sterile solutions can be prepared by dissolving the active component in the desired solvent system, and then passing the resulting solution through a membrane filter to sterilize it or, alternatively, by dissolving the sterile compound in a previously sterilized solvent under sterile conditions.

Solid dosage forms for oral administration can include capsules, tablets, pills, powders, and granules. The amount of a contemplated Compound of Formula I (neoseptin) in a solid dosage form is as discussed previously, an amount sufficient to provide a concentration of about 10 mM to about 100 mM, preferably about 1 nM to about 50 nM, in the serum or blood plasma. A solid dosage form can also be administered a plurality of times during a one week time period.

In such solid dosage forms, a compound of this invention is ordinarily combined with one or more adjuvants appropriate to the indicated route of administration. If administered per os, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, *acacia* gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

A mammal in need of treatment (a subject) and to which a pharmaceutical composition containing a Compound of Formula I is administered can be a primate such as a human, an ape such as a chimpanzee or gorilla, a monkey such as a cynomolgus monkey or a macaque, a laboratory animal such as a rat, mouse or rabbit, a companion animal such as a dog, cat, horse, or a food animal such as a cow or steer, sheep, lamb, pig, goat, llama or the like.

Where an in vitro assay is contemplated, a sample to be assayed such as cells and tissue can be used. These in vitro compositions typically contain water, sodium or potassium chloride, and one or more buffer salts such as and acetate and phosphate salts, Hepes or the like, a metal ion chelator such as EDTA that are buffered to a desired pH value such as pH 4.0-8.5, preferably about pH 7.2-7.4, depending on the assay to be performed, as is well known. Preferably, the pharmaceutical composition is in unit dosage form. In such form, the composition is divided into unit doses containing appropriate quantities of the active compound. The unit dosage form can be a packaged preparation, the package containing discrete quantities of the preparation, for example, in vials or ampules.

In another preferred embodiment, a contemplated Compound of Formula I is administered as an adjuvant along with one or more immunogenic materials as a vaccine. One such composition is illustrated herein in which olvalbumin was used as the immunogen in the vaccination of C57BL/6J mice.

Results

The mechanism by which Compound 1 (neoseptin-1) and related compounds were signaling was established to be TLR4 using macrophages derived from mice bearing disabling germline genetic mutations or knockouts of the genes encoding for each TLR or the downstream signaling molecules.

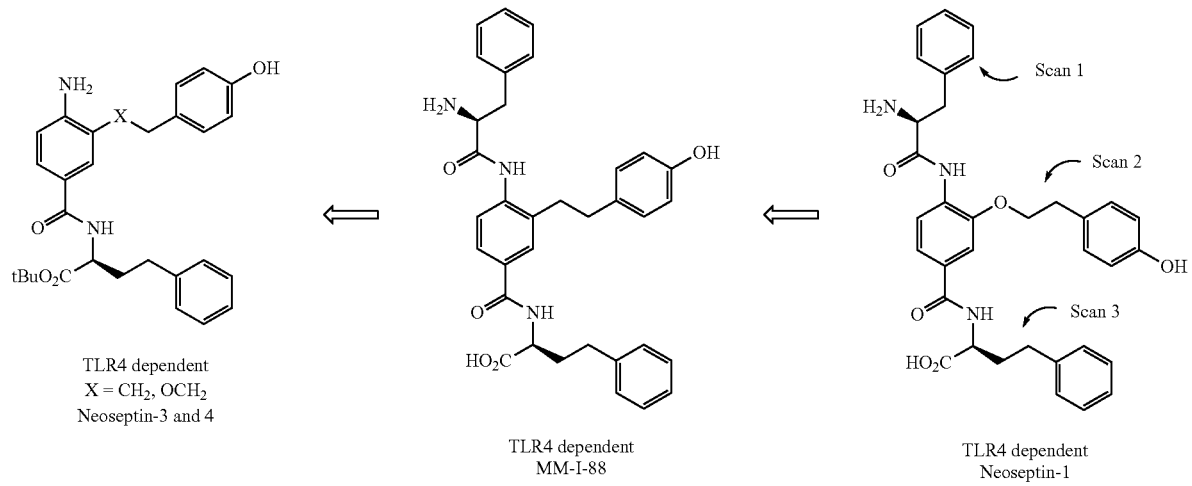

Representative of the SAR data available from the initial screening, activity was observed only with a central tyrosine side chain substituent and the closely related phenyl, 4-chlorophenyl, naphthyl, 4-methoxyphenyl, and indolyl derivative mixtures were inactive. Similarly, the two active mixtures contained either a homophenylalanine or methionine side chain at the carboxylic acid terminus and all other 18 residues were inactive including phenyl-, 4-chlorophenyl-, 4-methoxyphenyl-, naphthyl-alanine, tyrosine, tryptophan, leucine, valine, isoleucine, alanine, glycine, asparagine, lysine, serine, threonine, aspartate, histidine, and Abu.

In these two series, the amine terminus also exhibited a well-defined structural dependence where only those compounds containing a spatially well placed hydrophobic aromatic substituent exhibited activity. The activity of the initial screening lead, neoseptin-1, below, was optimized

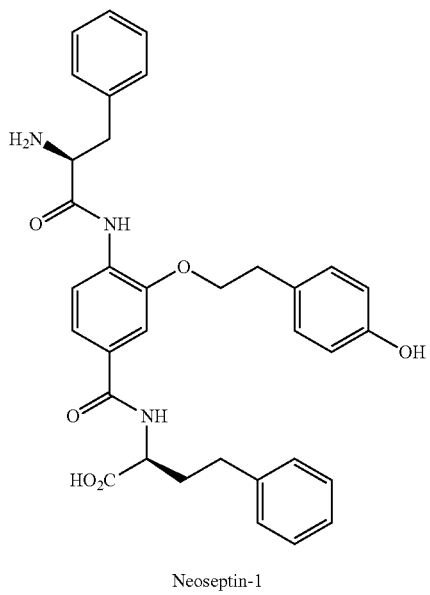 [SMILES: N[C@@H](Cc1ccccc1)C(=O)Nc1ccc(C(=O)N[C@@H](CCc2ccccc2)C(=O)O)cc1OCCc1ccc(O)cc1]

Neoseptin-1 via preparation of about 850 compounds, probing the two end portions of the structure.

Upon exploring the central region of neoseptin-1 (80 compounds), a significant enhancement in TLR4 agonist efficacy was discovered with Compound MM-1-88, below, where a single atom change in

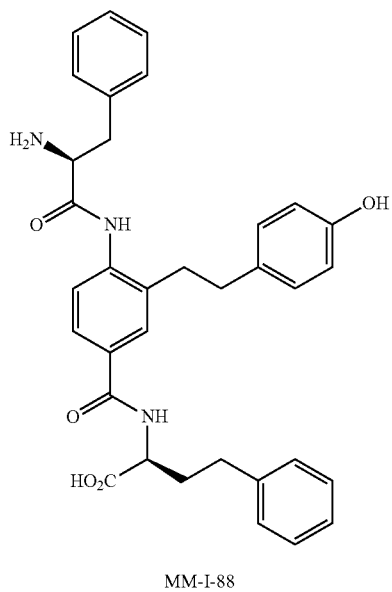 [SMILES: N[C@@H](Cc1ccccc1)C(=O)Nc1ccc(C(=O)N[C@@H](CCc2ccccc2)C(=O)O)cc1CCc1ccc(O)cc1]

MM-I-88 neoseptin-1 (removal of a single oxygen atom) provided the increased efficacy. Nearly all other changes to this region of the molecule led to a complete loss in activity. Further optimization led to additional simplifying structural modifications and two proved to be even more efficacious TLR4-dependent agonists (named neoseptin-3 and neoseptin-4), nearly matching the efficacy of LPS.

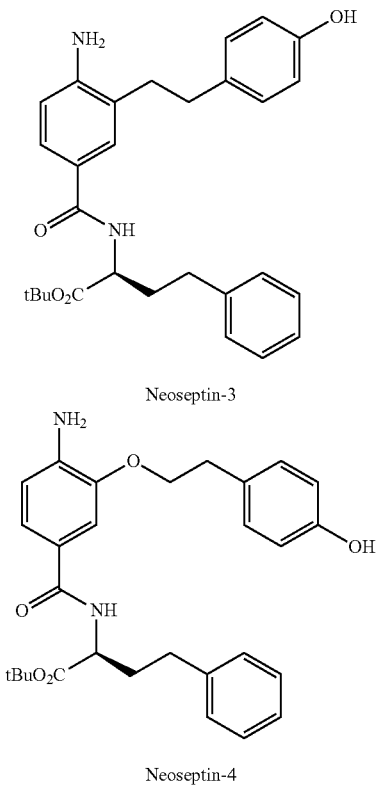

Neoseptin-3

Neoseptin-4

Systematic exploration of this more efficacious series (about 100 compounds) revealed that even minor changes to either compound completely disrupted activity. Key elements of the work include the observation of an exquisite SAR where the TLR4 agonist activity of neoseptin-3 and -4 is unique among many very closely related structures (>100 to date), that each of the components that make up the structure of neoseptin-3 is required for activity, and that both exhibit well-defined dose-response curves ($EC_{50}$ 15-25 µM).

Additionally, close structurally related analogs in the series act as antagonists of neoseptin-3 (bind but do not activate TLR4), and azide substitution of neoseptin-3 on the C-terminus phenyl group provided an active agonist that serves as a photoaffinity cross-linking reagent.

With the use of macrophages from mice bearing germline genetic defects or knockouts of each of the genes encoding the TLRs or their downstream signaling molecules uniquely available in the laboratories of Professor Bruce Beutler, (University of Texas Southwestern Medical Center, Dallas, Tex.) the induced TNF-α production by neoseptin-3 was established to be nearly identical to that of LPS, being dependent on TLR4, MD-2, MyD88, Trif, TRAM, MAL, IRAK4, and IKBKG. Neoseptin-3 has been additionally shown to activate the NF-κB, P38 MAPK, JNK, and Erk signaling pathways. However, unlike LPS, neoseptin-3 is independent of CD14. See, (a) mutagenetix.utsouthwestern.edu.; (b) Arnold et al., (2012) ENU-induced phenovariance in mice: Inferences from 587 mutations. *BMC Res. Notes.* 5, 577-0500-5-577.

Like LPS (lipolysaccharide, endotoxin) and MPLA (monophosphoryl lipid A), the TLR4 agonist activity of neoseptin-3 is blocked by the antagonist eritoran, suggesting that they bind to the same hydrophobic pocket of MD-2 in the activated MD-2/TLR4 complex. Consistent with this expectation, direct binding of neoseptin-3 to MD-2 was observed by isothermal titration calorimetry (figure x), displaying an affinity slightly better than that of MPLA itself.

Figure 2:
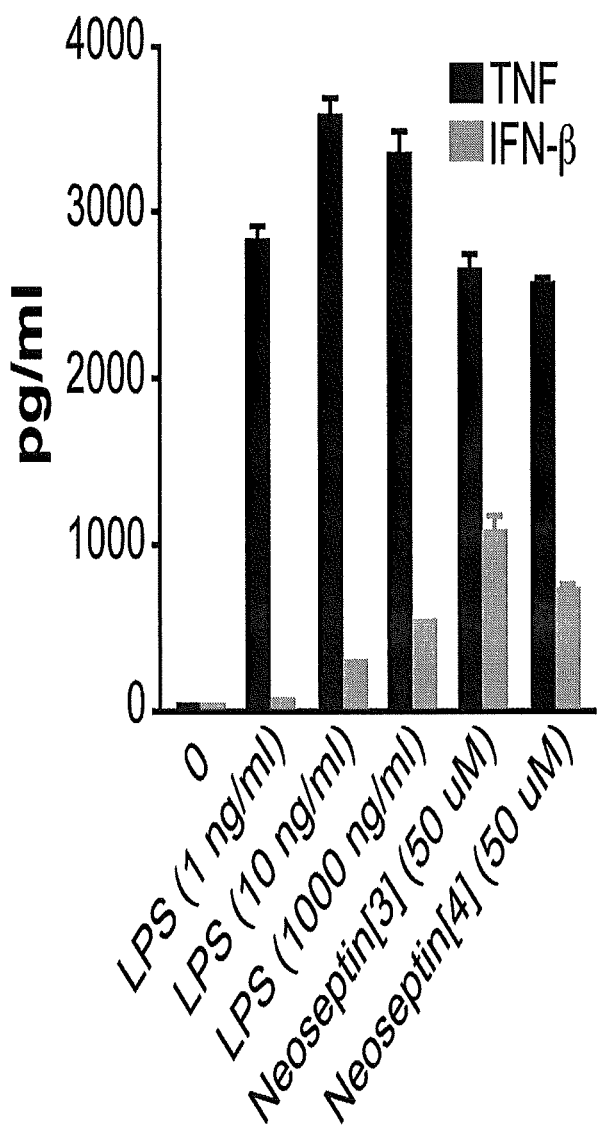
FIG. 2 is a graph that compares the activity of neosepin-3 and LPS and illustrates that neoseptin-3 much more effectively stimulates a type I interferon response resulting in the release of INF-β (but not INF-α), representing a potential advantage to its use as an adjuvant.

Further distinguishing the activity of neoseptin-3 and LPS (FIG. 2), neoseptin-3 much more effectively stimulates a type I interferon response resulting in the release of INF-$\beta$ (but not INF-$\alpha$), representing a potential advantage to its use as an adjuvant.

Figures 3, 3A:
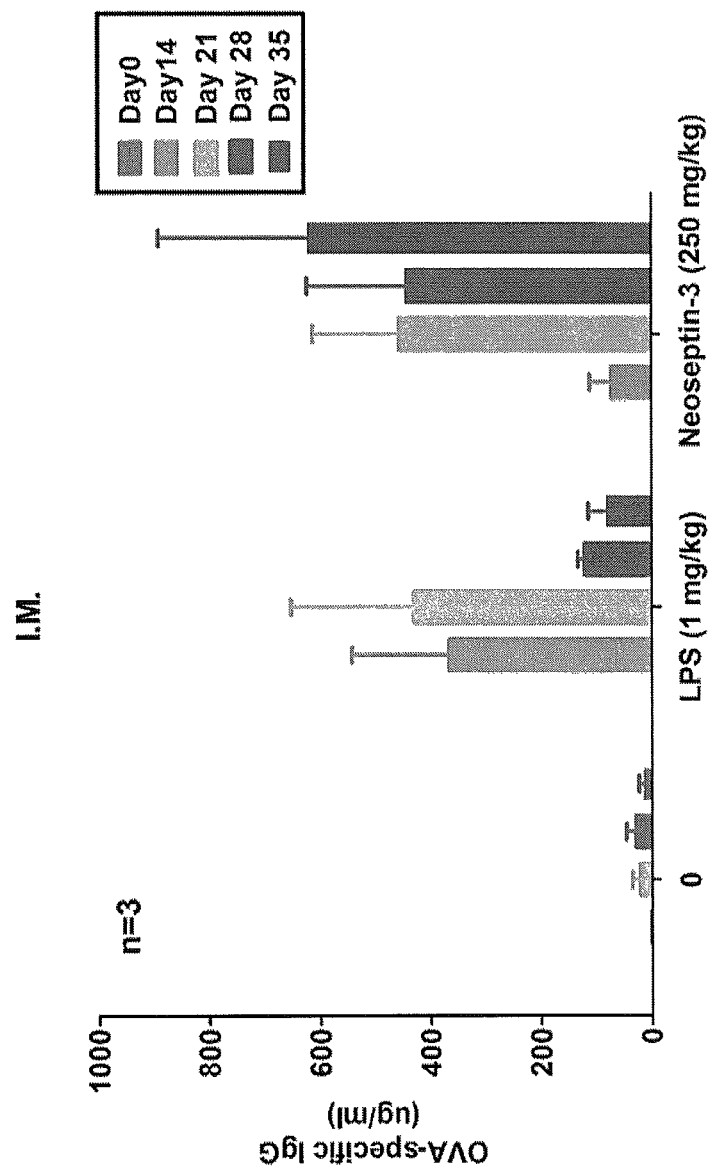
FIG. 3, in two panels as FIG. 3A and FIG. 3B, are graphs that illustrate ELIZA results for the adjuvant effect of neoseptin-3.
In FIG. 3A, adjuvants were mixed with ovalbumin (OVA, 100 µg) and injected intramuscularly into C57BL/6J mice at the indicated doses. Two immunizations were administered with a booster given at 7 days.
Figure 3B:
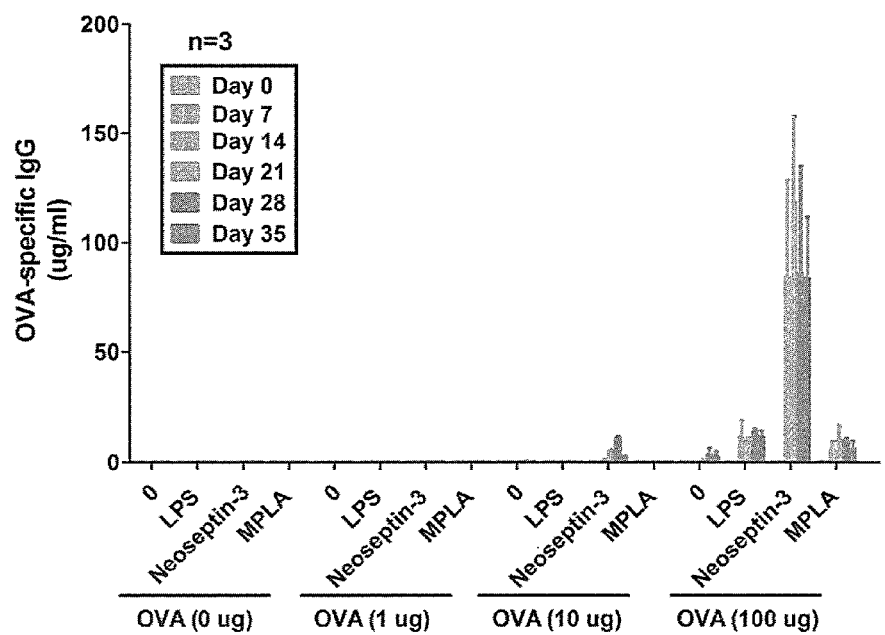
In FIG. 3B, LPS (0.2 mg/kg), neoseptin-3 (250 mg/kg) or monophosphoryl lipid A from *Salmonella minnesota* R595 (MPLA) (0.2 mg/kg) were mixed with ovalbumin (OVA, 0, 1, 10, and 100 µg) Serum levels of OVA-specific IgG were measured (ELISA) on indicated days post-immunization.
Figure 4:
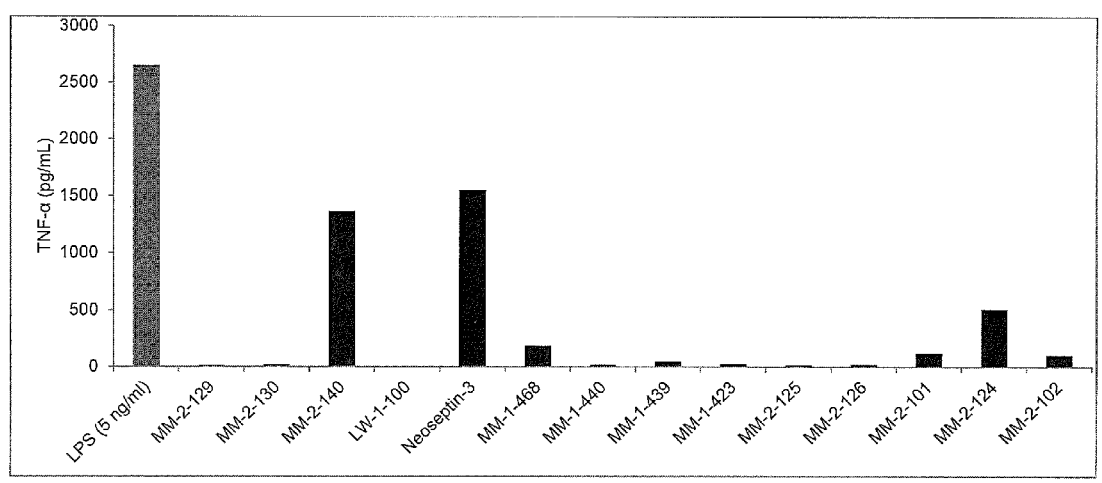
FIG. 4 is a graph whose bars illustrate the stimulation of TNF-α (pg/mL) in a mouse peritoneal macrophage agonist assay by various potential TLR-4 agonists, including LPS at 5 ng/mL, neoseptin-3 and several of its analogues that are substituted with various groups at the carboxyl group as are identified by their alphanumeric identifiers and are present in the assay at 50 µM.
Figure 5:
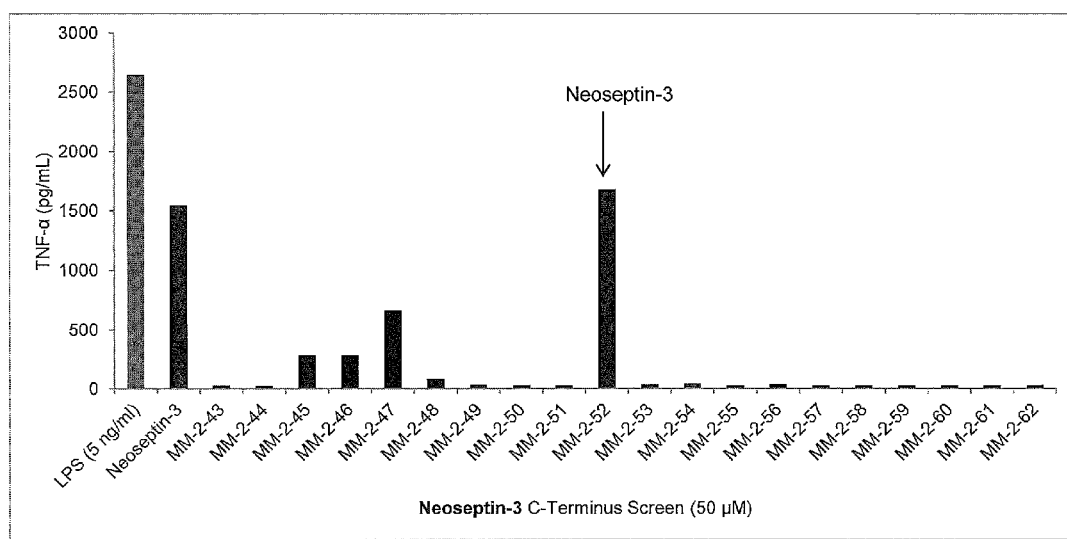
FIG. 5 is a graph similar to that of FIG. 4 in which the bars represent LPS (5 ng/mL), neoseptin-3 (twice) and further neoseptin-3 analogues (50 µM) that are substituted with differing substituents at the alpha-carbon atom as are identified by their alphanumeric identifiers.
Figure 6:
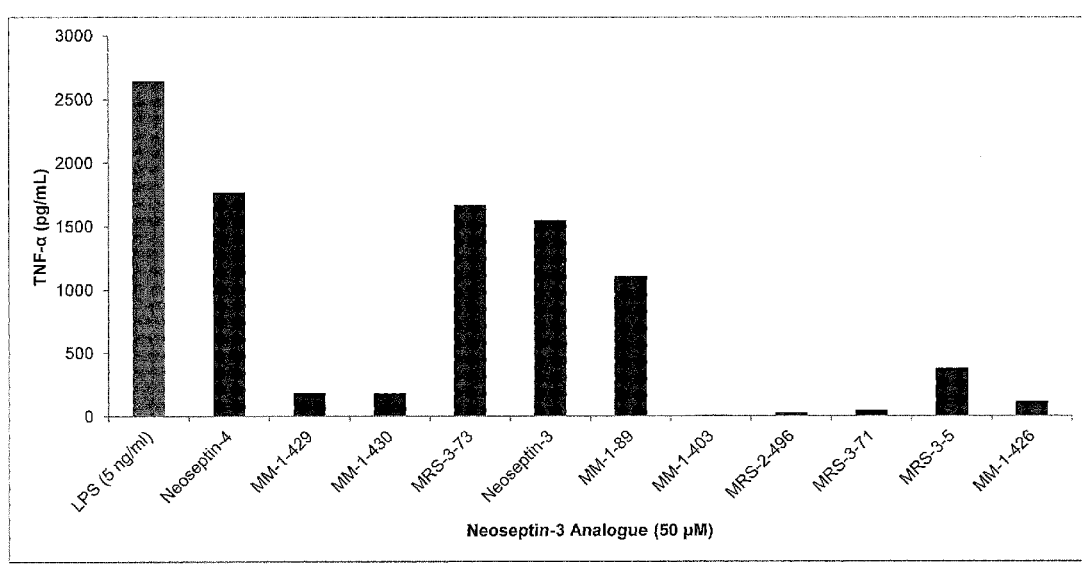
FIG. 6 is a graph similar to that of FIG. 4 in which the bars represent LPS (5 ng/mL), neoseptin-4, neoseptin-3 and further neoseptin-3 analogues (50 µM) that are substituted with differing linker groups between the phenolic and aniline ring portions as are identified by their alphanumeric identifiers.
Figure 7:
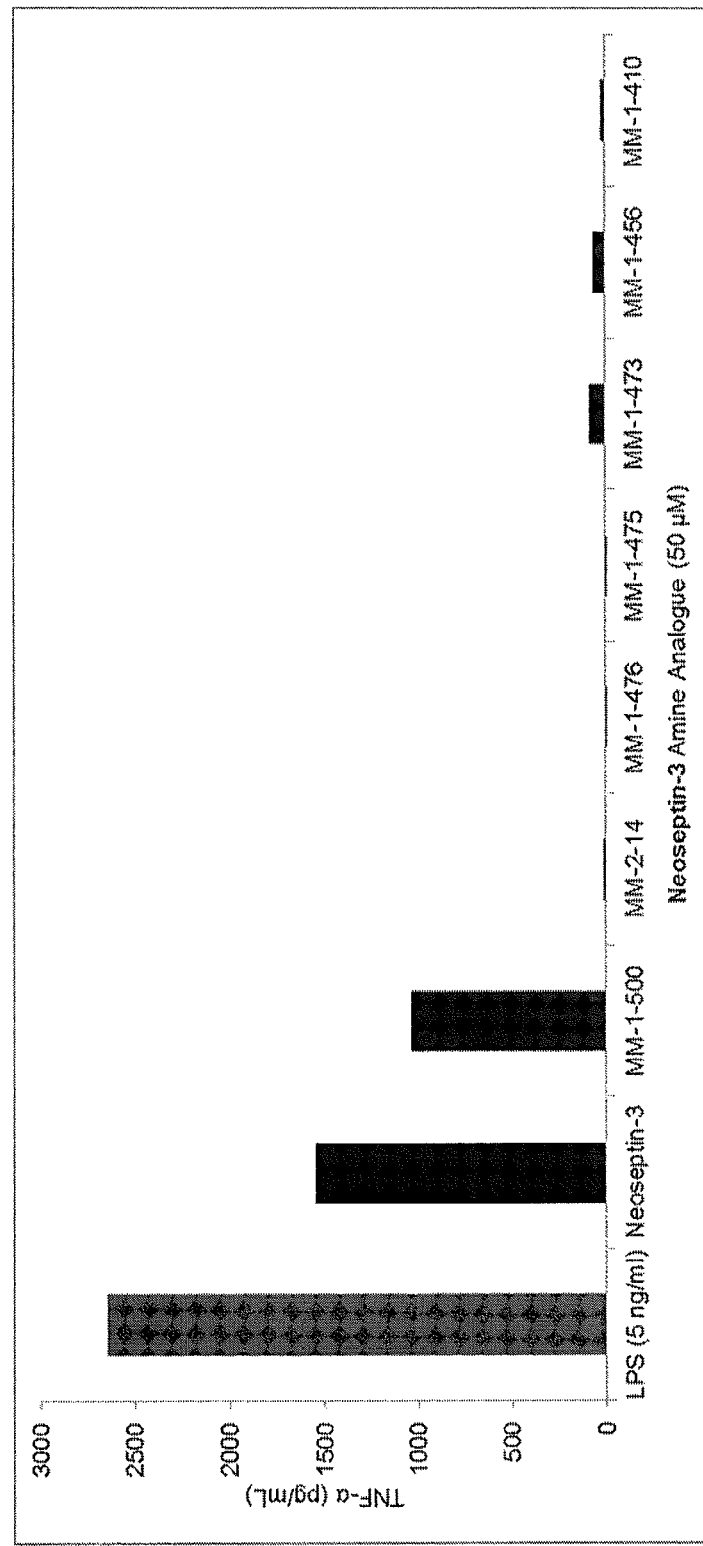
FIG. 7 is a graph similar to that of FIG. 4 in which the bars represent LPS (5 ng/mL), neoseptin-3 and further neoseptin-3 analogues (50 µM) whose aniline ring amino group is present at differing positions, with and without further nitrogen-bonded substituents as are identified by their alphanumeric identifiers.
Figure 8:
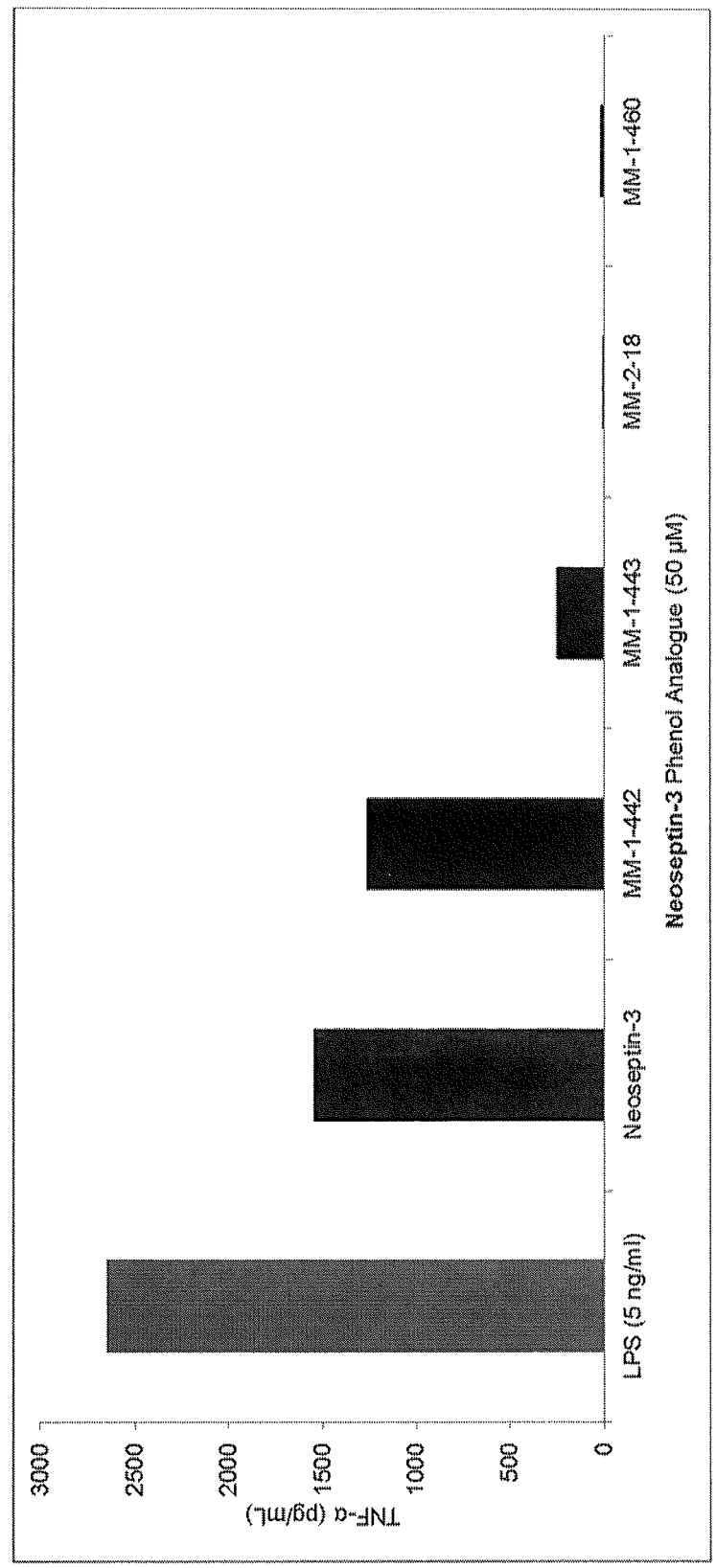
FIG. 8 is a graph similar to that of FIG. 4 in which the bars represent LPS (5 ng/mL), neoseptin-3 and further neoseptin-3 analogues (50 µM) whose phenolic ring hydroxyl group is present at differing positions as are identified by their alphanumeric identifiers.

Neoseptin-3 behaves as a robust in vivo adjuvant that evokes a more sustained immune response of equal or greater efficacy than LPS when co-injected with ovalbumin by an intramuscular route (FIG. 3). Moreover and at the maximum doses capable of administration, neoseptin-3 does not display the overt toxicity that is characteristic of LPS administration. It is remarkable that such a small molecule can display such exquisite structural selectivity for activating the immune response and to do so in a way that is so mechanistically specific and well-defined. {See, (a) Vogel *Clin. Infect. Dis.* 30 (Suppl 3):S266-S270 (2000); (b) Guy, *Nat. Rev. Microbiol.* 5:505-517 (2007); (c) Johnson, *Curr. Top. Med. Chem.* 8:64-79 (2008); and (d) Persing et al., *Trends Microbiol.* 10:S32-S37 (2002) and the citations therein for the procedures utilized.]

Figure 9:
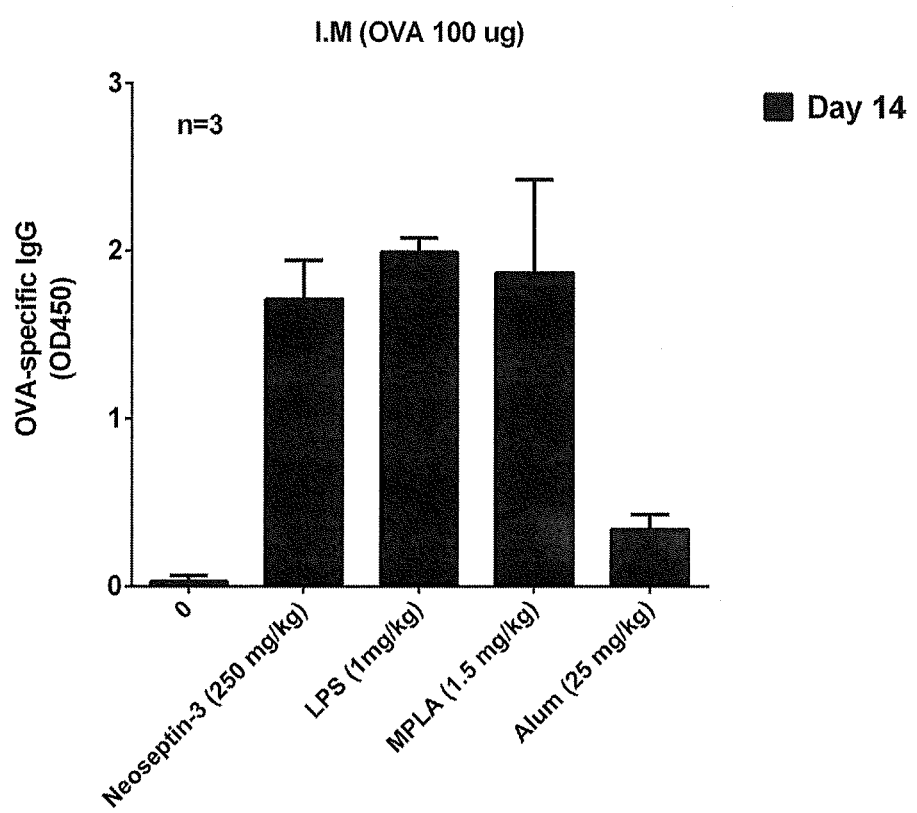
FIG. 9 is a graph similar to FIG. 3 showing anti-olvalbumin titers at 14 days post immunization using adjuvants with ovalbumin (OVA, 100 µg) and injected intramuscularly into C57BL/6J mice. The adjuvants used were neoseptin-3, LPS, MPLA, and alum in the amounts shown.
Figure 10:
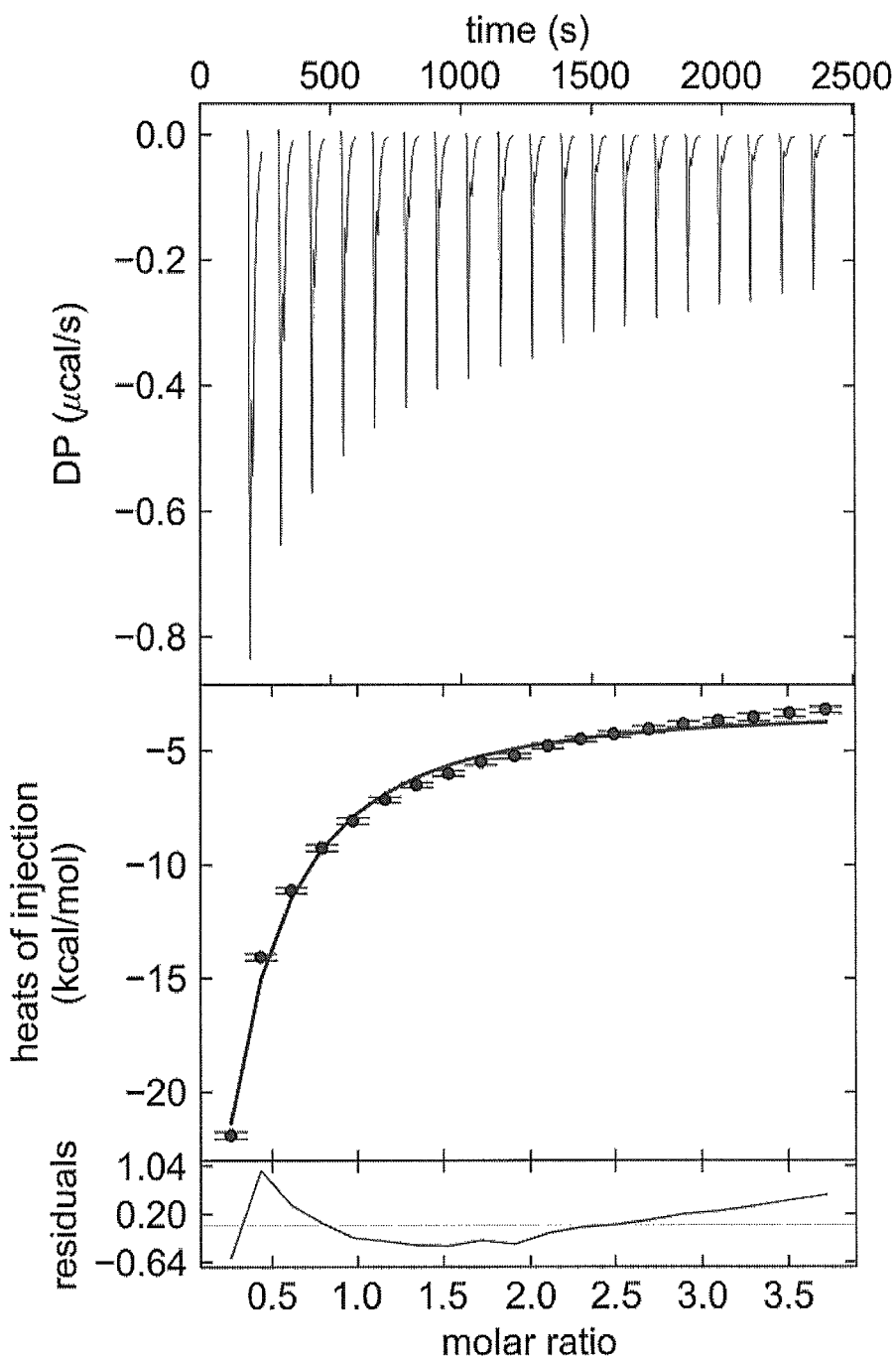
FIG. 10 shows the results of an isothermal titration calorimetry study of the binding of 20 µM neoseptin-3 with 350 µM MD-2. The Kd of neoseptin-3 binding to MD-2 is 11.7 µM, whereas MPLA binds to MD-2 with a Kd of 14.4 µM.
Figure 11A:
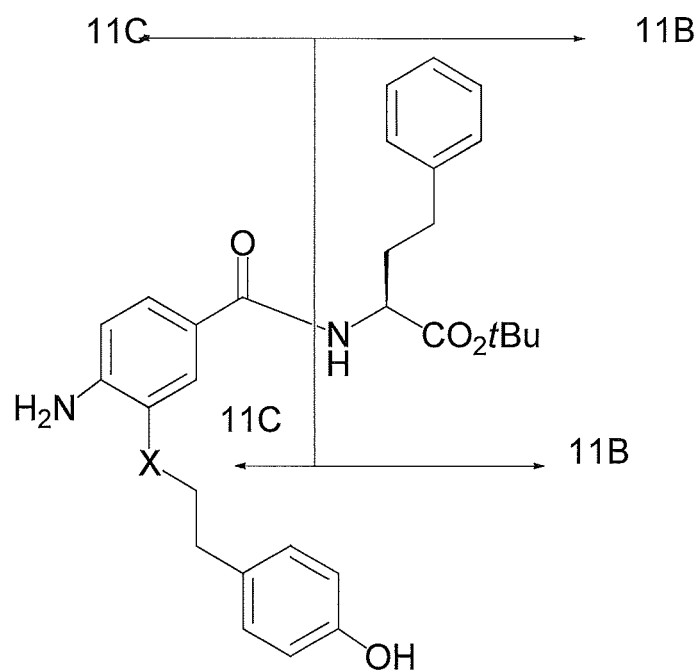
FIG. 11A shows a formula for such an embodiment divided by a line through the amide bond terminated by arrows to 11B and 11C, which FIG. 11B and FIG. 11C provide structure activity relationships determined to date for the preferred embodiments encompassed by compounds within the structural formula of FIG. 11A.
Figure 11B:
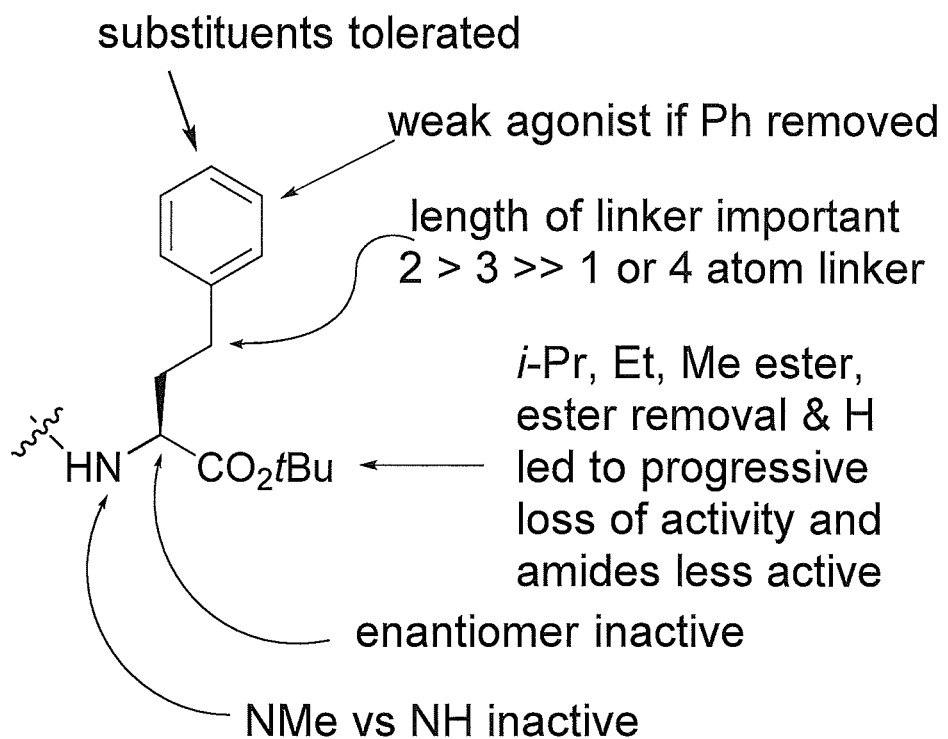
Figure 11C:
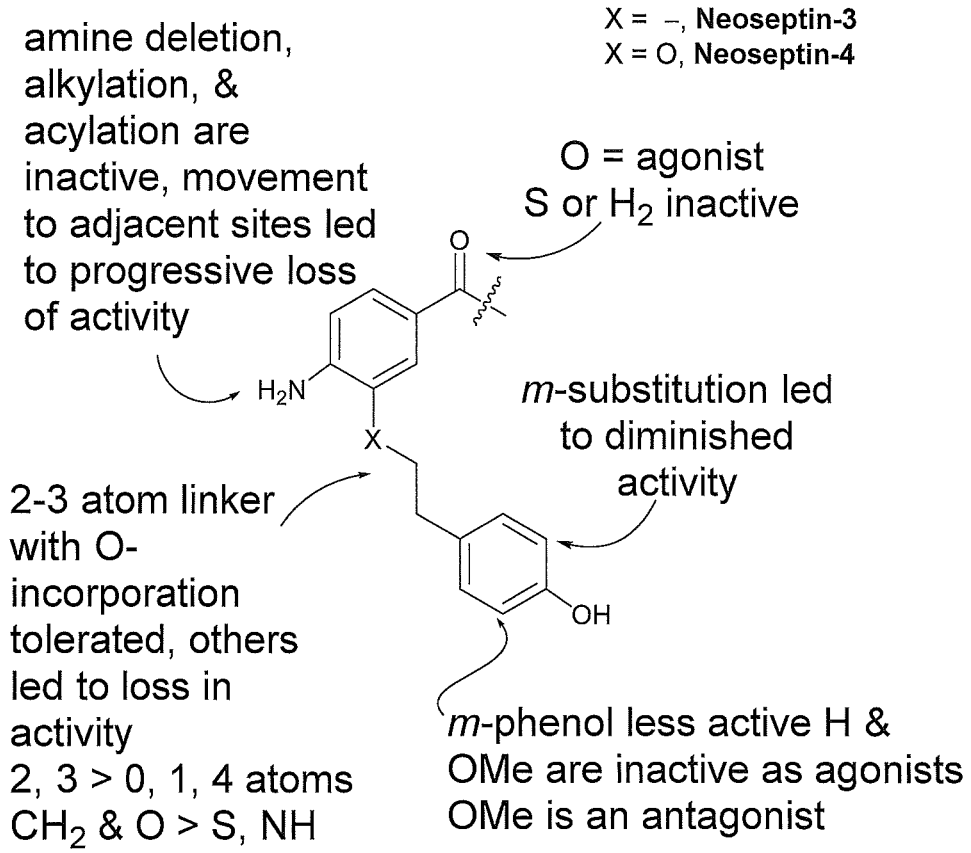

Further comparison of the adjuvant activity of neospetin-3 with alum, the only US approved vaccination adjuvant, is illustrated in FIG. 9. Neoseptin-3 stimulates a much more robust immune response in vivo than does alum.

Mouse Peritoneal Macrophage Agonist Assay

Reagents:
Brewer's Thioglycolate Medium, 4%
  4% (w/v) Brewer's thioglycolate medium powder (BBL Microbiology Systems, Cockeysville, Md.) is added to distilled water pre-warmed to 37° C. The solution is autoclaved to sterilize and stored away from light.
PEC Recovery Solution
  Hepes-buffered saline solution (Gibco, Invitrogen, Carlsbad, Calif.)
  5% (v/v) heat-inactivated fetal bovine serum (Atlanta Biologicals, Lawrenceville, Ga.)
  200 IU/mL penicillin (Gibco)
  200 mg/mL streptomycin (Gibco)
PEC Medium
  Dulbecco's modified eagle medium (Mediatech Inc., Herndon, Va.)
  5% (v/v) heat-inactivated fetal bovine serum
  200 IU/mL penicillin
  200 mg/mL streptomycin
MTT Solution
  5 mg MTT (Sigma)/mL sterile PBS
DMSO
Mouse TNF$\alpha$ ELISA Ready-SET-Go!® (eBioscience:88-7324-76)
  Wash Buffer: 1×PBS, 0.05% Tween-20
  Stop Solution: 2N $H_2SO_4$
  96-well plate (Corning Costar 9018 or NUNC Maxisorp (#44-2404))
  96-well ELISA plate reader
  DI water
Peritoneal Exudate Cell (PEC) (Peritoneal Macrophages) Isolation
  Three to four days prior to PEC isolation, 3 mL syringes filled with Brewer's thioglycolate medium are used to inject mice intraperitoneally with 1.5-2 mL through a 25-gauge needle.
  Immediately prior to isolation, mice are anaesthetized under isofluorane vapour (2-5% v/v, 2% $O_2$).
  5 mL syringes filled with sterile PBS are used to recover PECs by lavage through an 18-gauge needle. Once obtained, exudate is added to 5 mL of PEC recovery solution in a 15 mL conical tube, and stored on ice.
  Tubes containing exudate are centrifuged for 3 minutes at 1200 rpm in a tabletop centrifuge, and supernatant is replaced with 1-4 mL of PEC medium. Pelleted cells are resuspended by pipeting, and a 10 µL aliquot is taken for cell enumeration.
  The concentration of each cell sample is adjusted to $1\times10^6$ cells/mL using PEC medium, and 100 µL of each sample ($1\times10^5$ cells) is added to a tissue culture-treated 96 well flat-bottomed plate, leaving two columns (11 & 12) unoccupied per plate. Plates are incubated at 37° C./5% $CO_2$ in a humidified incubator for at least 1 hour to permit cells to adhere to the plate, during which time 125-03 solutions are prepared.
Compound Screen
  Following preincubation of PECs in the 96-well plate, non-adherent PECs are discarded along with residual medium, and 50 µM of compounds to be assayed are added to the cells. Plates are incubated for a further 4 hours.
  Conditioned supernatant is collected into another 96 well plate and retained for TNF ELISA Assay. The cells are replaced with 100 µL/well of a 1:4 MTT solution:PEC medium solution (MTT 1 mg/mL final concentration). PEC plates are incubated at 37° C./5% $CO_2$ overnight (about 18 hours). Supernatants are removed and 100 µL DMSO is added to each well. The plate is shaken for 10 minutes and read at 570 nM. This value is used to measure the cytotoxicity of the compounds.
TNF$\alpha$ ELISA
  Coat ELISA plate with 100 µL/well of capture antibody in Coating Buffer. Seal the plate and incubate overnight (about 18 hours) at 4° C.
  Aspirate wells and wash 4× with 300 µL/well Wash Buffer. Blot plate on absorbent paper to remove residual buffer.
  Dilute 1 part 5× concentrated Assay Diluent with 4 parts DI water. Block wells with 200 µL/well of 1× Assay Diluent. Incubate at room temperature for 1 hour or 4° C. overnight (about 18 hours).
  Aspirate and wash at twice with Wash Buffer.
  Using 1× Assay Diluent to perform 2-fold serial dilutions of the top standards to make the standard curve for a total of 8 points: 1000, 500, 250, 125, 62.5, 31.25, 15.625, 0 pg/ml. Add 100 µL/well of top standard concentration to the appropriate wells. Add 65 µL/well assay diluent plus 35 µL samples to the wells. Seal the plate and incubate at room temperature for 2 hours [or overnight (about 18 hours) at 4° C.]
  Aspirate/wash 4 times with wash buffer.
  Add 100 µL/well of detection antibody diluted in 1× Assay diluent. Seal the plate and incubate at room temperature for 1 hour.
  Aspirate/wash. Repeat for a total of 4 washes.
  Add 100 µL/well of Avidin-HRP diluted in 1× Assay diluent. Seal the plate and incubate at room temperature for 30 minutes.
  Aspirate and wash. Repeat for a total of 5 washes.
  Add 100 µL/well of Substrate Solution to each well. Incubate plate at room temperature for 2-3 minutes.
  Add 50 µL/well of Stop Solution, and read plate at 450 nm.

Compound Preparation

A contemplated Compound of Formula I, a neoceptin molecule, can be readily prepared using standard organic chemistry procedures. An illustrative synthesis of neoseptin-3 is illustrated schematically below in Schemes 1A and 1B.

Scheme 1A
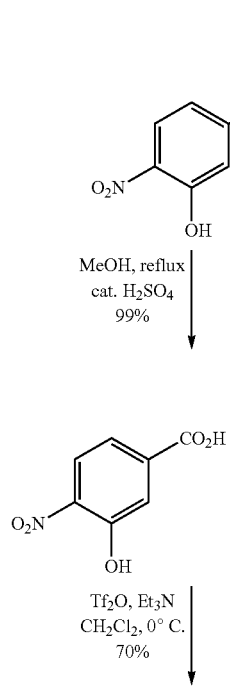
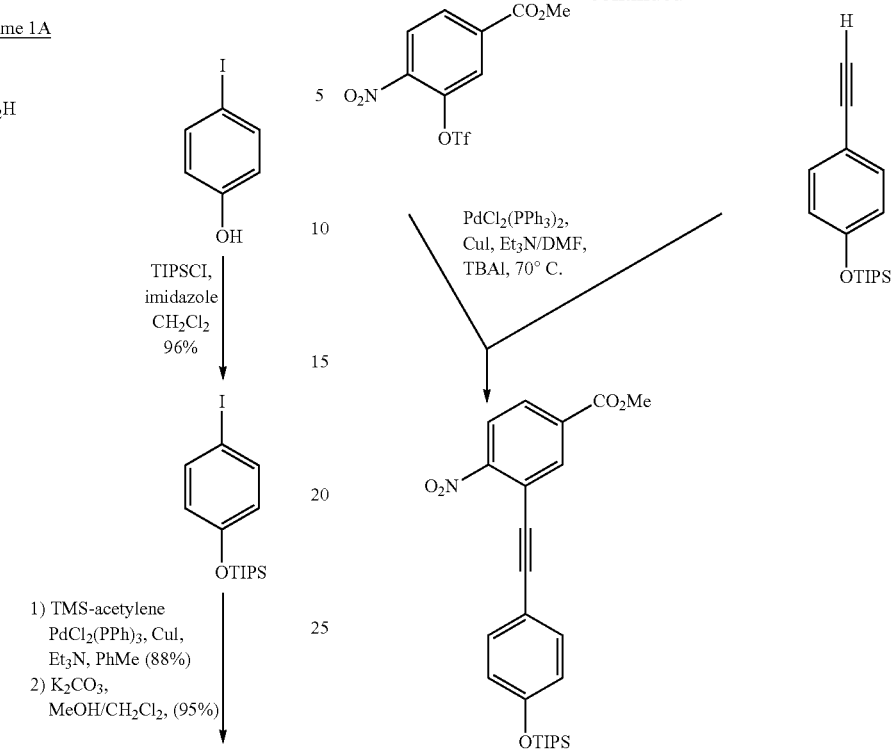
Scheme 1B
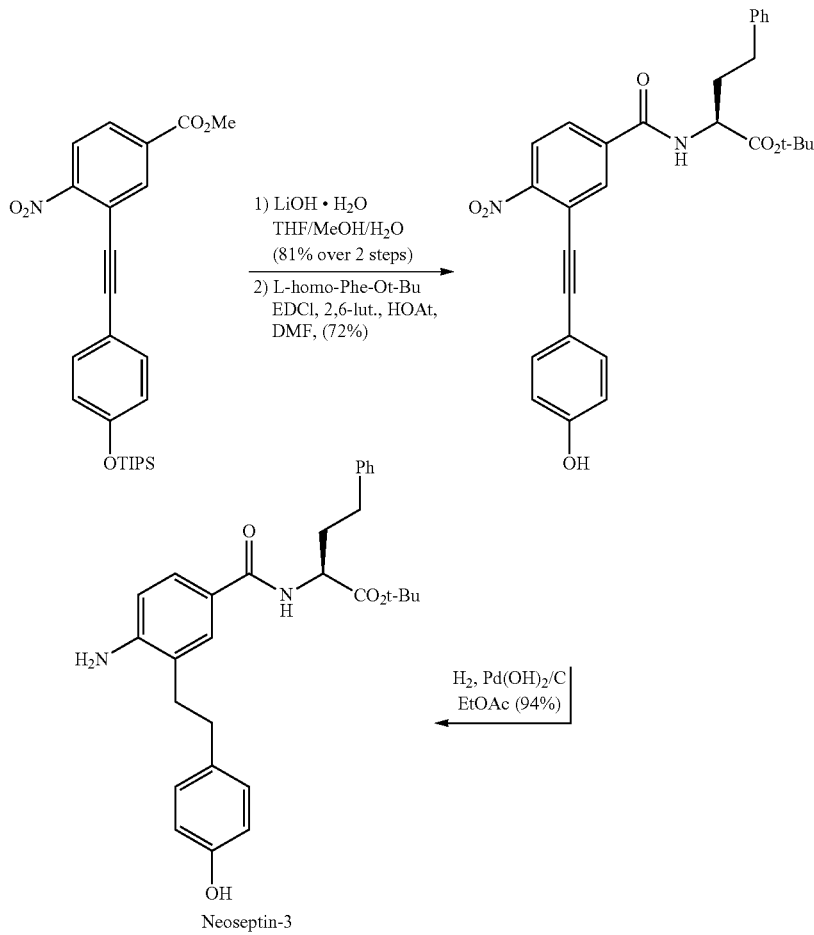

An alternative synthesis is set out in Schemes 2A and 2B, below.
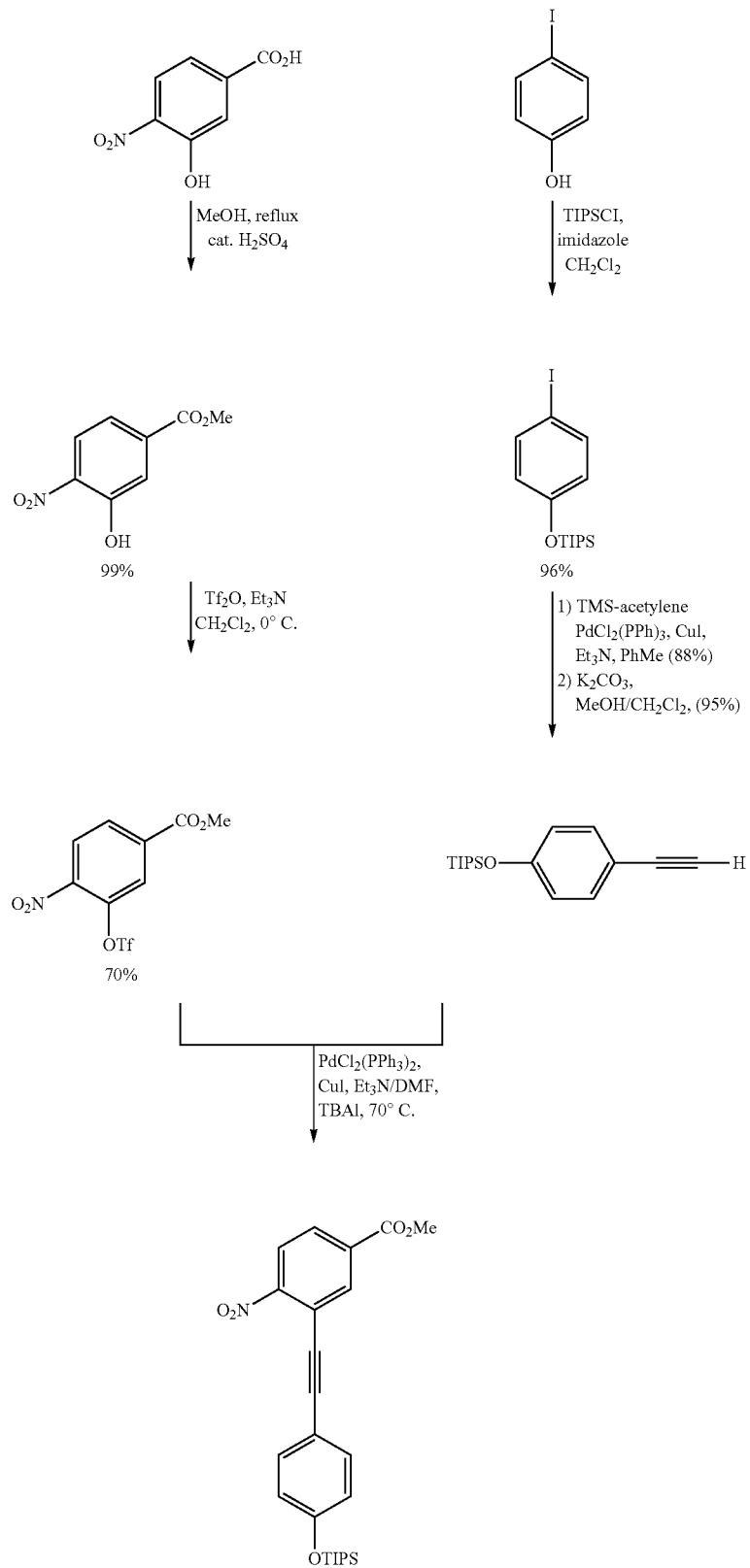
Scheme 2A

Scheme 2B

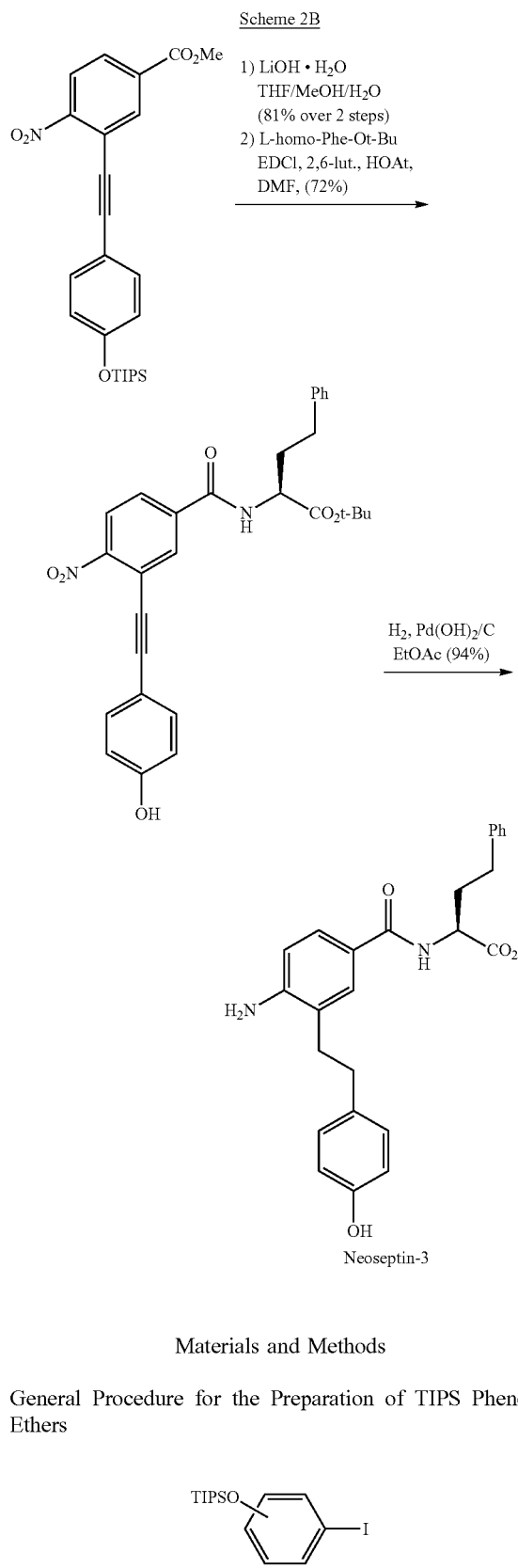

Neoseptin-3

Materials and Methods

General Procedure for the Preparation of TIPS Phenolic Ethers

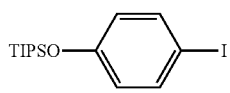

Iodophenol (11.4 mmol) was dissolved in anhydrous CH$_2$Cl$_2$ (50 mL). Imidazole (12.0 mmol, 1.05 equiv) was added to the mixture, followed by dropwise addition of TIPSCl (11.4 mmol, 1.00 equiv). After 16 hours, the cloudy reaction mixture was transferred to a 500 mL separatory funnel and washed with sat. NH$_4$Cl (25 mL) and H$_2$O (25 mL). The aqueous phase was extracted twice with CH$_2$Cl$_2$ (25 mL), and the combined extracts were dried over Na$_2$SO$_4$ and concentrated. Flash chromatography (SiO$_2$, hexanes to 10% EtOAc/hexanes) gave 4.12 g (96%) of the silyl ether.

(MM-1-58) 4-Iodophenol (2.50 g, 11.4 mmol), CH$_2$Cl$_2$ (50 mL), imidazole (815 mg, 12.0 mmol, 1.05 equiv) and TIPSCl (2.50 mL, 11.4 mmol, 1.00 equiv) were combined according to the general procedure. Flash chromatography (SiO$_2$, hexanes to 10% EtOAc/hexanes) gave 4.12 g (96%) of the silyl ether. $^1$H NMR (300 MHz, CDCl$_3$) δ 7.50 (dd, J=8.9, 0.7 Hz, 2H), 6.67 (dd, J=8.9, 0.7 Hz, 2H), 1.36-1.16 (m, 3H), 1.10 (d, J=6.9 Hz, 18H).

(MM-1-234) 3-Iodophenol (500 mg, 2.27 mmol), CH$_2$Cl$_2$ (10 mL), imidazole (162 mg, 2.39 mmol, 1.05 equiv) and TIPSCl (510 μL, 2.27 mmol, 1.00 equiv) were combined according to the general procedure. Flash chromatography (SiO$_2$, hexanes to 10% EtOAc/hexanes) gave 710 mg (83%) of the silyl ether.

(MM-1-235) 2-iodophenol (500 mg, 2.27 mmol), CH$_2$Cl$_2$ (10 mL), imidazole (162 mg, 2.39 mmol, 1.05 equiv) and TIPSCl (510 μL, 2.27 mmol, 1.00 equiv) were combined according to the general procedure. Flash chromatography (SiO$_2$, hexanes to 10% EtOAc/hexanes) gave 632 mg (74%) of the silyl ether.

General Procedure for Sonogashira Cross-Coupling with TMS-Acetylene

The TIPSO iodide (2.66 mmol) was dissolved in anhydrous toluene (12 mL). PdCl$_2$(PPh$_3$)$_2$ (0.133 mmol, 5 mol %) and CuI (0.266 mmol, 10 mol %) were added in one portion, followed by freshly distilled Et$_3$N (2.92 mmol, 1.1 equiv). After stirring for 15 minutes, trimethylsilylacetylene (2.92 mmol, 1.1 equiv) was added dropwise, upon complete addition of which the reaction mixture turned dark green.

After 12 hours at room temperature, the solvent was removed in vacuo. Flash chromatography of the resulting dark oil (SiO$_2$, 0 to 4% EtOAc/hexanes) afforded the cross-coupled alkyne.

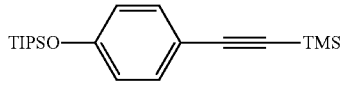

(MM-1-68) Compound MM-1-58 (1.00 g, 2.66 mmol), toluene (12 mL), PdCl$_2$(PPh$_3$)$_2$ (94 mg, 0.133 mmol, 5 mol %), CuI (56 mg, 0.266 mmol, 10 mol %), Et$_3$N (0.41 mL, 2.92 mmol, 1.1 equiv) and trimethylsilylacetylene (0.42 mL, 2.92 mmol, 1.1 equiv) were used according to the general procedure. Flash chromatography (SiO$_2$, 0 to 4% EtOAc/hexanes) afforded 0.809 g (88%) of the cross-coupled alkyne. $^1$H NMR (300 MHz, CDCl$_3$) δ 7.38-7.31 (m, 2H), 6.83-6.77 (m, 2H), 1.30-1.18 (m, 3H), 1.10 (d, J=3.6 Hz, 18H), 0.25 (s, 9H).

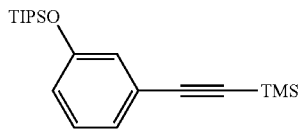

(MM-1-271) Compound MM-1-234 (1.00 g, 2.66 mmol), toluene (12 mL), PdCl$_2$(PPh$_3$)$_2$ (93 mg, 0.133 mmol, 5 mol %), CuI (51 mg, 0.266 mmol, 10 mol %), Et$_3$N (0.41 mL, 2.92 mmol, 1.1 equiv) and trimethylsilylacetylene (0.42 mL, 2.92 mmol, 1.1 equiv) were used according to the general procedure. The reaction mixture was filtered, concentrated, and used unpurified in the next step.

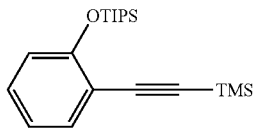

(MM-1-272) Compound MM-1-235 (1.00 g, 2.66 mmol), toluene (12 mL), PdCl$_2$(PPh$_3$)$_2$ (93 mg, 0.133 mmol, 5 mol %), CuI (51 mg, 0.266 mmol, 10 mol %), Et$_3$N (0.41 mL, 2.92 mmol, 1.1 equiv) and trimethylsilylacetylene (0.42 mL, 2.92 mmol, 1.1 equiv) were used according to the general procedure. The reaction mixture was filtered, concentrated, and used unpurified in the next step.

General Procedure for Selective TMS Cleavage

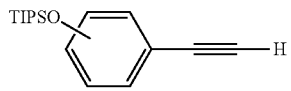

TIPSO TMS-alkyne (2.00 mmol) was suspended in MeOH (10 mL). CH$_2$Cl$_2$ was added until a homogeneous mixture was obtained (approx. 1-2 mL) with stirring. K$_2$CO$_3$ (2.22 mmol, 1.10 equiv) was added. The mixture was stirred at room temperature for 3 hours, after which the reaction was observed to be complete by TLC (hexanes eluent). The mixture was diluted with CH$_2$Cl$_2$ (30 mL) and washed with H$_2$O (20 mL). The aqueous phase was extracted with CH$_2$Cl$_2$ (3×10 mL) and the combined organic phases were dried over Na$_2$SO$_4$, decanted and concentrated in vacuo to yield the terminal alkyne, which was used without further purification.

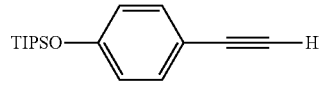

(MM-1-70) TMS-alkyne MM-1-68 (700 mg, 2.02 mmol), MeOH (10 mL), CH$_2$Cl$_2$, K$_2$CO$_3$ (320 mg, 2.22 mmol, 1.10 equiv.) were combined according to the general procedure to yield 524 mg (95%) of the terminal alkyne, which was used without further purification. $^1$H NMR (300 MHz, CDCl$_3$) δ 7.36 (d, J=8.6 Hz, 2H), 6.81 (d, J=8.8 Hz, 2H), 2.99 (s, 1H), 1.24 (m, 3H), 1.09 (d, J=6.8 Hz, 18H).

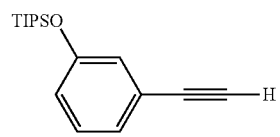

(MM-1-274) TMS-alkyne MM-1-271 (920 mg, 2.66 mmol), MeOH (10 mL), CH$_2$Cl$_2$ (~1 mL), K$_2$CO$_3$ (370 mg, 2.68 mmol, 1.01 equiv) were combined according to the general procedure to yield 474 mg (65%) of the terminal alkyne. $^1$H NMR (400 MHz, CDCl$_3$) δ 7.18 (td, J=7.9, 2.6 Hz, 1H), 7.12-7.06 (m, 1H), 7.02 (d, J=1.8 Hz, 1H), 6.92-6.87 (m, 1H), 3.05 (s, 1H), 1.27 (m, 3H), 1.11 (d, J=7.3 Hz, 18H).

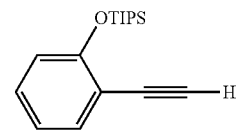

(MM-1-275) TMS-alkyne MM-1-272 (920 mg, 2.66 mmol), MeOH (10 mL), CH$_2$Cl$_2$ (~1 mL), K$_2$CO$_3$ (370 mg, 2.68 mmol, 1.01 equiv) were combined according to the general procedure to yield 243 mg (33%) of the terminal alkyne. $^1$H NMR (400 MHz, CDCl$_3$) δ 7.43 (dt, J=7.7, 2.2 Hz, 1H), 7.24-7.16 (m, 1H), 6.88 (dd, J=8.0, 2.6 Hz, 2H), 3.20 (s, 1H), 1.33 (m, 3H), 1.15 (d, J=7.5 Hz, 18H).

General Procedure for Benzoic Acid Fischer Esterification

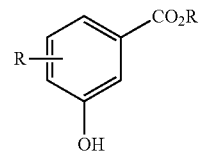

3-Hydroxybenzoic acid (8.00 mmol) was dissolved in MeOH (60 mL) in a two-neck 250 mL round-bottom flask fitted with a reflux condenser and stir bar. Conc. H$_2$SO$_4$ (about 0.5 mL) was added, and the mixture was stirred at reflux for 18 hours. After cooling to room temperature, the reaction solvent was concentrated in vacuo to ⅕ volume, diluted with EtOAc (50 mL) and washed with sat. NaHCO$_3$ (30 mL). The aqueous phase was acidified with 1 N HCl until pH 2, then extracted with EtOAc (3×15 mL). The combined organic phases were dried over Na₂SO₄ and concentrated under high vacuum to afford the methyl ester (95-99%). Where further purification was necessary, products were subjected to flash chromatography (SiO₂, 50% EtOAc/hexanes). [Börger et al., *Synlett*, 11:1698-1702 (2008); Charrier et al., *Synthesis*, 20:3467-3477 (2006).]

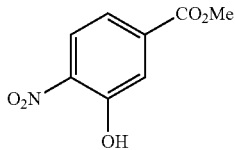 [SMILES: COC(=O)c1ccc([N+](=O)[O-])c(O)c1]

(MM-1-40) The general procedure for Fischer esterification was followed: 3-hydroxy-4-nitrobenzoic acid (3.00 g, 16.4 mmol), MeOH (120 mL), and H₂SO₄ (about 1.0 mL, conc.) were employed. Methyl 3-hydroxy-4-nitrobenzoate, 3.2 g (99%), was obtained as a yellow solid, which was used without further purification.

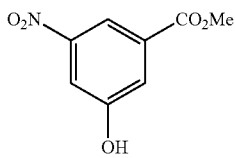 [SMILES: COC(=O)c1cc(O)cc([N+](=O)[O-])c1]

(MM-1-492) The general procedure for Fischer esterification was followed: 3-hydroxy-5-nitrobenzoic acid (1.50 g, 8.19 mmol), MeOH (60 mL), and H₂SO₄ (~0.5 mL, conc.) were employed. Methyl 3-hydroxy-5-nitrobenzoate, 1.6 g (99%), was obtained as a yellow solid, which was used without further purification.

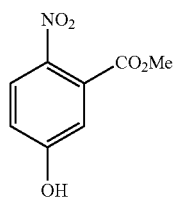

(MM-2-5) The general procedure for Fischer esterification was followed: 5-hydroxy-2-nitrobenzoic acid (1.5 g 8.19 mmol), MeOH (60 mL), and H₂SO₄ (~0.5 mL) were employed. Methyl 5-hydroxy-2-nitrobenzoate, 1.6 g (99%), was obtained as an off-white solid, used without further purification. $^1$H NMR (500 MHz, CDCl₃) δ 7.99 (d, J=8.7 Hz, 1H), 7.04-6.94 (m, 2H), 3.95 (s, 3H).

General Procedure for the Preparation of Aryl Triflates

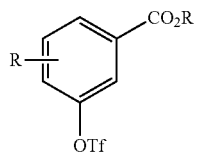

Methyl hydroxybenzoate (8.00 mmol) was dissolved in anhydrous CH₂Cl₂ (40 mL) and cooled to 0° C. under N₂ atmosphere. Et₃N (16.0 mmol, 3 equiv) was slowly added. After 15 minutes, trifluoromethane-sulfonic anhydride (8.80 mmol, 1.1 equiv) was added dropwise, producing a dark reaction medium. After 16 hours, the reaction mixture was washed with sat. NH₄Cl (30 mL) and H₂O (40 mL). The aqueous phase was extracted with CH₂Cl₂ (2×20 mL), and the combined extracts were dried over Na₂SO₄, decanted, and concentrated in vacuo. Flash chromatography (SiO₂, 10 to 20% EtOAc/hexanes) afforded the aryl triflate.

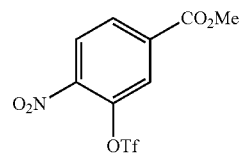

(MM-1-69) Methyl 3-hydroxy-4-nitrobenzoate (1.50 g, 7.61 mmol), CH₂Cl₂ (40 mL), Et₃N (2.21 mL, 15.2 mmol, 2.00 equiv), Tf₂O (1.45 mL, 8.37 mmol, 1.1 equiv) were employed according to the general procedure. Flash column chromatography (SiO₂, 10→20% EtOAc/hexanes) gave 1.98 g (79%) of the aryl triflate as a fluffy, off-white solid. $^1$H NMR (300 MHz, CDCl₃) δ 8.23 (t, J=1.2 Hz, 1H), 8.12-8.07 (m, 2H), 4.02 (s, 3H).

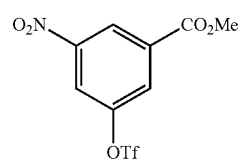 [SMILES: COC(=O)c1cc(OS(=O)(=O)C(F)(F)F)cc([N+](=O)[O-])c1]

(MM-1-494) Methyl 3-hydroxy-5-nitrobenzoate (1.50 g, 7.61 mmol), CH₂Cl₂ (40 mL), Et₃N (2.20 mL, 15.2 mmol, 2.00 equiv), Tf₂O (1.41 mL, 8.37 mmol, 1.10 equiv) were employed according to the general procedure. Flash chromatography (SiO₂, 10% EtOAc/hexanes) produced 2.31 g (92%) of the aryl triflate.

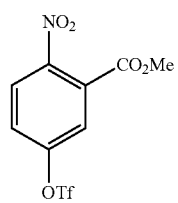 [SMILES: COC(=O)c1cc(OS(=O)(=O)C(F)(F)F)ccc1[N+](=O)[O-]]

(MM-2-6) Methyl 5-hydroxy-2-nitrobenzoate (1.60 g, 8.12 mmol), CH₂Cl₂ (40 mL), Et₃N (2.26 mL, 16.2 mmol, 2.00 equiv), Tf₂O (1.50 mL, 8.93 mmol, 1.10 equiv) were employed according to the general procedure. Flash chromatography (SiO₂, hexanes→30% EtOAc/hexanes) gave 2.39 g (90%) of the aryl triflate as a viscous orange oil.

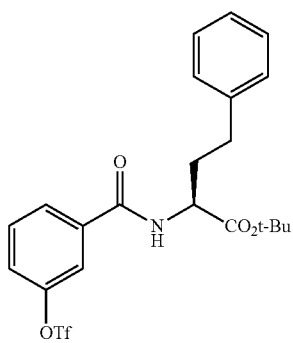 [SMILES: CC(C)(C)OC(=O)[C@H](CCc1ccccc1)NC(=O)c1cccc(OS(=O)(=O)C(F)(F)F)c1]

(MM-1-452) Phenol MRS-3-35 (412 mg, 1.16 mmol), CH₂Cl₂ (40 mL), Et₃N (0.325 mL, 2.32 mmol, 2.00 equiv), Tf$_2$O (0.215 mL, 1.28 mmol, 1.10 equiv) were employed according to the general procedure. Flash chromatography (SiO$_2$, 20% EtOAc/hexanes) gave 118 mg (21%) of the aryl triflate as a viscous amber oil. $^1$H NMR (400 MHz, CDCl$_3$) δ 7.52-7.44 (m, 1H), 7.15-6.97 (m, 7H), 6.86 (ddd, J=8.4, 2.5, 1.1 Hz, 1H), 6.54 (t, J=8.2 Hz, 1H), 4.62 (td, J=7.1, 5.2 Hz, 1H), 2.67-2.44 (m, 2H), 2.25-2.08 (m, 1H), 2.06-1.90 (m, 1H), 1.36 (s, 9H).

General Procedure for 2$^{nd}$ Sonogashira Cross-Coupling and Hydrolysis

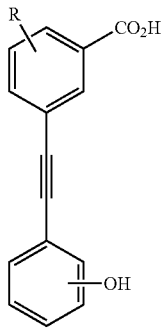

A 100 mL two-neck round-bottom flask was charged with triflate (7.29 mmol), PdCl$_2$(PPh$_3$)$_2$ (0.73 mmol, 10 mol %), CuI (2.18 mmol, 30 mol %), and TBAI (21.8 mmol, 3.00 equiv). The reagents were suspended in 5:1 DMF/Et$_3$N (30 mL/6 mL), and the reaction mixture was submerged in a preheated oil bath at 70° C. Aryl alkyne (14.6 mmol, 2.00 equiv) was added dropwise to the vigorously stirred reaction mixture. After 3 hours, the mixture was cooled to room temperature, diluted with 1:1 EtOAc/hexanes (60 mL ea.) and washed with sat. NH$_4$Cl/H2O (2×25 mL ea). The aqueous phase was extracted with the 1:1 mixture (3×30 mL), and combined organic phases were dried over Na$_2$SO$_4$, decanted and concentrated. The resultant dark oil was dissolved in 4:1:1 THF/MeOH/H$_2$O (20 mL/5 mL/5 mL, respectively). LiOH.H$_2$O (31.0 mmol, 4.25 equiv) was added, and the suspension stirred at room temperature overnight. After 16 hours, the reaction mixture was cooled to 0° C. and 2N HCl (approx. 8-10 mL) was added until a precipitate was observed. The mixture was diluted with EtOAc (100 mL) and washed with more aq. HCl until the aqueous phase remained pH about 2. The aqueous phase was extracted with EtOAc (2×30 mL), and the combined organic phases were dried over Na$_2$SO$_4$, decanted and concentrated in vacuo. Flash chromatography (SiO$_2$, 50:50:0.5 EtOAc: hexanes:AcOH) gave the cross-coupled carboxylic acid.

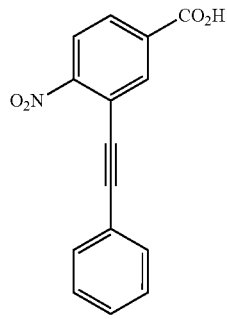 [SMILES: O=C(O)c1ccc([N+](=O)[O-])c(C#Cc2ccccc2)c1]

(MM-1-52/457) Triflate MM-1-69 (100 mg, 0.304 mmol), PdCl$_2$(PPh$_3$)$_2$ (21 mg, 0.030 mmol, 10 mol %), CuI (17 mg, 0.091 mmol, 30 mol %), TBAI (337 mg, 0.911 mmol, 3.00 equiv) and phenylacetylene were combined according to the general procedure. Flash chromatography at this stage afforded 52 mg (60%) of the cross-coupled product. LiOH.H$_2$O (28 mg, 0.668 mmol, 4.00 equiv) hydrolysis gave 44 mg (99%) of the depicted cross-coupled carboxylic acid. $^1$H NMR (methyl ester, 300 MHz, CDCl$_3$) δ 8.34 (s, 1H), 8.12-8.01 (m, 2H), 7.65-7.54 (m, 2H), 7.40 (dd, J=3.2, 1.9 Hz, 3H), 3.98 (s, 3H).

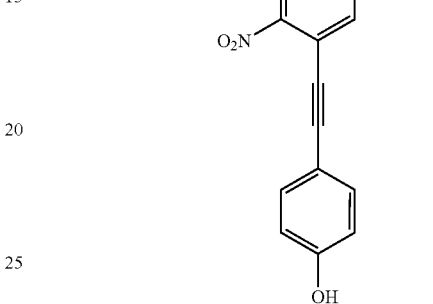

(MM-2-3) Triflate MM-1-69 (2.40 g, 7.29 mmol), PdCl$_2$(PPh$_3$)$_2$ (510 mg, 0.73 mmol, 10 mol %), CuI (415 mg, 2.18 mmol, 30 mol %), TBAI (8.06 g, 21.8 mmol, 3.00 equiv), alkyne MM-1-70 (4.00 g, 14.6 mmol, 2.00 equiv) and LiOH.H$_2$O (1.30 g, 31.0 mmol, 4.25 equiv) were combined according to the general procedure. Flash chromatography (50:50:0.5 EtOAc:hexanes:AcOH) gave 1.69 g (81%) of the depicted cross-coupled carboxylic acid. $^1$H NMR (500 MHz, CDCl$_3$) δ 8.35 (d, J=1.8 Hz, 1H), 8.10 (d, J=8.5 Hz, 1H), 8.05 (dd, J=8.6, 1.8 Hz, 1H), 7.50 (d, J=8.6 Hz, 2H), 6.89 (d, J=8.6 Hz, 2H), 4.19 (s, 1H).

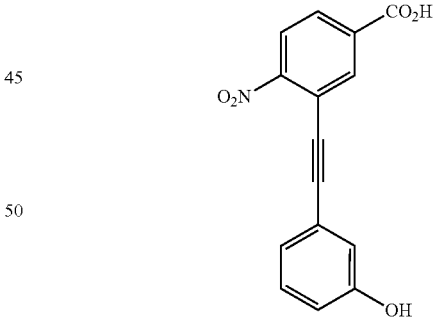

(MM-1-276/278) Triflate MM-1-69 (176 mg, 0.534 mmol), PdCl$_2$(PPh$_3$)$_2$ (38 mg, 0.053 mmol, 10 mol %), TBAI (590 mg, 1.60 mmol, 3.00 equiv) and alkyne MM-1-274 (220 mg, 0.800 mmol, 1.50 equiv) were combined according to the general procedure. Flash chromatography at this stage gave 117 mg (48%). LiOH.H$_2$O (43 mg, 1.03 mmol, 4.25 equiv) employed in the hydrolysis step gave 112 mg (99%) of the depicted carboxylic acid. $^1$H NMR (400 MHz, CDCl$_3$) δ 8.84 (d, J=1.9 Hz, 1H), 8.31 (d, J=1.7 Hz, 1H), 8.07-7.97 (m, 2H), 7.23-7.10 (m, 2H), 7.09-7.03 (m, 1H), 6.88 (ddd, J=8.1, 2.5, 1.4 Hz, 1H).

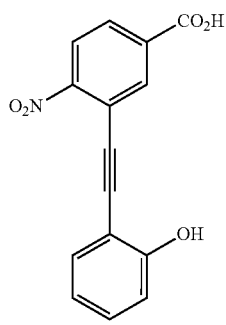 [SMILES: O=C(O)c1ccc([N+](=O)[O-])c(C#Cc2ccccc2O)c1]

(MM-1-277/279) Triflate XMM-1-69 (176 mg, 0.534 mmol), PdCl$_2$(PPh$_3$)$_2$ (38 mg, 0.053 mmol, 10 mol %), TBAI (590 mg, 1.60 mmol, 3.00 equiv) and alkyne MM-1-275 (220 mg, 0.800 mmol, 1.50 equiv) were combined according to the general procedure. Flash chromatography at this stage gave 50 mg (31%). LiOH.H$_2$O (28 mg, 1.03 mmol, 4.00 equiv) employed in the hydrolysis step gave 48 mg (99%) of the depicted carboxylic acid. $^1$H NMR (methyl ester, 400 MHz, CDCl$_3$) δ 8.39 (dd, J=3.6, 1.9 Hz, 1H), 8.23 (dd, J=8.8, 3.4 Hz, 1H), 8.10 (ddd, J=8.8, 3.6, 1.9 Hz, 1H), 7.46 (dq, J=5.4, 1.8 Hz, 1H), 7.39-7.31 (m, 1H), 7.03 (dd, J=8.3, 3.3 Hz, 1H), 6.94 (td, J=8.2, 3.4 Hz, 1H), 6.61 (d, J=3.4 Hz, 1H), 4.00 (s, 3H).

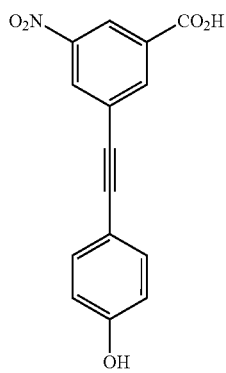 [SMILES: O=C(O)c1cc(C#Cc2ccc(O)cc2)cc([N+](=O)[O-])c1]

(MM-1-495/496) Triflate MM-1-494 (1.20 g, 3.64 mmol), PdCl$_2$(PPh$_3$)$_2$ (256 mg, 0.36 mmol, 10 mol %), CuI (208 mg, 1.09 mmol, 30 mol %), TBAI (4.00 g, 10.9 mmol, 3.00 equiv), alkyne MM-1-70 (2.00 g, 7.3 mmol, 2.00 equiv) and LiOH.H$_2$O (381 mg, 9.08 mmol, 2.50 equiv) were combined according to the general procedure. Flash chromatography (SiO$_2$, 50:50:1 EtOAc:hexanes:AcOH) gave 365 mg (57%) of the depicted cross-coupled carboxylic acid.

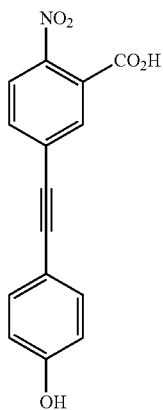 [SMILES: O=C(O)c1cc(C#Cc2ccc(O)cc2)ccc1[N+](=O)[O-]]

(MM-2-9/11) Triflate MM-2-6 (1.20 g, 3.64 mmol), PdCl$_2$(PPh$_3$)$_2$ (256 mg, 0.36 mmol, 10 mol %), CuI (208 mg, 1.09 mmol, 30 mol %), TBAI (4.00 g, 10.9 mmol, 3.00 equiv), alkyne MM-1-70 (2.00 g, 7.3 mmol, 2.00 equiv.) were combined according to the general procedure. Flash chromatography at this stage afforded 788 mg (48%) of the cross-coupled product. LiOH.H$_2$O (251 mg, 6.00 mmol, 4.00 equiv. based on 679 mg of the starting methyl ester) hydrolysis and flash chromatography (SiO$_2$, 50:50:1 EtOAc:hexanes:AcOH) gave 133 mg (31%) of the depicted cross-coupled carboxylic acid. $^1$H NMR (methyl ester, 500 MHz, CDCl$_3$) δ 7.94 (d, J=8.4 Hz, 1H), 7.79 (d, J=1.8 Hz, 1H), 7.68 (dd, J=8.4, 1.8 Hz, 1H), 7.43 (d, J=8.6 Hz, 2H), 6.89 (d, J=8.6 Hz, 2H), 3.95 (s, 3H), 1.34-1.23 (m, 3H), 1.12 (d, J=7.4 Hz, 18H).

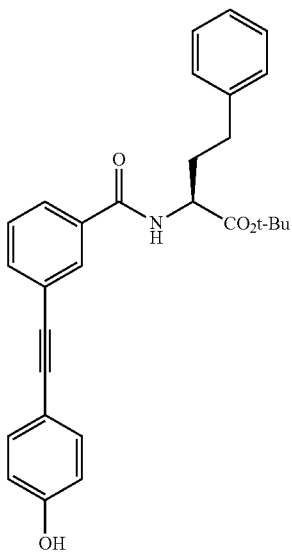 [SMILES: CC(C)(C)OC(=O)[C@H](CCc1ccccc1)NC(=O)c1cccc(C#Cc2ccc(O)cc2)c1]

(MM-1-454) Triflate MM-1-452 (99 mg, 0.203 mmol), PdCl$_2$(PPh$_3$)$_2$ (15 mg, 0.020 mmol, 10 mol %), CuI (8 mg, 0.040 mmol, 20 mol %), TBAI (225 mg, 0.609 mmol, 3.00 equiv), alkyne MM-1-70 (111 mg, 0.406 mmol, 2.00 equiv) were combined according to the general procedure. Flash chromatography (SiO$_2$, 20% EtOAc/hexanes) at this stage afforded 88 mg (71%) of the cross-coupled product. Silyl ether cleavage (TBAF, 1 M in THF, 1.0 mL, 1.00 mmol, 6.9 equiv) and flash chromatography (SiO$_2$, 30% EtOAc/hexanes) gave 14 mg (22%) of the depicted cross-coupled free phenol. $^1$H NMR (400 MHz, CDCl$_3$) δ 7.80 (t, J=1.9 Hz, 1H), 7.73-7.67 (m, 2H), 7.62 (dt, J=7.8, 1.3 Hz, 1H), 7.44-7.36 (m, 5H), 7.21 (d, J=7.1 Hz, 2H), 6.88 (d, J=7.1 Hz, 2H), 4.81 (td, J=7.0, 4.9 Hz, 1H), 2.83-2.66 (m, 2H), 2.40-2.27 (m, 1H), 2.14 (ddd, J=13.9, 9.9, 6.7 Hz, 1H), 1.13 (s, 9H).

General Procedure for Amine Coupling with Acid

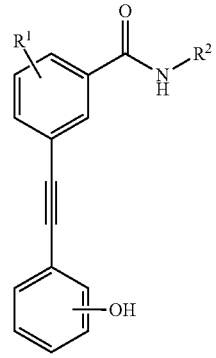

Carboxylic acid (1.00 mmol), amine (1.00 mmol, 1 equiv), and 1-hydroxy-7-aza-benzotriazole (HOAt) (1.10 mmol, 1.1 equiv) were combined in a 20 mL scintillation vial equipped with a stir bar. Anhydrous DMF (5 mL) and 2,6-lutidine (5.0 mmol, 5.0 equiv) were added, and the mixture stirred until complete dissolution of the reagents. 1-Ethyl-3-(3-dimethylaminopropyl)carbodiimide (EDCI.HCl) (1.05 mmol, 1.05 equiv) was added, and the mixture was stirred 12-24 hours. The reaction mixture was diluted with EtOAc (30 mL), washed with 0.1 N HCl (2×25 mL) and sat. aqueous NaCl (25 mL). The aqueous phase was extracted with EtOAc (2×10 mL), and combined organic phases were dried over $Na_2SO_4$, decanted and concentrated. Purified products were isolated by flash chromatography.

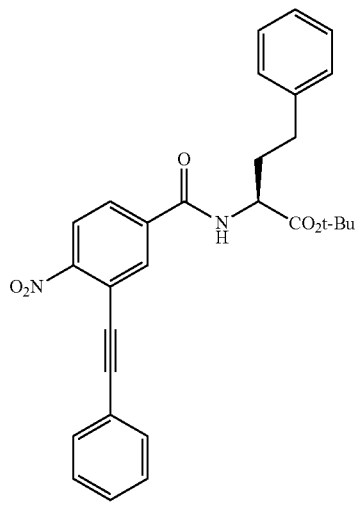 [SMILES: CC(C)(C)OC(=O)[C@H](CCc1ccccc1)NC(=O)c1ccc([N+](=O)[O-])c(C#Cc2ccccc2)c1]

(MM-1-458) The general procedure for amine coupling with acid was followed: Carboxylic acid MM-1-52/457 (44 mg, 0.165 mmol), HoPhe-OtBu (39 mg, 0.165 mmol, 1 equiv), HOAt (25 mg, 0.181 mmol, 1.1 equiv), 2,6-lutidine (95 µL, 0.823 mmol, 5.0 equiv) and EDCI.HCl (33 mg, 0.173 mmol, 1.05 equiv) were employed. Flash chromatography ($SiO_2$, 10% EtOAc/hexanes) afforded 11.4 mg (14%) of coupled product. $^1$H NMR (400 MHz, $CDCl_3$) δ 8.71-8.66 (m, 1H), 7.77-7.72 (m, 2H), 7.58-7.47 (m, 2H), 7.47-7.40 (m, 2H), 7.34-7.28 (m, 3H), 7.21 (d, J=7.3 Hz, 3H), 6.71 (d, J=7.7 Hz, 1H), 4.81 (ddd, J=7.6, 6.6, 5.1 Hz, 1H), 2.84-2.62 (m, 2H), 2.32 (dddd, J=13.8, 10.3, 6.5, 5.1 Hz, 1H), 2.13 (dddd, J=13.8, 12.3, 10.9, 6.0 Hz, 1H), 1.53 (s, 9H).

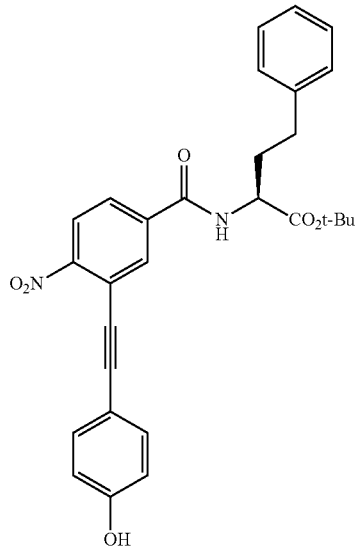 [SMILES: CC(C)(C)OC(=O)[C@H](CCc1ccccc1)NC(=O)c1ccc([N+](=O)[O-])c(C#Cc2ccc(O)cc2)c1]

(MM-1-466) The general procedure for amine coupling with acid was followed: carboxylic acid MM-2-3 (320 mg, 1.13 mmol, 1.00 equiv), HoPhe-OtBu (266 mg, 1.13 mmol), HOAt (170 mg, 1.24 mmol, 1.10 equiv), 2,6-lutidine (0.66 mL, 5.65 mmol, 5.00 equiv) and EDCI.HCl (230 mg, 1.18 mmol, 1.05 equiv) were employed. Flash column chromatography ($SiO_2$, hexanes→30% EtOAc/hexanes) afforded 555 mg (98%) of the amide product. $^1$H NMR (400 MHz, $CDCl_3$) δ 8.07 (d, J=8.5 Hz, 1H), 7.85 (d, J=1.9 Hz, 1H), 7.64 (dd, J=8.6, 2.0 Hz, 1H), 7.49 (d, J=8.6 Hz, 2H), 7.35-7.28 (m, 2H), 7.25-7.17 (m, 3H), 6.86 (d, J=8.6 Hz, 2H), 6.74 (d, J=7.6 Hz, 1H), 4.80 (td, J=7.0, 4.8 Hz, 1H), 2.76 (t, J=7.7 Hz, 2H), 2.37 (dtd, J=13.1, 8.1, 4.8 Hz, 1H), 2.26-2.15 (m, 1H), 1.56 (s, 9H).

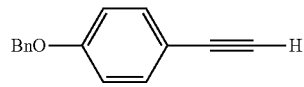

1-(Benzyloxy)-4-ethynylbenzene was prepared from 4-benzyloxyacetophenone (commercially available from Fisher) according to the method described by: Frontier et al., *J. Am. Chem. Soc.*, 130:1003-1011 (2008).

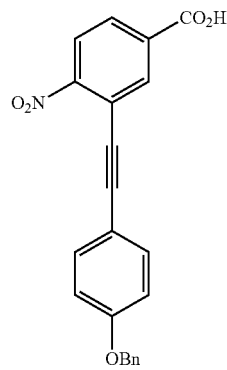 [SMILES: O=C(O)c1ccc([N+](=O)[O-])c(C#Cc2ccc(OCc3ccccc3)cc2)c1]

(MM-1-369/370) Triflate MM-1-69 (2.77 g, 8.40 mmol), $PdCl_2(PPh_3)_2$ (590 mg, 0.84 mmol, 10 mol %), CuI (240 mg, 1.26 mmol, 15 mol %), TBAI (9.3 g, 25.2 mmol, 3.00 equiv), 1-(benzyloxy)-4-ethynylbenzene (3.5 g, 16.8 mmol, 2.00 equiv) and $LiOH.H_2O$ (0.46 g, 11.0 mmol, 4.00 equiv) were combined according to the general procedure for $2^{nd}$ Sonogashira cross-coupling and hydrolysis (below). Flash chromatography (50:50:0.5 EtOAc:hexanes:AcOH) gave 1.05 g (33%) of the cross-coupled carboxylic acid. $^1$H NMR (MM-1-369, Me Ester, 400 MHz, $CDCl_3$) δ 8.35 (d, J=1.8 Hz, 1H), 8.10 (d, J=8.6 Hz, 1H), 8.05 (dd, J=8.5, 1.8 Hz, 1H), 7.56 (d, J=8.7 Hz, 2H), 7.49-7.32 (m, 9H), 7.00 (d, J=8.8 Hz, 2H), 6.93 (d, J=8.8 Hz, 1H), 5.11 (s, 2H), 3.99 (s, 3H).

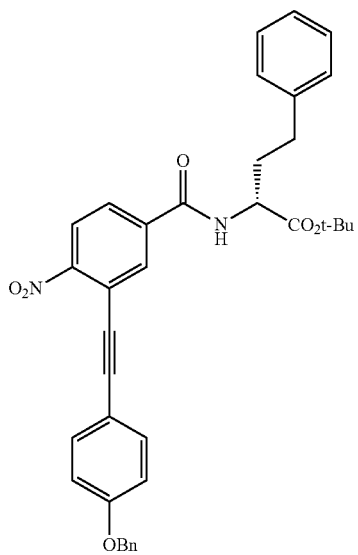 [SMILES: CC(C)(C)OC(=O)[C@@H](CCc1ccccc1)NC(=O)c1ccc([N+](=O)[O-])c(C#Cc2ccc(OCc3ccccc3)cc2)c1]

(MM-1-477) The general procedure for amine coupling with acid was followed: carboxylic acid MM-2-3 (71 mg, 0.191 mmol, 1.00 equiv), D-HoPhe-OtBu (45 mg, 0.191 mmol, 1.00 equiv), HOAt (30 mg, 0.210 mmol, 1.10 equiv), 2,6-lutidine (0.111 mL, 0.960 mmol, 5.00 equiv) and EDCI.HCl (39 mg, 0.200 mmol, 1.05 equiv) were employed. Flash chromatography (SiO$_2$, 10 to 30% EtOAc/hexanes) afforded 20 mg (18%) of the desired amide product.

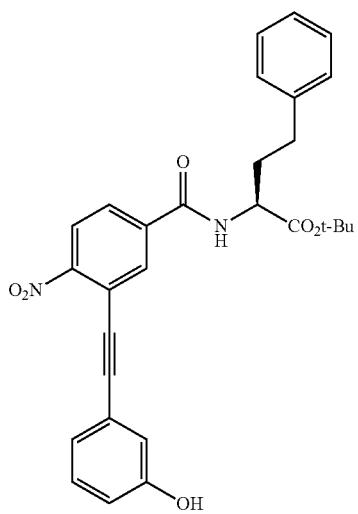 [SMILES: CC(C)(C)OC(=O)[C@H](CCc1ccccc1)NC(=O)c1ccc([N+](=O)[O-])c(C#Cc2cccc(O)c2)c1]

(MM-1-281) The general procedure for amine coupling with acid was followed: carboxylic acid MM-1-276/278 (73 mg, 0.258 mmol, 1.00 equiv), HoPhe-OtBu (61 mg, 0.258 mmol, 1.00 equiv), HOAt (39 mg, 0.284 mmol, 1.10 equiv), 2,6-lutidine (0.150 mL, 1.29 mmol, 5.00 equiv) and EDCI.HCl (52 mg, 0.271 mmol, 1.05 equiv) were employed. Flash chromatography (SiO$_2$, 50% EtOAc/hexanes) afforded 58 mg (48%) of the amide product.

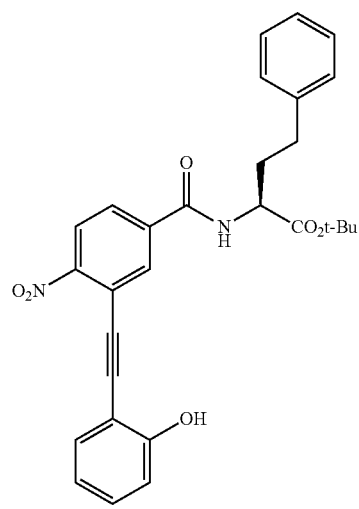 [SMILES: CC(C)(C)OC(=O)[C@H](CCc1ccccc1)NC(=O)c1ccc([N+](=O)[O-])c(C#Cc2ccccc2O)c1]

(MM-1-282) The general procedure for amine coupling with acid was followed: carboxylic acid MM-1-277/279 (48 mg, 0.169 mmol, 1.00 equiv), HoPhe-OtBu (40 mg, 0.169 mmol, 1.00 equiv), HOAt (25 mg, 0.186 mmol, 1.10 equiv), 2,6-lutidine (0.100 mL, 0.847 mmol, 5.00 equiv) and EDCI.HCl (34 mg, 0.178 mmol, 1.05 equiv) were employed. Flash chromatography (SiO$_2$, 50% EtOAc/hexanes) afforded 36 mg (45%) of the amide product.

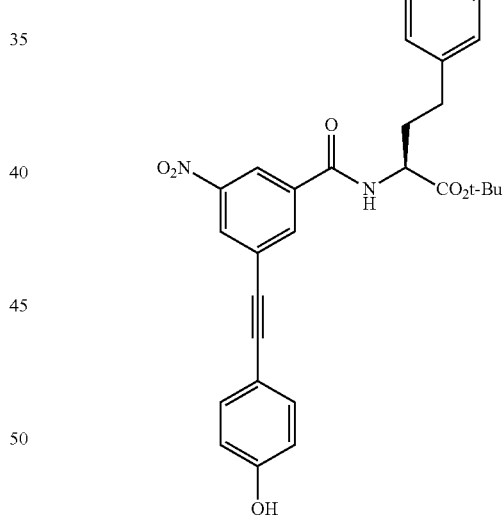

(MM-1-497) The general procedure for amine coupling with acid was followed: carboxylic acid MM-1-495/496 (100 mg, 0.353 mmol, 1.00 equiv), HoPhe-OtBu (83 mg, 0.353 mmol, 1.00 equiv), HOAt (53 mg, 0.388 mmol, 1.10 equiv), 2,6-lutidine (0.205 mL, 1.77 mmol, 5.00 equiv) and EDCI.HCl (71 mg, 0.371 mmol, 1.05 equiv) were employed. Flash chromatography (SiO$_2$, 30 to 40% EtOAc/hexanes) afforded 88 mg (50%) of the amide product. $^1$H NMR (500 MHz, CDCl$_3$) δ 8.37 (dt, J=9.4, 2.0 Hz, 2H), 7.95-7.93 (m, 1H), 7.39 (d, J=8.6 Hz, 2H), 7.32-7.16 (m, 5H), 6.83 (d, J=8.6 Hz, 2H), 4.84 (dd, J=7.6, 4.8 Hz, 1H), 2.78 (t, J=7.8 Hz, 2H), 2.40-2.28 (m, 1H), 2.26-2.15 (m, 1H), 1.56 (s, 9H).

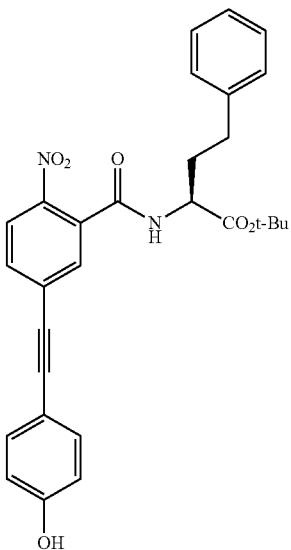 [SMILES: CC(C)(C)OC(=O)[C@H](CCc1ccccc1)NC(=O)c1cc(C#Cc2ccc(O)cc2)ccc1[N+](=O)[O-]]

(MM-2-12) The general procedure for amine coupling with acid was followed: carboxylic acid MM-2-9/11 (100 mg, 0.353 mmol, 1.00 equiv), HoPhe-OtBu (83 mg, 0.353 mmol, 1.00 equiv), HOAt (53 mg, 0.388 mmol, 1.10 equiv), 2,6-lutidine (0.205 mL, 1.77 mmol, 5.00 equiv) and EDCI.HCl (71 mg, 0.371 mmol, 1.05 equiv) were employed. Flash chromatography (SiO₂, 30% EtOAc/hexanes) afforded 154 mg (87%) of the amide product. ¹H NMR (500 MHz, CDCl₃) δ 8.06 (d, J=8.5 Hz, 1H), 7.61 (dd, J=8.5, 1.8 Hz, 1H), 7.46 (d, J=1.8 Hz, 1H), 7.42 (d, J=8.6 Hz, 2H), 7.31 (d, J=7.5 Hz, 2H), 7.26-7.15 (m, 3H), 6.81 (d, J=8.6 Hz, 2H), 6.56 (d, J=7.7 Hz, 1H), 4.80 (ddd, J=7.7, 6.4, 4.9 Hz, 1H), 2.88-2.67 (m, 2H), 2.45-2.34 (m, 1H), 2.18-2.09 (m, 1H), 1.55 (s, 9H).

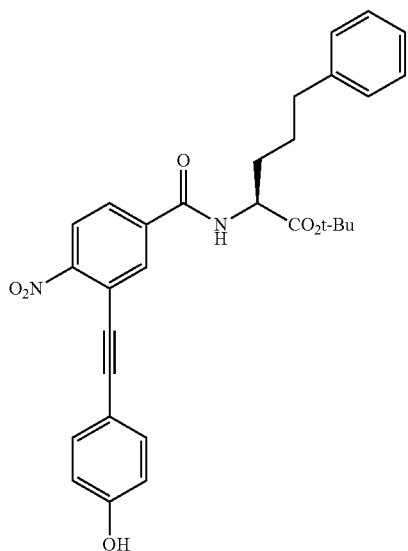 [SMILES: CC(C)(C)OC(=O)[C@H](CCCc1ccccc1)NC(=O)c1ccc([N+](=O)[O-])c(C#Cc2ccc(O)cc2)c1]

(MM-2-99) The general procedure for amine coupling with acid was followed: H-Nva(5-Ph)-OtBu (18 mg, 0.071 mmol) was added to a 1 dram scintillation vial equipped with stir bar and charged with carboxylic acid MM-2-3 (20 mg, 0.071 mmol, 1.00 equiv) and HOAt (11 mg, 0.077 mmol, 1.10 equiv). The reagents were dissolved in anhydrous DMF (0.35 mL) and 2,6-lutidine (0.041 mL, 0.35 mmol, 5.00 equiv). EDCI.HCl (14 mg, 0.074 mmol, 1.05 equiv.) was added in one portion, and the reaction mixture stirred overnight. After 16 hours, the mixture was diluted with EtOAc (5 mL) and washed twice with 0.1 N HCl (5 mL). The aqueous phase was extracted with EtOAc (2×2.5 mL), and the combined extracts were dried over Na₂SO₄, decanted and concentrated. Flash chromatography (SiO₂, 40% EtOAc/hexanes) produced 30 mg (83%) of the amide product.

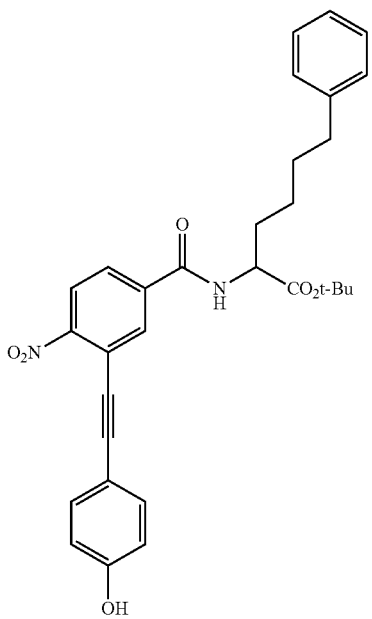 [SMILES: CC(C)(C)OC(=O)C(CCCCc1ccccc1)NC(=O)c1ccc([N+](=O)[O-])c(C#Cc2ccc(O)cc2)c1]

(MM-2-83) The general procedure for amine coupling with acid was followed: tert-Butyl ester (75 mg, 0.285 mmol), carboxylic acid MM-2-3 (81 mg, 0.285 mmol, 1.00 equiv), HOAt (43 mg, 0.313 mmol, 1.10 equiv), 2,6-lutidine (0.166 mL, 1.42 mmol, 5.00 equiv) and EDCI.HCl (57 mg, 0.299 mmol, 1.05 equiv) in anhydrous DMF (1.5 mL). Flash chromatography (SiO₂, 30% EtOAc/hexanes) afforded 45 mg (30%) of the racemic amide product.

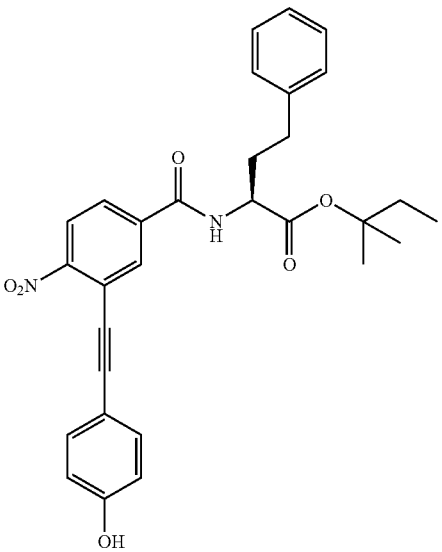 [SMILES: CCC(C)(C)OC(=O)[C@H](CCc1ccccc1)NC(=O)c1ccc([N+](=O)[O-])c(C#Cc2ccc(O)cc2)c1]

(MM-2-138) The general procedure for amine coupling with acid was followed: carboxylic acid MM-2-3(20 mg, 0.071 mmol, 1.00 equiv), tert-pentyl ester (20 mg, 0.071 mmol, 1.00 equiv), HOAt (11 mg, 0.078 mmol, 1.10 equiv), 2,6-lutidine (0.040 mL, 0.353 mmol, 5.00 equiv.) and EDCI.HCl (14 mg, 0.074 mmol, 1.05 equiv) were employed. Flash chromatography (SiO$_2$, 20→30% EtOAc/hexanes) afforded 15 mg (42%) of the amide product. $^1$H NMR (500 MHz, CDCl$_3$) δ 8.07 (d, J=8.5 Hz, 1H), 7.86 (d, J=2.0 Hz, 1H), 7.64 (dd, J=8.6, 2.0 Hz, 1H), 7.49 (d, J=8.6 Hz, 2H), 7.34-7.28 (m, 2H), 7.24-7.19 (m, 3H), 6.86 (d, J=8.5 Hz, 2H), 6.75 (d, J=7.6 Hz, 1H), 4.85-4.76 (m, 1H), 2.82-2.71 (m, 2H), 2.37 (dd, J=10.8, 3.3 Hz, 1H), 2.25-2.14 (m, 1H), 1.86 (m, 2H), 1.53 (d, J=2.5 Hz, 6H), 0.96 (t, J=7.5 Hz, 3H).

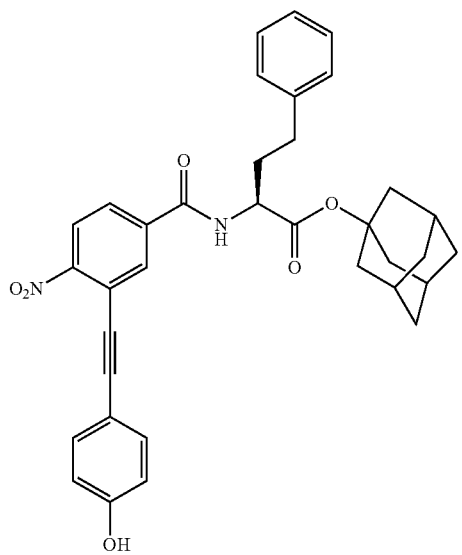 [SMILES: O=C(N[C@@H](CCc1ccccc1)C(=O)OC12CC3CC(CC(C3)C1)C2)c1ccc([N+](=O)[O-])c(C#Cc2ccc(O)cc2)c1]

(MM-2-128) The general procedure for amine coupling with acid was followed: carboxylic acid MM-2-3 (20 mg, 0.071 mmol, 1.00 equiv), adamantyl ester (25 mg, 0.071 mmol, 1.00 equiv), HOAt (11 mg, 0.078 mmol, 1.10 equiv), 2,6-lutidine (0.040 mL, 0.353 mmol, 5.00 equiv) and EDCI.HCl (14 mg, 0.074 mmol, 1.05 equiv) were employed. Flash chromatography (SiO$_2$, 30% EtOAc/hexanes) afforded 32 mg (78%) of the amide product.

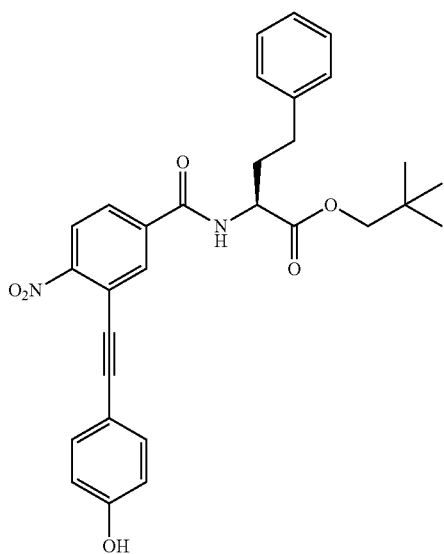 [SMILES: CC(C)(C)COC(=O)[C@H](CCc1ccccc1)NC(=O)c1ccc([N+](=O)[O-])c(C#Cc2ccc(O)cc2)c1]

(MM-2-127) The general procedure for amine coupling with acid was followed: carboxylic acid MM-2-3 (20 mg, 0.071 mmol, 1.00 equiv), neopentyl ester (20 mg, 0.071 mmol, 1.00 equiv), HOAt (11 mg, 0.078 mmol, 1.10 equiv), 2,6-lutidine (0.040 mL, 0.353 mmol, 5.00 equiv) and EDCI.HCl (14 mg, 0.074 mmol, 1.05 equiv) were employed. Flash chromatography (SiO$_2$, 40% EtOAc/hexanes) afforded 26 mg (72%) of the amide product.

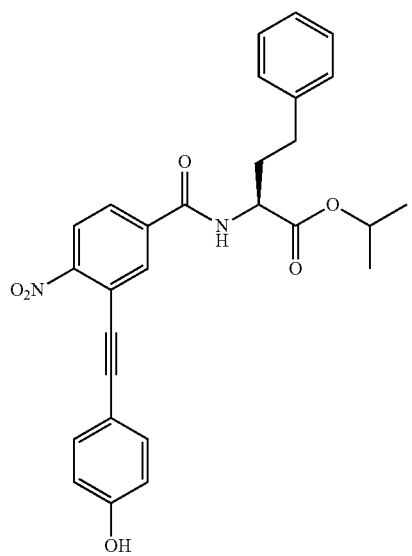 [SMILES: CC(C)OC(=O)[C@H](CCc1ccccc1)NC(=O)c1ccc([N+](=O)[O-])c(C#Cc2ccc(O)cc2)c1]

(MM-1-467) The general procedure for amine coupling with acid was followed: carboxylic acid MM-2-3 (10 mg, 0.036 mmol, 1.00 equiv), isopropyl ester (8 mg, 0.036 mmol, 1.00 equiv), HOAt (5.4 mg, 0.040 mmol, 1.10 equiv), 2,6-lutidine (0.020 mL, 0.180 mmol, 5.00 equiv) and EDCI.HCl (7.2 mg, 0.038 mmol, 1.05 equiv) were employed. Flash chromatography (SiO$_2$ 30% EtOAc/hexanes) afforded 17 mg (97%) of the amide product. $^1$H NMR (400 MHz, CDCl$_3$) δ 8.09-8.02 (m, 1H), 7.83 (d, J=2.0 Hz, 1H), 7.63 (d, J=8.5 Hz, 1H), 7.49-7.42 (m, 2H), 7.34-7.26 (m, 2H), 7.22 (q, J=3.5 Hz, 3H), 6.88-6.82 (m, 2H), 6.33-6.24 (m, 1H), 5.15 (p, J=6.3 Hz, 1H), 4.85 (td, J=7.7, 3.5 Hz, 1H), 2.77 (q, J=7.7, 6.5 Hz, 2H), 2.36 (qd, J=8.7, 8.3, 4.8 Hz, 1H), 2.27-2.16 (m, 1H), 1.34 (d, J=6.2 Hz, 6H).

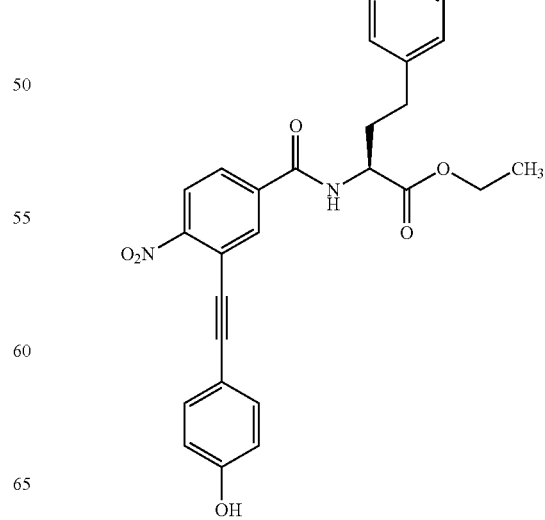

(MM-1-438) The general procedure for amine coupling with acid was followed: carboxylic acid MM-2-3 (80 mg, 0.282 mmol, 1.00 equiv), ethyl ester (59 mg, 0.282 mmol, 1.00 equiv), HOAt (42 mg, 0.310 mmol, 1.10 equiv), 2,6-lutidine (0.165 mL, 1.41 mmol, 5.00 equiv) and EDCI.HCl (57 mg, 0.2.97 mmol, 1.05 equiv) were employed. Flash chromatography (SiO$_2$, 30% EtOAc/hexanes) afforded 16 mg (12%) of the amide product.

0.116 mmol, 1.00 equiv), carboxamide (25 mg, 0.116 mmol, 1.00 equiv), HOAt (17 mg, 0.128 mmol, 1.10 equiv), 2,6-lutidine (0.068 mL, 0.582 mmol, 5.00 equiv) and EDCI.HCl (23 mg, 0.122 mmol, 1.05 equiv) were employed. Unpurified reaction product was used in the reduction step.

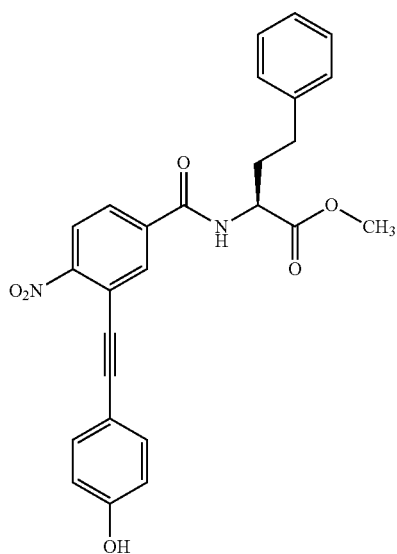 [SMILES: COC(=O)[C@H](CCc1ccccc1)NC(=O)c1ccc([N+](=O)[O-])c(C#Cc2ccc(O)cc2)c1]

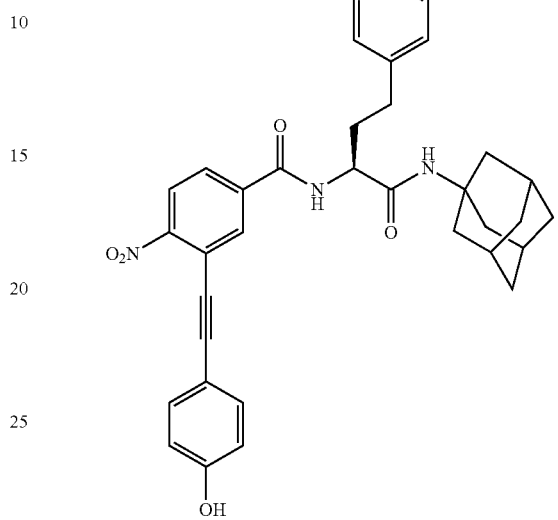

(MM-1-437) The general procedure for amine coupling with acid was followed: carboxylic acid MM-2-3 (70 mg, 0.247 mmol, 1.00 equiv), methyl ester (48 mg, 0.247 mmol, 1.00 equiv), HOAt (37 mg, 0.272 mmol, 1.10 equiv), 2,6-lutidine (0.144 mL, 1.24 mmol, 5.00 equiv) and EDCI.HCl (50 mg, 0.259 mmol, 1.05 equiv) were employed. Flash chromatography (SiO$_2$, 40% EtOAc/hexanes) afforded 19 mg (17%) of the amide product.

(MM-2-121) The general procedure for amine coupling with acid was followed: carboxylic acid MM-2-3 (20 mg, 0.071 mmol, 1.00 equiv), adamantyl amide (25 mg, 0.071 mmol, 1.00 equiv), HOAt (11 mg, 0.078 mmol, 1.10 equiv), 2,6-lutidine (0.040 mL, 0.353 mmol, 5.00 equiv) and EDCI.HCl (14 mg, 0.074 mmol, 1.05 equiv) were employed. Flash chromatography (SiO$_2$, 40 to 50% EtOAc/hexanes) afforded 29 mg (71%) of the amide product.

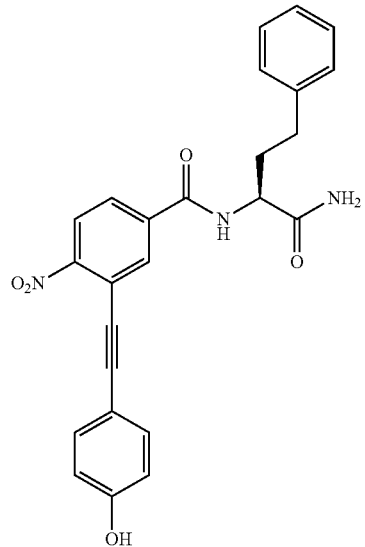 [SMILES: NC(=O)[C@H](CCc1ccccc1)NC(=O)c1ccc([N+](=O)[O-])c(C#Cc2ccc(O)cc2)c1]

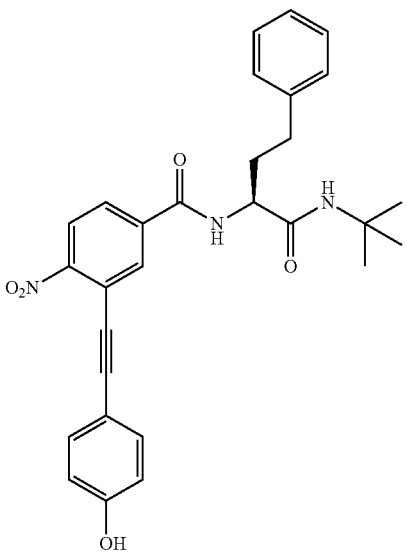 [SMILES: CC(C)(C)NC(=O)[C@H](CCc1ccccc1)NC(=O)c1ccc([N+](=O)[O-])c(C#Cc2ccc(O)cc2)c1]

(MM-2-94) The general procedure for amine coupling with acid was followed: carboxylic acid MM-2-3 (33 mg, (MM-2-93) The general procedure for amine coupling with acid was followed: carboxylic acid MM-2-3 (21 mg, 0.074 mmol, 1.00 equiv), t-butyl amide (20 mg, 0.074 mmol, 1.00 equiv), HOAt (11 mg, 0.081 mmol, 1.10 equiv), 2,6- lutidine (0.043 mL, 0.353 mmol, 5.00 equiv) and EDCI.HCl (15 mg, 0.078 mmol, 1.05 equiv) were employed. Flash chromatography (SiO$_2$, 40% EtOAc/hexanes) afforded 31 mg (84%) of the amide product.

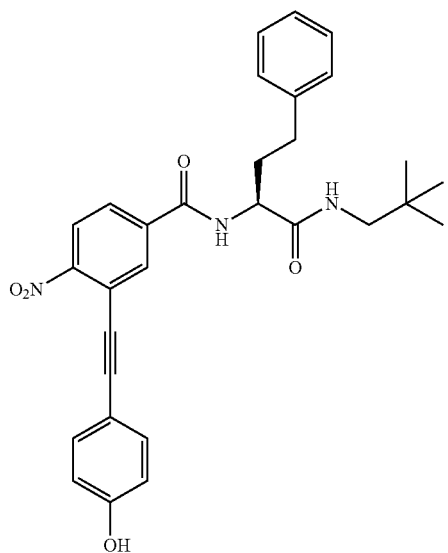 [SMILES: CC(C)(C)CNC(=O)[C@H](CCc1ccccc1)NC(=O)c1ccc([N+](=O)[O-])c(C#Cc2ccc(O)cc2)c1]

(MM-2-120) The general procedure for amine coupling with acid was followed: carboxylic acid MM-2-3 (20 mg, 0.071 mmol, 1.00 equiv), neopentyl amide (20 mg, 0.071 mmol, 1.00 equiv), HOAt (11 mg, 0.078 mmol, 1.10 equiv), 2,6-lutidine (0.040 mL, 0.353 mmol, 5.00 equiv) and EDCI.HCl (14 mg, 0.074 mmol, 1.05 equiv) were employed. Flash chromatography (SiO$_2$, 40 to 50% EtOAc/hexanes) afforded 28 mg (78%) of the amide product.

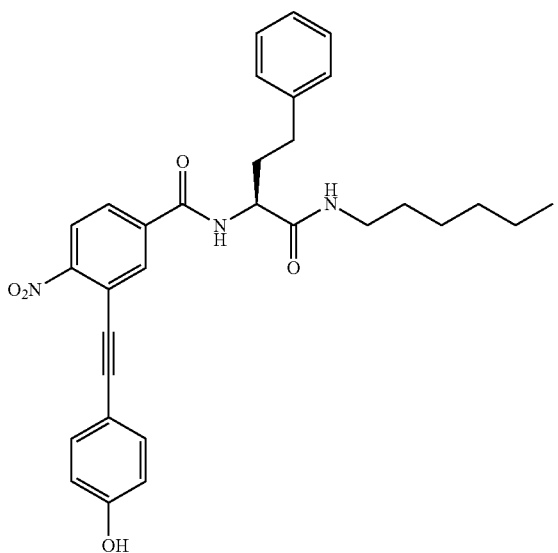 [SMILES: CCCCCCNC(=O)[C@H](CCc1ccccc1)NC(=O)c1ccc([N+](=O)[O-])c(C#Cc2ccc(O)cc2)c1]

(MM-2-119) The general procedure for amine coupling with acid was followed: carboxylic acid MM-2-3 (20 mg, 0.071 mmol, 1.00 equiv), n-hexyl amide (21 mg, 0.071 mmol, 1.00 equiv), HOAt (11 mg, 0.078 mmol, 1.10 equiv), 2,6-lutidine (0.040 mL, 0.353 mmol, 5.00 equiv) and EDCI.HCl (14 mg, 0.074 mmol, 1.05 equiv) were employed. Flash chromatography (SiO$_2$, 40 to 50% EtOAc/hexanes) afforded 13 mg (35%) of the amide product.

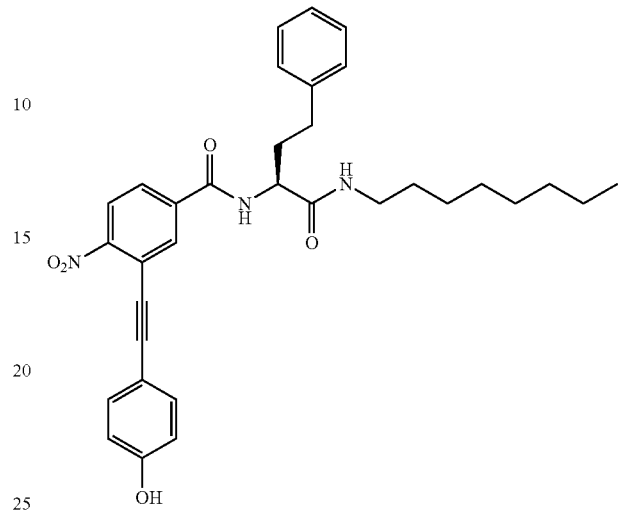

(MM-2-155) The general procedure for amine coupling with acid was followed: carboxylic acid MM-2-3 (20 mg, 0.071 mmol, 1.00 equiv), n-octyl amide (23 mg, 0.071 mmol, 1.00 equiv), HOAt (11 mg, 0.078 mmol, 1.10 equiv), 2,6-lutidine (0.040 mL, 0.353 mmol, 5.00 equiv) and EDCI.HCl (14 mg, 0.074 mmol, 1.05 equiv) were employed. Flash chromatography (SiO$_2$, 40% EtOAc/hexanes) afforded 22 mg (56%) of the amide product.

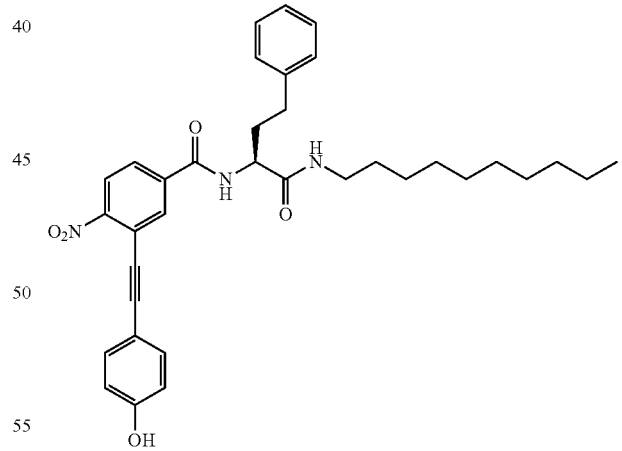

(MM-2-156) The general procedure for amine coupling with acid was followed: carboxylic acid MM-2-3 (20 mg, 0.071 mmol, 1.00 equiv), n-decyl amide (25 mg, 0.071 mmol, 1.00 equiv), HOAt (11 mg, 0.078 mmol, 1.10 equiv), 2,6-lutidine (0.040 mL, 0.353 mmol, 5.00 equiv) and EDCI.HCl (14 mg, 0.074 mmol, 1.05 equiv) were employed. Flash chromatography (SiO$_2$, 40% EtOAc/hexanes) afforded 23 mg (56%) of the amide product.

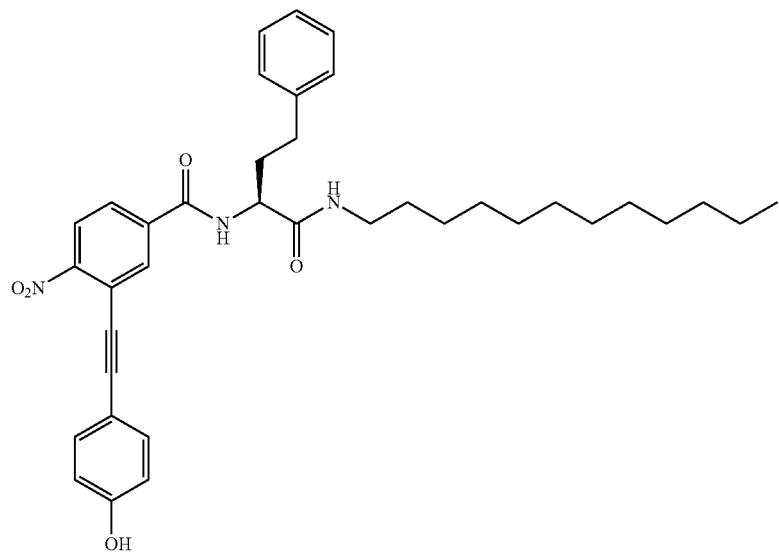 [SMILES: CCCCCCCCCCCCNC(=O)[C@H](CCc1ccccc1)NC(=O)c1ccc([N+](=O)[O-])c(C#Cc2ccc(O)cc2)c1]

(MM-2-157) The general procedure for amine coupling with acid was followed: carboxylic acid MM-2-3 (20 mg, 0.071 mmol, 1.00 equiv), n-dodecyl amide (27 mg, 0.071 mmol, 1.00 equiv), HOAt (11 mg, 0.078 mmol, 1.10 equiv), 2,6-lutidine (0.040 mL, 0.353 mmol, 5.00 equiv) and EDCI.HCl (14 mg, 0.074 mmol, 1.05 equiv) were employed. Flash chromatography (SiO$_2$, 40% EtOAc/hexanes) afforded 23 mg (53%) of the amide product.

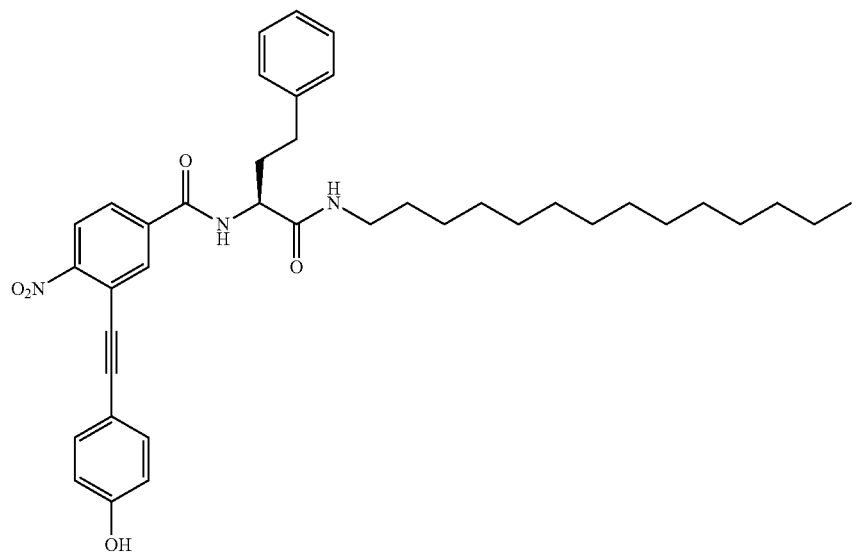 [SMILES: CCCCCCCCCCCCCCNC(=O)[C@H](CCc1ccccc1)NC(=O)c1ccc([N+](=O)[O-])c(C#Cc2ccc(O)cc2)c1]

(MM-2-158) The general procedure for amine coupling with acid was followed: carboxylic acid MM-2-3 (20 mg, 0.071 mmol, 1.00 equiv), n-tetradecyl amide (29 mg, 0.071 mmol, 1.00 equiv), HOAt (11 mg, 0.078 mmol, 1.10 equiv), 2,6-lutidine (0.040 mL, 0.353 mmol, 5.00 equiv) and EDCI.HCl (14 mg, 0.074 mmol, 1.05 equiv) were employed. Flash chromatography (SiO$_2$, 40% EtOAc/hexanes) afforded 30 mg (67%) of the amide product.

47

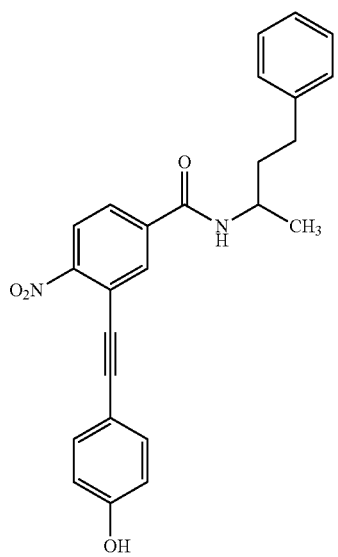 [SMILES: CC(CCc1ccccc1)NC(=O)c1ccc([N+](=O)[O-])c(C#Cc2ccc(O)cc2)c1]

(MM-2-175) Carboxylic acid MM-2-3 (10 mg, 0.035 mmol, 1.00 equiv), α-methyl-3-phenylpropylamine XX (5.3 mg, 0.035 mmol, 1.00 equiv) and Et$_3$N (10 μL, 0.071 mmol, 2.00 equiv) were combined in a 1 dram scintillation vial. THF (200 μL) was added, followed by 3-(diethoxyphosphoryloxy)-1,2,3-benzotriazin-4(3H)-one (DEPBT, 11.6 mg, 0.039 mmol, 1.10 equiv) After 16 hours, the reaction mixture was diluted with EtOAc (5 mL) and washed with 0.1 N HCl (5 mL). The organic phase was dried over Na$_2$SO$_4$ and concentrated. Flash chromatography (SiO$_2$, 40% EtOAc/hexanes) afforded 8.5 mg (58%) of the amide product. $^1$H NMR (500 MHz, CDCl$_3$) δ 8.06 (d, J=8.6 Hz, 1H), 7.83 (d, J=1.9 Hz, 1H), 7.60 (dd, J=8.6, 2.0 Hz, 1H), 7.49 (d, J=8.6 Hz, 2H), 7.30 (dd, J=8.3, 6.8 Hz, 2H), 7.26-7.18 (m, 3H), 6.88 (d, J=8.6 Hz, 2H), 5.99 (d, J=8.2 Hz, 1H), 4.37-4.25 (m, 1H), 2.77 (m, 2H), 2.02-1.93 (m, 2H), 1.34 (d, J=6.6 Hz, 3H).

General Procedure for Nitroaryl Alkyne Reduction

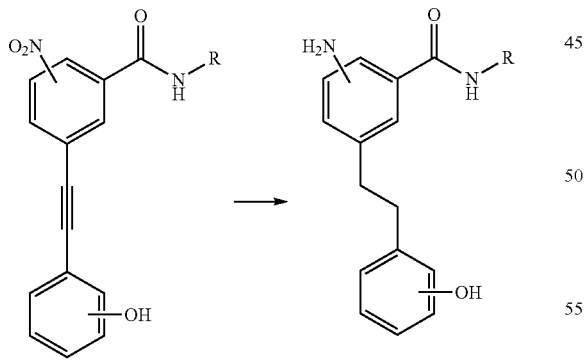

Nitroaryl alkyne (1.00 mmol) was dissolved in EtOAc (10 mL) in a two-neck round-bottom flask equipped with a stir bar and 3-way vacuum adapter. Pearlman's catalyst (5 mol %, 20% Pd w/w on carbon) was suspended in the reaction solvent, and the solvent was sparged with N$_2$ for 10 minutes. The reaction headspace was evacuated briefly until the solvent began to boil, and then back-filled with H$_2$. This process was repeated 15-20 times to ensure maximum H$_2$ atmosphere above the reaction mixture. After stirring for 16

48 hours, the mixture was filtered through a plug of sand/Celite with a 2 mm top layer of SiO$_2$, washing thoroughly with EtOAc. Solvent was removed in vacuo and the residue subjected to flash/preparative thin layer chromatography to yield the fully reduced aniline.

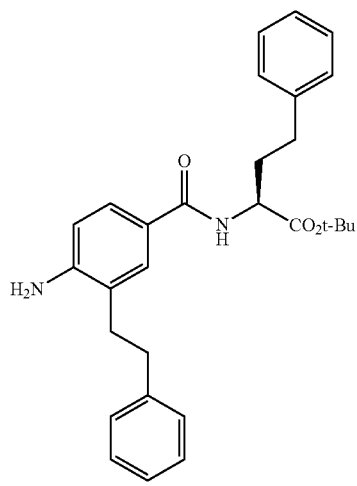 [SMILES: CC(C)(C)OC(=O)[C@H](CCc1ccccc1)NC(=O)c1ccc(N)c(CCc2ccccc2)c1]

(MM-1-460) The general procedure for nitroaryl alkyne reduction was followed: Nitroalkyne MM-1-458 (11.4 mg, 0.024 mmol), EtOAc (1.20 mL), Pearlman's catalyst (20 mg) were employed. Preparative thin-layer chromatography (SiO$_2$, 20% EtOAc/hexanes) gave 7.3 mg (68%) of the fully reduced product. $^1$H NMR (500 MHz, CDCl$_3$) δ 7.75 (d, J=7.8 Hz, 2H), 7.51 (t, J=7.1 Hz, 2H), 7.44 (t, J=7.5 Hz, 2H), 7.36-7.26 (m, 3H), 7.21 (d, J=7.6 Hz, 3H), 6.73 (m, 1H), 4.87-4.77 (m, 1H), 2.88-2.63 (m, 4H), 2.32 (dt, J=9.8, 4.9 Hz, 1H), 2.12 (td, J=15.6, 14.3, 6.7 Hz, 1H), 1.53 (s, 9H).

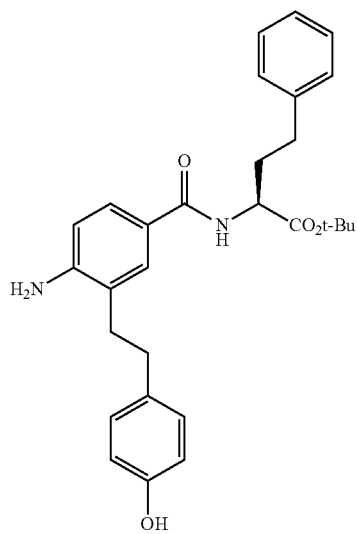 [SMILES: CC(C)(C)OC(=O)[C@H](CCc1ccccc1)NC(=O)c1ccc(N)c(CCc2ccc(O)cc2)c1]

(MM-1-406/470/Neoseptin-3) The general procedure for nitroaryl alkyne reduction was followed: Nitroalkyne MM-1-466 (530 mg, 1.06 mmol), EtOAc (10 mL), Pearlman's catalyst (250 mg) were employed. Flash chromatography (SiO$_2$, 30 to 50% EtOAc/hexanes) gave 411 mg (82%) of the fully reduced product, Neoseptin-3. $^1$H NMR (500 MHz, CDCl$_3$) δ 7.44 (dd, J=8.3, 2.2 Hz, 1H), 7.34 (d, J=2.2

Hz, 1H), 7.32-7.28 (m, 2H), 7.25-7.16 (m, 3H), 6.99 (d, J=8.4 Hz, 2H), 6.78 (d, J=8.4 Hz, 2H), 6.63 (d, J=8.3 Hz, 1H), 6.49 (d, J=7.8 Hz, 1H), 4.82-4.76 (m, 1H), 2.90-2.61 (m, 6H), 2.28 (dddd, J=13.7, 10.2, 6.3, 5.1 Hz, 1H), 2.10 (m, 1H), 1.53 (s, 9H). $^{13}$C NMR (101 MHz, CDCl$_3$) δ 172.1, 167.2, 154.5, 147.8, 141.2, 133.0, 129.5, 129.1, 128.49, 128.48, 128.37, 126.3, 126.1, 125.2, 123.4, 115.6, 114.7, 82.5, 53.0, 34.5, 34.2, 33.4, 31.6, 28.1. HRMS (ESI-TOF) m/z calcd for C$_{29}$H$_{35}$N$_2$O$_4$ [M+H]$^+$ 475.2591. found 475.2592.

7.19-7.13 (m, 3H), 7.10 (t, J=7.8 Hz, 1H), 6.70 (dd, J=9.9, 7.5 Hz, 2H), 6.61 (d, J=2.1 Hz, 1H), 6.57 (d, J=8.2 Hz, 1H), 4.79 (td, J=7.3, 5.1 Hz, 1H), 3.83 (s, 2H), 2.83-2.58 (m, 6H), 2.34-2.19 (m, 1H), 2.13-2.00 (m, 1H), 1.49 (s, 9H).

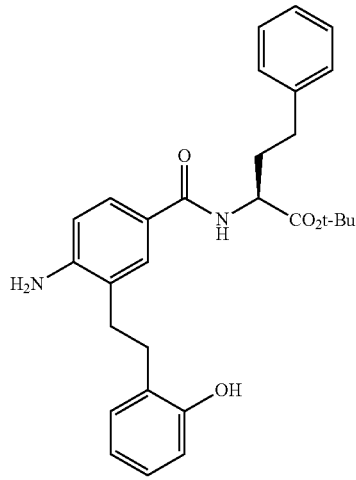

(MM-1-443) The general procedure for nitroaryl alkyne reduction was followed: Nitroalkyne MM-1-282 (5.7 mg, 0.012 mmol), EtOAc (0.5 mL), Pearlman's catalyst (10 mg) were employed. Product obtained after filtration, 5.6 mg (98%), was homogeneous by TLC and not purified further. $^1$H NMR (400 MHz, CDCl$_3$) δ 7.57 (d, J=2.1 Hz, 1H), 7.50 (dd, J=8.2, 2.2 Hz, 1H), 7.32-7.27 (m, 2H), 7.24-7.14 (m, 3H), 7.08 (dd, J=7.7, 1.7 Hz, 1H), 6.88 (td, J=7.3, 1.0 Hz, 1H), 6.84-6.79 (m, 1H), 6.66 (d, J=7.8 Hz, 1H), 6.63 (d, J=8.3 Hz, 1H), 6.32 (s, 1H), 4.87-4.78 (m, 1H), 4.27 (s, 2H), 3.00-2.61 (m, 6H), 2.29 (ddt, J=15.4, 11.1, 5.7 Hz, 1H), 2.16-2.06 (m, 1H), 1.53 (s, 9H).

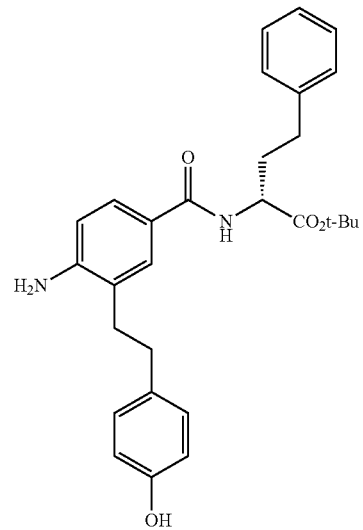 [SMILES: CC(C)(C)OC(=O)[C@@H](CCc1ccccc1)NC(=O)c1ccc(N)c(CCc2ccc(O)cc2)c1]

(MM-1-481) The general procedure for nitroaryl alkyne reduction was followed: Nitroalkyne MM-1-477 (20 mg, 0.0389 mmol), EtOAc (10 mL), Pearlman's catalyst (20 mg) were employed. Preparative thin-layer chromatography (SiO$_2$, 60% EtOAc/hexanes) gave 3.7 mg (23%) of the fully reduced product. $^1$H NMR data matched that of Neoseptin-3.

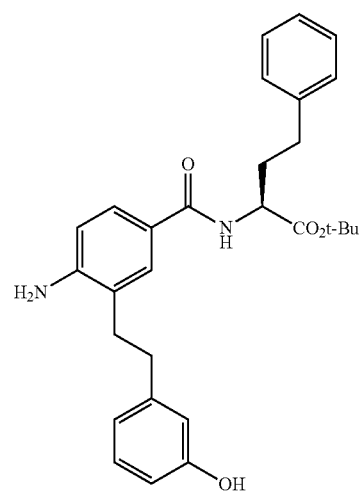 [SMILES: CC(C)(C)OC(=O)[C@H](CCc1ccccc1)NC(=O)c1ccc(N)c(CCc2cccc(O)c2)c1]

(MM-1-442) The general procedure for nitroaryl alkyne reduction was followed: Nitroalkyne MM-1-281 (21.6 mg, 0.046 mmol), EtOAc (1.00 mL), Pearlman's catalyst (20 mg) were employed. Product obtained after filtration, 21.4 mg (99%), was homogeneous by TLC and not purified further. $^1$H NMR (400 MHz, CDCl$_3$) δ 7.47 (d, J=2.1 Hz, 1H), 7.41 (dd, J=8.3, 2.1 Hz, 1H), 7.26-7.21 (m, 2H),

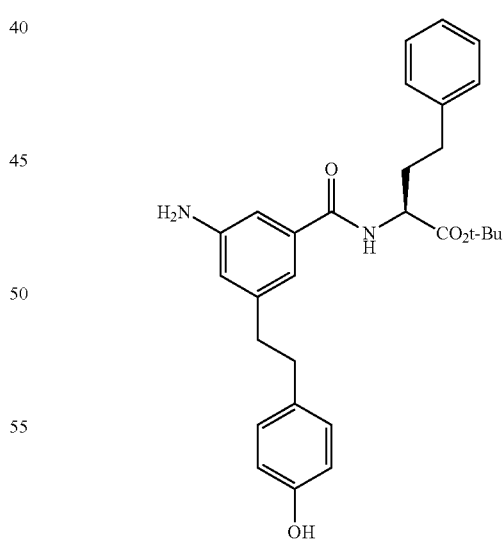

(MM-1-500) The general procedure for nitroaryl alkyne reduction was followed: Nitroalkyne MM-1-497 (88 mg, 0.176 mmol), EtOAc (1.5 mL), Pearlman's catalyst (50 mg) were employed. Product obtained after filtration, 65 mg (78%), was homogeneous by TLC and not purified further. $^1$H NMR (400 MHz, CDCl$_3$) δ 7.31-7.26 (m, 2H), 7.21-7.18 (m, 3H), 6.94 (d, J=7.6 Hz, 2H), 6.89 (s, 1H), 6.76 (d, J=7.6

Hz, 2H), 6.67 (s, 1H), 6.61 (s, 1H), 6.49 (d, J=6.0 Hz, 1H), 4.77 (dd, J=6.0, 2.0 Hz, 1H), 2.86-2.67 (m, 6H), 2.25 (m, 1H), 2.13 (m, 1H), 1.52 (s, 9H). HRMS (ESI-TOF) m/z calcd for $C_{29}H_{35}N_2O_4$ [M+H]$^+$ 475.2591. found 475.2590.

1H), 4.74 (dt, J=7.8, 5.7 Hz, 1H), 2.87-2.57 (m, 6H), 2.03-1.91 (m, 1H), 1.77 (m, 2H), 1.71-1.58 (m, 1H), 1.48 (s, 9H). HRMS (ESI-TOF) m/z calcd for $C_{30}H_{37}N_2O_4$ [M+H]$^+$ 489.2748. found 489.2757.

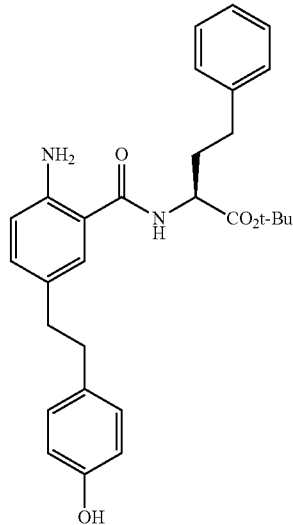 [SMILES: CC(C)(C)OC(=O)[C@H](CCc1ccccc1)NC(=O)c1cc(CCc2ccc(O)cc2)ccc1N]

(MM-2-14) The general procedure for nitroaryl alkyne reduction was followed: Nitroalkyne MM-2-12 (65 mg, 0.130 mmol), EtOAc (1.2 mL), Pearlman's catalyst (50 mg) were employed. Product obtained after filtration, 58 mg (94%), was homogeneous by TLC and not purified further. $^1$H NMR (500 MHz, CDCl$_3$) δ 7.33-7.28 (m, 2H), 7.24-7.17 (m, 3H), 7.03 (dd, J=8.3, 2.0 Hz, 1H), 6.97 (d, J=8.4 Hz, 2H), 6.85 (d, J=2.1 Hz, 1H), 6.82-6.76 (m, 2H), 6.62 (d, J=8.3 Hz, 1H), 6.49 (d, J=7.9 Hz, 1H), 4.76 (d, J=5.2 Hz, 1H), 2.86-2.62 (m, 6H), 2.27 (dddd, J=13.7, 9.9, 6.7, 5.1 Hz, 1H), 2.10 (m, 1H), 1.54 (s, 9H). HRMS (ESI-TOF) m/z calcd for $C_{29}H_{35}N_2O_4$ [M+H]$^+$ 475.2591. found 475.2605.

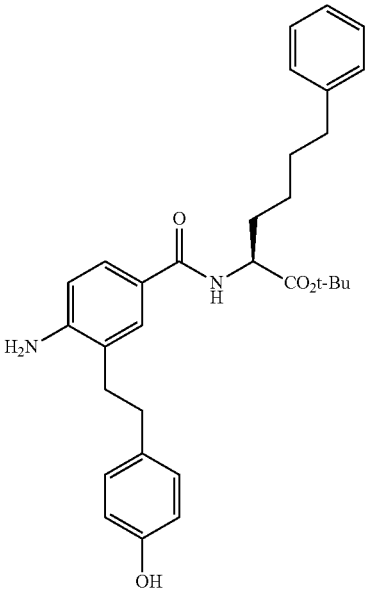

(MM-2-100) The general procedure for nitroaryl alkyne reduction was followed: Nitroalkyne MM-2-83 (45 mg, 0.085 mmol), EtOAc (0.5 mL), Pearlman's catalyst (10 mg). Preparative thin-layer chromatography of the filtered material (SiO$_2$, 50% EtOAc/hexanes) gave 19.6 mg (47%) of the fully reduced product. $^1$H NMR (500 MHz, CDCl$_3$) δ 7.47 (dd, J=8.2, 2.2 Hz, 1H), 7.45 (d, J=2.1 Hz, 1H), 7.24 (d, J=7.5 Hz, 2H), 7.19-7.13 (m, 3H), 6.98 (d, J=8.4 Hz, 2H), 6.80 (d, J=8.4 Hz, 2H), 6.62 (d, J=8.2 Hz, 1H), 6.55 (d, J=7.7 Hz, 1H), 4.75-4.67 (m, 1H), 2.86-2.65 (m, 4H), 2.61 (t, J=7.6 Hz, 2H), 1.95 (ddd, J=10.9, 8.2, 5.4 Hz, 1H), 1.84-1.74 (m, 1H), 1.73-1.62 (m, 2H), 1.47 (s, 9H). HRMS (ESI-TOF) m/z calcd for $C_{31}H_{39}N_2O_4$ [M+H]$^+$ 503.2904. found 503.2912.

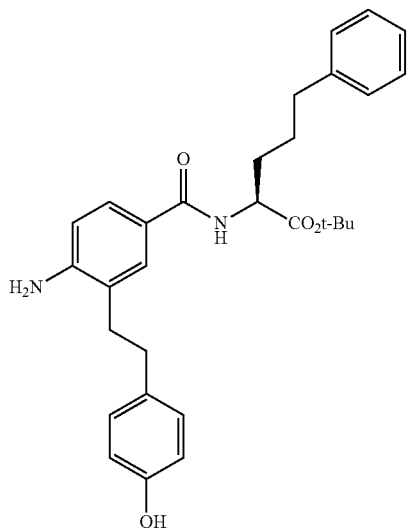 [SMILES: CC(C)(C)OC(=O)[C@H](CCCc1ccccc1)NC(=O)c1ccc(N)c(CCc2ccc(O)cc2)c1]

(MM-2-103) The general procedure for nitroaryl alkyne reduction was followed: Nitroalkyne MM-2-99 (30 mg, 0.058 mmol), EtOAc (0.5 mL), Pearlman's catalyst (10 mg). Preparative thin-layer chromatography of the filtered material (SiO$_2$, 50% EtOAc/hexanes) gave 13.1 mg (47%) of the fully reduced product. $^1$H NMR (500 MHz, CDCl$_3$) δ 7.48 (dd, J=8.2, 2.2 Hz, 1H), 7.42 (d, J=2.1 Hz, 1H), 7.31-7.24 (m, 2H), 7.21-7.13 (m, 3H), 6.97 (d, J=8.4 Hz, 2H), 6.77 (d, J=8.4 Hz, 2H), 6.62 (d, J=8.3 Hz, 1H), 6.53 (d, J=7.8 Hz,

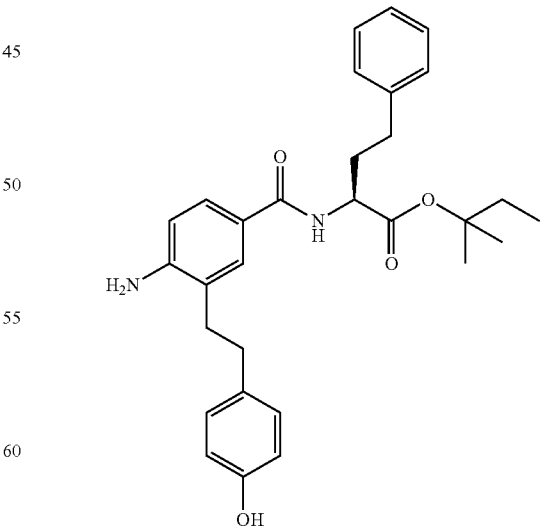

(MM-2-140) The general procedure for nitroaryl alkyne reduction was followed: Nitroalkyne MM-2-138 (15 mg, 0.029 mmol), EtOAc (0.25 mL), Pearlman's catalyst (10 mg). Preparative thin-layer chromatography of the filtered material (SiO$_2$, 60% EtOAc/hexanes) gave 2.2 mg (16%) of the fully reduced product. $^1$H NMR (500 MHz, CDCl$_3$) δ 7.45 (dd, J=8.3, 2.2 Hz, 1H), 7.32 (d, J=2.1 Hz, 1H), 7.31-7.28 (m, 2H), 7.22-7.17 (m, 3H), 7.01 (d, J=8.4 Hz, 2H), 6.78 (d, J=8.4 Hz, 2H), 6.64 (d, J=8.3 Hz, 1H), 6.44 (d, J=7.8 Hz, 1H), 4.81 (td, J=7.0, 5.0 Hz, 1H), 2.94-2.63 (m, 6H), 2.29 (ddt, J=15.6, 11.1, 5.8 Hz, 1H), 2.13-2.03 (m, 1H), 1.90-1.75 (m, 2H), 1.50 (d, J=2.9 Hz, 6H), 0.94 (t, J=7.5 Hz, 3H). HRMS (ESI-TOF) m/z calcd for C$_{30}$H$_{37}$N$_2$O$_4$ [M+H]$^+$ 489.2748. found 489.2740.

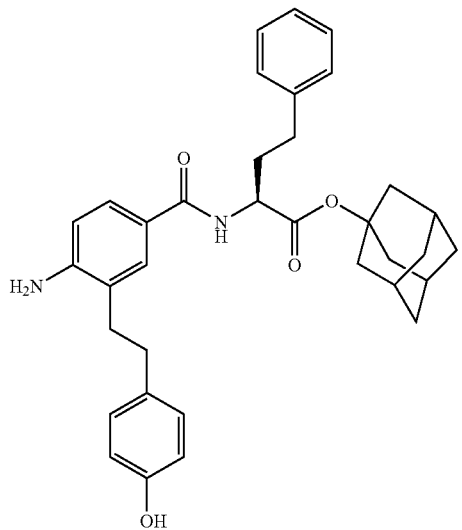 [SMILES: Nc1ccc(C(=O)N[C@@H](CCc2ccccc2)C(=O)OC23CC4CC(CC(C4)C2)C3)cc1CCc1ccc(O)cc1]

(MM-2-130) The general procedure for nitroaryl alkyne reduction was followed: Nitroalkyne MM-2-128 (32 mg, 0.055 mmol), EtOAc (0.5 mL), Pearlman's catalyst (15 mg). Preparative thin-layer chromatography of the filtered material (SiO$_2$, 50% EtOAc/hexanes) gave 11.3 mg (38%) of the fully reduced product. $^1$H NMR (500 MHz, CDCl$_3$) δ 7.43 (dd, J=8.3, 2.2 Hz, 1H), 7.37 (d, J=2.2 Hz, 1H), 7.29 (d, J=1.2 Hz, 2H), 7.20 (dd, J=7.7, 2.4 Hz, 3H), 6.99 (d, J=8.3 Hz, 2H), 6.79 (d, J=8.3 Hz, 2H), 6.62 (d, J=8.3 Hz, 1H), 6.51 (d, J=7.7 Hz, 1H), 4.83-4.76 (m, 1H), 3.82 (s, 2H), 2.86-2.63 (m, 6H), 2.33-2.24 (m, 1H), 2.21 (q, J=3.3 Hz, 3H), 2.17 (d, J=2.9 Hz, 6H), 2.14-2.05 (m, 1H), 1.70 (d, J=3.6 Hz, 6H). HRMS (ESI-TOF) m/z calcd for C$_{35}$H$_{41}$N$_2$O$_4$ [M+H]$^+$ 553.3061. found 553.3072.

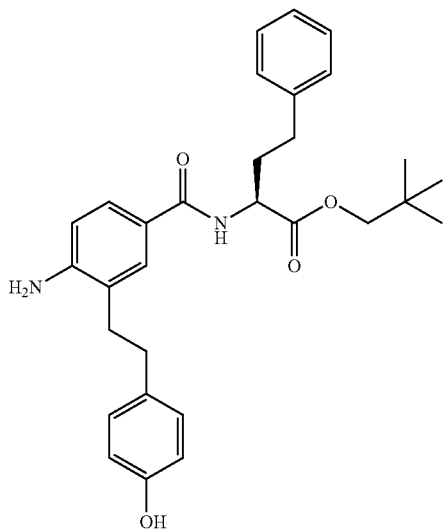 [SMILES: CC(C)(C)COC(=O)[C@H](CCc1ccccc1)NC(=O)c1ccc(N)c(CCc2ccc(O)cc2)c1]

(MM-2-129) The general procedure for nitroaryl alkyne reduction was followed: Nitroalkyne MM-2-127 (26 mg, 0.051 mmol), EtOAc (0.5 mL), Pearlman's catalyst (10 mg). Preparative thin-layer chromatography of the filtered material (SiO$_2$, 50% EtOAc/hexanes) gave 8.6 mg (34%) of the fully reduced product. $^1$H NMR (500 MHz, CDCl$_3$) δ 7.43 (dd, J=8.3, 2.2 Hz, 1H), 7.36 (d, J=2.2 Hz, 1H), 7.29 (d, J=7.9 Hz, 2H), 7.20 (dt, J=5.9, 1.4 Hz, 3H), 6.99 (d, J=8.3 Hz, 2H), 6.79 (d, J=8.4 Hz, 2H), 6.63 (d, J=8.3 Hz, 1H), 6.48 (d, J=7.8 Hz, 1H), 4.94 (td, J=7.3, 5.1 Hz, 1H), 3.88 (q, J=10.5 Hz, 2H), 3.83 (s, 2H), 2.88-2.63 (m, 6H), 2.33 (ddd, J=10.0, 5.0, 3.0 Hz, 1H), 2.21-2.08 (m, 1H), 0.98 (s, 9H). HRMS (ESI-TOF) m/z calcd for C$_{30}$H$_{37}$N$_2$O$_4$ [M+H]$^+$ 489.2748. found 489.2746.

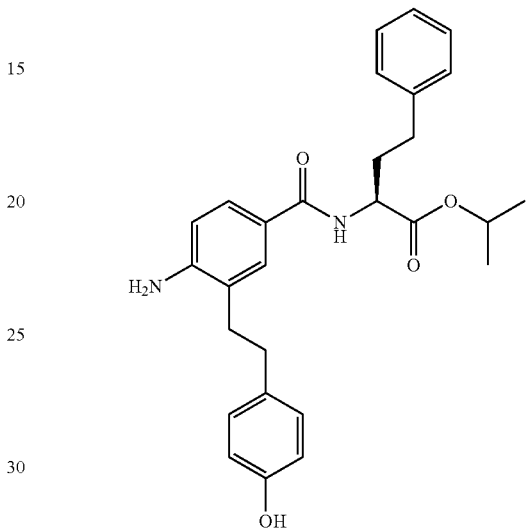

(MM-1-468) The general procedure for nitroaryl alkyne reduction was followed: Nitroalkyne MM-1-467 (18 mg, 0.037 mmol), EtOAc (0.25 mL), Pearlman's catalyst (15 mg). Preparative thin-layer chromatography of the filtered material (SiO$_2$, 50% EtOAc/hexanes) gave 10 mg (59%) of the fully reduced product. $^1$H NMR (400 MHz, CDCl$_3$) δ 7.43 (dd, J=8.3, 2.1 Hz, 1H), 7.35-7.28 (m, 2H), 7.25-7.15 (m, 3H), 6.98 (d, J=8.4 Hz, 2H), 6.78 (d, J=8.4 Hz, 2H), 6.63 (d, J=8.3 Hz, 1H), 6.51 (d, J=7.9 Hz, 1H), 6.28 (q, J=5.7 Hz, 1H), 5.12 (tt, J=12.5, 6.2 Hz, 1H), 4.85 (ddt, J=12.3, 7.3, 4.1 Hz, 1H), 2.91-2.62 (m, 6H), 2.40-2.22 (m, 1H), 2.14 (m, 1H), 1.31 (dd, J=6.2, 2.3 Hz, 6H). HRMS (ESI-TOF) m/z calcd for C$_{28}$H$_{33}$N$_2$O$_4$ [M+H]$^+$ 461.2435. found 461.2434.

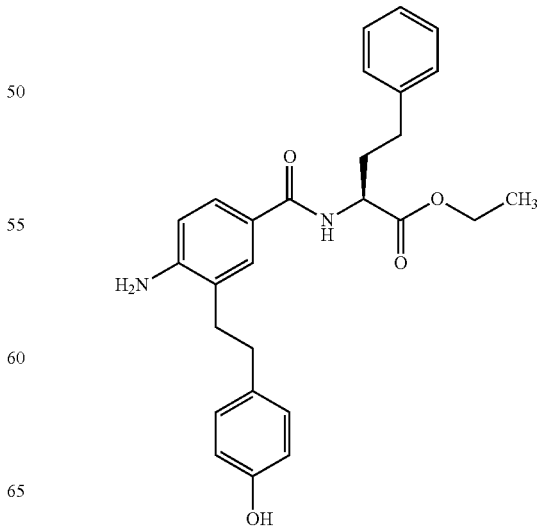

(MM-1-440) The general procedure for nitroaryl alkyne reduction was followed: Nitroalkyne MM-1-438 (16 mg, 0.034 mmol), EtOAc (0.4 mL), Pearlman's catalyst (15 mg). Preparative thin-layer chromatography of the filtered material (SiO$_2$, 50% EtOAc/hexanes) gave 5.2 mg (35%) of the fully reduced product. $^1$H NMR (400 MHz, CD$_3$OD) δ 7.77 (d, J=8.7 Hz, 2H), 7.34-7.16 (m, 5H), 6.87 (d, J=8.7 Hz, 2H), 4.55 (dd, J=9.3, 5.1 Hz, 1H), 4.21 (q, J=7.1 Hz, 2H), 2.92-2.68 (m, 4H), 2.22 (dd, J=28.3, 6.5 Hz, 4H), 1.29 (t, J=7.1 Hz, 3H).

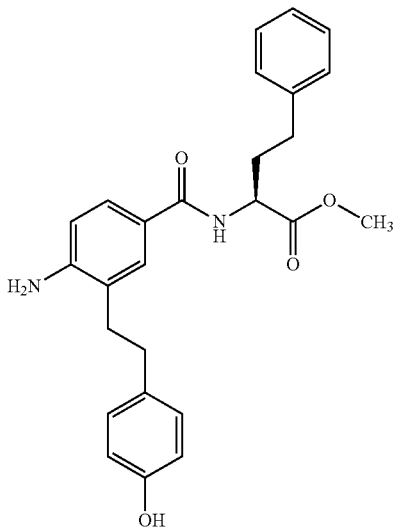 [SMILES: COC(=O)[C@H](CCc1ccccc1)NC(=O)c1ccc(N)c(CCc2ccc(O)cc2)c1]

(MM-1-439) The general procedure for nitroaryl alkyne reduction was followed: Nitroalkyne MM-1-437 (19 mg, 0.041 mmol), EtOAc (0.4 mL), Pearlman's catalyst (15 mg). Preparative thin-layer chromatography of the filtered material (SiO$_2$, 50% EtOAc/hexanes) gave 9 mg (50%) of the fully reduced product. $^1$H NMR (400 MHz, CD$_3$OD) δ 8.64 (d, J=2.1 Hz, 1H), 8.26 (dd, J=8.5, 2.1 Hz, 1H), 8.15 (d, J=8.8 Hz, 2H), 7.70 (dd, J=10.3, 8.6 Hz, 2H), 7.30-7.11 (m, 5H), 6.91 (d, J=8.8 Hz, 2H), 6.82 (d, J=8.7 Hz, 1H), 4.58 (dd, J=9.6, 4.9 Hz, 1H), 3.72 (s, 3H), 2.88-2.62 (m, 4H), 2.32-2.07 (m, 4H).

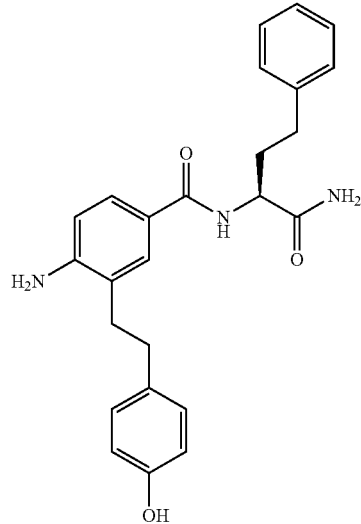 [SMILES: NC(=O)[C@H](CCc1ccccc1)NC(=O)c1ccc(N)c(CCc2ccc(O)cc2)c1]

(MM-2-102) The general procedure for nitroaryl alkyne reduction was followed: Nitroalkyne MM-2-94 (50 mg, 0.113 mmol), EtOAc (0.5 mL), Pearlman's catalyst (15 mg). Preparative thin-layer chromatography of the filtered material (SiO$_2$, 10% MeOH/CH$_2$Cl$_2$) gave 40 mg (85%) of the fully reduced product. HRMS (ESI-TOF) m/z calcd for C$_{25}$H$_{28}$N$_3$O$_3$ [M+H]$^+$ 418.2125. found 418.2128.

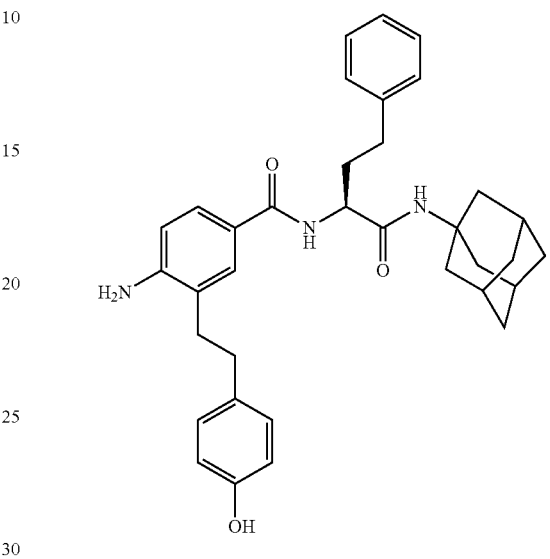

(MM-2-126) The general procedure for nitroaryl alkyne reduction was followed: Nitroalkyne MM-2-121 (29 mg, 0.050 mmol), EtOAc (0.5 mL), Pearlman's catalyst (10 mg). Preparative thin-layer chromatography of the filtered material (SiO$_2$, 75% EtOAc/hexanes) gave 22.4 mg (81%) of the fully reduced product. $^1$H NMR (500 MHz, CDCl$_3$) δ 7.54-7.45 (m, 1H), 7.34-7.28 (m, 2H), 7.26-7.17 (m, 3H), 6.90-6.84 (m, 2H), 6.79 (dd, J=9.1, 2.4 Hz, 2H), 6.71 (d, J=2.2 Hz, 1H), 6.65 (d, J=8.3 Hz, 1H), 6.15 (m, 1H), 5.88 (s, 1H), 4.47 (m, 1H), 3.89 (br s, 2H), 3.00-2.53 (m, 6H), 2.13-2.07 (m, 3H), 2.03 (d, J=6.8 Hz, 6H), 1.74-1.67 (m, 6H). HRMS (ESI-TOF) m/z calcd for C$_{35}$H$_{42}$N$_3$O$_3$ [M+H]$^+$ 552.3221. found 552.3225.

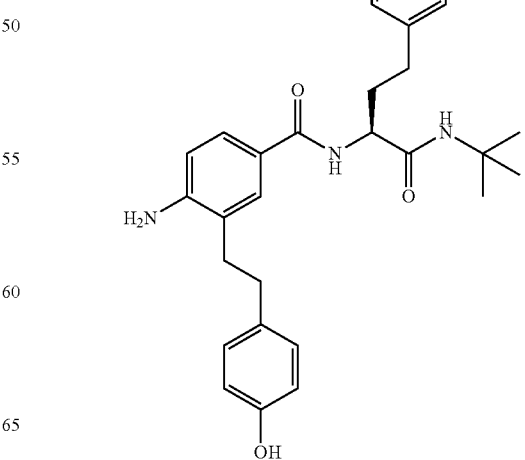

(MM-2-101) The general procedure for nitroaryl alkyne reduction was followed: Nitroalkyne MM-2-93 (31 mg, 0.063 mmol), EtOAc (0.5 mL), Pearlman's catalyst (10 mg). Preparative thin-layer chromatography of the filtered material (SiO$_2$, 50% EtOAc/hexanes) gave 16.2 mg (55%) of the fully reduced product. $^1$H NMR (500 MHz, CDCl$_3$) δ 7.47 (dd, J=8.4, 2.2 Hz, 1H), 7.26-7.23 (m, 2H), 7.19-7.14 (m, 3H), 6.99 (d, J=2.1 Hz, 1H), 6.86 (d, J=8.5 Hz, 2H), 6.78 (d, J=8.3 Hz, 2H), 6.59 (d, J=8.3 Hz, 1H), 6.56 (m, 1H), 4.53 (m, 1H), 2.88-2.62 (m, 6H), 2.57 (dt, J=13.9, 7.5 Hz, 1H), 2.12-2.02 (m, 1H), 1.35 (s, 9H). HRMS (ESI-TOF) m/z calcd for C$_{29}$H$_{36}$N$_3$O$_3$ [M+H]$^+$ 474.2751. found 474.2754.

(MM-2-124) The general procedure for nitroaryl alkyne reduction was followed: Nitroalkyne MM-2-119 (13 mg, 0.025 mmol), EtOAc (0.25 mL), Pearlman's catalyst (10 mg). Preparative thin-layer chromatography of the filtered material (SiO$_2$, 75% EtOAc/hexanes) gave 4.2 mg (34%) of the fully reduced product. $^1$H NMR (400 MHz, CDCl$_3$) δ 7.45 (dd, J=8.6, 2.3 Hz, 1H), 7.18 (t, J=6.5 Hz, 5H), 7.02 (s, 1H), 6.83 (d, J=8.2 Hz, 2H), 6.76 (d, J=8.2 Hz, 2H), 6.61 (d, J=8.4 Hz, 1H), 6.56 (d, J=4.1 Hz, 1H), 6.29 (d, J=8.7 Hz, 1H), 4.57 (q, J=7.8 Hz, 1H), 3.23 (m, 2H), 2.71 (m, 6H), 2.21 (m, 1H), 2.10 (m, 1H), 1.32-1.14 (m, 8H), 0.86 (t, J=6.4 Hz, 3H). HRMS (ESI-TOF) m/z calcd for C$_{31}$H$_{40}$N$_3$O$_3$ [M+H]$^+$ 502.3064. found 502.3069.

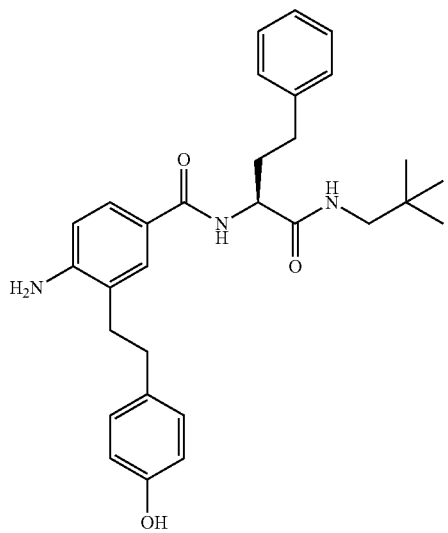 [SMILES: CC(C)(C)CNC(=O)[C@H](CCc1ccccc1)NC(=O)c1ccc(N)c(CCc2ccc(O)cc2)c1]

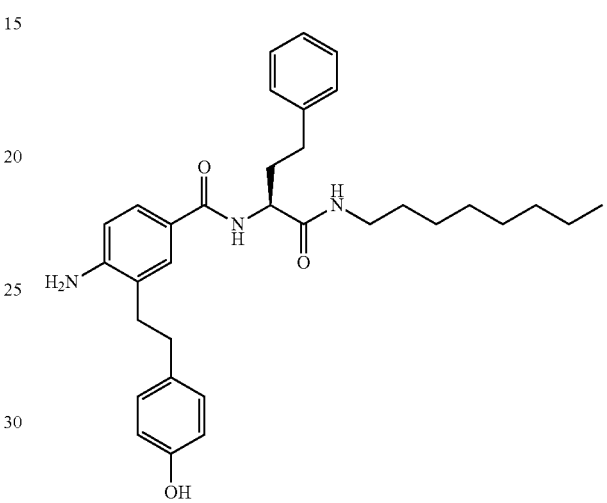

(MM-2-125) The general procedure for nitroaryl alkyne reduction was followed: Nitroalkyne MM-2-120 (28 mg, 0.055 mmol), EtOAc (0.5 mL), Pearlman's catalyst (10 mg). Preparative thin-layer chromatography of the filtered material (SiO$_2$, 75% EtOAc/hexanes) gave 23 mg (87%) of the fully reduced product. $^1$H NMR (500 MHz, CDCl$_3$) δ 7.51-7.43 (m, 1H), 7.27 (dt, J=4.7, 2.5 Hz, 2H), 7.23-7.15 (m, 3H), 6.86-6.82 (m, 2H), 6.77 (dd, J=8.3, 1.3 Hz, 2H), 6.69 (d, J=2.1 Hz, 1H), 6.66-6.61 (m, 1H), 6.56 (t, J=6.3 Hz, 1H), 6.09 (d, J=8.7 Hz, 1H), 4.60 (q, J=7.5 Hz, 1H), 3.91 (br s, 2H), 3.15-3.05 (m, 2H), 2.90 (dd, J=12.7, 6.4 Hz, 1H), 2.82 (dt, J=12.5, 5.6 Hz, 1H), 2.78-2.51 (m, 4H), 2.30-2.18 (m, 1H), 2.16-2.02 (m, 1H), 1.74 (s, 1H), 0.91 (d, J=1.2 Hz, 9H). HRMS (ESI-TOF) m/z calcd for C$_{30}$H$_{38}$N$_3$O$_3$ [M+H]$^+$ 488.2908. found 488.2913.

(MM-2-160) The general procedure for nitroaryl alkyne reduction was followed: Nitroalkyne MM-2-155 (22 mg, 0.040 mmol), EtOAc (1.0 mL), Pearlman's catalyst (10 mg). Preparative thin-layer chromatography of the filtered material (SiO$_2$, 60% EtOAc/hexanes) gave 20.5 mg (98%) of the fully reduced product. $^1$H NMR (400 MHz, CDCl$_3$) δ 7.46 (dd, J=8.3, 2.1 Hz, 1H), 7.31-7.24 (m, 2H), 7.19 (m, 3H), 6.85 (d, J=8.5 Hz, 2H), 6.79 (d, J=8.4 Hz, 2H), 6.70 (d, J=2.1 Hz, 1H), 6.63 (d, J=8.4 Hz, 1H), 6.17 (d, J=8.7 Hz, 1H), 4.54 (td, J=8.1, 6.4 Hz, 1H), 3.90 (s, 2H), 3.25 (m, 2H), 2.89 (m, 1H), 2.81 (dt, J=13.6, 5.7 Hz, 1H), 2.76-2.52 (m, 4H), 2.26-2.14 (m, 1H), 2.07 (dtd, J=14.2, 8.5, 6.7 Hz, 1H), 1.49 (q, J=7.0 Hz, 2H), 1.33-1.15 (m, 10H), 0.87 (t, J=6.8 Hz, 3H). HRMS (ESI-TOF) m/z calcd for C$_{33}$H$_{44}$N$_3$O$_3$ [M+H]$^+$ 530.3377. found 530.3378.

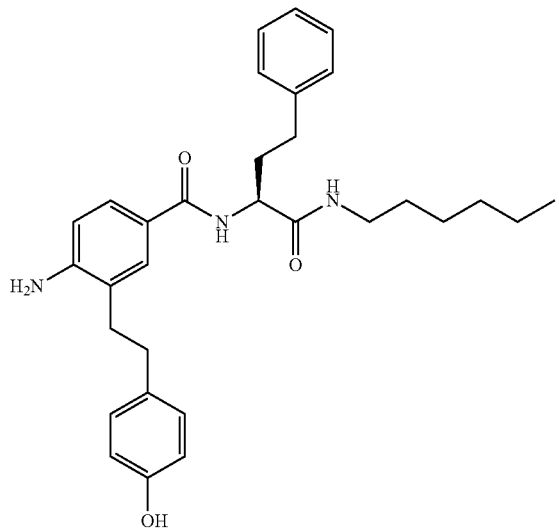 [SMILES: CCCCCCNC(=O)[C@H](CCc1ccccc1)NC(=O)c1ccc(N)c(CCc2ccc(O)cc2)c1]

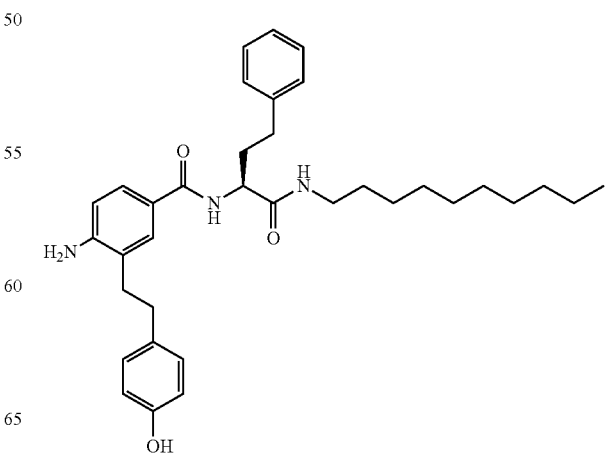

(MM-2-161) The general procedure for nitroaryl alkyne reduction was followed: Nitroalkyne MM-2-156 (23 mg, 0.039 mmol), EtOAc (1.0 mL), Pearlman's catalyst (10 mg). Preparative thin-layer chromatography of the filtered material (SiO$_2$, 60% EtOAc/hexanes) gave 7.6 mg (35%) of the fully reduced product. $^1$H NMR (400 MHz, CDCl$_3$) δ 7.46 (dd, J=8.3, 2.1 Hz, 1H), 7.32-7.23 (m, 2H), 7.19 (m, 3H), 6.85 (d, J=8.4 Hz, 2H), 6.79 (d, J=8.4 Hz, 2H), 6.68 (d, J=2.1 Hz, 1H), 6.64 (d, J=8.3 Hz, 1H), 6.48 (t, J=5.8 Hz, 1H), 6.12 (d, J=8.7 Hz, 1H), 4.63-4.47 (m, 1H), 3.90 (s, 2H), 3.25 (m, 2H), 2.90 (dd, J=12.1, 6.0 Hz, 1H), 2.86-2.77 (m, 1H), 2.77-2.48 (m, 4H), 2.31-2.14 (m, 1H), 2.09 (m, 1H), 1.50 (m, 2H), 1.35-1.14 (m, 14H), 0.88 (t, J=6.9 Hz, 3H). HRMS (ESI-TOF) m/z calcd for C$_{35}$H$_{48}$N$_3$O$_3$ [M+H]$^+$ 558.3690. found 558.3685.

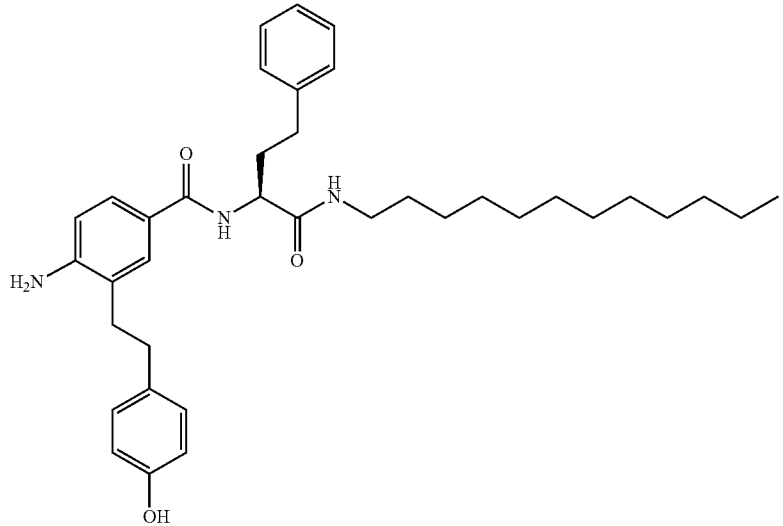 [SMILES: CCCCCCCCCCCCNC(=O)[C@H](CCc1ccccc1)NC(=O)c1ccc(N)c(CCc2ccc(O)cc2)c1]

(MM-2-162) The general procedure for nitroaryl alkyne reduction was followed: Nitroalkyne MM-2-157 (23 mg, 0.038 mmol), EtOAc (1.0 mL), Pearlman's catalyst (15 mg). Preparative thin-layer chromatography of the filtered material (SiO$_2$, 60% EtOAc/hexanes) gave 8.0 mg (36%) of the fully reduced product. $^1$H NMR (400 MHz, CDCl$_3$) δ 7.46 (d, J=8.4 Hz, 1H), 7.28 (d, J=7.7 Hz, 2H), 7.23-7.14 (m, 3H), 6.84 (d, J=8.0 Hz, 2H), 6.78 (d, J=8.0 Hz, 2H), 6.71 (s, 1H), 6.62 (d, J=8.5 Hz, 1H), 6.49 (t, J=5.6 Hz, 1H), 6.16 (d, J=8.7 Hz, 1H), 4.56 (m, 1H), 3.89 (s, 2H), 3.36-3.15 (m, 2H), 2.95-2.51 (m, 6H), 2.29-2.15 (m, 1H), 2.14-2.01 (m, 1H), 1.50 (t, J=7.2 Hz, 2H), 1.26 (d, J=11.2 Hz, 18H), 0.88 (t, J=6.7 Hz, 3H). HRMS (ESI-TOF) m/z calcd for C$_{37}$H$_{52}$N$_3$O$_3$ [M+H]$^+$ 586.4003. found 586.3989.

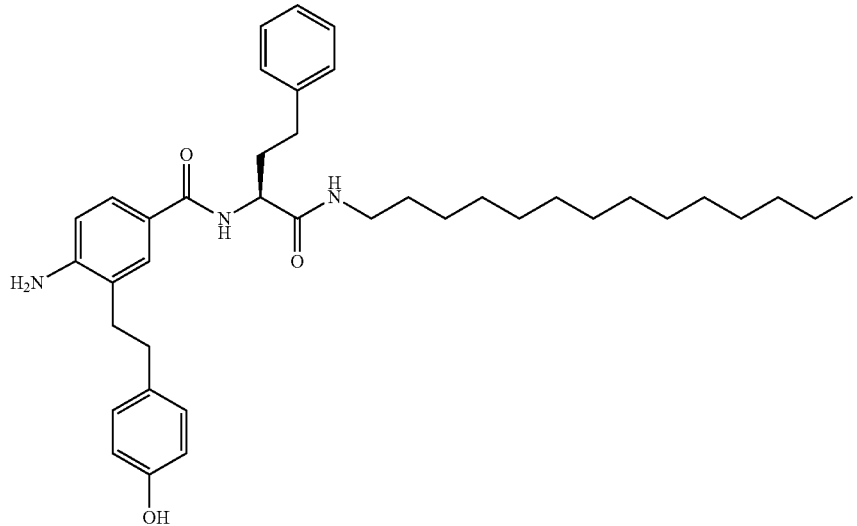 [SMILES: CCCCCCCCCCCCCCNC(=O)[C@H](CCc1ccccc1)NC(=O)c1ccc(N)c(CCc2ccc(O)cc2)c1]

(MM-2-163) The general procedure for nitroaryl alkyne reduction was followed: Nitroalkyne MM-2-158 (30 mg, 0.047 mmol), EtOAc (1.0 mL), Pearlman's catalyst (15 mg). Preparative thin-layer chromatography of the filtered material (SiO$_2$, 60% EtOAc/hexanes) gave 12.2 mg (42%) of the fully reduced product. $^1$H NMR (400 MHz, CDCl$_3$) δ 7.46 (dd, J=8.3, 2.1 Hz, 1H), 7.31-7.23 (m, 2H), 7.18 (dd, J=7.6, 5.2 Hz, 3H), 6.85 (d, J=8.4 Hz, 2H), 6.78 (d, J=8.9 Hz, 2H), 6.62 (d, J=8.3 Hz, 1H), 6.56 (t, J=5.8 Hz, 1H), 6.24 (d, J=8.6 Hz, 1H), 4.58 (q, J=7.6 Hz, 1H), 3.89 (s, 2H), 3.25 (m, 2H), 2.93-2.50 (m, 6H), 2.21 (ddt, J=13.4, 8.8, 6.6 Hz, 1H), 2.14-2.03 (m, 1H), 1.50 (m, 2H), 1.25 (d, J=5.7 Hz, 22H), 0.88 (t, J=6.8 Hz, 3H). HRMS (ESI-TOF) m/z calcd for C$_{39}$H$_{56}$N$_3$O$_3$ [M+H]$^+$ 614.4316. found 614.4311.

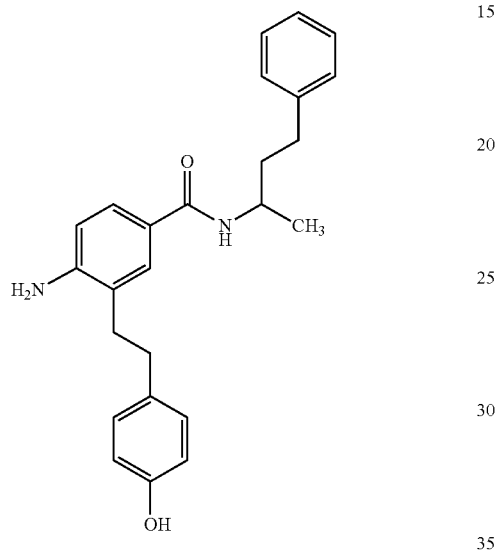

(MM-2-176) The general procedure for nitroaryl alkyne reduction was followed: Nitroalkyne MM-2-175 (8.5 mg, 0.021 mmol), EtOAc (0.75 mL), Pearlman's catalyst (10 mg). Preparative thin-layer chromatography of the filtered material (SiO$_2$, 60% EtOAc/hexanes) gave 2.8 mg (35%) of the fully reduced product. $^1$H NMR (400 MHz, CDCl$_3$) δ 7.39 (d, J=2.2 Hz, 1H), 7.35 (dd, J=8.2, 2.2 Hz, 1H), 7.30 (m, 2H), 7.24-7.16 (m, 3H), 7.02 (d, J=8.4 Hz, 2H), 6.78 (d, J=8.4 Hz, 2H), 6.62 (d, J=8.2 Hz, 1H), 5.69 (d, J=8.5 Hz, 1H), 4.27 (m, 1H), 3.80 (s, 2H), 2.84 (dd, J=8.9, 6.1 Hz, 2H), 2.76-2.69 (m, 4H), 1.92-1.83 (m, 2H), 1.27 (d, J=6.7 Hz, 3H). HRMS (ESI-TOF) m/z calcd for C$_{25}$H$_{29}$N$_2$O$_2$ [M+H]$^+$ 389.2223. found 389.2228.

Amino Acid Coupling with Acid and Reduction

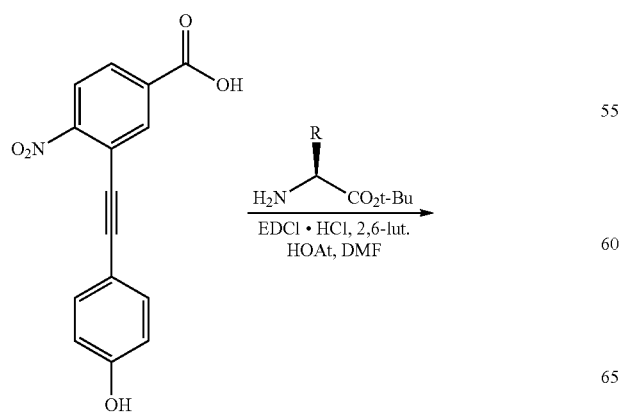

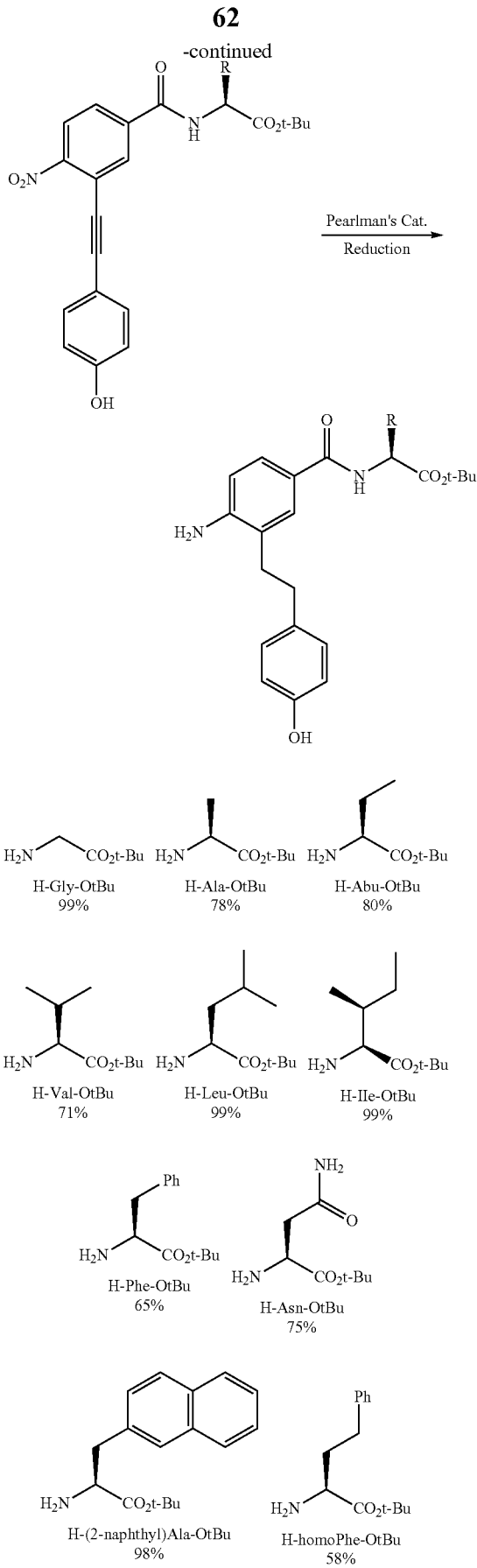

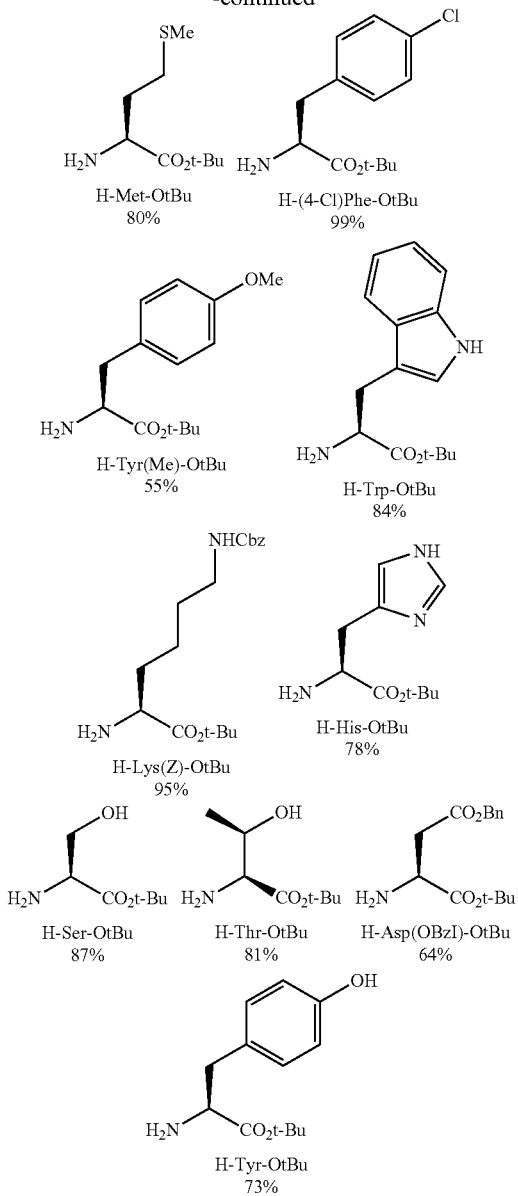

(MM-2-43-62) The general procedures for amine coupling with acid and nitroaryl alkyne reduction with Pearlman's catalyst were employed (0.035 mmol scale amine/acid) with the following amines. Yields are over two steps after preparative thin-layer chromatography (SiO$_2$, 50% EtOAc/hexanes) purification:

(MM-2-43-Gly) $^1$H NMR (500 MHz, CDCl$_3$) δ 7.53-7.45 (m, 2H), 7.01 (d, J=8.5 Hz, 1H), 6.98 (d, J=8.0 Hz, 2H), 6.78 (d, J=8.2 Hz, 1H), 6.62 (d, J=8.1 Hz, 1H), 6.52 (m, 1H), 4.19-4.07 (m, 2H), 2.80 (dd, J=9.3, 6.3 Hz, 1H), 2.70 (dd, J=9.2, 6.4 Hz, 1H), 1.51 (s, 9H). HRMS (ESI-TOF) m/z calcd for C$_{21}$H$_{27}$N$_2$O$_4$ [M+H]$^+$ 371.1965. found 371.1979.

(MM-2-44-Ala) $^1$H NMR (500 MHz, CDCl$_3$) δ 7.51-7.47 (m, 1H), 7.45 (d, J=2.3 Hz, 1H), 7.04-6.95 (m, 2H), 6.80 (d, J=8.3 Hz, 2H), 6.62 (d, J=8.0 Hz, 1H), 4.68 (m, 1H), 2.86-2.78 (m, 2H), 2.75-2.66 (m, 2H), 1.51 (s, 9H), 1.48 (d, J=5.0 Hz, 3H). HRMS (ESI-TOF) m/z calcd for C$_{22}$H$_{29}$N$_2$O$_4$ [M+H]$^+$ 385.2122. found 385.2139.

(MM-2-45-Abu) $^1$H NMR (500 MHz, CDCl$_3$) δ 7.50 (dd, J=8.2, 2.2 Hz, 1H), 7.45 (d, J=2.2 Hz, 1H), 6.99 (d, J=8.4 Hz, 2H), 6.80 (d, J=8.4 Hz, 2H), 6.63 (d, J=8.3 Hz, 1H), 6.57 (d, J=7.7 Hz, 1H), 4.69 (m, 1H), 2.87-2.77 (m, 2H), 2.75-2.66 (m, 2H), 2.04-1.93 (m, 1H), 1.87-1.77 (m, 1H), 1.51 (s, 9H), 0.95 (t, J=7.4 Hz, 3H). HRMS (ESI-TOF) m/z calcd for C$_{23}$H$_{31}$N$_2$O$_4$ [M+H]±399.2278. found 399.2278.

(MM-2-46-Val) $^1$H NMR (500 MHz, CDCl$_3$) δ 7.50 (dd, J=8.2, 2.2 Hz, 1H), 7.41 (d, J=2.1 Hz, 1H), 6.98 (d, J=8.4 Hz, 2H), 6.80 (d, J=8.4 Hz, 2H), 6.64 (d, J=8.3 Hz, 1H), 6.47 (d, J=8.6 Hz, 1H), 4.68 (dd, J=8.6, 4.6 Hz, 1H), 2.91-2.64 (m, 4H), 2.30-2.20 (sept, J=6.9 Hz, 1H), 1.51 (s, 9H), 1.00 (d, J=6.8 Hz, 3H), 0.97 (d, J=6.9 Hz, 3H). HRMS (ESI-TOF) m/z calcd for C$_{24}$H$_{33}$N$_2$O$_4$ [M+H]$^+$ 413.2435. found 413.2430.

(MM-2-47-Leu) $^1$H NMR (500 MHz, CDCl$_3$) δ 7.48 (dd, J=8.2, 2.2 Hz, 1H), 7.39 (d, J=2.1 Hz, 1H), 6.98 (d, J=8.3 Hz, 2H), 6.79 (d, J=8.4 Hz, 2H), 6.63 (d, J=8.3 Hz, 1H), 6.36 (d, J=8.3 Hz, 1H), 4.74 (td, J=8.5, 5.2 Hz, 1H), 3.83 (br s, 2H), 2.89-2.62 (m, 4H), 1.79-1.58 (m, 3H), 1.50 (s, 9H), 0.99 (d, J=3.4 Hz, 3H), 0.98 (d, J=3.5 Hz, 3H). HRMS (ESI-TOF) m/z calcd for C$_{25}$H$_{35}$N$_2$O$_4$ [M+H]$^+$ 427.2591. found 427.2599.

(MM-2-48-Ile) $^1$H NMR (500 MHz, CDCl$_3$) δ 7.49 (dd, J=8.3, 2.2 Hz, 1H), 7.41 (d, J=2.1 Hz, 1H), 6.99 (d, J=8.4 Hz, 2H), 6.79 (d, J=8.4 Hz, 2H), 6.64 (d, J=8.2 Hz, 1H), 6.51 (d, J=8.4 Hz, 1H), 4.71 (dd, J=8.3, 4.6 Hz, 1H), 3.87 (br s, 2H), 2.89-2.67 (m, 4H), 2.02-1.92 (m, 1H), 1.51 (s, 9H), 0.98 (t, J=7.4 Hz, 3H), 0.96 (d, J=6.8 Hz, 3H). HRMS (ESI-TOF) m/z calcd for C$_{25}$H$_{35}$N$_2$O$_4$ [M+H]$^+$ 427.2591. found 427.2591.

(MM-2-49-Phe) $^1$H NMR (500 MHz, CDCl$_3$) δ 7.42 (dd, J=8.2, 2.1 Hz, 1H), 7.37 (d, J=2.1 Hz, 1H), 7.33-7.28 (m, 2H), 7.26-7.15 (m, 3H), 6.99 (d, J=8.5 Hz, 2H), 6.78 (d, J=8.4 Hz, 2H), 6.62 (d, J=8.2 Hz, 1H), 6.43 (d, J=7.5 Hz, 1H), 4.96 (dt, J=7.5, 5.8 Hz, 1H), 3.83 (br s, 2H), 3.21 (d, J=5.9 Hz, 2H), 2.90-2.64 (m, 4H), 1.44 (s, 9H). HRMS (ESI-TOF) m/z calcd for C$_{28}$H$_{33}$N$_2$O$_4$ [M+H]$^+$ 461.2435. found 461.2437.

(MM-2-50-Asn) $^1$H NMR (500 MHz, Acetone-d$_6$) δ 7.59 (d, J=8.7 Hz, 1H), 7.57 (d, J=2.1 Hz, 1H), 7.50 (dd, J=8.3, 2.2 Hz, 1H), 7.11 (d, J=8.4 Hz, 2H), 6.75 (d, J=8.4 Hz, 2H), 6.73 (d, J=8.3 Hz, 1H), 5.00 (s, 1H), 4.77 (ddd, J=8.1, 5.8, 4.9 Hz, 1H), 2.83-2.71 (m, 6H), 1.44 (s, 9H). HRMS (ESI-TOF) m/z calcd for C$_{23}$H$_{30}$N$_3$O$_5$ [M+H]$^+$ 428.2180. found 428.2184.

(MM-2-51-2-Nap-Ala) $^1$H NMR (500 MHz, CDCl$_3$) δ 7.86-7.69 (m, 4H), 7.64-7.61 (m, 1H), 7.52-7.38 (m, 2H), 7.33 (dd, J=8.3, 1.7 Hz, 1H), 7.30 (d, J=2.2 Hz, 1H), 6.93 (d, J=8.4 Hz, 2H), 6.72 (d, J=8.4 Hz, 2H), 6.59 (d, J=8.2 Hz, 1H), 6.42 (d, J=7.6 Hz, 1H), 5.10-5.01 (m, 1H), 3.38 (d, J=5.6 Hz, 2H), 2.93-2.60 (m, 4H), 1.44 (s, 9H). HRMS (ESI-TOF) m/z calcd for C$_{32}$H$_{35}$N$_2$O$_4$ [M+H]$^+$ 511.2591. found 511.2593.

(MM-2-52-HoPhe) $^1$H NMR (500 MHz, CDCl$_3$) δ 7.44 (dd, J=8.2, 2.1 Hz, 1H), 7.34 (d, J=2.2 Hz, 1H), 7.32-7.28 (m, 2H), 7.25-7.16 (m, 3H), 7.00 (d, J=8.4 Hz, 2H), 6.79 (d, J=8.4 Hz, 2H), 6.63 (d, J=8.3 Hz, 1H), 6.47 (d, J=7.8 Hz, 1H), 4.80 (td, J=7.2, 5.0 Hz, 1H), 3.83 (br s, 2H), 2.90-2.63 (m, 6H), 2.29 (m, 1H), 2.13-2.07 (m, 1H), 1.53 (s, 9H). HRMS (ESI-TOF) m/z calcd for C$_{29}$H$_{35}$N$_2$O$_4$ [M+H]$^+$ 475.2591. found 475.2581.

(MM-2-53-Met) $^1$H NMR (500 MHz, CDCl$_3$) δ 7.57 (m, 1H), 7.48 (m, 1H), 7.37 (d, J=2.3 Hz, 1H), 6.99-6.96 (m, 2H), 6.90 (d, J=8.5 Hz, 1H), 6.78 (d, J=8.5 Hz, 2H), 6.69 (d, J=8.6 Hz, 1H), 4.78 (m, 1H), 2.78-2.40 (m, 6H), 2.23 (m, 2H), 2.11 (s, 3H), 1.51 (s, 9H). HRMS (ESI-TOF) m/z calcd for C$_{24}$H$_{33}$N$_2$O$_4$S [M+H]$^+$ 445.2155. found 445.2154.

(MM-2-54-4-Cl-Phe) $^1$H NMR (500 MHz, CDCl$_3$) δ 7.42 (dd, J=8.3, 2.1 Hz, 1H), 7.36 (d, J=2.2 Hz, 1H), 7.25 (d, J=8.4 Hz, 2H), 7.11 (d, J=8.4 Hz, 2H), 6.99 (d, J=8.5 Hz, 2H), 6.78 (d, J=8.4 Hz, 2H), 6.63 (d, J=8.2 Hz, 1H), 6.44 (d, J=7.1 Hz, 1H), 4.94 (m, 1H), 3.26-3.14 (m, 2H), 2.91-2.66 (m, 4H), 1.45 (s, 9H). HRMS (ESI-TOF) m/z calcd for C$_{28}$H$_{32}$ClN$_2$O$_4$ [M+H]$^+$ 495.2045. found 495.2044.

(MM-2-55-TyrMe) $^1$H NMR (500 MHz, CDCl$_3$) δ 7.43 (dd, J=8.3, 2.1 Hz, 1H), 7.37 (d, J=2.2 Hz, 1H), 7.10 (d, J=8.6 Hz, 2H), 6.99 (d, J=8.4 Hz, 2H), 6.82 (d, J=8.6 Hz, 2H), 6.77 (d, J=8.4 Hz, 2H), 6.62 (d, J=8.3 Hz, 1H), 6.41 (d, J=7.6 Hz, 1H), 4.96-4.90 (m, 1H), 3.78 (s, 3H), 3.15 (t, J=6.1 Hz, 2H), 2.88-2.66 (m, 4H), 1.46 (s, 9H). HRMS (ESI-TOF) m/z calcd for C$_{29}$H$_{35}$N$_2$O$_5$ [M+H]$^+$ 491.2540. found 491.2544.

(MM-2-56-Trp) $^1$H NMR (500 MHz, CDCl$_3$) δ 8.33 (s, 1H), 7.61 (d, J=7.7 Hz, 1H), 7.40 (dd, J=8.3, 2.1 Hz, 1H), 7.35-7.32 (m, 1H), 7.19 (d, J=2.1 Hz, 1H), 7.18-7.14 (m, 1H), 7.07 (ddd, J=8.0, 7.1, 1.0 Hz, 1H), 6.98 (dd, J=5.1, 2.7 Hz, 2H), 6.89 (d, J=8.6 Hz, 2H), 6.73 (d, J=8.4 Hz, 2H), 6.54 (d, J=8.3 Hz, 1H), 6.49 (d, J=7.7 Hz, 1H), 5.03 (m, 1H), 3.37 (qd, J=14.8, 5.5 Hz, 2H), 2.80-2.70 (m, 2H), 2.68-2.60 (m, 2H), 1.41 (s, 9H). HRMS (ESI-TOF) m/z calcd for C$_{30}$H$_{34}$N$_3$O$_4$ [M+H]$^+$ 500.2544. found 500.2548.

(MM-2-57-Lys) $^1$H NMR (500 MHz, CDCl$_3$) δ 7.51-7.45 (m, 2H), 6.96 (d, J=7.7 Hz, 2H), 6.64 (d, J=7.1 Hz, 2H), 6.29 (m, 1H), 6.18 (d, J=12.0 Hz, 1H), 4.98 (m, 1H), 3.15 (m, 2H), 2.83-2.64 (m, 6H), 1.87 (m, 2H), 1.45 (s, 9H), 1.32-1.17 (m, 2H). HRMS (ESI-TOF) m/z calcd for C$_{25}$H$_{36}$N$_3$O$_4$ [M+H]$^+$ 442.2700. found 442.2690.

(MM-2-58-His) $^1$H NMR (500 MHz, Acetone-d$_6$) δ 8.23 (dd, J=5.2, 3.3 Hz, 1H), 8.04 (dd, J=8.6, 1.9 Hz, 1H), 7.96 (m, 1H), 7.70 (m, 1H), 7.50 (d, J=8.7 Hz, 2H), 6.87 (d, J=8.7 Hz, 2H), 6.77-6.72 (m, 1H), 6.68-6.63 (m, 1H), 4.78-4.72 (m, 1H), 3.23-3.02 (m, 4H), 2.91-2.79 (m, 2H), 1.39 (s, 9H). HRMS (ESI-TOF) m/z calcd for C$_{25}$H$_{31}$N$_4$O$_4$ [M+H]$^+$ 451.2340. found 451.2340.

(MM-2-59-Ser) $^1$H NMR (500 MHz, Acetone-d$_6$) δ 8.08 (s, 1H), 7.65 (d, J=2.2 Hz, 1H), 7.56 (dd, J=8.3, 2.2 Hz, 1H), 7.22 (d, J=7.8 Hz, 1H), 7.12 (d, J=8.4 Hz, 2H), 6.76 (d, J=8.5 Hz, 2H), 6.73 (d, J=8.3 Hz, 1H), 5.00 (br s, 1H), 4.59 (ddd, J=8.1, 4.7, 3.6 Hz, 1H), 4.00-3.85 (m, 2H), 2.85 (s, 2H), 2.83-2.76 (m, 4H), 1.47 (s, 9H). HRMS (ESI-TOF) m/z calcd for C$_{22}$H$_{29}$N$_2$O$_5$ [M+H]' 401.2071. found 401.2072.

(MM-2-60-Thr) $^1$H NMR (500 MHz, Acetone-d$_6$) δ 7.65 (d, J=2.1 Hz, 1H), 7.57 (dd, J=8.3, 2.2 Hz, 1H), 7.12 (d, J=8.4 Hz, 2H), 7.00 (d, J=7.5 Hz, 1H), 6.76 (d, J=5.9 Hz, 2H), 6.74 (d, J=5.6 Hz, 1H), 4.54 (dd, J=8.8, 3.2 Hz, 1H), 4.33 (m, 1H), 2.89-2.76 (m, 6H), 1.47 (s, 9H), 1.20 (d, J=6.4 Hz, 3H). HRMS (ESI-TOF) m/z calcd for C$_{23}$H$_{31}$N$_2$O$_5$ [M+H]$^+$ 415.2227. found 415.2226.

(MM-2-61-Asp) $^1$H NMR (500 MHz, Acetone-d$_6$) δ 7.62 (d, J=2.1 Hz, 1H), 7.53 (dd, J=8.1, 2.2 Hz, 1H), 7.45 (d, J=8.1 Hz, 1H), 7.12 (d, J=8.4 Hz, 2H), 6.75 (d, J=8.4 Hz, 2H), 6.72 (d, J=8.3 Hz, 1H), 4.86 (m, 1H), 2.91 (d, J=5.8 Hz, 2H), 2.86-2.74 (m, 4H), 1.45 (s, 9H). HRMS (ESI-TOF) m/z calcd for C$_{23}$H$_{29}$N$_2$O$_6$ [M+H]$^+$ 429.2020. found 429.2020.

(MM-2-62-Tyr) $^1$H NMR (500 MHz, Acetone-d$_6$) δ 8.13 (d, J=45.8 Hz, 1H), 7.58 (d, J=2.1 Hz, 1H), 7.50 (dd, J=8.3, 2.2 Hz, 1H), 7.15 (d, J=8.0 Hz, 1H), 7.12 (d, J=2.9 Hz, 2H), 7.11 (d, J=2.8 Hz, 2H), 6.77 (d, J=2.2 Hz, 2H), 6.75 (d, J=2.1 Hz, 2H), 6.70 (d, J=8.4 Hz, 1H), 4.98 (s, 1H), 4.70 (td, J=7.7, 6.1 Hz, 1H), 3.08 (dd, J=13.8, 6.1 Hz, 1H), 3.01 (dd, J=13.9, 7.6 Hz, 1H), 2.85 (br s, 2H), 2.84-2.73 (m, 4H), 1.41 (s, 9H). HRMS (ESI-TOF) m/z calcd for C$_{28}$H$_{33}$N$_2$O$_5$ [M+H]$^+$ 477.2384. found 477.2388.

N- and O-Alkyl Neoseptin-3 Analogues

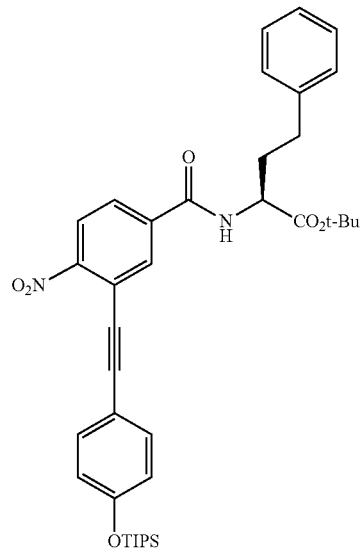

(MM-1-469) Free phenol MM-1-466 (80 mg, 0.200 mmol) was dissolved in CH$_2$Cl$_2$ (1 mL). Imidazole (15 mg, 0.209 mmol, 1.05 equiv) was added, followed by slow addition of TIPSCl (43 μL, 0.200 mmol, 1.00 equiv). After stirring 12 hours at room temperature, the reaction mixture was diluted with CH$_2$Cl$_2$ (10 mL) and washed with sat. NH$_4$Cl (10 mL). The aqueous phase was extracted with CH$_2$Cl$_2$ (2×5 mL), and the combined extracts were dried over Na$_2$SO$_4$, decanted and concentrated. Flash chromatography (SiO$_2$, 10% EtOAc/hexanes) afforded 85 mg (81%) of the silyl ether.

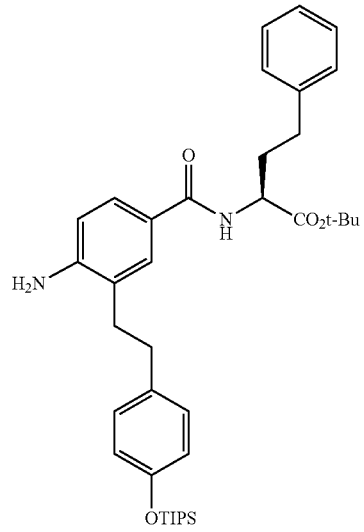

(MM-1-471) Silyl ether MM-1-469 was subjected to the general procedure for nitroalkyne reduction: Silyl ether MM-1-469 (85 mg, 0.129 mmol), Pearlman's catalyst (40 mg) in EtOAc (0.75 mL) for 3.5 hours. After filtration and concentration, the residue was subjected to flash column chromatography (SiO$_2$, 20 to 50% EtOAc/hexanes) to yield 56 mg (70%) of the reduced aniline as a yellow foam. $^1$H NMR (400 MHz, CDCl₃) δ 7.60 (t, J=2.1 Hz, 1H), 7.50 (dt, J=8.5, 2.2 Hz, 1H), 7.38-7.30 (m, 2H), 7.30-7.21 (m, 3H), 7.13-7.06 (m, 2H), 6.87 (dd, J=8.3, 2.4 Hz, 2H), 6.66 (dd, J=8.5, 2.3 Hz, 2H), 4.86 (dt, J=7.4, 2.4 Hz, 1H), 3.83 (s, 2H), 2.98-2.88 (m, 2H), 2.87-2.67 (m, 4H), 2.42-2.27 (m, 1H), 2.21-2.07 (m, 1H), 1.58 (s, 9H), 1.37-1.24 (m, 3H), 1.16 (dd, J=7.1, 2.4 Hz, 18H).

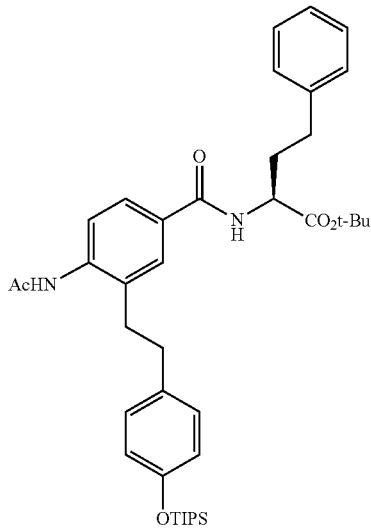

(MM-1-472) Aniline MM-1-471 (13 mg, 0.021 mmol) and 4-dimethylaminopyridine (DMAP, 10.3 mg, 0.085 mmol, 4.00 equiv) were dissolved in CH₂Cl₂ (220 μL) at room temperature. Acetyl chloride (approx. 2 μL, 1.10 equiv) was added dropwise, resulting in a slight exotherm. After stirring overnight (about 18 hours), the reaction solvent was removed under a stream of N₂ and the resulting residue subjected to preparative thin-layer chromatography (SiO₂, 50% EtOAc/hexanes) to afford 7.6 mg (55%) of the acetamide as a white solid. ¹H NMR (500 MHz, CDCl₃) δ 7.77 (d, J=8.4 Hz, 1H), 7.70 (d, J=2.1 Hz, 1H), 7.50 (dd, J=8.4, 2.1 Hz, 1H), 7.32-7.27 (m, 2H), 7.21 (dt, J=8.1, 1.8 Hz, 3H), 6.92 (d, J=8.4 Hz, 2H), 6.81 (d, J=8.4 Hz, 2H), 6.66 (d, J=7.6 Hz, 1H), 6.35 (s, 1H), 4.86-4.74 (m, 1H), 2.88 (s, 4H), 2.76 (dd, J=9.9, 5.9 Hz, 1H), 2.71 (dd, J=9.9, 5.9 Hz, 1H), 2.36-2.27 (m, 1H), 2.14 (m, 1H), 1.95 (s, 3H), 1.53 (s, 9H), 1.33-1.18 (m, 3H), 1.10 (d, J=7.4 Hz, 18H).

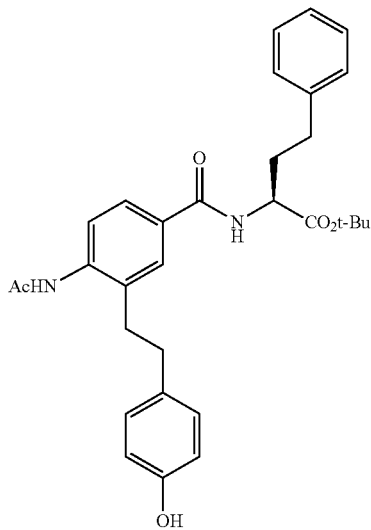 [SMILES: CC(=O)Nc1ccc(C(=O)N[C@@H](CCc2ccccc2)C(=O)OC(C)(C)C)cc1CCc1ccc(O)cc1]

(MM-1-473) Acetamide MM-1-472 (7.6 mg, 0.011 mmol) was dissolved in TBAF solution (200 μL, 0.200 mmol, 175 equiv, 1 M in THF) at room temperature. After 1 hour, the reaction mixture was transferred directly to a plate for preparative thin-layer chromatography (10% MeOH:CH₂Cl₂), which provided 3.2 mg (56%) of the free phenol. ¹H NMR (500 MHz, CDCl₃) δ 7.81 (d, J=8.4 Hz, 1H), 7.57 (s, 1H), 7.50 (d, J=8.3 Hz, 1H), 7.33-7.27 (m, 2H), 7.21 (d, J=7.4 Hz, 3H), 6.90 (d, J=8.4 Hz, 2H), 6.79 (d, J=8.3 Hz, 2H), 6.61 (d, J=7.8 Hz, 1H), 6.46 (s, 1H), 4.79 (td, J=7.0, 5.0 Hz, 1H), 3.30-3.20 (m, 1H), 2.86 (dd, J=9.3, 6.9 Hz, 4H), 2.76 (dd, J=9.8, 6.0 Hz, 1H), 2.69 (dd, J=9.8, 6.0 Hz, 1H), 2.34-2.26 (m, 1H), 2.17-2.07 (m, 1H), 1.96 (s, 3H), 1.53 (s, 9H). HRMS (ESI-TOF) m/z calcd for $C_{31}H_{37}N_2O_5$ [M+H]⁺ 517.2697. found 517.2703.

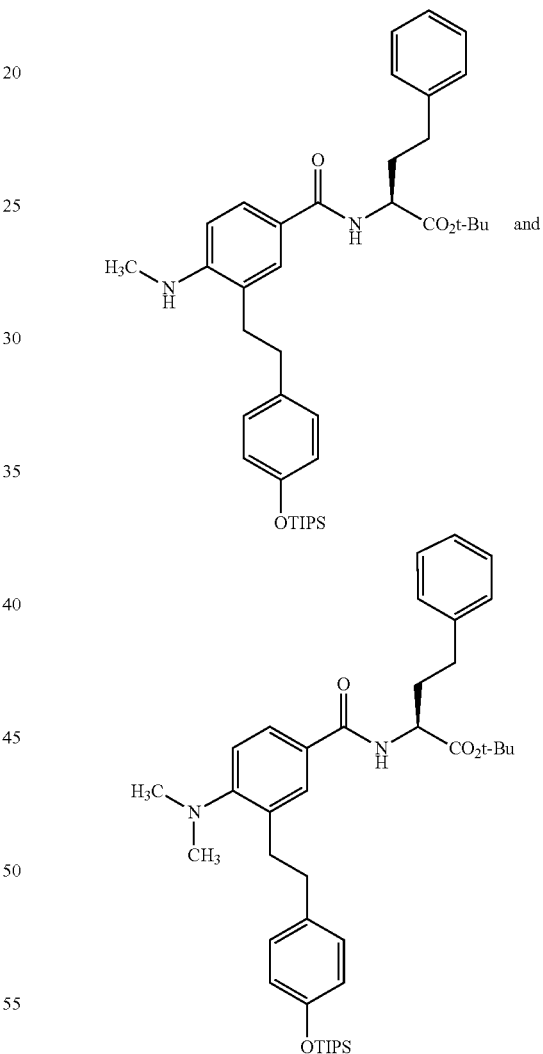

(MM-1-474) Aniline MM-1-471 (10.2 mg, 0.016 mmol) was dissolved in anhydrous DMF (150 μL) at room temperature. K₂CO₃ (2.2 mg, 0.016 mmo, 1.00 equiv) was suspended in the mixture, follow by addition of methyl iodide (approx. 1.5 μL, 0.024 mmol, 1.5 equiv). After stirring for 24 hours, the mixture was diluted with EtOAc (2 mL) and washed with H₂O (2 mL). The organic phase was concentrated and the residual oil subjected to preparative thin-layer chromatography (SiO₂, 30% EtOAc/hexanes) to afford the mono-N-methylated compound ($R_f$=0.57, 4.1 mg) and the N,N-dimethyl compound ($R_f$=0.70, 2.0 mg), along with recovered starting material ($R_f$=0.50, 2.2 mg). $^1$H NMR (MM-1-474-Mid, N-methyl, 500 MHz, CDCl$_3$) δ 7.60-7.55 (m, 2H), 7.31-7.28 (m, 2H), 7.24-7.16 (m, 3H), 7.05 (d, J=8.5 Hz, 2H), 6.82 (d, J=8.4 Hz, 2H), 6.57 (d, J=8.3 Hz, 2H), 4.81 (ddd, J=7.6, 6.6, 5.1 Hz, 1H), 3.88 (s, 1H), 2.87 (dd, J=9.7, 6.2 Hz, 2H), 2.84 (s, 3H), 2.81-2.64 (m, 4H), 2.30 (ddt, J=13.7, 11.0, 5.5 Hz, 1H), 2.14-2.05 (m, 1H), 1.52 (s, 9H), 1.30-1.21 (m, 3H), 1.11 (d, J=7.3 Hz, 18H). $^1$H NMR (MM-1-474-Higher, N,N-dimethyl, 500 MHz, CDCl$_3$) δ 7.68 (d, J=2.3 Hz, 1H), 7.54 (dd, J=8.3, 2.3 Hz, 1H), 7.29 (m, 2H), 7.21 (d, J=7.7 Hz, 3H), 7.09 (d, J=8.6 Hz, 2H), 7.06 (d, J=8.7 Hz, 1H), 6.81 (d, J=8.6 Hz, 2H), 6.62 (d, J=8.0 Hz, 1H), 4.85-4.77 (m, 1H), 3.03-2.65 (m, 2H), 2.74 (d, J=1.0 Hz, 6H), 2.30 (td, J=13.8, 10.9, 5.7 Hz, 1H), 2.11 (m, 1H), 1.53 (s, 9H), 1.30-1.21 (m, 3H), 1.11 (d, J=7.2 Hz, 18H).

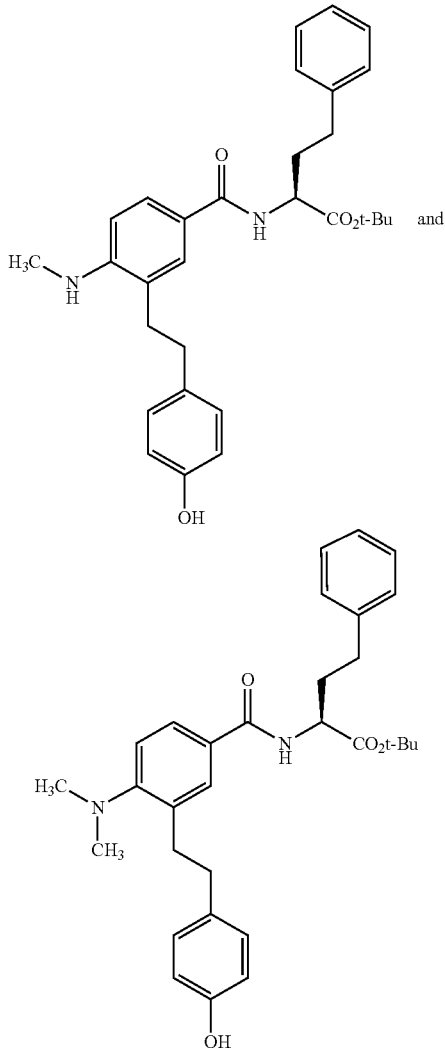 [SMILES: CNc1ccc(C(=O)N[C@@H](CCc2ccccc2)C(=O)OC(C)(C)C)cc1CCc1ccc(O)cc1 ; CN(C)c1ccc(C(=O)N[C@@H](CCc2ccccc2)C(=O)OC(C)(C)C)cc1CCc1ccc(O)cc1]

(MM-1-475/476) N-Alkyl compounds MM-1-474-Mid and MM-1-474-Higher were individually dissolved in 1 M TBAF (0.100 mL, 0.100 mmol, about 16 equiv, 1.0 M in THF) at room temperature, and stirred for 1 hour. Each reaction mixture was transferred directly to a plate for preparative thin-layer chromatography (SiO$_2$, 50% EtOAc/hexanes) to give 1.2 mg of the N-methyl product and 0.9 mg of the N,N-dimethyl product. HRMS (MM-1-475, N-methyl, ESI-TOF) m/z calcd for C$_{30}$H$_{37}$N$_2$O$_4$ [M+H]$^+$ 489.2748. found 489.2756. HRMS (MM-1-476, dimethyl, ESI-TOF) m/z calcd for C$_{31}$H$_{39}$N$_2$O$_4$ [M+H]$^+$ 503.2904. found 503.2901.

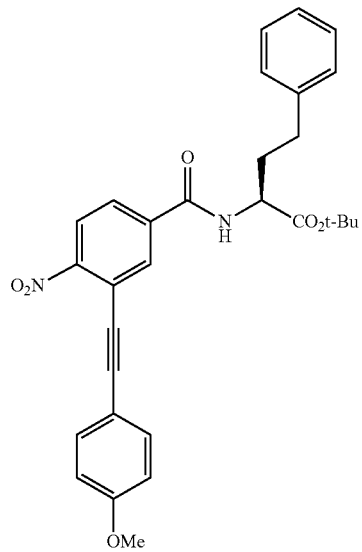 [SMILES: COc1ccc(C#Cc2cc(C(=O)N[C@@H](CCc3ccccc3)C(=O)OC(C)(C)C)ccc2[N+](=O)[O-])cc1]

(MM-2-15) Nitroalkyne free phenol MM-1-466 (20 mg, 0.040 mmol) was dissolved in anhydrous DMF (250 µL) in a ½ dram scintillation vial. K$_2$CO$_3$ (11 mg, 0.080 mmol, 2.00 equiv) was suspended in the reaction solvent, and methyl iodide (about 3 µL, 0.044, 1.10 equiv) was added. After stirring overnight (about 19 hours), the mixture was diluted with EtOAc (3 mL) and washed with 1:1 sat. NH$_4$Cl and H$_2$O (1.5 mL each). The aqueous phase was extracted once with EtOAc (1 mL), and the combined EtOAc extracts were dried over Na$_2$SO$_4$, decanted and concentrated. Preparative thin-layer chromatography (SiO$_2$, 30% EtOAc/hexanes) gave 12.8 mg (62%) of the methyl ether. $^1$H NMR (500 MHz, CDCl$_3$) δ 8.08 (d, J=8.5 Hz, 1H), 7.89 (d, J=2.0 Hz, 1H), 7.68 (dd, J=8.5, 2.0 Hz, 1H), 7.58 (d, J=8.8 Hz, 2H), 7.35-7.28 (m, 2H), 7.26-7.18 (m, 3H), 6.93 (d, J=8.8 Hz, 2H), 6.73 (d, J=7.5 Hz, 1H), 4.85-4.74 (m, 1H), 3.86 (s, 3H), 2.75 (td, J=7.2, 6.2, 2.3 Hz, 2H), 2.42-2.30 (m, 1H), 2.19 (m, 1H), 1.55 (s, 9H).

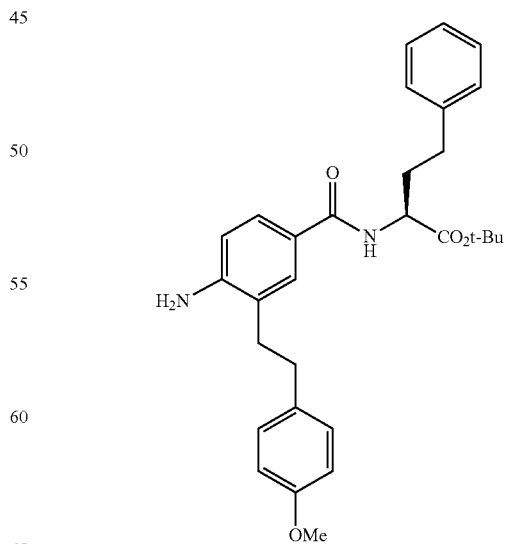

(MM-2-18) Methyl ether MM-2-15 was subjected to the general procedure for nitroalkyne reduction: Nitroalkyne MM-2-15 (12.8 mg, 0.025 mmol), Pearlman's catalyst (10 mg) and EtOAc (1 mL) hydrogenated for 3 hours. Filtration and concentration produced 7.8 mg (64%) of the aniline product which was not further purified. $^1$H NMR (500 MHz, CDCl$_3$) δ 7.51 (d, J=2.1 Hz, 1H), 7.46 (dd, J=8.2, 2.2 Hz, 1H), 7.32-7.28 (m, 2H), 7.23-7.17 (m, 3H), 7.12 (d, J=8.5 Hz, 2H), 6.85 (d, J=8.6 Hz, 2H), 6.64 (d, J=8.3 Hz, 1H), 6.53 (d, J=7.7 Hz, 1H), 4.79 (td, J=7.0, 5.0 Hz, 1H), 3.79 (br s, 5H), 2.90 (dd, J=9.4, 6.4 Hz, 2H), 2.82-2.62 (m, 4H), 2.35-2.24 (m, 1H), 2.14-2.06 (m, 1H), 1.52 (s, 9H). HRMS (ESI-TOF) m/z calcd for C$_{30}$H$_{37}$N$_2$O$_4$ [M+H]$^+$ 489.2748. found 489.2751.

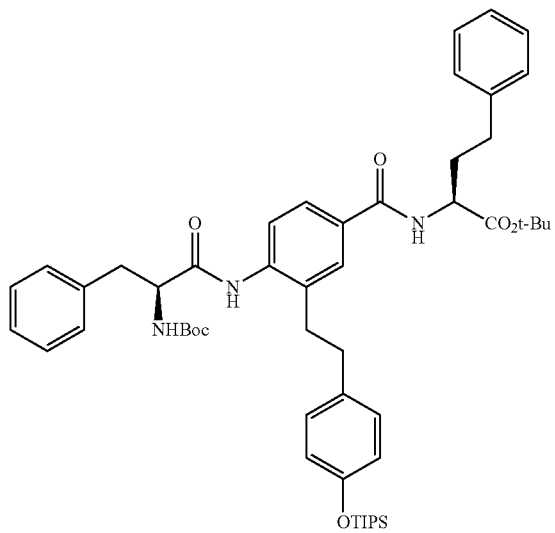

(MM-1-379) Aniline MM-2-18 (255 mg, 0.404 mmol), HOAt (61 mg, 0.445 mmol, 1.10 equiv) and Boc-Phe-OH (107 mg, 0.404 mmol, 1.00 equiv) were dissolved in anhydrous DMF (1.35 mL) at room temperature. 2,6-Lutidine (0.190 mL, 1.62 mmol, 4.00 equiv) and EDCI.HCl (81 mg, 0.424 mmol, 1.10 equiv) were added, and the mixture was stirred for 48 hours. After dilution with EtOAc (10 mL), the mixture was washed with 0.1 N HCl (10 mL) and saturated NaHCO$_3$ (5 mL). The organic phase was washed with brine, dried over Na$_2$SO$_4$, decanted and concentrated. Flash chromatography (SiO$_2$, 25% EtOAc/hexanes) gave 226 mg (64%) of the amide product.

(MM-1-381) Amide MM-1-379 (226 mg, 0.257 mmol) was dissolved in anhydrous THF (1.5 mL). TBAF (1.00 mL, 1.00 mmol, 4.00 equiv) was added dropwise, and the mixture was stirred for 1.5 hours at room temperature. The mixture was diluted with EtOAc (10 mL) and washed with H$_2$O (10 mL) and brine (10 mL). The aqueous phase was extracted once with EtOAc (10 mL), and the combined extracts were dried over Na$_2$SO$_4$, decanted and concentrated. Flash chromatography (SiO$_2$, 40% EtOAc/hexanes) afforded 141 mg (76%) of the phenolic product.

Carboxylic Acid Analogues

General Procedure for Tert-Butyl Ester Cleavage

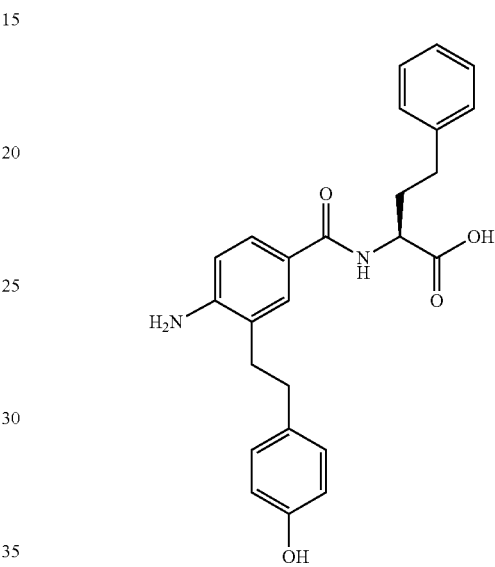

(MM-1-423) Representative procedure: Neoseptin-3 (4.0 mg, 0.015 mmol, 1.00 equiv) was dissolved in 4 N HCl (200 µL, 0.800 mmol, approx. 54 equiv) in a 0.5 dram scintillation vial, and stirred for 8 hours, after which the t-butyl ester was observed by LCMS to have been completely consumed. Concentration of the solvent provided 3.5 mg (99%) of the carboxylic acid product.

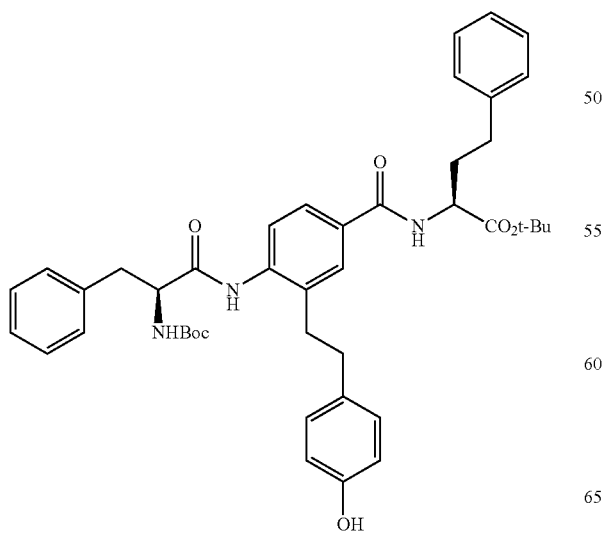

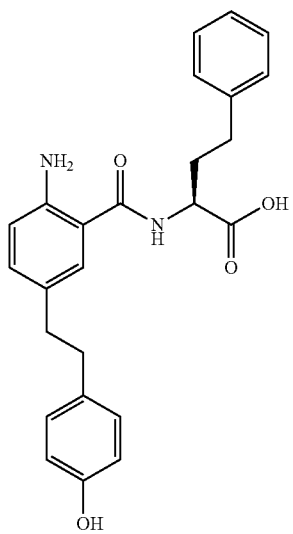 [SMILES: Nc1ccc(CCc2ccc(O)cc2)cc1C(=O)N[C@@H](CCc1ccccc1)C(=O)O]

(MM-2-17) The general procedure for t-butyl ester cleavage was followed: ortho-Amine MM-2-14 (18.5 mg, 0.039 mmol, 1.00 equiv) in 4 N HCl (500 μL, 2.00 mmol, approx. 50 equiv) provided 12.9 mg (80%) of the carboxylic acid product. HRMS (ESI-TOF) m/z calcd for $C_{25}H_{37}N_2O_4$ [M+H]$^+$ 419.1965. found 419.1963.

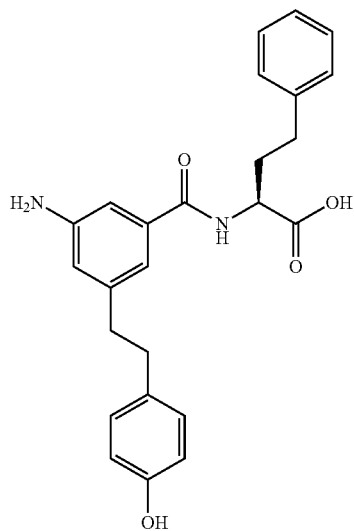 [SMILES: Nc1cc(CCc2ccc(O)cc2)cc(C(=O)N[C@@H](CCc2ccccc2)C(=O)O)c1]

(MM-2-4) The general procedure for t-butyl ester cleavage was followed: meta-Amine MM-1-500 (6.7 mg, 0.014 mmol, 1.00 equiv) in 4 N HCl (250 μL, 2.00 mmol, approx. 50 equiv) gave 6.0 mg (99%) of the carboxylic acid product. HRMS (ESI-TOF) m/z calcd for $C_{25}H_{27}N_2O_4$ [M+H]$^+$ 419.1965. found 419.1971.

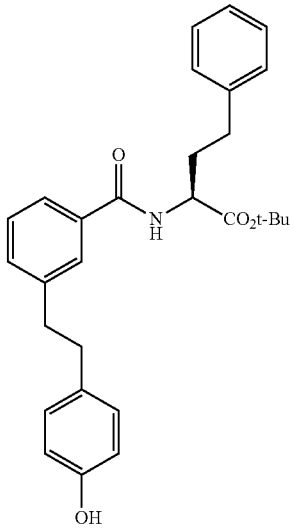 [SMILES: CC(C)(C)OC(=O)[C@H](CCc1ccccc1)NC(=O)c1cccc(CCc2ccc(O)cc2)c1]

(MM-2-456) The general procedure for nitroaryl alkyne reduction was followed: Nitroalkyne MM-1-454 (13 mg, 0.029 mmol), EtOAc (1.00 mL), Pearlman's catalyst (10 mg) were employed. Preparative thin-layer chromatography (SiO$_2$, 20% EtOAc/hexanes) gave 8.0 mg (62%) of the fully reduced product. $^1$H NMR (400 MHz, CDCl$_3$) δ 7.51-7.47 (m, 1H), 7.31-7.22 (m, 4H), 7.15 (d, J=7.2 Hz, 2H), 6.97 (d, J=8.4 Hz, 2H), 6.93 (d, J=8.4 Hz, 1H), 6.71 (dd, J=9.6, 8.4 Hz, 3H), 6.52 (d, J=7.8 Hz, 1H), 4.75 (d, J=5.9 Hz, 1H), 2.89-2.76 (m, 4H), 2.74-2.59 (m, 2H), 2.50 (m, 2H), 2.37-2.18 (m, 1H), 2.05 (d, J=7.1 Hz, 1H), 1.48 (s, 9H).

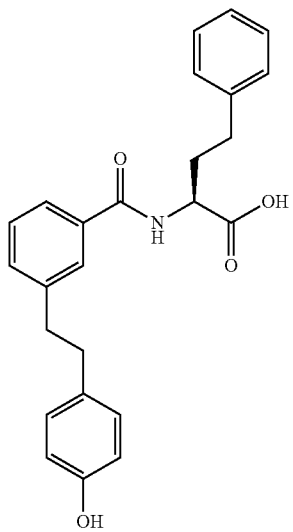 [SMILES: O=C(N[C@@H](CCc1ccccc1)C(=O)O)c1cccc(CCc2ccc(O)cc2)c1]

(MM-1-463) The general procedure for t-butyl ester cleavage was followed: t-Butyl ester XX (3.6 mg, 0.007 mmol, 1.00 equiv) in 4 N HCl (100 μL, 0.400 mmol, approx. 57 equiv) provided 3.2 mg (99%) of the carboxylic acid product.

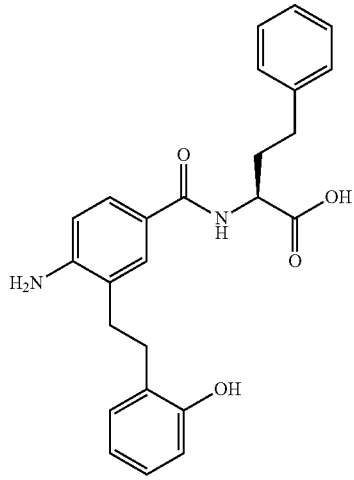 [SMILES: Nc1ccc(C(=O)N[C@@H](CCc2ccccc2)C(=O)O)cc1CCc1ccccc1O]

(MM-1-462) The general procedure for t-butyl ester cleavage was followed: o-Phenol MM-1-443 (1.3 mg, 0.003 mmol, 1.00 equiv) in 4 N HCl (100 μL, 0.400 mmol, approx. 266 equiv) gave 1.2 mg (99%) of the carboxylic acid product.

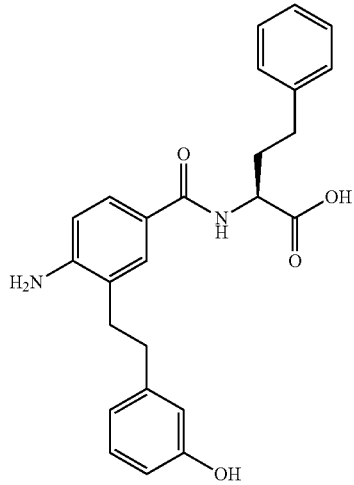 [SMILES: Nc1ccc(C(=O)N[C@@H](CCc2ccccc2)C(=O)O)cc1CCc1cccc(O)c1]

(MM-1-461) The general procedure for t-butyl ester cleavage was followed: m-Phenol MM-1-442 (5.2 mg, 0.003 mmol, 1.00 equiv) in 4 N HCl (100 μL, 0.400 mmol, approx. 364 equiv) afforded 4.6 mg (99%) of the carboxylic acid product.

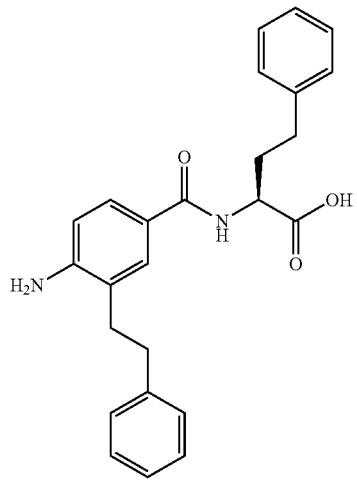 [SMILES: Nc1ccc(C(=O)N[C@@H](CCc2ccccc2)C(=O)O)cc1CCc1ccccc1]

(MM-1-464) The general procedure for t-butyl ester cleavage was followed: t-Butyl ester MM-1-460 (4.5 mg, 0.010 mmol, 1.00 equiv) in 4 N HCl (100 μL, 0.400 mmol, about 41 equiv) provided 3.2 mg (80%) of the carboxylic acid product.

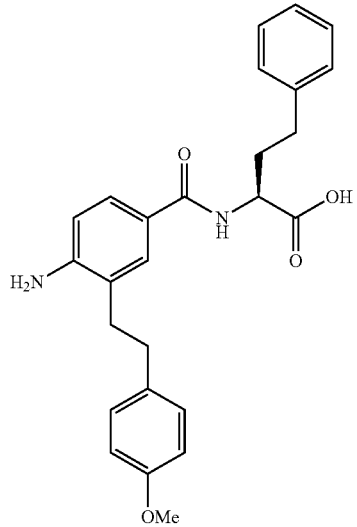 [SMILES: COc1ccc(CCc2cc(C(=O)N[C@@H](CCc3ccccc3)C(=O)O)ccc2N)cc1]

(MM-2-19) The general procedure for t-butyl ester cleavage was followed: t-Butyl ester MM-2-18 (3.0 mg, 0.006 mmol, 1.00 equiv) in 4 N HCl (500 μL, 2.00 mmol, approx. 333 equiv) gave 2.5 mg (93%) of the carboxylic acid product.

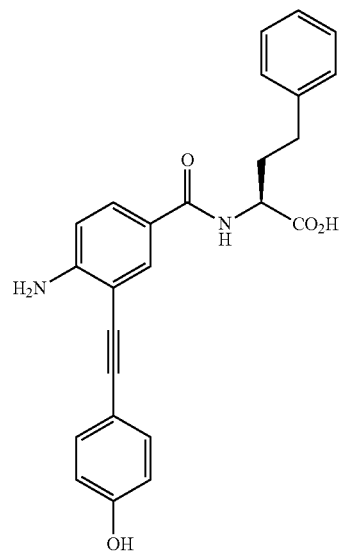 [SMILES: Nc1ccc(C(=O)N[C@@H](CCc2ccccc2)C(=O)O)cc1C#Cc1ccc(O)cc1]

(MM-1-433) The general procedure for t-butyl ester cleavage was followed: t-Butyl ester MM-1-403 (2.7 mg, 0.006 mmol, 1.00 equiv) in 4 N HCl (200 μL, 0.800 mmol, approx. 133 equiv) gave 1.5 mg (65%) of the carboxylic acid product. HRMS (ESI-TOF) m/z calcd for $C_{25}H_{23}N_2O_4$ [M+H]$^+$ 415.1652. found 415.1661.

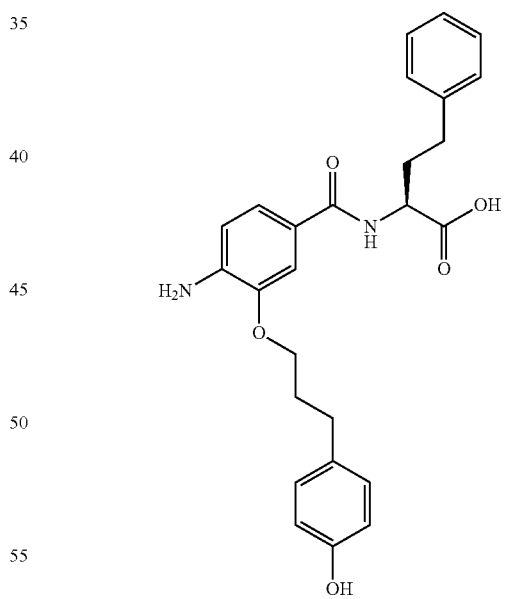

(MM-1-435) The general procedure for t-butyl ester cleavage was followed: t-butyl ester MM-1-429 (2.2 mg, 0.004 mmol, 1.00 equiv) in 4 N HCl (200 μL, 0.800 mmol) gave 2.0 mg (99%) of the carboxylic acid product. HRMS (ESI-TOF) m/z calcd for $C_{26}H_{29}N_2O_5$ [M+H]$^+$ 449.2071. found 449.2072.

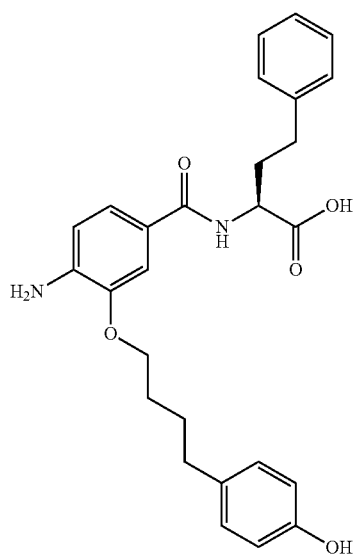 [SMILES: Nc1ccc(C(=O)N[C@@H](CCc2ccccc2)C(=O)O)cc1OCCCCc1ccc(O)cc1]

(MM-1-436) The general procedure for t-butyl ester cleavage was followed: t-butyl ester MM-1-430 (2.2 mg, 0.004 mmol, 1.00 equiv) in 4 N HCl (200 µL, 0.800 mmol) gave 1.9 mg (99%) of the carboxylic acid product. HRMS (ESI-TOF) m/z calcd for $C_{27}H_{31}N_2O_5$ [M+H]$^+$ 463.2227. found 463.2230.

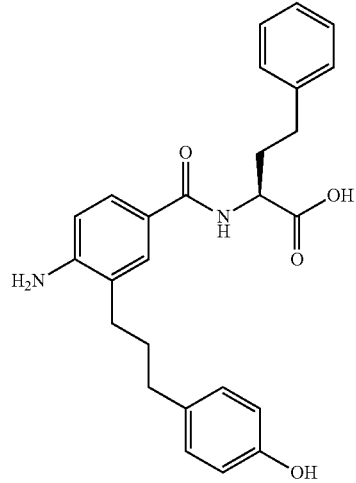

(MM-1-432) The general procedure for t-butyl ester cleavage was followed: t-butyl ester MM-1-89 (6.2 mg, 0.013 mmol, 1.00 equiv) in 4 N HCl (200 µL, 0.800 mmol) gave 5.5 mg (99%) of the carboxylic acid product. HRMS (ESI-TOF) m/z calcd for $C_{26}H_{29}N_2O_4$ [M+H]$^+$ 433.2122. found 433.2130.

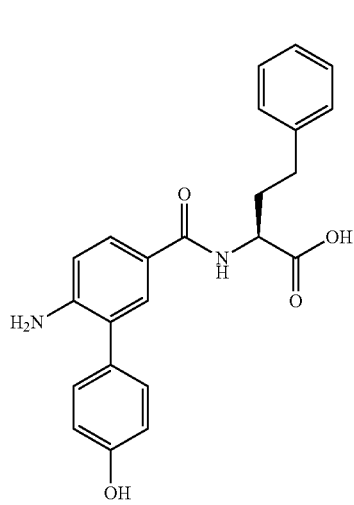 [SMILES: Nc1ccc(C(=O)N[C@@H](CCc2ccccc2)C(=O)O)cc1-c1ccc(O)cc1]

(MM-1-434) The general procedure for t-butyl ester cleavage was followed: t-butyl ester MM-1-430 (2.0 mg, 0.005 mmol, 1.00 equiv) in 4 N HCl (200 µL, 0.800 mmol) gave 1.7 mg (99%) of the carboxylic acid product. HRMS (ESI-TOF) m/z calcd for $C_{23}H_{23}N_2O_4$ [M+H]$^+$ 391.1652. found 391.1658.

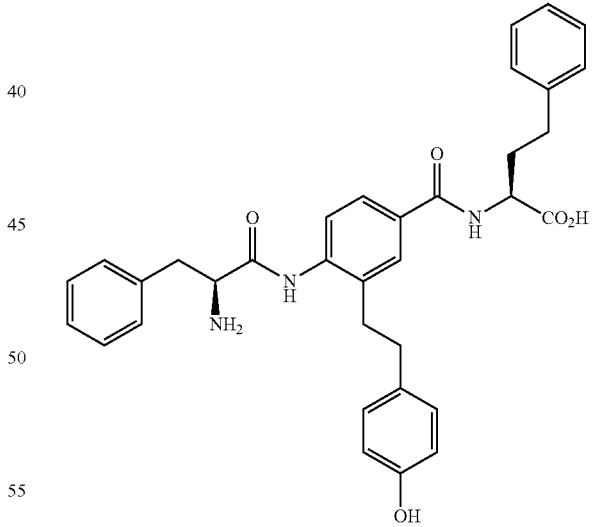

(MM-1-88) Boc-carbamate MM-1-379 (7 mg, 0.010 mmol) was dissolved in 4 N HCl (0.200 mL, 0.800 mmol, approx 80 equiv). The solution was stirred for 6 hours, then concentrated under a stream of $N_2$ to reveal 5 mg (86%) of the amino acid as the HCl salt.

Linker Analogues

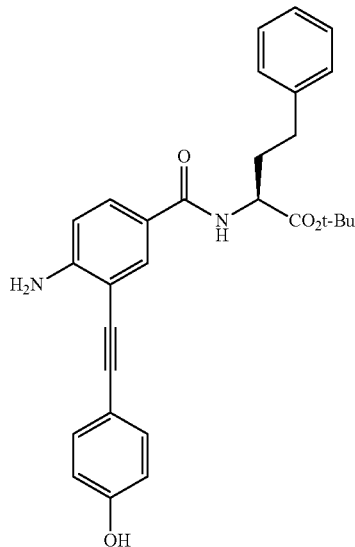

(MM-1-403) Nitroalkyne MM-1-466 (800 mg, 1.60 mmol, 1.00 equiv) was dissolved in acetone (60 mL) at room temperature. Zinc nanopowder (1.57 g, 23.4 mmol, 15.0 equiv) was suspended in the medium, and the mixture was stirred vigorously. Sat. $NH_4Cl$ (12 mL) was added slowly, resulting in a zinc salt precipitate, accompanied by a lightening of the reaction mixture from dark red to pale yellow. After 15 minutes, the reaction mixture was filtered through a cotton plug and diluted with EtOAc (50 mL). The organic phase was washed with sat. $NaHCO_3$ (30-50 mL) and the aqueous phase extracted with EtOAc (2×30 mL). The combined extracts were dried over $Na_2SO_4$, decanted and concentrated. Flash chromatography ($SiO_2$, 40 to 50% EtOAc/hexanes) gave 463 mg (62%) of the aniline product. $^1$H NMR (400 MHz, $CDCl_3$) δ 7.72 (d, J=2.1 Hz, 1H), 7.55 (dd, J=8.5, 2.2 Hz, 1H), 7.42 (d, J=8.6 Hz, 2H), 7.30 (m, 2H), 7.23-7.16 (m, 3H), 6.87 (d, J=8.6 Hz, 2H), 6.71 (d, J=8.5 Hz, 1H), 6.60 (d, J=7.6 Hz, 1H), 4.59 (ddd, J=7.9, 6.7, 5.1 Hz, 1H), 2.83-2.55 (m, 2H), 2.35-2.25 (m, 1H), 2.23-2.08 (m, 1H), 1.53 (s, 9H). HRMS (ESI-TOF) m/z calcd for $C_{29}H_{31}N_2O_4$ $[M+H]^+$ 471.2278. found 471.2270.

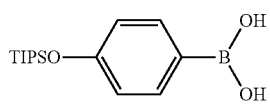

(MM-1-188) TIPSO iodide MM-1-58 (700 mg, 1.86 mmol) was dissolved in anhydrous THF (9 mL) and cooled to −78° C. n-BuLi (0.89 mL, 2.23 mmol, 2.5 M in hexanes) was added dropwise. After 30 minutes, triisopropyl borate (0.86 mL, 3.72 mmol, 2.00 equiv) was added. After an additional 20 minutes, the cold bath was removed, and the mixture was stirred for 1 hours. 2 N HCl (10 mL) was added slowly, and the mixture was diluted and extracted with EtOAc (2×10 mL). The combined organic phases were washed with sat. aqueous NaCl, dried over $Na_2SO_4$, decanted and concentrated. Flash chromatography ($SiO_2$, 40% EtOAc/hexanes) gave 523 mg (96%) of the aryl boronic acid as a white solid.

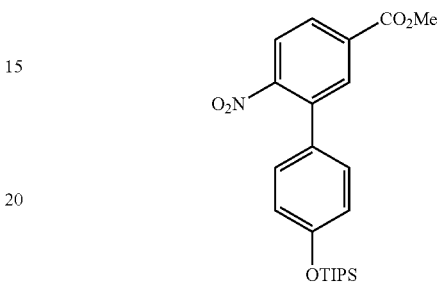

(MM-1-190) Aryl boronic acid MM-1-188 (300 mg, 1.00 mmol) and aryl triflate MM-1-69 (272 mg, 0.820 mmol, 0.800 equiv) were dissolved in anhydrous 1,2-DME (4 mL). The yellow reaction solution was sparged 15 min with $N_2$. $Pd(PPh_3)_4$ (120 mg, 0.100 mmol, 0.100 equiv) was added, followed by $K_3PO_4$ (145 mg, 0.700 equiv) as a solution in $H_2O$ (1 mL). A condenser was attached to the reaction vessel, and the reaction medium heated to 85° C. under $N_2$ atmosphere. After 1.5 hours, the mixture was cooled to room temperature and diluted with EtOAc (25 mL). The organic phase was washed with sat. $NH_4Cl$ (10 mL) and the aqueous phase extracted with EtOAc. The combined extracts were dried over $Na_2SO_4$, decanted and concentrated. Flash chromatography ($SiO_2$, 10% EtOAc/hexanes) gave 345 mg (98%) of the Suzuki-coupling product. $^1$H NMR (400 MHz, $CDCl_3$) δ 8.14 (d, J=1.8 Hz, 1H), 8.09 (dd, J=8.4, 1.9 Hz, 1H), 7.81 (d, J=8.4 Hz, 1H), 7.21 (d, J=8.6 Hz, 2H), 6.95 (d, J=8.6 Hz, 2H), 3.98 (s, 3H), 1.29 (m, 3H), 1.13 (d, J=7.4 Hz, 18H).

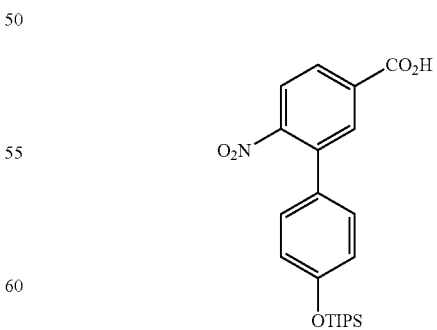

(MM-1-191) Suzuki-coupling product MM-1-190 (335 mg, 0.78 mmol) was dissolved in t-BuOH/$H_2O$ (2 mL ea.). $LiOH·H_2O$ (36 mg, 0.85 mmol, 1.10 equiv) was added, and the suspension stirred vigorously for 2 hours. The reaction was quenched with 0.1 N HCl (about 10 mL), which was continuously added until the carboxylic acid was observed to precipitate. The mixture was diluted with EtOAc (10 mL) and extracted (3×5 mL), dried over Na₂SO₄, decanted and concentrated to give 273 mg (84%) of the biaryl carboxylic acid.

Celite and concentrated to give 132 mg (98%) of the aniline. The product was used directly in the next step without further purification.

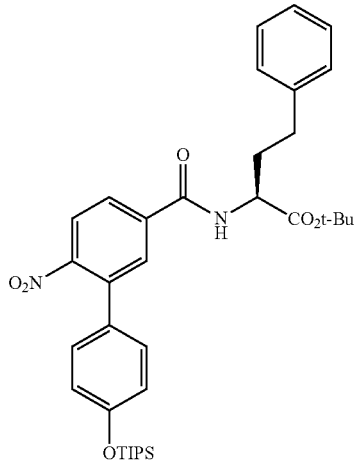

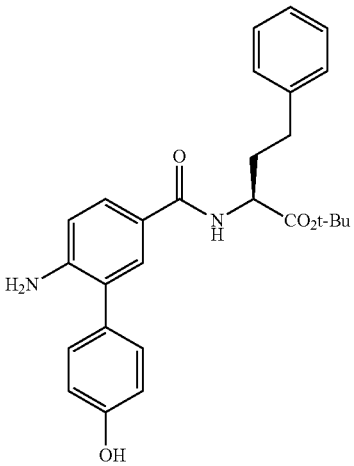 [SMILES: CC(C)(C)OC(=O)[C@H](CCc1ccccc1)NC(=O)c1ccc(N)c(-c2ccc(O)cc2)c1]

(MM-1-192) The general procedure for amine coupling with acid was followed: biaryl carboxylic acid MM-1-191 (100 mg, 0.241 mmol, 1.00 equiv), hoPhe-OtBu (57 mg, 0.241 mmol, 1.00 equiv), HOAt (36 mg, 2.65 mmol, 1.10 equiv), 2,6-lutidine (0.140 mL, 1.20 mmol, 5.00 equiv) and EDCI.HCl (48 mg, 0.253 mmol, 1.05 equiv) were employed. Flash chromatography (SiO₂, 25% EtOAc/hexanes) afforded 142 mg (93%) of the amide product. ¹H NMR (400 MHz, CDCl₃) δ 7.81 (d, J=8.2 Hz, 1H), 7.78-7.72 (m, 1H), 7.73 (d, J=1.5 Hz, 1H), 7.29 (t, J=7.3 Hz, 2H), 7.26-7.18 (m, 5H), 7.16 (d, J=7.8 Hz, 1H), 7.02-6.95 (m, 2H), 6.90 (d, J=7.8 Hz, 1H), 4.83 (dd, J=6.9, 2.2 Hz, 1H), 4.16 (dd, J=7.0, 1.3 Hz, 1H), 2.78 (t, J=7.7 Hz, 2H), 2.37 (d, J=8.0 Hz, 1H), 2.26-2.13 (m, 1H), 1.40-1.25 (m, 3H), 1.17 (d, J=7.4 Hz, 18H).

(MM-1-426) Aniline MM-1-195 (23 mg, 0.036 mmol) was dissolved in TBAF solution (100 µL, 0.100 mmol, 2.75 equiv, 1 M in THF) at room temperature. After stirring 2 hours, the mixture was diluted with EtOAc (5 mL) and washed with H₂O (5 mL) and sat. aqueous NaCl (2 mL). The aqueous phase was extracted once with EtOAc (5 mL) and the combined extracts were dried over Na₂SO₄, decanted and concentrated. Flash chromatography (SiO₂, 50% EtOAc/hexanes) afforded 10 mg (63%) of the free phenol. ¹H NMR (400 MHz, CDCl₃) δ 7.62 (d, J=2.1 Hz, 1H), 7.56 (dd, J=8.4, 2.2 Hz, 1H), 7.35-7.19 (m, 7H), 7.01 (d, J=8.3 Hz, 2H), 6.77 (d, J=8.5 Hz, 1H), 6.74 (d, J=7.6 Hz, 1H), 4.89 (td, J=7.1, 5.1 Hz, 1H), 4.20 (br s, 2H), 2.79 (m, 2H), 2.37 (td, J=9.5, 5.2 Hz, 1H), 2.17 (ddd, J=10.4, 7.6, 4.9 Hz, 1H), 1.59 (s, 9H). HRMS (ESI-TOF) m/z calcd for $C_{27}H_{31}N_2O_4$ [M+H]⁺ 447.2278. found 447.2277.

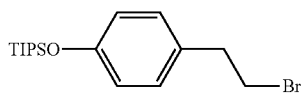

(MM-1-73) 4-(2-Bromoethyl)phenol (1.00 g, 4.97 mmol, 1.00 equiv) was dissolved in anhydrous CH₂Cl₂ (30 mL) at room temperature. Imidazole (360 mg, 5.22 mmol, 1.05 equiv) was added in one portion. Upon dissolution of the base, TIPSCl (1.06 mL, 4.97 mmol, 1.00 equiv) was added dropwise. After 16 hours, the mixture was washed with sat. NH₄Cl (20 mL) and H₂O (10 mL). The aqueous phase was extracted with CH₂Cl₂ (3×15 mL), and the combined extracts were dried over Na₂SO₄, decanted and concentrated. Flash chromatography (SiO₂, 5% EtOAc/hexanes) gave 1.75 g (99%) of the silyl ether. ¹H NMR (300 MHz, CDCl₃) δ 7.06 (d, J=8.3 Hz, 2H), 6.83 (d, J=8.4 Hz, 2H), 3.53 (t, J=7.8 Hz, 2H), 3.09 (t, J=7.8 Hz, 1H), 1.29-1.20 (m, 3H), 1.11 (d, J=7.0 Hz, 18H).

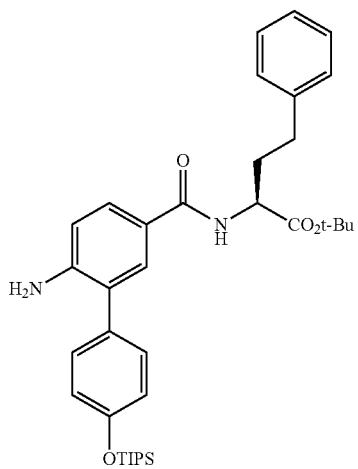

(MM-1-195) The general procedure for hydrogenation was employed: Nitroarene MM-1-192 (142 mg, 0.224 mmol), Pd/C (27 mg, 10% by wt. on carbon) in EtOAc (2 mL). After 3 hours, the mixture was filtered through sand/

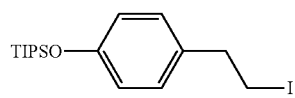

(MM-1-82) Alkyl bromide MM-1-73 (800 mg, 2.24 mmol) was dissolved in acetone at room temperature. Sodium iodide (1.67 g, 11.2 mmol, 5.00 equiv) was added in one portion. The reaction vessel covered in aluminum foil, and the mixture was vigorously stirred for 36 hours. $Et_2O$ (30 mL) was added, and the organic phase was washed with $H_2O$ (30 mL). The aqueous phase was extracted with $Et_2O$ (3×10 mL), and the combined extracts dried over $Na_2SO_4$, decanted and concentrated to give 875 mg (97%) of the alkyl iodide, which was used without further purification. $^1$H NMR (300 MHz, $CDCl_3$) δ 7.03 (d, J=8.1 Hz, 2H), 6.85-6.80 (d, J=8.1 Hz, 2H), 3.35-3.26 (t, J=7.9 Hz, 2H), 3.10 (t, J=7.9 Hz, 2H), 1.27-1.19 (m, 3H), 1.10 (d, J=7.3 Hz, 18H).

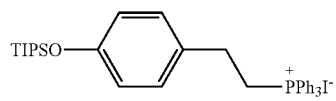

(MM-1-83) In a two-neck round-bottomed (r.b.) flask equipped with condenser, alkyl iodide MM-1-82 (800 mg, 1.98 mmol) was dissolved in acetonitrile (3 mL). Triphenylphosphine (570 mg, 1.1 equiv) was added, and the reaction mixture was heated to 85° C. After 16 hours, the mixture was cooled to room temperature and reconcentrated from $CH_2Cl_2$ (3×20 mL) to afford the phosphonium salt (1.30 g, 99%) as a sticky white foam.

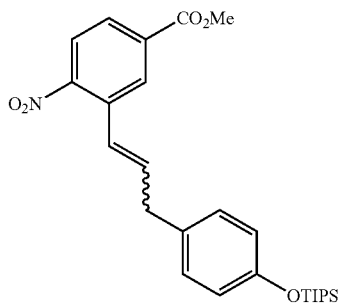

(MM-1-85) Wittig salt X MM-1-82 (1.20 g, 1.80 mmol, 1.2 equiv) was dissolved in anhydrous THF (6 mL) and cooled to 0° C. Freshly prepared lithium diisopropylamide (LDA; 6 mL, 2.10 mmol, 1.4 equiv, 0.35 M in THF) was added dropwise, producing a brilliant orange solution. After 30 minutes, methyl 3-formyl-4-nitrobenzoate (314 mg, 1.50 mmol, 1.00 equiv) was added dropwise as a solution in anhydrous THF (2 mL). After 1 hour, the reaction was quenched with $H_2O$ (25 mL) and diluted with $Et_2O$ (25 mL). The aqueous phase was extracted with $Et_2O$ (3×20 mL), dried over $Na_2SO_4$, decanted and concentrated. Flash chromatography ($SiO_2$, 10% EtOAc/hexanes) afforded 561 mg (66%) of the alkene product as a 3:1 mixture of Z/E isomers. $^1$H NMR (Z, major isomer, 300 MHz, $CDCl_3$) δ 8.04 (dd, J=2.5, 1.7 Hz, 1H), 8.02-7.96 (m, 1H), 6.94 (d, J=8.6 Hz, 2H), 6.79 (d, J=11.4 Hz, 1H), 6.74 (d, J=8.4 Hz, 2H), 6.01 (dt, J=11.4, 7.6 Hz, 1H), 3.89 (s, 3H), 3.33 (dd, J=7.8, 1.2 Hz, 2H), 1.21-1.12 (m, 3H), 1.00 (d, J=7.0 Hz, 18H).

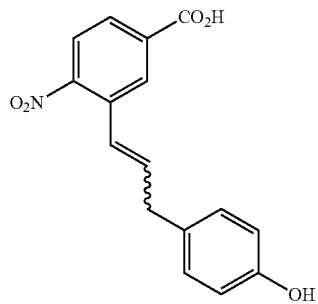 [SMILES: O=C(O)c1ccc([N+](=O)[O-])c(C=CCc2ccc(O)cc2)c1]

(MM-1-86) Methyl ester MM-1-85 (500 mg, 1.06 mmol) was dissolved in a 4:1:1 mixture of $THF/MeOH/H_2O$ (12 mL total). $LiOH.H_2O$ (180 mg, 4.25 mmol, 4.00 equiv) was added in one portion. After 30 minutes, 1 N HCl (5 mL) was added, followed by 0.1 N HCl until the reaction pH=3, whereupon the product was observed to precipitate. The aqueous phase was extracted with EtOAc (3×25 mL) and the combined extracts were washed with sat. aqueous NaCl, dried over $Na_2SO_4$, decanted and concentrated to give 480 mg (99%) of the carboxylic acid lacking the silyl ether.

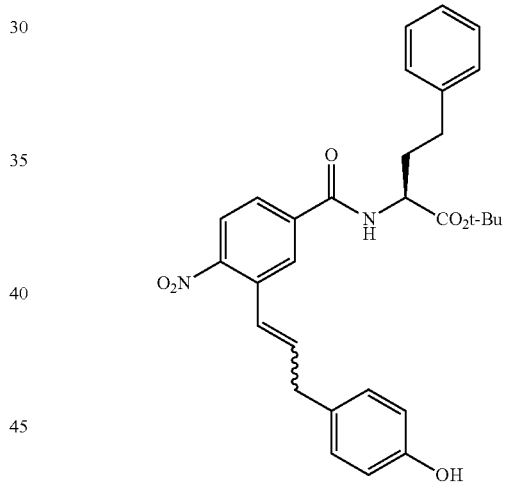

(MM-1-87) The general procedure for amine coupling with acid was followed: alkene carboxylic acid MM-1-86 (300 mg, 0.66 mmol, 1.00 equiv), HoPhe-OtBu (155 mg, 0.66 mmol, 1.00 equiv), HOAt (99 mg, 0.72 mmol, 1.10 equiv), 2,6-lutidine (0.385 mL, 3.29 mmol, 5.00 equiv) and EDCI.HCl (133 mg, 0.69 mmol, 1.05 equiv) were employed. Flash column chromatography ($SiO_2$, 20% EtOAc/hexanes) afforded 292 mg (86%) of the amide product. $^1$H NMR (Z, major isomer, 300 MHz, $CDCl_3$) δ 8.03 (d, J=8.5 Hz, 1H), 7.83 (d, J=1.9 Hz, 1H), 7.72 (dd, J=8.4, 1.9 Hz, 1H), 7.41-7.19 (m, 5H), 7.11 (d, J=7.9 Hz, 2H), 7.00 (d, J=8.4 Hz, 2H), 6.87 (d, J=11.4 Hz, 1H), 6.81 (d, J=8.5 Hz, 2H), 6.08 (dt, J=11.4, 7.5 Hz, 1H), 4.85 (td, J=7.4, 3.5 Hz, 1H), 3.44-3.33 (m, 2H), 2.88-2.73 (m, 2H), 2.38 (ddd, J=13.2, 9.4, 5.3 Hz, 1H), 2.22 (dd, J=14.6, 7.4 Hz, 1H), 1.61 (s, 9H).

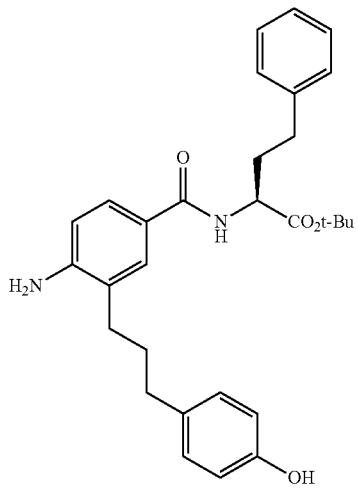

(MM-1-89) The general procedure for hydrogenation with Pearlman's catalyst was followed: Nitroalkene MM-1-87 (150 mg, 0.290 mmol), Pd(OH)$_2$ (50 mg, 20% Pd by wt.) in EtOAc (5 mL). Filtration, concentration and flash chromatography (SiO$_2$, 40→50% EtOAc/hexanes) afforded 115 mg (81%) of the fully reduced aniline product. $^1$H NMR (300 MHz, CDCl$_3$) δ 7.59 (d, J=2.1 Hz, 1H), 7.49 (dd, J=8.3, 2.1 Hz, 1H), 7.39-7.20 (m, 5H), 7.05 (d, J=8.4 Hz, 2H), 6.93 (d, J=7.9 Hz, 1H), 6.89 (d, J=8.4 Hz, 2H), 6.62 (d, J=8.3 Hz, 1H), 4.90 (d, J=5.3 Hz, 1H), 3.99 (s, 2H), 2.81 (dd, J=7.0, 2.8 Hz, 1H), 2.63 (t, J=7.4 Hz, 2H), 2.52-2.42 (m, 2H), 2.37 (tdd, J=11.7, 5.7, 3.5 Hz, 1H), 2.28-2.16 (m, 1H), 1.96-1.82 (m, 2H), 1.60 (s, 9H). HRMS (ESI-TOF) m/z calcd for C$_{30}$H$_{37}$N$_2$O$_4$ [M+H]$^+$ 489.2748. found 489.2753.

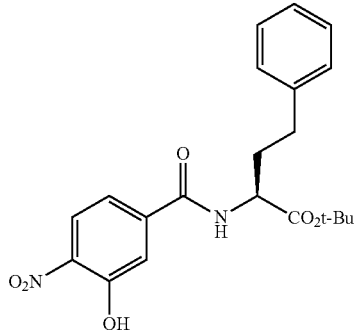 [SMILES: CC(C)(C)OC(=O)[C@H](CCc1ccccc1)NC(=O)c1ccc([N+](=O)[O-])c(O)c1]

(MM-1-22) 3-Hydroxy-4-nitrobenzoic acid (272 mg, 1.49 mmol), HoPhe-OtBu (350 mg, 1.49 mmol, 1.00 equiv) and HOAt (223 mg, 1.64 mmol, 1.10 equiv) were combined in a 25 mL round bottom flask with stir bar. Anhydrous DMF (8 mL) and 2,6-lutidine (0.87 mL, 7.44 mmol, 5.00 equiv) were added, and the mixture was stirred until dissolution of the reagents. EDCI.HCl (300 mg, 1.56 mmol, 1.05 equiv) was added, and the mixture stirred for 4 hours, then diluted with EtOAc (30 mL). The organic phase was washed with 1 N HCl (3×15 mL), then washed with H$_2$O (10 mL) and sat. aqueous NaCl (20 mL). After drying with Na$_2$SO$_4$, the organic phase was decanted and concentrated. Flash chromatography (SiO$_2$, 15→30% EtOAc/hexanes) provided 180 mg (30%) of the coupled amide. $^1$H NMR (300 MHz, CDCl$_3$) δ 10.55 (s, 1H), 8.15 (dd, J=8.8, 0.7 Hz, 1H), 7.42 (dd, J=1.9, 0.7 Hz, 1H), 7.36-7.16 (m, 5H), 6.70 (d, J=7.6 Hz, 1H), 4.82-4.70 (m, 1H), 2.79-2.66 (m, 2H), 2.33 (m, 1H), 2.23-2.08 (m, 1H), 1.54 (s, 9H).

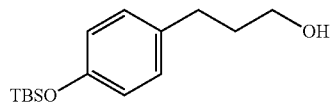 [SMILES: CC(C)(C)[Si](C)(C)Oc1ccc(CCCO)cc1]

(MM-1-28) An oven dried 50 mL round bottom flask equipped with stir bar was charged with NaH (80 mg, 60% dispersion in mineral oil). THF (5 mL) was added, and the mixture cooled to 0° C. 4-(3-Hydroxypropyl)phenol (300 mg, 1.97 mmol) was added dropwise as a solution in THF (4 mL+1 mL rinse). After effervescence ceased, the mixture was warmed to room temperature, and an additional 5 mL THF was added. After 1 hour at room temperature, TBSCl (312 mg, 2.07 mmol, 1.05 equiv) was added, and the mixture was allowed to stir for an additional hour, whereupon the mixture was diluted with Et$_2$O (15 mL). The ethereal phase was washed with sat. NH$_4$Cl (10 mL) and H$_2$O (5 mL). The aqueous phase was extracted with Et$_2$O (3×15 mL), and the combined extracts were dried over sat. aqueous NaCl (10 mL), Na$_2$SO$_4$, decanted and concentrated. Flash chromatography (SiO$_2$, 30% EtOAc/hexanes) gave 377 mg (72%) of the silyl ether. $^1$H NMR (300 MHz, CDCl$_3$) δ 7.05 (s, J=8.4 Hz, 2H), 6.77 (d, J=8.4 Hz, 2H), 3.67 (m, 2H), 2.64 (dd, J=8.5, 6.8 Hz, 2H), 1.95-1.79 (m, 2H), 0.99 (s, 9H), 0.20 (s, 6H).

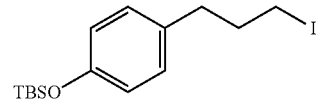 [SMILES: CC(C)(C)[Si](C)(C)Oc1ccc(CCCI)cc1]

(MM-1-27) TBS-ether MM-1-28 (200 mg, 0.751 mmol) and triphenylphosphine (197 mg, 0.751 mmol, 1.00 equiv) were dissolved in anhydrous CH$_2$Cl$_2$ (4 mL). After cooling to 0° C., imidazole (61 mg, 0.901 mmol, 1.20 equiv) was added, and the mixture stirred until dissolution of the base. Iodine (200 mg, 0.788 mmol, 1.05 equiv) was added dropwise as a solution in CH$_2$Cl$_2$ (4 mL). Upon complete addition of the iodine, the reaction mixture maintained an orange color. After 20 minutes at 0° C., the reaction was quenched with Na$_2$S$_2$O$_3$.5H$_2$O (5 mL, 10% w/v). The aqueous phase was extracted once with CH$_2$Cl$_2$ (5 mL), and the combined organic phases were washed with sat. aqueous NaCl (5 mL), dried over Na$_2$SO$_4$, decanted and concentrated. Flash chromatography (SiO$_2$, 10% EtOAc/hexanes) gave 229 mg (81%) of the alkyl iodide. $^1$H NMR (300 MHz, CDCl$_3$) δ 7.08-7.02 (m, 2H), 6.80-6.73 (m, 2H), 3.17 (t, J=6.8 Hz, 2H), 2.66 (t, J=6.8 Hz, 2H), 2.11 (p, J=6.8 Hz, 2H), 0.99 (s, 9H), 0.20 (s, 6H).

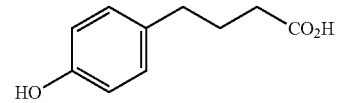 [SMILES: O=C(O)CCCc1ccc(O)cc1]

(MM-1-31) A 50 mL round bottom flask equipped with reflux condenser was charged with 4-(4-methoxyphenyl) butanoic acid (5.00 g, 25.7 mmol). Aqueous HBr (48% solution, approx 6 mL) was added. A tygon line was fed from the top of the condenser to the rear of the fume hood, to allow for complete exhaust of the HBr. The reaction mixture was heated to reflux for 6 hours. After cooling to about 50° C., the mixture was poured into chilled H$_2$O (45 mL), causing immediate precipitation of the product as white solid needles. After 1 hour at 0° C., the mixture was vacuum filtered and the needles collected, affording 3.86 g (83%) of the phenolic product. ¹H NMR (300 MHz, Acetone-d₆) δ 10.48 (s, 1H), 8.07 (s, 1H), 7.07-6.99 (m, 2H), 6.79-6.71 (m, 2H), 2.60-2.50 (m, 2H), 2.29 (t, J=7.4 Hz, 2H), 1.92-1.77 (m, 2H).

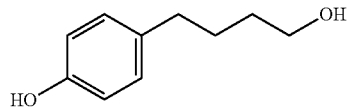 [SMILES: OCCCCc1ccc(O)cc1]

(MM-1-34) Carboxylic acid MM-1-31 (1.00 g, 5.55 mmol) was dissolved in anhydrous THF (10 mL) and cooled to 0° C. Lithium aluminum hydride (1.0 M in THF, 12 mL) was added dropwise. An additional 15 mL THF was added, and the heterogeneous mixture was heated to reflux. After 2 hours, the mixture was cooled to room temperature and allo stirred overnight (about 19 hours). Fieser workup: H₂O (1 mL), aqueous NaOH (15% w/v, 1 mL) and H₂O (3 mL) were respectively added. After 20 minutes, the mixture was filtered, and the Al₂O₃ filter cake was washed with Et₂O (3×50 mL), and the ethereal phase concentrated to give 700 mg (76%) of the primary alcohol. ¹H NMR (300 MHz, Acetone-d₆) δ 8.07 (s, 1H), 7.01 (d, J=8.5 Hz, 2H), 6.74 (d, J=8.5 Hz, 2H), 3.56 (t, J=6.3 Hz, 2H), 2.52 (t, J=7.4 Hz, 2H), 1.55 (m, 4H).

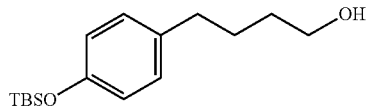 [SMILES: CC(C)(C)[Si](C)(C)Oc1ccc(CCCCO)cc1]

(MM-1-35) An oven dried 100 mL round bottom flask equipped with stir bar was charged with NaH (145 mg, 60% dispersion in mineral oil). THF (10 mL) was added, and the mixture cooled to 0° C. Primary alcohol MM-1-34 (600 mg, 3.61 mmol) was added dropwise as a solution in THF (6 mL+2 mL rinse). After effervescence ceased, the mixture was warmed to room temperature, and an additional 6 mL THF was added. After 1 hour at room temperature, TBSCl (570 mg, 3.79 mmol, 1.05 equiv) was added, and the mixture was stirred for an additional hour, whereupon the mixture was diluted with Et₂O (30 mL). The ethereal phase was washed with sat. NH₄Cl (20 mL) and H₂O (10 mL). The aqueous phase was extracted with Et₂O (3×20 mL), and the combined ether extracts were dried over sat. aqueous NaCl (20 mL), Na₂SO₄, decanted and concentrated. Flash chromatography (SiO₂, 30% EtOAc/hexanes) gave 412 mg (41%) of the silyl ether. ¹H NMR (300 MHz, CDCl₃) δ 7.07-7.00 (m, 2H), 6.78-6.73 (m, 2H), 3.66 (t, J=6.1 Hz, 2H), 2.58 (t, J=7.2 Hz, 2H), 1.74-1.53 (m, 2H), 0.99 (s, 9H), 0.19 (s, 6H).

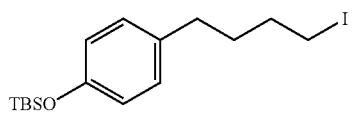 [SMILES: CC(C)(C)[Si](C)(C)Oc1ccc(CCCCI)cc1]

(MM-1-36) TBS-ether MM-1-35 (300 mg, 1.07 mmol) and triphenylphosphine (281 mg, 1.07 mmol, 1.00 equiv) were dissolved in anhydrous CH₂Cl₂ (6 mL). After cooling to 0° C., imidazole (87 mg, 1.28 mmol, 1.20 equiv) was added, and the mixture stirred until dissolution of the base. Iodine (285 mg, 1.12 mmol, 1.05 equiv) was added dropwise as a solution in CH₂Cl₂ (4 mL). Upon complete addition of the iodine, the reaction mixture maintained an orange color. After 20 minutes at 0° C., the reaction was quenched with Na₂S₂O₃.5H₂O (8 mL, 10% w/v). The aqueous phase was extracted once with CH₂Cl₂ (10 mL), and the combined organic phases were washed with sat. aqueous NaCl (10 mL), dried over Na₂SO₄, decanted and concentrated. Flash chromatography (SiO₂, 10% EtOAc/hexanes) gave 343 mg (82%) of the alkyl iodide.

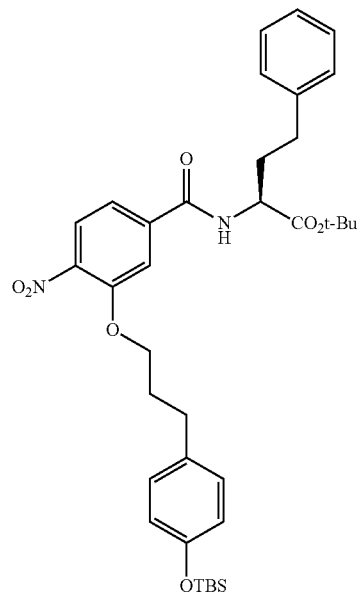 [SMILES: CC(C)(C)OC(=O)[C@H](CCc1ccccc1)NC(=O)c1ccc([N+](=O)[O-])c(OCCCc2ccc(O[Si](C)(C)C(C)(C)C)cc2)c1]

(MM-1-427) Arylnitro phenol MM-1-22 (30 mg, 0.075 mmol) and alkyl iodide MM-1-27 (30 mg, 0.080 mmol, 1.05 equiv) were dissolved in anhydrous DMF (0.375 mL). K₃CO₃ (31 mg, 0.225 mmol, 3.00 equiv) was added, and the heterogeneous mixture was stirred overnight (about 18 hours), after which the reaction mixture had changed from orange to yellow. The mixture was diluted with EtOAc (5 mL) and washed with sat. NH₄Cl (5 mL). The organic phase was dried over Na₂SO₄, decanted and concentrated. Flash chromatography (SiO₂, 25% EtOAc/hexanes) yielded 32 mg (67%) of the $S_N2$ alkylation product.

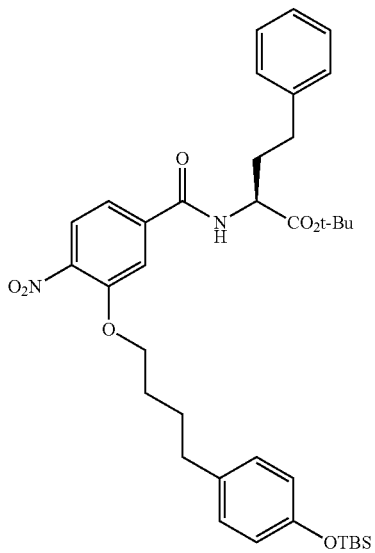 [SMILES: CC(C)(C)OC(=O)[C@H](CCc1ccccc1)NC(=O)c1ccc([N+](=O)[O-])c(OCCCCc2ccc(O[Si](C)(C)C(C)(C)C)cc2)c1]

(MM-1-428) Arylnitro phenol MM-1-22 (30 mg, 0.075 mmol) and alkyl iodide MM-1-35 (31 mg, 0.080 mmol, 1.05 equiv) were dissolved in anhydrous DMF (0.375 mL). $K_3CO_3$ (31 mg, 0.225 mmol, 3.00 equiv) was added, and the heterogeneous mixture was stirred overnight, after which the reaction mixture had changed from orange to yellow. The mixture was diluted with EtOAc (5 mL) and washed with sat. $NH_4Cl$ (5 mL). The organic phase was dried over $Na_2SO_4$, decanted and concentrated. Flash chromatography ($SiO_2$, 25% EtOAc/hexanes) yielded 36 mg (72%) of the $S_N2$ alkylation product.

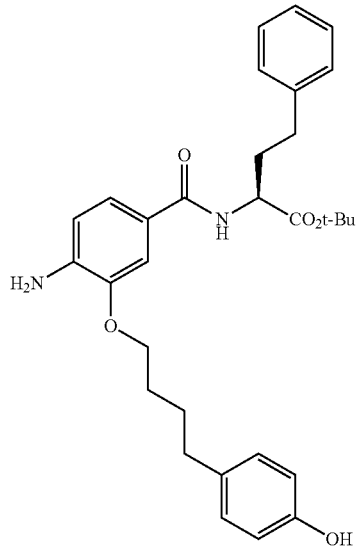

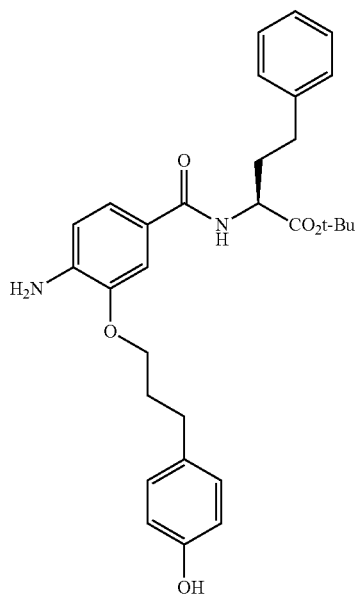 [SMILES: CC(C)(C)OC(=O)[C@H](CCc1ccccc1)NC(=O)c1ccc(N)c(OCCCc2ccc(O)cc2)c1]

(MM-1-429) Nitroarene MM-1-427 (20 mg, 0.0308 mmol) was dissolved in acetone (0.5 mL). Zinc nanopowder (30 mg, 0.462 mmol, 15 equiv) was suspended in the medium and vigorous stirring was applied. Sat. $NH_4Cl$ (0.1 mL) was added dropwise, producing a precipitate of zinc salts. After 20 minutes, the mixture was diluted with EtOAc (10 mL) and filtered through a 1 cm plug of Celite, washing with EtOAc. The filtrate was washed with sat. $NaHCO_3$ (5 mL), and the organic phase was dried over $Na_2SO_4$, decanted and concentrated. The resulting residue was dissolved in TBAF (0.200 mL, 1 M in THF). After 20 minutes, the mixture was diluted again with EtOAc (10 mL) and washed with $H_2O$ (10 mL). After drying over $Na_2SO_4$, the extracts were decanted and concentrated. Flash chromatography ($SiO_2$, 40% EtOAc/hexanes) gave 11 mg (71%) of the desired product as a white foam. $^1H$ NMR (400 MHz, $CDCl_3$) δ 7.32-7.23 (m, 2H), 7.19 (d, J=6.9 Hz, 3H), 7.11 (dd, J=8.1, 1.8 Hz, 1H), 7.03 (d, J=8.4 Hz, 2H), 6.77 (d, J=8.4 Hz, 2H), 6.65 (d, J=8.1 Hz, 1H), 6.64 (d, J=7.8 Hz, 1H), 4.79 (td, J=7.1, 5.1 Hz, 1H), 4.24-4.05 (br s, 2H), 4.01 (t, J=6.2 Hz, 2H), 2.71 (m, 4H), 2.34-2.22 (m, 1H), 2.15-2.01 (m, 3H), 1.52 (s, 9H). HRMS (ESI-TOF) m/z calcd for $C_{30}H_{37}N_2O_5$ $[M+H]^+$ 505.2697. found 505.2694.

(MM-1-430) Nitroarene MM-1-428 (22 mg, 0.0332 mmol) was dissolved in acetone (0.5 mL). Zinc nanopowder (33 mg, 0.462 mmol, 15 equiv) was suspended in the medium and vigorous stirring was applied. Saturated $NH_4Cl$ (0.1 mL) was added dropwise, producing a ppt. of zinc salts. After 20 minutes, the mixture was diluted with EtOAc (10 mL) and filtered through a 1 cm plug of Celite, washing with EtOAc. The filtrate was washed with sat. $NaHCO_3$ (5 mL), and the organic phase was dried over $Na_2SO_4$, decanted and concentrated. The resulting residue was dissolved in TBAF (0.200 mL, 1 M in THF). After 20 minutes, the mixture was diluted again with EtOAc (10 mL) and washed with $H_2O$ (10 mL). After drying over $Na_2SO_4$, the extracts were decanted and concentrated. Flash chromatography ($SiO_2$, 40% EtOAc/hexanes) gave 13 mg (76%) of the desired product as a white foam. $^1H$ NMR (400 MHz, $CDCl_3$) δ 7.37 (d, J=2.0 Hz, 1H), 7.34 (dd, J=5.6, 2.0 Hz, 2H), 7.26 (dd, J=7.8, 1.6 Hz, 3H), 7.16 (dd, J=8.1, 1.8 Hz, 1H), 7.07 (d, J=8.3 Hz, 2H), 6.84 (d, J=8.4 Hz, 2H), 6.71 (t, J=8.4 Hz, 2H), 4.86 (td, J=7.1, 5.2 Hz, 1H), 4.19 (br s, 2H), 4.00 (t, J=6.3 Hz, 2H), 2.90-2.69 (m, 2H), 2.63 (t, J=7.4 Hz, 2H), 2.42-2.30 (m, 1H), 2.22-2.10 (m, 1H), 1.91-1.71 (m, 4H), 1.59 (s, 9H). HRMS (ESI-TOF) m/z calcd for $C_{31}H_{39}N_2O_5$ $[M+H]^+$ 519.2853. found 519.2857.

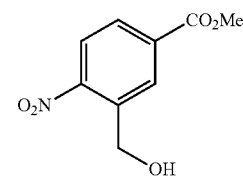 [SMILES: COC(=O)c1ccc([N+](=O)[O-])c(CO)c1]

(MRS-3-49) Methyl 3-formyl-4-nitrobenzoate (1.20 g, 5.73 mmol) was dissolved in MeOH (10 mL) and cooled to 0° C. Sodium borohydride (69 mg, 1.72 mmol) was added in one portion, and the reaction mixture was stirred for 20 minutes. The reduction was quenched with 1 N HCl (10 mL) and the methanol portion evaporated in vacuo. The aqueous phase was extracted with $CH_2Cl_2$ (3×10 mL) to afford 1.06 g of benzylic alcohol, which was used without further purification.

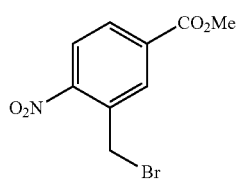 [SMILES: COC(=O)c1ccc([N+](=O)[O-])c(CBr)c1]

(MRS-3-53) Benzylic alcohol MRS-3-49 (1.06 g, 5.35 mmol) was dissolved in Et$_2$O (15 mL) and cooled to 0° C. Phosphorus tribromide (0.254 mL, 2.67 mmol) was carefully added dropwise. After 1 hour, the reaction mixture was poured into ice water (50 mL) and extracted with Et$_2$O (3×20 mL). The ethereal phases were washed with sat. NaHCO$_3$ (20 mL), water (10 mL) and sat. aqueous NaCl (10 mL), and dried over Na$_2$SO$_4$. Evaporation of the Et$_2$O revealed 440 mg (30%) of the primary alkyl bromide.

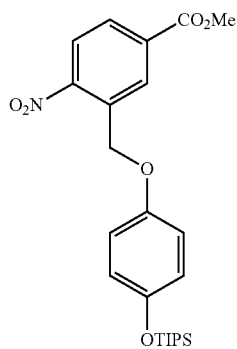

(MRS-3-57) Benzylic bromide MRS-3-49 (150 mg, 0.547 mmol, 1.00 equiv.) and 4-((triisopropylsilyl)oxy)phenol (175 mg, 0.656 mmol, 1.20 equiv) were dissolved in acetone (10 mL). Potassium carbonate (113 mg, 0.820 mmol, 1.50 equiv) was added, and the mixture was heated at reflux overnight (about 18 hours). Evaporation of the solvent and flash chromatography (SiO$_2$, 5% EtOAc/hexanes) returned 170 mg (68%) of the alkylation product and 50 mg of starting bromide.

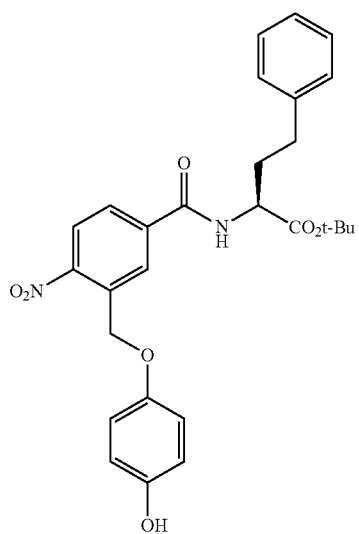 [SMILES: CC(C)(C)OC(=O)[C@H](CCc1ccccc1)NC(=O)c1ccc([N+](=O)[O-])c(COc2ccc(O)cc2)c1]

(MRS-3-59) TIPS-ether MRS-3-57 (170 mg, 0.370 mmol) was dissolved in THF/MeOH/H$_2$O (4 mL: 1 mL: 1 mL). LiOH.H$_2$O (1.48 mmol, 4.00 equiv) was added in one portion, and the reaction stirred for 1 hour, after which the reaction was observed to be complete by TLC. After diluting with H$_2$O (10 mL), the mixture was washed with Et$_2$O (10 mL) to remove the silyl alcohol byproduct. The aqueous phase was acidified with 1 N HCl to pH about 1, then extracted with EtOAc (3×10 mL). The EtOAc extracts were dried over Na$_2$SO$_4$, decanted and concentrated. To the resulting residue, HoPhe-OtBu (122 mg, 0.518 mmol, approx. 1.00 equiv), HOAt (85 mg, 0.622 mmol, 1.20 equiv) and 2,6-lutidine (0.180 mL, 1.55 mmol, 3.00 equiv) were added, and the mixture dissolved in anhydrous DMF (2.5 mL). EDCI.HCl (119 mg, 0.622 mmol, 1.20 equiv) was added, and the reaction stirred overnight (about 18 hours). The mixture was diluted with EtOAc (10 mL) and washed with 0.1 N HCl (10 mL), sat. NaHCO$_2$ (10 mL) and sat. aqueous NaCl (5 mL). The organic phase was dried over Na$_2$SO$_4$, filtered and concentrated to give the coupled amide, which was not further purified.

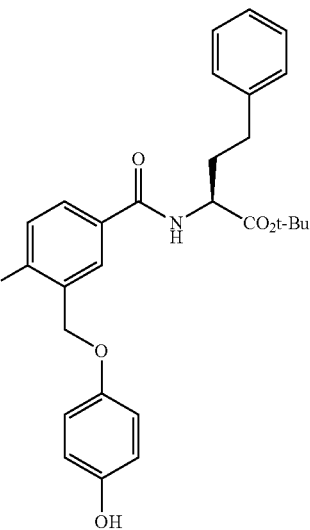

(MRS-3-73) Arylnitro MRS-3-59 (48 mg, 0.094 mmol) was dissolved in acetone (0.4 mL). Zn nanopowder (62 mg, 0.94 mmol, 10 equiv) was suspended in the mixture with vigorous stirring. Sat. NH$_4$Cl (0.1 mL) was added slowly. After 20 minutes, the mixture was filtered through cotton, diluted with EtOAc (5 mL) and washed with sat. NaHCO$_3$ (5 mL) and sat. aqueous NaCl (2 mL). Flash chromatography (SiO$_2$, 50% EtOAc/hexanes) afforded 40 mg (91%) of the aniline product. $^1$H NMR (600 MHz, DMSO-d$_6$) δ 8.22 (s, 1H), 8.17 (d, J=7.8 Hz, 1H), 7.70 (d, J=7.4 Hz, 1H), 7.30-7.20 (m, 5H), 6.90 (d, J=7.2 Hz, 2H), 6.80 (d, J=6.9 Hz, 2H), 5.40 (s, 2H), 4.80 (q, J=6.4 Hz, 1H), 2.70-2.65 (m, 2H), 2.50-2.30 (m, 1H), 2.25-2.10 (m, 1H), 1.52 (s, 9H); MS-ESI (m/z) calcd for [C$_{28}$H$_{30}$N$_2$O$_7$+Na]$^+$ 529.2. found: 529.2.

(MRS-2-53) Methyl-3-formyl-4-nitrobenzoate (500 mg, 2.39 mmol, commercially available from Aldrich) was dissolved in MeOH (12 mL) and cooled to 0° C. Sodium borohydride (28 mg, 0.700 mmol, 0.3 equiv) was added, and the mixture was stirred for 20 minutes. Water (10 mL) was added and the mixture was warmed to room temperature and diluted with EtOAc (30 mL). After extracting once with EtOAc (15 mL), the combined organic phases were dried over $Na_2SO_4$, filtered and concentrated to provide 450 mg (89%) of the benzylic alcohol, which was used without further purification.

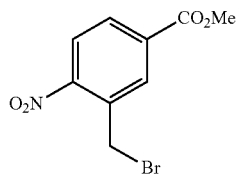 [SMILES: COC(=O)c1ccc([N+](=O)[O-])c(CBr)c1]

(MRS-2-55) Benzylic alcohol MRS-2-53 (615 mg, 2.91 mmol) was dissolved in anhydrous $Et_2O$ (15 mL) and cooled to 0° C. Phosphorus tribromide (0.138 mL, 1.45 mmol, 0.5 equiv) was slowly added drop-wise to the stirring solution. After 40 minutes at 0° C., the reaction was quenched with sat. $NaHCO_3$ (20 mL) and the mixture was diluted with EtOAc. The aqueous phase was extracted once with EtOAc (10 mL), and the combined extracts were dried over $Na_2SO_4$ and concentrated. Flash chromatography ($SiO_2$, 25% EtOAc/hexanes) gave 240 mg (30%) of the benzylic bromide.

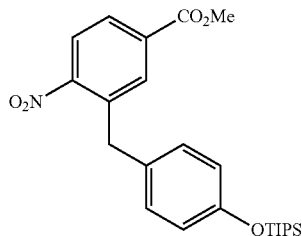

(MRS-2-497) Benzylic bromide MRS-2-55 (170 mg, 0.620 mmol) and arylboronic acid MM-1-188 (274 mg, 0.930 mmol, 1.50 equiv) were dissolved in acetone/$H_2O$ (3:1, 4 mL). Potassium carbonate (214 mg, 1.55 mmol, 2.50 equiv) and $PdCl_2$ (5.5 mg, 0.03 mmol, 5 mol %) were added, and the reaction mixture stirred at room temperature for 1 h. The reaction mixture was filtered through Celite, washing with EtOAc, and concentrated. Flash chromatography ($SiO_2$, 25% EtOAc/hexanes) gave 160 mg (58%) of the cross-coupled product. $^1$H NMR (600 MHz, DMSO-$d_5$) δ 8.20 (d, J=8.2 Hz, 1H), 7.95 (s, 1H), 7.80 (d, J=7.4 Hz, 1H), 7.00 (d, J=7.2 Hz, 2H), 6.65 (d, J=7.2 Hz, 2H), 4.25 (s, 2H), 3.96 (s, 3H), 1.30-1.20 (m, 3H), 1.09 (d, J=7.1 Hz, 18H); MS-ESI (m/z) calcd for $[C_{24}H_{33}NO_5Si+H]^+$ 444.2. found: 444.2.

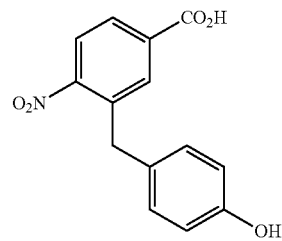 [SMILES: O=C(O)c1ccc([N+](=O)[O-])c(Cc2ccc(O)cc2)c1]

(MRS-2-498) TIPS-ether MM-1-188 (160 mg, 0.360 mmol) was dissolved in THF/MeOH/$H_2O$ (4 mL: 1 mL: 1 mL). $LiOH.H_2O$ (1.44 mmol, 4.00 equiv) was added in one portion, and the reaction stirred for 1 hour, after which the reaction was observed to be complete by TLC. After diluting with $H_2O$ (10 mL), the mixture was washed with $Et_2O$ (10 mL) to remove the silyl alcohol byproduct. The aqueous phase was acidified with 1 N HCl to pH about 1, then extracted with EtOAc (3×10 mL). The extracts were dried over $Na_2SO_4$, decanted and concentrated to give 130 mg of the hydrolyzed product.

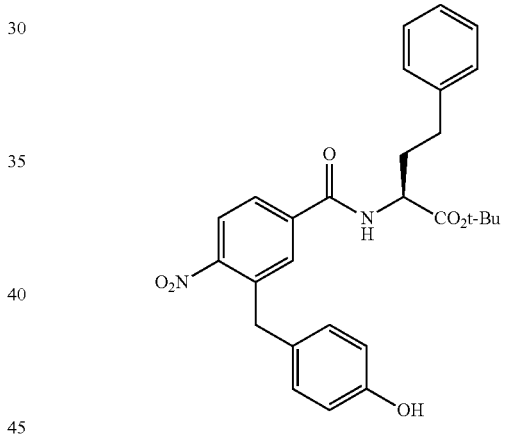

(MRS-3-1) Carboxylic acid MRS-2-498 (130 mg, 0.475 mmol) and HoPhe-OtBu (112 mg, 0.475 mmol, 1.00 equiv) were dissolved in anhydrous DMF. HOAt (78 mg, 0.570 mmol, 1.20 equiv), 2,6-lutidine (0.165 mL, 1.42 mmol, 3.00 equiv) and EDCI.HCl (109 mg, 0.570 mmol, 1.20 equiv) were added. After 12 hours, the reaction mixture was washed with 0.1 N HCl (10 mL) and extracted with EtOAc (3×10 mL), dried over $Na_2SO_4$, filtered and concentrated. Flash chromatography ($SiO_2$, 25% EtOAc/hexanes) produced 120 mg (51%) of the coupled amide. $^1$H NMR (600 MHz, DMSO-$d_6$) δ 8.15 (d, J=8.2 Hz, 1H), 7.50 (d, J=7.6 Hz, 1H), 7.45 (s, 1H), 7.30-7.20 (m, 5H), 7.00 (d, J=7.2 Hz, 2H), 6.60 (d, J=7.2 Hz, 2H), 4.25 (q, J=6.4 Hz, 1H), 3.46 (s, 2H), 2.80 (t, J=7.1 Hz, 2H), 2.70-2.50 (m, 2H), 1.45 (s, 9H); MS-ESI (m/z) calcd for $[C_{28}H_{30}N_2O_6+H]^+$ 491.2. found: 491.2.

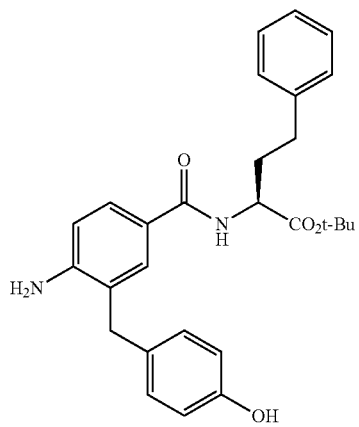 [SMILES: CC(C)(C)OC(=O)[C@H](CCc1ccccc1)NC(=O)c1ccc([N+](=O)[O-])c(Cc2ccc(O)cc2)c1]

(MRS-3-5) Amide MRS-3-1 (120 mg, 0.244 mmol) was dissolved in acetone/NH$_4$Cl (4 mL, 1 mL, respectively). Zinc nanopowder (159 mg, 2.44 mmol, 10 equiv) was suspended in the reaction mixture. After vigorous stirring for 1 hour, the reaction mixture was filtered through Celite, diluted with EtOAc (10 mL) and washed with sat. NaHCO$_3$ (10 mL) and sat. aqueous NaCl (5 mL). The organic phase was dried over Na$_2$SO$_4$, filtered and concentrated. Flash chromatography (SiO$_2$, 25% EtOAc/hexanes) gave 90 mg (80%) of the aniline compound. $^1$H NMR (600 MHz, DMSO-d$_6$) δ 9.10 (s, 1H), 8.10 (d, J=8.3 Hz, 1H), 7.50 (d, J=7.6 Hz, 1H), 7.45 (s, 1H), 7.40-7.25 (m, 5H), 7.00 (d, J=7.2 Hz, 2H), 6.65 (d, J=7.4 Hz, 2H), 5.40 (s, 2H), 4.15 (q, J=6.6 Hz, 1H), 3.46 (s, 2H), 2.85 (t, J=7.2 Hz, 2H), 2.70-2.50 (m, 2H), 1.49 (s, 9H); MS-ESI (m/z) calcd for [C$_{28}$H$_{32}$N$_2$O$_4$+H]$^+$ 461.2. found: 461.2.

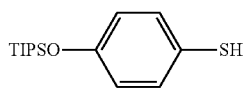

4-((Triisopropylsilyl)oxy)benzenethiol (above) was prepared according to the procedure described by Bubert et al., *Chem Med Chem*, 3:1708-1730 (2008).

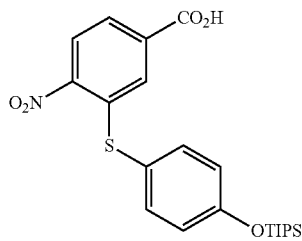

(MRS-1-500) 4-((Triisopropylsilyl)oxy)-benzenethiol (710 mg, 2.51 mmol, 0.93 equiv) was dissolved in anhydrous DMF (10 mL) at room temperature. K$_2$CO$_3$ (420 mg, 3.08 mmol, 1.14 equiv) was added, and the mixture stirred for 15 minutes. 3-Fluoro-4-nitrobenzoic acid (500 mg, 2.70 mmol, solution in 4 mL DMF) was added dropwise, and the mixture allowed to stir overnight (about 18 hours), then quenched with sat. NH$_4$Cl (15 mL) and diluted with EtOAc (30 mL). The organic phase was further washed with 0.1 N HCl (2×10 mL), and the combined aqueous phases were extracted with EtOAc (2×10 mL). The extracts were dried over Na$_2$SO$_4$, filtered and concentrated. Flash chromatography (3:2:0.1 hexanes:Et$_2$O:AcOH) gave 810 mg (72%) of the adduct.

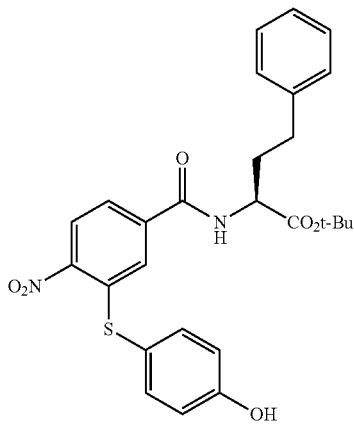 [SMILES: CC(C)(C)OC(=O)[C@H](CCc1ccccc1)NC(=O)c1ccc([N+](=O)[O-])c(Sc2ccc(O)cc2)c1]

(MRS-2-1) Carboxylic acid MRS-1-500 (150 mg, 0.514 mmol), HoPhe-OtBu (121 mg, 0.514 mmol, 1.00 equiv) and HOAt (84 mg, 0.617 mmol, 1.20 equiv) were dissolved in anhydrous DMF (15 mL). 2,6-Lutidine (0.11 mL, 1.54 mmol, 3.00 equiv) and EDCI.HCl (118 mg, 0.617 mmol, 1.20 equiv) were added, and the mixture stirred overnight. The reaction mixture was diluted with EtOAc (25 mL) and washed with 0.1 N HCl (20 mL), sat. NaHCO$_3$ (20 mL) and sat. aqueous NaCl (10 mL), and the organic phase was concentrated. Flash chromatography (SiO$_2$, 25% EtOAc/hexanes) produced 200 mg (76%) of coupled amide. $^1$H NMR (600 MHz, DMSO-d$_6$) δ 8.30 (d, J=8.9 Hz, 1H), 7.50 (s, 1H), 7.40-7.21 (m, 6H), 7.15 (d, J=7.5 Hz, 2H), 6.95 (d, J=7.3 Hz, 2H), 4.80-4.73 (m, 1H), 2.72 (t, J=6.9 Hz, 2H), 2.50-2.30 (m, 2H), 1.50 (s, 9H); MS-ESI (m/z) calcd for [C$_{27}$H$_{28}$N$_2$O$_6$S+H]$^+$ 509.1. found: 509.2.

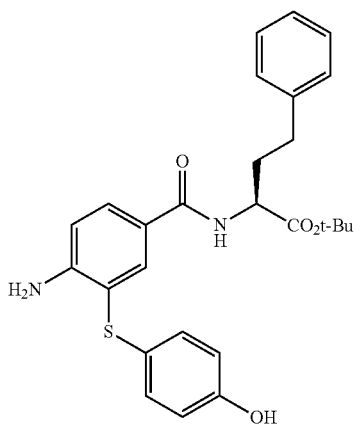

(MRS-2-7) Nitroarene MRS-2-1 (180 mg, 0.270 mmol) was dissolved in acetone/sat. NH$_4$Cl (10 mL, 2 mL, respectively). Zinc nanopowder (230 mg, 3.51 mmol, 13 equiv) was added, and the reaction mixture was stirred for 30 minutes. The heterogeneous mixture was filtered through Celite, diluted with EtOAc (30 mL) and washed with sat. NaHCO$_3$ (20 mL). The organic phase was washed with sat. aqueous NaCl (10 mL), dried over Na$_2$SO$_4$ and concentrated to give 125 mg (97%) of the aniline. $^1$H NMR (600 MHz, DMSO-d$_6$) δ 8.30 (d, J=8.4 Hz, 1H), 7.90 (s, 1H), 7.60 (d, J=7.1 Hz, 1H), 7.45-7.25 (m, 5H), 7.00 (d, J=7.5 Hz, 2H), 6.65 (d, J=7.2 Hz, 2H), 5.80 (s, 2H), 4.25-4.10 (m, 1H), 2.80 (t, J=7.1 Hz, 2H), 2.70-2.50 (m, 2H), 1.45 (s, 9H); MS-ESI (m/z) calcd for [C$_{27}$H$_{30}$N$_2$O$_4$S+H]$^+$ 479.2. found: 479.2.

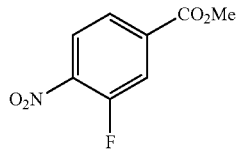 [SMILES: COC(=O)c1ccc([N+](=O)[O-])c(F)c1]

(MRS-2-33) 3-Fluoro-4-nitrobenzoic acid (720 mg, 3.89 mmol) was dissolved in PhMe:MeOH (8 mL ea) and cooled to 0° C. (Diazomethyl)trimethylsilane (4.3 mL, 8.56 mmol, 2.2 equiv, 2 M in n-hexane) was added dropwise over 5 minutes. The reaction mixture was stirred 30 minutes, then quenched with slow addition of AcOH. Solvent was removed in vacuo and the residue purified by flash chromatography (SiO$_2$, 10% EtOAc/hexanes) to give 770 mg (99%) of the methyl ester.

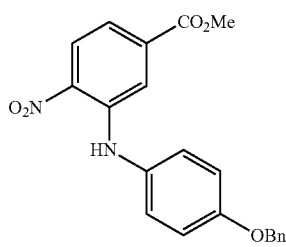 [SMILES: COC(=O)c1ccc([N+](=O)[O-])c(Nc2ccc(OCc3ccccc3)cc2)c1]

(MRS-2-35) Methyl ester MRS-2-33 (500 mg, 2.51 mmol) was dissolved in DMSO (10 mL). 4-(Benzyloxy)aniline (1.18 g, 5.02 mmol, 2.00 equiv) was added and the reaction mixture was heated to 110° C. for 6 hours. The reaction was cooled to room temperature and diluted with EtOAc. The organic layer was washed with H$_2$O and sat. aqueous NaCl, dried over MgSO$_4$, filtered and concentrated. Flash chromatography (SiO$_2$, 10% EtOAc/hexanes) gave 864 mg (91%) of the biaryl aniline. [Saitoh. et al., *J. Med. Chem.* 52:6270-6276 (2009).]

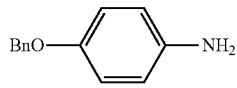

4-(benzyloxy)aniline was prepared according to the method described by Yang et al., *Bioorg. Med. Chem. Lett.,* 18:1135-1139 (2008).

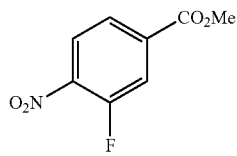 [SMILES: COC(=O)c1ccc([N+](=O)[O-])c(F)c1]

(MRS-2-33) 3-Fluoro-4-nitrobenzoic acid (720 mg, 3.89 mmol) was dissolved in toluene:MeOH (1:1 v/v) and cooled to 0° C. Trimethylsilyl-diazomethane (4.3 mL, 8.56 mmol, 2 M in n-hexane) was added dropwise over 5 minutes. After stirring for 30 minutes, AcOH was added to the reaction mixture slowly until N$_2$ evolution ceased, and the solvent was removed under reduced pressure. Flash chromatography (SiO$_2$, 10% EtOAc/hexanes) gave 770 mg (99%) of the arylfluoride methyl ester.

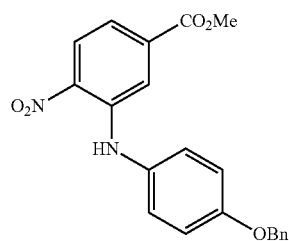 [SMILES: COC(=O)c1ccc([N+](=O)[O-])c(Nc2ccc(OCc3ccccc3)cc2)c1]

(MRS-2-35) Arylfluoride methyl ester MRS-2-33 (500 mg, 2.51 mmol) and 4-(benzyloxy)aniline (1.18 g, 5.02 mmol, 2.00 equiv) were dissolved in DMSO (10 mL) and heated to 110° C. for 6 hours. After cooling to room temperature, the reaction mixture was diluted with EtOAc (50 mL) and washed with H$_2$O (50 mL). The organic phase was dried over Na$_2$SO$_4$, decanted and concentrated. Flash chromatography (SiO$_2$, 10% EtOAc/hexanes) afforded 865 mg (91%) of the biaryl aniline.

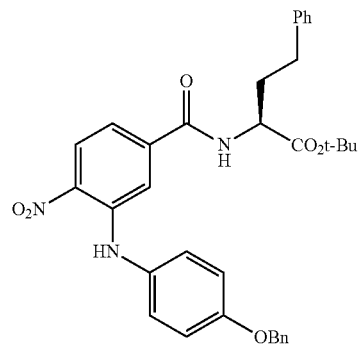

(MRS-3-9) Carboxylic acid XX (150 mg, 0.411 mmol), HoPhe-OtBu (97 mg, 0.411 mmol, 1.00 equiv) and HOAt (67 mg, 0.494 mmol, 1.2 equiv) were dissolved in anhydrous DMF (2 mL). 2,6-Lutidine (0.143 mL, 1.23 mmol, 3.00 equiv) and EDCI.HCl (95 mg, 0.494 mmol, 1.20 equiv) were added, and the mixture was stirred overnight (about 18 hours). The reaction mixture was diluted with EtOAc (10 mL) and washed with 0.1 N HCl (10 mL), sat. NaHCO$_3$ (10 mL) and sat. aqueous NaCl (5 mL), and the organic phase was concentrated. Flash chromatography (SiO$_2$, 25% EtOAc/hexanes) produced 155 mg (65%) of coupled amide. $^1$H NMR (600 MHz, DMSO-d$_6$) δ 8.20 (d, J=8.4 Hz, 1H), 7.50 (s, 1H), 7.40-7.20 (m, 13H), 7.00 (d, J=7.5 Hz, 2H), 5.10 (s, 2H), 4.80-4.70 (m, 1H), 2.72-2.60 (m, 2H), 2.25-2.20 (m, 1H), 2.10-2.00 (m, 1H), 1.40 (s, 9H); MS-ESI (m/z) calcd for [C$_{34}$H$_{35}$N$_3$O$_6$+H]$^+$ 582.2. found: 582.2.

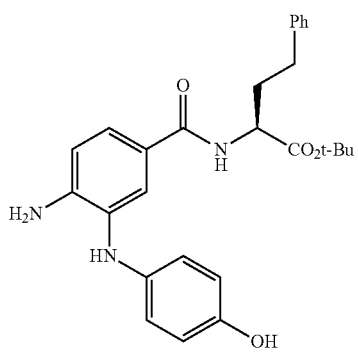 [SMILES: CC(C)(C)OC(=O)[C@H](CCc1ccccc1)NC(=O)c1ccc([N+](=O)[O-])c(Nc2ccc(OCc3ccccc3)cc2)c1]

(MRS-3-71) Nitroaryl benzyl ether MM-3-9 (80 mg, 0.138 mmol) was dissolved in MeOH (1.0 mL) Palladium on carbon (5 mol %, 20% Pd w/w on carbon) was suspended in the reaction solvent, and the solvent was sparged with $N_2$ for 10 minutes. After stirring for 2 hours under $H_2$ atmosphere, the mixture was filtered through a plug of sand/Celite, washing thoroughly with EtOAc. Solvent was removed in vacuo to yield the fully reduced aniline. $^1$H NMR (600 MHz, DMSO-$d_6$) δ 8.25 (d, J=8.2 Hz, 1H), 7.90 (s, 1H), 7.45-7.21 (m, 8H), 7.10 (d, J=7.8 Hz, 2H), 5.80 (s, 2H), 4.83-4.70 (m, 1H), 2.70-2.60 (m, 2H), 2.35-2.20 (m, 1H), 2.10-2.00 (m, 1H), 1.45 (s, 9H); MS-ESI (m/z) calcd for $[C_{27}H_{31}N_3O_4+H]^+$ 462.2. found: 462.2.

HoPhe Analogue Intermediate Preparation

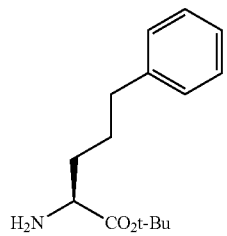 [SMILES: CC(C)(C)OC(=O)[C@@H](N)CCCc1ccccc1]

(MM-2-84) H-Nva(5-Ph)-OH (500 mg, 2.59 mmol) was suspended in anhydrous dioxane (5 mL) in a sealed tube reaction vessel. Conc. $H_2SO_4$ (200 μL) was added, and the mixture was cooled to −78° C. Condensed isobutylene (approx. 4 mL) was transferred via cannula onto the frozen reaction mixture. The reaction vessel was sealed tightly and warmed to room temperature overnight (about 18 hours). After stirring 2 days, pressure was slowly released, the mixture was diluted with $Et_2O$ (50 mL) and washed with sat. $NaHCO_3$ (25 mL). The aqueous phase was extracted with $Et_2O$ (2×25 mL), and the combined ethereal phases were dried over $Na_2SO_4$ and concentrated thoroughly. H-Nva(5-Ph)-OtBu (464 mg, 72%) obtained as a yellow oil was used without further purification. $^1$H NMR (500 MHz, CDCl$_3$) δ 7.30-7.25 (m, 2H), 7.21-7.16 (m, 3H), 3.37-3.28 (m, 1H), 2.65 (m, 2H), 1.71 (m, 4H), 1.45 (s, 9H).

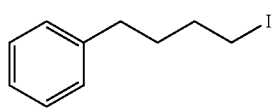 [SMILES: ICCCCc1ccccc1]

(MM-2-68) 4-Phenyl-1-butanol (543 mg, 3.58 mmol) was dissolved in $CH_2Cl_2$ (20 mL). Imidazole (810 mg, 11.8 mmol, 3.00 equiv) was added, followed by PPh$_3$ (986 mg, 3.76 mmol, 1.05 equiv). Upon complete dissolution of the PPh$_3$, iodine (1.00 g, 3.94 mmol, 1.10 equiv) was added portionwise. After 1 hour, the reaction was quenched with $Na_2S_2O_3$ (10% w/v, 15 mL). The aqueous layer was extracted once with $CH_2Cl_2$ (10 mL), dried over $Na_2SO_4$, decanted and concentrated to reveal a white solid. The solid was triturated with n-pentane (3×15 mL) and filtered through a 6 cm silica plug, washing with 50% EtOAc/n-pentane, to remove the phosphine oxide. Solvent removal in vacuo revealed the alkyl iodide (868 mg, 93%) as a clear oil. $^1$H NMR (500 MHz, CDCl$_3$) δ 7.34-7.27 (m, 2H), 7.25-7.17 (m, 3H), 3.22 (t, J=6.9 Hz, 2H), 2.66 (t, J=7.6 Hz, 2H), 1.93-1.83 (m, 2H), 1.82-1.70 (m, 2H).

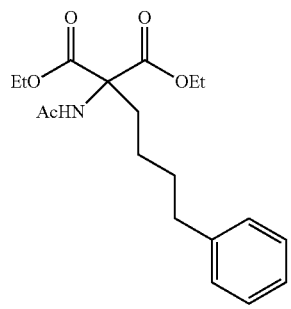 [SMILES: CCOC(=O)C(CCCCc1ccccc1)(NC(C)=O)C(=O)OCC]

(MM-2-71) Sodium hydride (350 mg, 60% dispersion in mineral oil) was carefully added to EtOH (20 mL) in a 50 mL two-neck round bottom flask equipped with condenser. Upon cooling to room temperature, diethyl acetamidomalonate (1.38 g, 6.34 mmol) was added and the mixture was heated to reflux. After 15 minutes at reflux, 4-phenyl-1-iodobutane (1.57 g, 6.04 mmol) was added dropwise. After 16 hours at reflux, the mixture was cooled to room temperature and poured into 0.05 M KHSO$_4$ (60 mL)/hexanes (30 mL), pre-cooled to 0° C. The product crystallized at the phase interface. Filtration and recrystallization from boiling hexanes/EtOAc gave 736 mg (35%) of the alkylation product. [Procedure adopted from: Varnavas et al., *J. Med. Chem.* 54:5769-5785 (2011).] $^1$H NMR (500 MHz, Acetone-$d_6$) δ 7.25 (t, J=7.7 Hz, 2H), 7.20-7.11 (m, 3H), 4.15 (q, J=7.1 Hz, 2H), 2.58 (t, J=7.6 Hz, 2H), 2.36-2.24 (m, 2H), 1.96 (s, 3H), 1.68-1.55 (m, 2H), 1.18 (dt, J=9.5, 5.8 Hz, 8H).

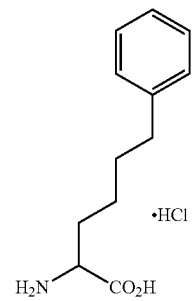

(MM-2-72) Alkylation product MM-2-71 prepared by the methods discussed in Pevan et al., *J. Med. Chem.*, 54:5769-5785 (2011) (700 mg, 2.00 mmol) was suspended in dioxane and 6 N HCl (7 mL ea) and the mixture was heated to reflux. After 3 hours, the reaction mixture was cooled to room temperature and the solvent removed under a stream of $N_2$.

The remaining residue was triturated with cold Et$_2$O (10 mL) and filtered to give 327 mg (67%) of the amino acid hydrochloride salt. $^1$H NMR (500 MHz, DMSO-d$_6$) δ 8.47-8.26 (br s, 1H), 7.27 (t, J=7.5 Hz, 2H), 7.23-7.12 (m, 3H), 3.86 (q, J=5.6 Hz, 1H), 3.64-3.23 (br s, 2H), 2.57 (t, J=7.7 Hz, 2H), 1.86-1.77 (m, 2H), 1.63-1.51 (m, 2H), 1.51-1.39 (m, 1H), 1.39-1.27 (m, 1H).

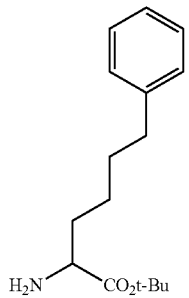 [SMILES: CC(C)(C)OC(=O)C(N)CCCCc1ccccc1]

(MM-2-76) Ammonium salt MM-2-72 (325 mg, 1.34 mmol) was suspended in anhydrous dioxane (5 mL). Conc. H$_2$SO$_4$ (about 0.2 mL) was added, after which the starting material dissolved. The reaction mixture was cooled to −78° C., and condensed isobutylene (5 mL) was added via cannula. The reaction vessel was sealed tightly, warmed to room temperature and stirred for 4 days. Pressure was slowly released, and the mixture was poured into Et$_2$O (50 mL). The ethereal phase was washed with sat. NaHCO$_3$ (50 mL). The aqueous phase was extracted with Et$_2$O (2×15 mL), and the combined ethereal layers were dried over Na$_2$SO$_4$, decanted and concentrated to reveal the t-butyl ester MM-2-76 (284 mg, 80%), which was used without further purification. $^1$H NMR (500 MHz, CDCl$_3$) δ 7.31-7.24 (m, 2H), 7.21-7.14 (m, 3H), 3.36 (dd, J=7.2, 5.6 Hz, 1H), 2.63 (t, J=7.7 Hz, 2H), 2.19 (s, 2H), 1.80-1.55 (m, 4H), 1.48-1.40 (m, 2H), 1.44 (s, 9H).

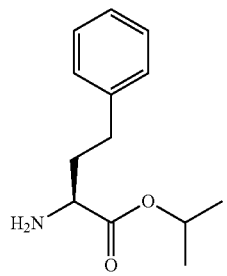 [SMILES: CC(C)OC(=O)[C@@H](N)CCc1ccccc1]

(MM-1-448) Boc-HoPhe-OH (427 mg, 1.53 mmol, 1.00 equiv) was dissolved in anhydrous isopropanol and cooled to 0° C. Thionyl chloride (155 μL, 2.14 mmol, 1.40 equiv) was added dropwise, and the mixture stirred overnight (about 18 hours), warming to room temperature. The reaction was quenched with sat. NaHCO$_3$ (10 mL) and H$_2$O (10 mL) and diluted with Et$_2$O (20 mL). The aqueous phase was extracted with Et$_2$O (5×10 mL), and the combined extracts dried over Na$_2$SO$_4$, decanted and concentrated to give 150 mg (44%) of the isopropyl ester. $^1$H NMR (400 MHz, CDCl$_3$) δ 7.33-7.26 (m, 2H), 7.24-7.17 (m, 3H), 5.06 (sept, J=6.3 Hz, 1H), 3.42 (dd, J=7.7, 5.3 Hz, 1H), 2.73 (ddd, J=9.4, 6.5, 4.5 Hz, 2H), 2.06 (dddd, J=13.4, 9.6, 6.9, 5.3 Hz, 1H), 1.92-1.79 (m, 1H), 1.56 (s, 2H), 1.27 (d, J=6.3 Hz, 2H).

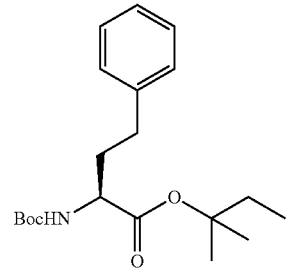 [SMILES: CCC(C)(C)OC(=O)[C@H](CCc1ccccc1)NC(=O)OC(C)(C)C]

(MM-2-135) Boc-HoPhe-OH (100 mg, 0.358 mmol), dicyclohexylcarbodiimide (DCC, 78 mg, 0.376 mmol, 1.05 equiv) and 4-dimethylaminopyridine (DMAP, 9 mg, 0.072 mmol, 0.200 equiv) were dissolved in CH$_2$Cl$_2$ (2 mL) at room temperature in a 20 mL scintillation vial. tert-Amyl alcohol (400 μL, 3.58 mmol, 10 equiv) was added, and the reaction mixture stirred for 2 days. The cloudy mixture was filtered through a 3 cm plug of Celite, diluted with CH$_2$Cl$_2$ (10 mL) and washed with aqueous citric acid (10% w/v, 10 mL) and sat. NaHCO$_3$. The halogenated phase was dried over Na$_2$SO$_4$, decanted, and concentrated. Flash chromatography (SiO$_2$, 5% EtOAc/hexanes) returned 83 mg (66%) of the tert-pentyl ester. $^1$H NMR (400 MHz, CDCl$_3$) δ 7.47-7.38 (m, 2H), 7.37-7.29 (m, 3H), 5.27 (d, J=8.4 Hz, 1H), 4.41 (td, J=7.8, 4.9 Hz, 1H), 2.91-2.72 (m, 2H), 2.34-2.20 (m, 1H), 2.05 (dddd, J=13.9, 11.2, 7.5, 5.6 Hz, 1H), 1.93 (p, J=7.2 Hz, 2H), 1.60 (s, 9H), 1.59 (s, 6H), 1.04 (t, J=7.5 Hz, 3H).

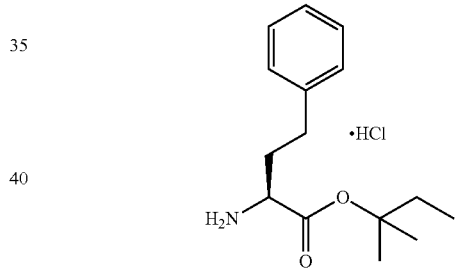

(MM-2-137) tert-Pentyl ester MM-2-135 (73 mg, 0.209 mmol) was dissolved in EtOAc (2 mL) in a 20 mL scintillation vial with stir bar. 4 N HCl in dioxane (0.5 mL, approx. 10 equiv) was added dropwise. After 5 hours, the stir bar was removed and the solvents were concentrated under an N$_2$ stream overnight (about 18 hours) to reveal 51 mg (86%) of ammonium salt as a white powder.

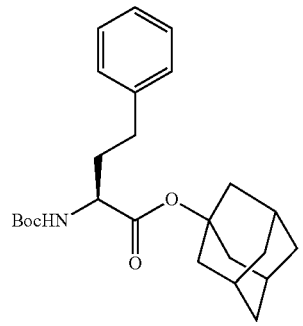 [SMILES: CC(C)(C)OC(=O)N[C@@H](CCc1ccccc1)C(=O)OC12CC3CC(CC(C3)C1)C2]

(MM-2-118) Boc-HoPhe-OH (100 mg, 0.358 mmol), dicyclohexylcarbodiimide (DCC, 78 mg, 0.376 mmol, 1.05 equiv) and 4-dimethylaminopyridine (DMAP, 9 mg, 0.072 mmol, 0.200 equiv) were dissolved in CH$_2$Cl$_2$ (2 mL) at room temperature in a 20 mL scintillation vial. 1-Adamantanol (57 mg, 0.376 mmol, 1.05 equiv) was added, and the reaction mixture stirred for 24 hours. The cloudy mixture was filtered through a 3 cm plug of Celite, diluted with CH$_2$Cl$_2$ (10 mL) and washed with aqueous citric acid (10% w/v, 10 mL) and sat. NaHCO$_3$. The halogenated phase was dried over Na$_2$SO$_4$, decanted, and concentrated. Flash chromatography (SiO$_2$, 5 to 10% EtOAc/hexanes) provided 74 mg (50%) of the adamantyl ester. $^1$H NMR (500 MHz, CDCl$_3$) δ 7.40-7.33 (m, 2H), 7.30-7.22 (m, 3H), 5.18 (d, J=9.1 Hz, 1H), 4.33 (q, J=6.8 Hz, 1H), 2.78 (dt, J=10.8, 6.5 Hz, 1H), 2.71 (dt, J=10.8, 6.5 Hz, 1H), 2.26 (m, 3H), 2.21 (d, J=3.0 Hz, 6H), 2.08-1.94 (m, 1H), 1.75 (d, J=3.2 Hz, 6H), 1.54 (s, 9H).

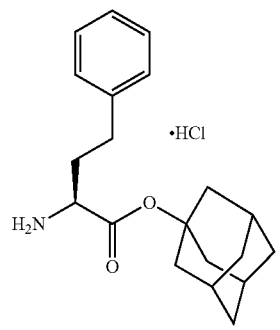 [SMILES: N[C@@H](CCc1ccccc1)C(=O)OC12CC3CC(CC(C3)C1)C2 ; Cl]

(MM-2-123) Adamantyl ester MM-2-118 (74 mg, 0.179 mmol) was dissolved in 4 N HCl in dioxane (2.0 mL, approx. 45 equiv). After 3 hours, the stir bar was removed and the solvent was concentrated under an N$_2$ stream overnight (about 18 hours) to reveal 61 mg (97%) of ammonium salt as a white powder.

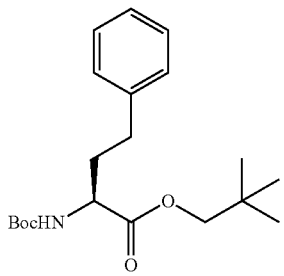 [SMILES: CC(C)(C)COC(=O)[C@H](CCc1ccccc1)NC(=O)OC(C)(C)C]

(MM-2-117) Boc-HoPhe-OH (100 mg, 0.358 mmol), dicyclohexylcarbodiimide (DCC, 78 mg, 0.376 mmol, 1.05 equiv) and 4-dimethylaminopyridine (DMAP, 9 mg, 0.072 mmol, 0.200 equiv) were dissolved in CH$_2$Cl$_2$ (2 mL) at room temperature in a 20 mL scintillation vial. Neopentyl alcohol (66 mg, 0.749 mmol, 2.10 equiv) was added, and the reaction mixture stirred for 24 hours. The cloudy mixture was filtered through a 3 cm plug of Celite, diluted with CH$_2$Cl$_2$ (10 mL) and washed with aqueous citric acid (10% w/v, 10 mL) and sat. NaHCO$_3$. The halogenated phase was dried over Na$_2$SO$_4$, decanted, and concentrated. Flash chromatography (SiO$_2$, 5% EtOAc/hexanes) provided 83 mg (66%) of the neopentyl ester. $^1$H NMR (500 MHz, CDCl$_3$) δ 7.30 (d, J=7.6 Hz, 2H), 7.23-7.15 (m, 3H), 5.09 (d, J=8.4 Hz, 1H), 4.40 (q, J=7.0 Hz, 1H), 3.83 (q, J=10.5 Hz, 2H), 2.76-2.60 (m, 2H), 2.17 (m, 1H), 1.98 (m, 1H), 1.46 (s, 9H), 0.96 (s, 9H).

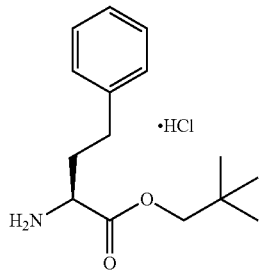 [SMILES: CC(C)(C)COC(=O)[C@@H](N)CCc1ccccc1 ; Cl]

(MM-2-122) Neopentyl ester MM-2-117 (83 mg, 0.238 mmol) was dissolved in 4 N HCl in dioxane (2.0 mL, approx. 34 equiv). After 3 hours, the stir bar was removed and the solvent was concentrated under an N$_2$ stream overnight (about 18 hours) to reveal 58 mg (85%) of ammonium salt as a white powder.

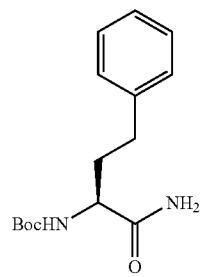 [SMILES: CC(C)(C)OC(=O)N[C@@H](CCc1ccccc1)C(N)=O]

(MM-2-81) Boc-HoPhe-OH (250 mg, 0.895 mmol), ammonium chloride (150 mg, 2.69 mmol, 3.00 equiv), HOAt (134 mg, 0.984 mmol, 1.10 equiv) and 2,6-lutidine (520 μL, 4.47 mmol, 5.00 equiv) were dissolved at room temperature in anhydrous DMF (4.5 mL). EDCI.HCl (180 mg, 0.940 mmol, 1.05 equiv) was added, and the mixture stirred 2 days. The mixture was diluted with EtOAc (50 mL) and washed with 0.1 N HCl (2×25 mL) and sat. aqueous NaCl (10 mL). The aqueous phase was extracted once with EtOAc (20 mL), and the combined organic phases were dried over Na$_2$SO$_4$, decanted and concentrated. The residual material was redissolved in EtOAc, rewashed with H$_2$O and dried to give 236 mg of the carboxamide as a white solid.

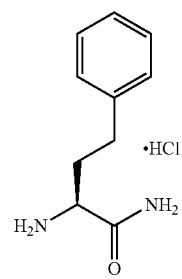 [SMILES: NC(=O)[C@@H](N)CCc1ccccc1 ; Cl]

(MM-2-92) Carboxamide MM-2-81 (100 mg, 0.359 mmol) was dissolved in EtOAc (4 mL) and cooled to 0° C. 4 N HCl in dioxane (1 mL) was added dropwise, and the mixture warmed to room temperature. After 5 hours, solvent was removed under an N$_2$ stream to give 75 mg (97%) of the caboxamide HCl salt.

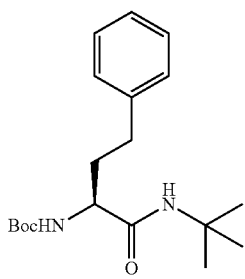 [SMILES: CC(C)(C)NC(=O)[C@H](CCc1ccccc1)NC(=O)OC(C)(C)C]

(MM-2-89) Boc-HoPhe-OH (100 mg, 0.358 mmol), DEPBT (118 mg, 0.394 mmol, 1.10 equiv) and Et$_3$N (100 µL, 0.716 mmol, 2.00 equiv) were dissolved at room temperature in anhydrous THF (2 mL). After 15 minutes, tert-butylamine (41 □L, 0.394 mmol, 1.10 equiv) was added dropwise. After 12 hours, the mixture was diluted with EtOAc (15 mL) and washed with citric acid (10 mL, 10% w/v) and sat. NaHCO$_3$ (20 mL). The organic phase was dried over Na$_2$SO$_4$, filtered and concentrated. Flash chromatography (SiO$_2$, 10% EtOAc/hexanes) gave 120 mg (99%) of the t-butyl amide. $^1$H NMR (500 MHz, CDCl$_3$) δ 7.22 (dd, J=8.2, 6.9 Hz, 2H), 7.13 (td, J=6.0, 3.3 Hz, 3H), 6.18 (s, 1H), 5.42 (d, J=8.4 Hz, 1H), 4.01 (q, J=8.0 Hz, 1H), 2.63 (m, 1H), 2.09-2.00 (m, 1H), 1.88 (dt, J=13.7, 7.9 Hz, 1H), 1.41 (s, 9H), 1.30 (s, 9H).

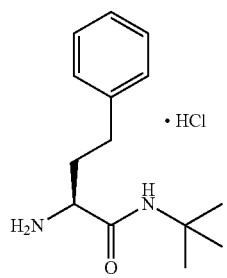 [SMILES: CC(C)(C)NC(=O)[C@@H](N)CCc1ccccc1 ; "· HCl"]

(MM-2-91) tert-Butyl amide MM-2-89 (60 mg, 0.179 mmol) was dissolved in EtOAc (2 mL) at 0° C. 4 N HCl in dioxane (0.5 mL, approx. 11 equiv.) was added dropwise. After 2 hours, the stir bar was removed and the solvent was concentrated under an N$_2$ stream overnight (about 18 hours) to reveal 41 mg (98%) of ammonium salt as a white powder.

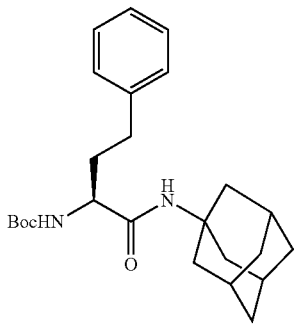 [SMILES: CC(C)(C)OC(=O)N[C@@H](CCc1ccccc1)C(=O)NC12CC3CC(CC(C3)C1)C2]

(MM-2-113) Boc-HoPhe-OH (100 mg, 0.358 mmol), DEPBT (118 mg, 0.394 mmol, 1.10 equiv.) and Et$_3$N (100 µL, 0.716 mmol, 2.00 equiv) were dissolved at room temperature in anhydrous THF (2 mL). After 15 minutes, 1-adamantylamine (60 mg, 0.394 mmol, 1.10 equiv) was added in one portion. After 12 hours, the mixture was diluted with EtOAc (15 mL) and washed with aqueous citric acid (10 mL, 10% w/v) and sat. NaHCO$_3$ (20 mL). The organic phase was dried over Na$_2$SO$_4$, filtered and concentrated. Flash chromatography (SiO$_2$, 20% EtOAc/hexanes) gave 132 mg (89%) of the adamantyl amide. $^1$H NMR (400 MHz, CDCl$_3$) δ 7.42-7.33 (m, 2H), 7.28 (dt, J=8.1, 3.8 Hz, 3H), 5.71 (s, 1H), 5.17 (d, J=6.0 Hz, 1H), 4.03 (m, 1H), 2.86-2.64 (m, 2H), 2.16 (t, J=5.5 Hz, 3H), 2.07 (t, J=2.6 Hz, 6H), 2.01-1.91 (m, 1H), 1.80-1.70 (m, 6H), 1.54 (d, J=2.7 Hz, 9H).

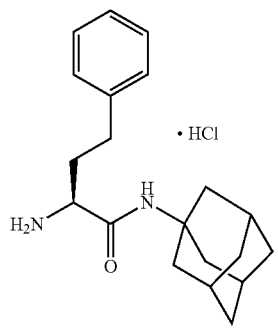 [SMILES: N[C@@H](CCc1ccccc1)C(=O)NC12CC3CC(CC(C3)C1)C2 ; "· HCl"]

(MM-2-116) Adamantyl amide MM-2-113 (54 mg, 0.131 mmol) was dissolved in 4 N HCl in dioxane (2.0 mL, approx. 61 equiv). After 3 hours, the stir bar was removed and the solvent was concentrated under an N$_2$ stream overnight (about 18 hours) to reveal 46 mg (99%) of ammonium salt as a white powder.

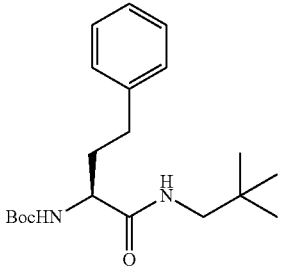 [SMILES: CC(C)(C)CNC(=O)[C@H](CCc1ccccc1)NC(=O)OC(C)(C)C]

(MM-2-111) Boc-HoPhe-OH (100 mg, 0.358 mmol), DEPBT (118 mg, 0.394 mmol, 1.10 equiv) and Et$_3$N (100 µL, 0.716 mmol, 2.00 equiv) were dissolved at room temperature in anhydrous THF (2 mL). After 15 min, neopentyl amine (46 µL, 0.394 mmol, 1.10 equiv) was added in one portion. After 12 hours, the mixture was diluted with EtOAc (15 mL) and washed with citric acid (10 mL, 10% w/v) and sat. NaHCO$_3$ (20 mL). The organic phase was dried over Na$_2$SO$_4$, filtered and concentrated. Flash chromatography (SiO$_2$, 20% EtOAc/hexanes) gave 85 mg (68%) of the neopentyl amide. $^1$H NMR (400 MHz, CDCl$_3$) δ 7.33-7.26 (m, 2H), 7.20 (td, J=7.6, 6.8 Hz, 3H), 6.25-6.09 (m, 1H), 5.02 (s, 1H), 4.05 (q, J=7.4 Hz, 1H), 3.06 (m, 2H), 2.70 (t, J=7.9 Hz, 2H), 2.19 (m, 1H), 1.92 (m, 1H), 1.46 (s, 9H), 0.91 (s, 9H).

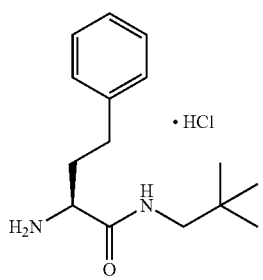 [SMILES: CC(C)(C)CNC(=O)[C@@H](N)CCc1ccccc1 ; "· HCl"]

(MM-2-115) Neopentyl amide MM-2-111 (46 mg, 0.132 mmol) was dissolved in 4 N HCl in dioxane (2.0 mL, approx. 60 equiv). After 3 hours, the stir bar was removed and the solvent was concentrated under an $N_2$ stream overnight (about 18 hours) to reveal 40 mg (99%) of ammonium salt as a white powder.

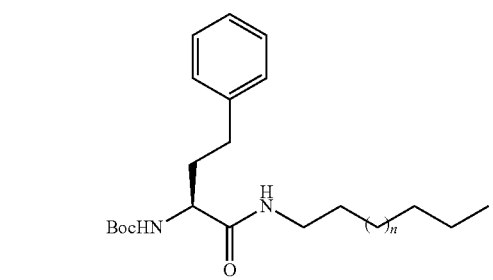

n = 1-5

(MM-2-109/150/151/152/154) Representative procedure for n-hexylamine: Boc-HoPhe-OH (100 mg, 0.358 mmol), n-hexylamine (47 µL, 0.358 mmol, 1.00 equiv), HOAt (54 mg, 0.394 mmol, 1.10 equiv) and 2,6-lutidine (208 µL, 1.79 mmol, 5.00 equiv) were dissolved at room temperature in anhydrous DMF (2 mL). EDCI.HCl (72 mg, 0.376 mmol, 1.05 equiv) was added, and the mixture stirred overnight. The mixture was diluted with EtOAc (20 mL) and washed with 0.1 N HCl (2×10 mL) and sat. aqueous NaCl (10 mL). The aqueous phase was extracted once with EtOAc (10 mL), and the combined organic phases were dried over $Na_2SO_4$, decanted and concentrated. Flash chromatography ($SiO_2$, 20% EtOAc/hexanes) returned 85 mg (65%) of the hexyl amide. By the same procedure, 122 mg (87%) of the n-octyl amide, 140 mg (94%) of the n-decyl amide, 148 mg (93%) of the n-dodecyl amide, and 156 mg (92%) of the n-tetradecyl amide were obtained. $^1$H NMR (MM-2-109, n=1, 500 MHz, CDCl$_3$) δ 7.31-7.24 (m, 2H), 7.21-7.15 (m, 3H), 6.47 (s, 1H), 5.36 (d, J=9.0 Hz, 1H), 4.23-4.01 (m, 1H), 3.34-3.13 (m, 2H), 2.68 (t, J=8.0 Hz, 2H), 2.22-2.05 (m, 1H), 1.94 (m, 1H), 1.46 (m, 2H), 1.46 (s, 9H), 1.37-1.22 (m, 6H), 0.89 (t, J=6.7 Hz, 3H).

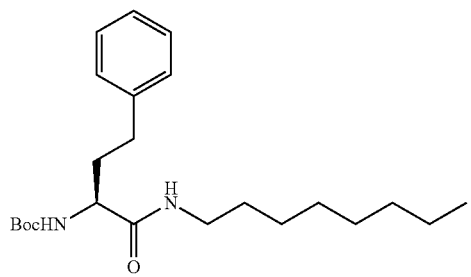 [SMILES: CCCCCCCCNC(=O)[C@H](CCc1ccccc1)NC(=O)OC(C)(C)C]

$^1$H NMR (MM-2-150, n=3, 500 MHz, CDCl$_3$) δ 7.32-7.25 (m, 2H), 7.23-7.16 (m, 3H), 6.04 (t, J=5.7 Hz, 1H), 5.05 (s, 1H), 4.04 (m, 1H), 3.24 (q, J=6.7 Hz, 2H), 2.68 (t, J=8.4 Hz, 2H), 2.15 (dq, J=7.1, 6.6 Hz, 1H), 1.93 (dt, J=12.9, 7.7 Hz, 1H), 1.53-1.47 (m, 2H), 1.45 (s, 9H), 1.29 (m, 10H), 0.88 (t, J=6.8 Hz, 3H).

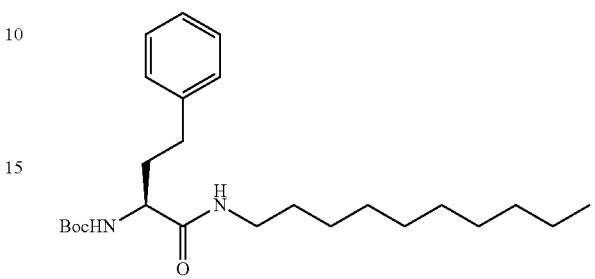

$^1$H NMR (MM-2-151, n=5, 500 MHz, CDCl$_3$) δ 7.31-7.26 (m, 2H), 7.22-7.16 (m, 3H), 6.03 (t, J=5.5 Hz, 1H), 5.06 (d, J=8.9 Hz, 1H), 4.04 (q, J=9.1 Hz, 1H), 3.24 (q, J=6.7 Hz, 2H), 2.68 (t, J=8.1 Hz, 2H), 2.15 (m, 1H), 1.92 (m, 1H), 1.52-1.47 (m, 2H), 1.45 (s, 9H), 1.34-1.21 (m, 14H), 0.88 (t, J=6.9 Hz, 3H).

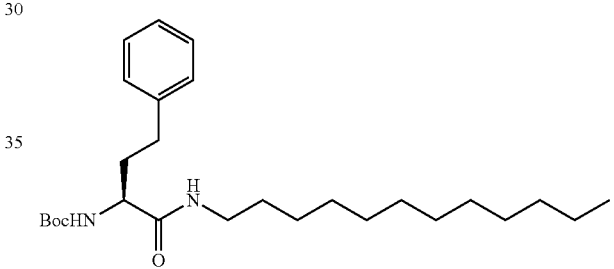

$^1$H NMR (MM-2-152, n=7, 500 MHz, CDCl$_3$) δ 7.31-7.26 (m, 2H), 7.22-7.16 (m, 3H), 6.07 (t, J=5.7 Hz, 1H), 5.07 (s, 1H), 4.04 (d, J=8.1 Hz, 1H), 3.24 (q, J=6.8 Hz, 2H), 2.72-2.61 (m, 2H), 2.24-2.07 (m, 1H), 1.92 (m, 1H), 1.49 (t, J=7.2 Hz, 2H), 1.45 (s, 9H), 1.27 (m, 18H), 0.89 (t, J=6.9 Hz, 3H).

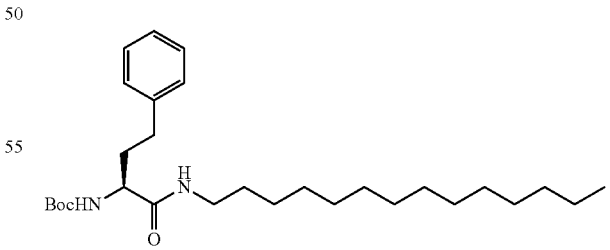

$^1$H NMR (MM-2-154, n=9, 500 MHz, CDCl$_3$) δ 7.31-7.27 (m, 2H), 7.22-7.16 (m, 3H), 6.05 (t, J=5.7 Hz, 1H), 5.06 (s, 1H), 4.04 (q, J=6.9 Hz, 1H), 3.24 (q, J=6.7 Hz, 2H), 2.68 (t, J=8.1 Hz, 2H), 2.15 (m, 1H), 1.92 (m, 1H), 1.48 (d, J=7.0 Hz, 2H), 1.45 (s, 9H), 1.34-1.22 (m, 22H), 0.89 (t, J=6.8 Hz, 3H).

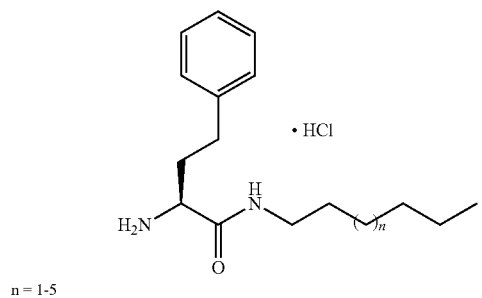

n = 1-5

(MM-2-114/153A-D) Representative procedure for n-hexyl amide: Hexyl amide MM-2-109 (72 mg, 0.199 mmol) was dissolved in 4 N HCl in dioxane (2.0 mL, approx. 40 equiv). After 3 hours, the stir bar was removed and the solvent was concentrated under an $N_2$ stream overnight (about 18 hours) to reveal 57 mg (97%) of amine HCl salt as a white powder. By the same procedure, 92 mg (90%) of the n-octyl amide, 107 mg (90%) of the n-decyl amide, 109 mg (86%) of the n-dodecyl amide, and 126 mg (93%) of the n-tetradecyl amide were obtained.

Preparation of Neoseptin-4 and its Intermediates/Analogues

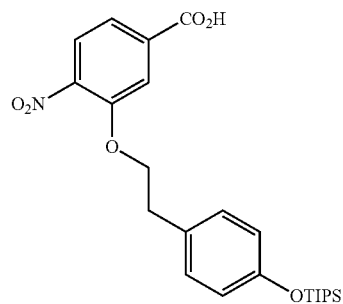

Sodium hydride (60%, 0.50 g, 12.4 mmol) was suspended in THF (10 mL) and 2-[4-(tri-isopropyl-silyloxy)phenyl]ethanol (0.67 mL, 6.48 mmol) was added dropwise at 0° C. The mixture was stirred at 0° C. for 15 minutes under an atmosphere of argon before 3-fluoro-4-nitrobenzoic acid (1.0 g, 5.4 mmol) was added. The mixture was stirred at 0° C. for 5 minutes and room temperature for 2 hours, quenched with saturated aqueous $NH_4Cl$, diluted with EtOAc, and extracted with aqueous HCl (0.1 M, ×2). The organic layer was collected, concentrated, and the product purified by flash chromatography ($SiO_2$, 3:2:0.1 hexanes/$Et_2O$/HOAc) to give the depicted Compound as a solid (1.26 g, 85%). $^1$H NMR (600 MHz, DMSO-$d_6$) δ 11.78 (s, 1H), 7.90 (d, J=8.3 Hz, 1H), 7.83 (d, J=6.1 Hz, 1H), 7.73 (dd, J=8.3, 1.6 Hz, 1H), 7.24 (d, J=8.5 Hz, 2H), 6.86 (d, J=8.5 Hz, 2H), 4.45 (t, J=6.7 Hz, 2H), 3.08 (t, J=6.7 Hz, 2H), 1.34-1.22 (m, 3H), 1.11 (d, J=7.2 Hz, 18H); MS-ESI (m/z) calcd for $[C_{24}H_{33}NO_6Si+Na]^+$ 482.1969. found: 482.1964.

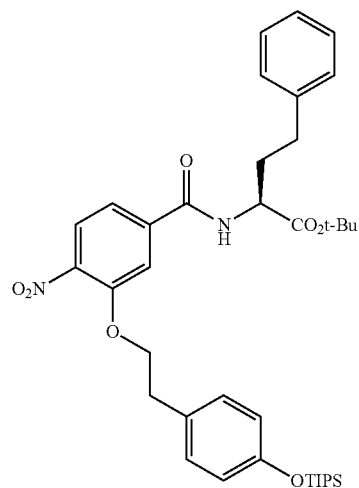

The above compound (95 mg, 0.30 mmol) was combined with HoPhe-OtBu (88 mg, 0.35 mmol) in DMF (0.75 mL) in a 0.5 dram vial. HOAt (61 mg, 0.45 mmol), EDCI (69 mg, 0.36 mmol), and 2,6-lutidine (0.17 mL, 1.5 mmol) were added. After stirring at room temperature for 12 hours, the reaction mixture was poured into aqueous 1 N HCl. The aqueous layer was extracted with EtOAc (2×). The combined ETOAc extract was washed with aqueous 1 N HCl, saturated aqueous $NaHCO_3$ and saturated aqueous NaCl, dried over $Na_2SO_4$, filtered and evaporated in vacuo. Flash chromatography ($SiO_2$) yielded pure product amide (90%). $^1$H NMR (600 MHz, DMSO-$d_6$) δ 7.80 (d, J=8.3 Hz, 1H), 7.50 (s, 1H), 7.30-7.21 (m, 6H), 7.12 (d, J=8.1 Hz, 2H), 6.85 (d, J=7.3 Hz, 2H), 4.74-4.50 (m, 1H), 4.30 (t, J=6.9 Hz, 2H), 3.10 (t, J=6.7 Hz, 2H), 2.80-2.72 (m, 2H), 2.40-2.26 (m, 1H), 2.20-2.11 (m, 1H), 1.50 (s, 9H), 1.30-1.24 (m, 3H), 1.09 (d, J=7.0 Hz, 18H); MS-ESI (m/z) calcd for $[C_{38}H_{52}N_2O_7Si+H]^+$ 677.3. found: 677.3.

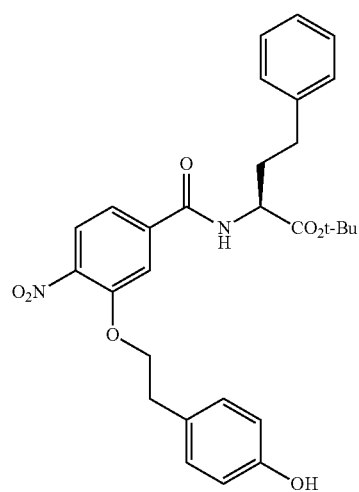 [SMILES: CC(C)(C)OC(=O)[C@H](CCc1ccccc1)NC(=O)c1ccc([N+](=O)[O-])c(OCCc2ccc(O)cc2)c1]

(MRS-2-477) The previous amide compound (250 mg, 350 mmol) was dissolved in anhydrous THF (8 mL) and treated with TBAF (0.43 mL, 1M solution in THF, 1.20 equiv). The reaction mixture was stirred at room temperature for 1 hour, and the solvent was removed in vacuo. Flash chromatography of the residue (25% EtOAc/hexanes)

afforded 166 mg (91%) of the phenolic product MRS-2-477. $^1$H NMR (600 MHz, DMSO-d$_6$) δ 7.82 (d, J=7.9 Hz, 1H), 7.50 (s, 1H), 7.40-7.11 (m, 8H), 6.85 (d, J=7.3 Hz, 2H), 5.40 (brs, 1H), 4.80-4.65 (m, 1H), 4.38 (t, J=7.0 Hz, 2H), 3.10 (t, J=6.7 Hz, 2H), 2.80-2.72 (m, 2H), 2.50-2.30 (m, 1H), 2.25-2.10 (m, 1H), 1.50 (s, 9H); MS-ESI (m/z) calcd for [C$_{29}$H$_{32}$N$_2$O$_7$+Na]$^+$ 543.2. found: 543.2.

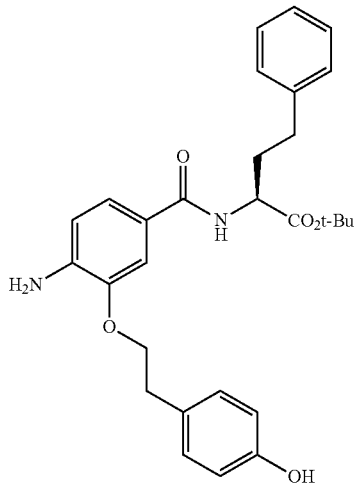

(MRS-2-481) Arylnitro Compound MRS-2-477 (120 mg, 0.23 mmol) was dissolved in acetone/saturated aqueous NH$_4$Cl (1:1, 5 mL each). Zn nanopowder (151 mg, 2.30 mmol, 10 equiv) was added portion-wise to the reaction mixture, which was stirred vigorously at room temperature for 1 hour. The heterogeneous mixture was filtered through Celite to remove the Zn salts, and the filtrate was diluted with EtOAc (50 mL) and washed with H$_2$O (50 mL). The organic phase was dried over Na$_2$SO$_4$, decanted and concentrated to give 113 mg (99%) of the aniline Compound 4 (Neoseptin-4). $^1$H NMR (600 MHz, DMSO-d$_6$) δ 9.30 (s, 1H), 8.20 (d, J=8.2 Hz, 1H), 7.50-7.30 (m, 7H), 7.20 (d, J=7.1 Hz, 2H), 6.65 (d, J=7.3 Hz, 2H), 5.25 (s, 2H), 4.80 (q, J=6.0 Hz, 1H), 4.18 (t, J=7.0 Hz, 2H), 3.00 (t, J=6.7 Hz, 2H), 2.70-2.65 (m, 1H), 2.55-2.50 (m, 1H), 2.10-2.00 (m, 2H), 1.49 (s, 9H); MS-ESI (m/z) calcd for [C$_{29}$H$_{34}$N$_2$O$_5$+H]$^+$ 491.2. found: 491.2.

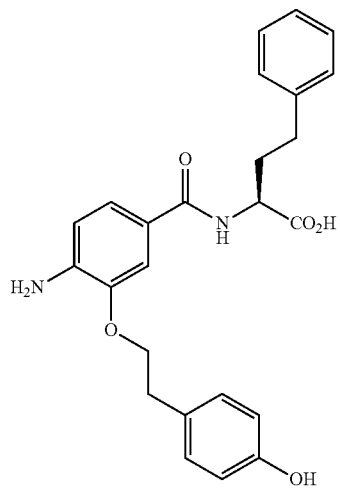 [SMILES: Nc1ccc(C(=O)N[C@@H](CCc2ccccc2)C(=O)O)cc1OCCc1ccc(O)cc1]

(MRS-2-491) MRS-2-481 (20 mg, 0.041 mmol) was dissolved in 4 N HCl/dioxane (1 mL), and the reaction medium was stirred for 8 hours. Solvent and excess HCl were evaporated under a stream of N$_2$ to reveal 17 mg (99%) of the carboxylic acid 5 MRS-2-491, which was not purified.

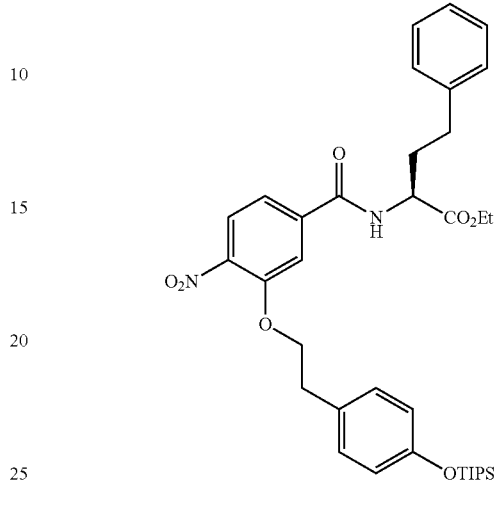

(MRS-3-23) The general procedure for amine coupling was followed: The above-depicted carboxylic acid (120 mg, 0.261 mmol), HoPhe-OEt (54 mg, 0.261 mmol, 1 equiv), 2,6-lutidine (0.91 mL, 0.783 mmol, 3 equiv), HOAt (43 mg, 0.313 mmol, 1.2 equiv) and EDCI.HCl (60 mg, 0.313 mmol, 1.2 equiv) were employed. Flash chromatography (25% EtOAc/hexanes) gave 150 mg (88%) of the coupled product MRS-3-23. $^1$H NMR (600 MHz, DMSO-d$_6$) δ 7.75 (d, J=8.1 Hz, 1H), 7.50 (s, 1H), 7.30-7.20 (m, 6H), 7.15 (d, J=8.1 Hz, 2H), 6.50 (d, J=7.3 Hz, 2H), 4.74-4.60 (m, 1H), 4.30-4.15 (m, 4H), 3.15 (t, J=6.7 Hz, 2H), 2.80-2.72 (m, 2H), 2.40-2.26 (m, 1H), 2.20-2.10 (m, 1H), 1.30-1.20 (m, 6H), 1.10 (d, J=7.2 Hz, 18H); MS-ESI (m/z) calcd for [C$_{36}$H$_{48}$N$_2$O$_7$Si+H]$^+$ 649.3. found: 649.3.

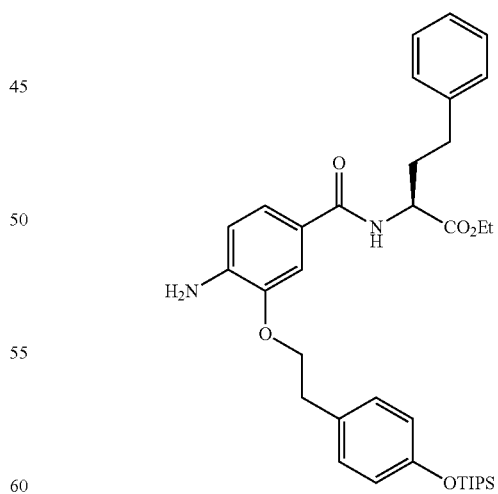

(MRS-3-29) The general procedure for zinc-nitro reduction was used: arylnitro MRS-3-23 (150 mg, 0.231 mmol), Zn nanopowder (150 mg, 2.31 mmol, 10 equiv) and acetone/saturated aqueous NH$_4$Cl (5 mL each) were employed to give 130 mg (86%) of aniline MRS-3-29, which was used without further purification.

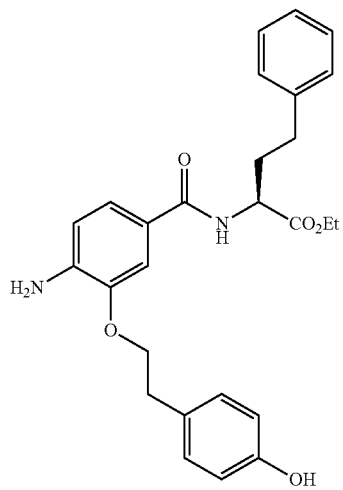 [SMILES: CCOC(=O)[C@H](CCc1ccccc1)NC(=O)c1ccc(N)c(OCCc2ccc(O)cc2)c1]

(MRS-3-37) TIPS-ether MRS-3-29 (120 mg, 0.19 mmol) was dissolved in anhydrous THF (3 mL) and treated with TBAF (0.39 mL, 0.39 mmol, 2 equiv). After stirring at room temperature for 1 hour, the mixture was diluted with EtOAc (20 mL) and washed with brine (20 mL). The organic phase was dried over $Na_2SO_4$, decanted and concentrated. Flash chromatography (50% EtOAc/hexanes) produced 76 mg (85%) of the phenolic product MRS-3-37. $^1$H NMR (600 MHz, DMSO-$d_6$) δ 9.25 (s, 1H), 8.40 (d, J=8.2 Hz, 1H), 7.50-7.30 (m, 7H), 7.20 (d, J=8.1 Hz, 2H), 6.50 (d, J=7.3 Hz, 2H), 5.30 (s, 2H), 4.45-4.30 (m, 1H), 4.20-4.05 (m, 4H), 2.95 (t, J=6.7 Hz, 2H), 2.80-2.60 (m, 2H), 2.00-1.90 (m, 2H), 1.20 (t, J=6.1 Hz, 3H); MS-ESI (m/z) calcd for $[C_{27}H_{30}N_2O_5+H]^+$ 463.2. found: 463.2.

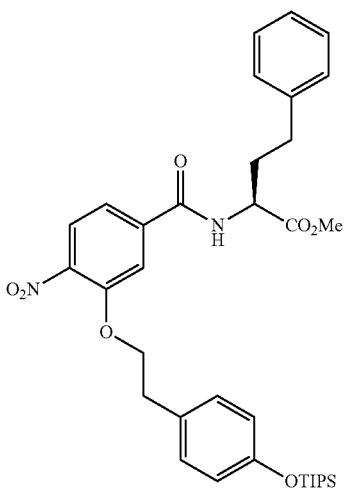

(MRS-3-31) The general procedure for amine coupling was followed: The above carboxylic acid (120 mg, 0.261 mmol), HoPhe-OMe (51 mg, 0.261 mmol, 1 equiv), 2,6-lutidine (0.91 mL, 0.783 mmol, 3 equiv), HOAt (43 mg, 0.313 mmol, 1.2 equiv) and EDCI.HCl (60 mg, 0.313 mmol, 1.2 equiv) were employed. Flash chromatography (25% EtOAc/hexanes) gave 129 mg (78%) of MRS-3-31. $^1$H NMR (600 MHz, DMSO-$d_6$) δ 7.80 (d, J=8.2 Hz, 1H), 7.50 (s, 1H), 7.40-7.20 (m, 6H), 7.15 (d, J=8.3 Hz, 2H), 6.60 (d, J=7.3 Hz, 2H), 4.74 (q, J=6.9 Hz, 1H), 4.45 (t, J=6.6 Hz, 2H), 3.86 (s, 3H), 3.15 (t, J=6.7 Hz, 2H), 2.72 (t, J=6.4 Hz, 2H), 2.45-2.40 (m, 1H), 2.20-2.10 (m, 1H), 1.40-1.20 (m, 3H), 1.10 (d, J=7.2 Hz, 18H); MS-ESI (m/z) calcd for $[C_{35}H_{46}N_2O_7Si+H]^+$ 635.3. found: 635.3.

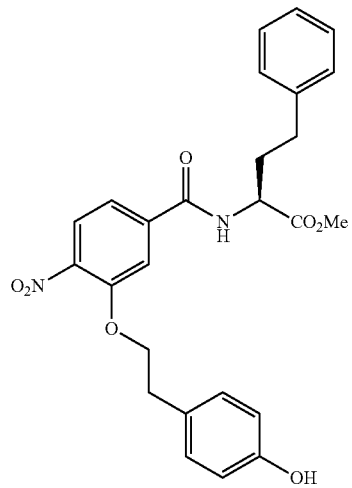 [SMILES: COC(=O)[C@H](CCc1ccccc1)NC(=O)c1ccc([N+](=O)[O-])c(OCCc2ccc(O)cc2)c1]

(MRS-3-45) TIPS-ether MRS-3-31 (123 mg, 0.19 mmol) was dissolved in anhydrous THF (3 mL) and treated with TBAF (0.39 mL, 0.39 mmol, 2 equiv). After stirring at room temperature for 1 hour, the mixture was diluted with EtOAc (20 mL) and washed with brine (20 mL). The organic phase was dried over $Na_2SO_4$, decanted and concentrated. The residue MRS-3-45 was used directly in the next step.

(MRS-3-45-II) The general procedure for zinc-nitro reduction was used: arylnitro MRS-3-45 (100 mg, 0.208 mmol), Zn nanopowder (137 mg, 2.08 mmol, 10 equiv) and acetone/saturated aqueous $NH_4Cl$ (5 mL each) were employed. Flash chromatography (50% EtOAC/hexanes) gave 130 mg (86%, 2 steps) of MRS-3-45-II. $^1$H NMR (600 MHz, DMSO-$d_6$) δ 9.15 (s, 1H), 8.40 (d, J=8.2 Hz, 1H), 7.40-7.15 (m, 7H), 7.10 (d, J=8.2 Hz, 2H), 6.65 (d, J=7.3 Hz, 2H), 5.20 (s, 2H), 4.25 (q, J=6.2 Hz, 1H), 4.10 (t, J=6.9 Hz, 2H), 3.60 (s, 3H), 2.95 (t, J=6.7 Hz, 2H), 2.75-2.70 (m, 1H), 2.60-2.50 (m, 2H); MS-ESI (m/z) calcd for $[C_{26}H_{28}N_2O_5+H]^+$ 449.2. found: 449.2.

J=6.4 Hz, 2H), 2.95 (t, J=6.7 Hz, 2H), 2.85-2.70 (m, 1H), 2.62-2.40 (m, 1H), 2.00-1.85 (m, 2H), 1.14-1.10 (m, 6H); MS-ESI (m/z) calcd for $[C_{28}H_{32}N_2O_5+H]^+$ 477.2. found: 477.2.

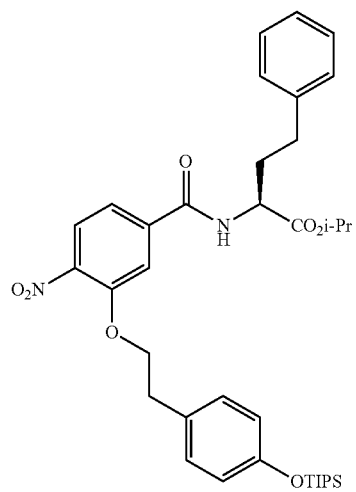

(MRS-3-121) The general procedure for amine coupling was followed: the above carboxylic acid (145 mg, 0.316 mmol), HoPhe-Oi-Pr (70 mg, 0.316 mmol, 1 equiv), 2,6-lutidine (0.110 mL, 0.95 mmol, 3 equiv), HOAt (52 mg, 0.380 mmol, 1.2 equiv) and EDCI.HCl (73 mg, 0.380 mmol, 1.2 equiv) were employed. Flash chromatography (25% EtOAc/hexanes) gave 130 mg (62%) of the coupled product MRS-3-121. $^1$H NMR (600 MHz, DMSO-d$_6$) δ 8.20 (d, J=8.5 Hz, 1H), 7.45 (s, 1H), 7.30-7.20 (m, 6H), 7.10 (d, J=8.3 Hz, 2H), 6.62 (d, J=7.4 Hz, 2H), 4.75 (q, J=6.6 Hz, 1H), 4.40-4.30 (m, 1H), 4.10 (t, J=6.5 Hz, 2H), 2.90 (t, J=6.7 Hz, 2H), 2.80-2.70 (m, 1H), 2.60-2.40 (m, 1H), 2.00-1.95 (m, 2H), 1.30-1.20 (m, 9H), 1.10 (d, J=7.1 Hz, 18H); MS-ESI (m/z) calcd for $[C_{37}H_{50}N_2O_7Si+H]^+$ 663.3. found: 663.3.

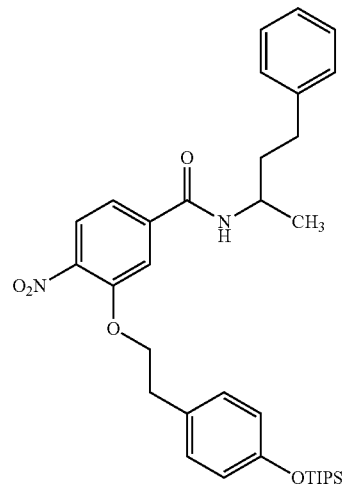

(MRS-3-25) The general procedure for amine coupling was followed: the above carboxylic acid Compound 1 (120 mg, 0.261 mmol), 1-methyl-3-phenylpropylamine (39 mg, 0.261 mmol, 1 equiv), 2,6-lutidine (0.084 mL, 0.783 mmol, 3 equiv), HOAt (43 mg, 0.313 mmol, 1.2 equiv) and EDCI.HCl (60 mg, 0.313 mmol, 1.2 equiv) were employed. Flash chromatography (25% EtOAc/hexanes) gave 126 mg (82%) of MRS-3-25. $^1$H NMR (600 MHz, DMSO-d$_6$) δ 7.76 (d, J=8.2 Hz, 1H), 7.50 (s, 1H), 7.30-7.20 (m, 6H), 7.10 (d, J=8.3 Hz, 2H), 6.80 (d, J=7.4 Hz, 2H), 4.30-4.20 (m, 3H), 3.05 (t, J=6.4 Hz, 2H), 2.80-2.70 (m, 2H), 2.00-1.95 (m, 2H), 1.30 (d, J=6.2 Hz, 3H), 1.20-1.10 (m, 3H), 1.09 (d, J=7.2 Hz, 18H); MS-ESI (m/z) calcd for $[C_{34}H_{46}N_2O_5Si+H]^+$ 591.3. found: 591.3.

(MRS-3-153) The general procedures for TBAF deprotection and Zn nitro reduction were employed: Isopropyl ester MRS-3-121 (120 mg, 0.181 mmol), TBAF (0.105 mL, 2 equiv, 1 M in THF), Zn nanopowder (181 mg, 2.76 mmol, 10 equiv). Flash chromatography (50% EtOAc/hexanes) produced 80 mg (93%) of MRS-3-153. $^1$H NMR (600 MHz, DMSO-d$_6$) δ 8.35 (d, J=8.1 Hz, 1H), 7.40 (s, 1H), 7.35-7.20 (m, 6H), 7.12 (d, J=8.4 Hz, 2H), 6.70 (d, J=7.4 Hz, 2H), 5.25 (s, 2H), 4.80 (q, J=6.8 Hz, 1H), 4.50-4.40 (m, 1H), 4.15 (t, (MRS-3-39) The general procedures for TBAF deprotection and Zn nitro reduction were employed: Amide MRS-3-25 (120 mg, 0.203 mmol), TBAF (0.106 mL, 2 equiv, 1 M in THF), Zn nanopowder (120 mg, 1.84 mmol, 10 equiv). Flash chromatography (50% EtOAc/hexanes) produced 51 mg (62%) of aniline MRS-3-39. $^1$H NMR (600 MHz, DMSO-d$_6$) δ 9.20 (s, 1H), 7.90 (d, J=8.4 Hz, 1H), 7.30-7.20 (m, 7H), 7.15 (d, J=8.1 Hz, 2H), 6.69 (d, J=7.4 Hz, 2H), 5.10 (s, 2H), 4.10 (t, J=6.8 Hz, 2H), 3.95-3.70 (m, 1H), 2.95 (t, J=6.7 Hz, 2H), 2.55-2.45 (m, 2H), 1.80-1.60 (m, 2H), 1.10 (d, J=6.2 Hz 3H); MS-ESI (m/z) calcd for [C$_{25}$H$_{28}$N$_2$O$_3$+H]$^+$ 405.2. found: 405.2.

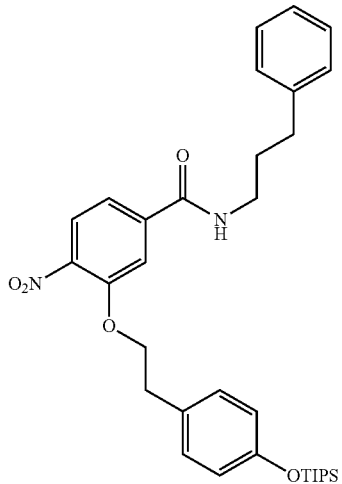

(MRS-3-27) The general procedure for amine coupling was followed: the above carboxylic acid Compound 1 (120 mg, 0.261 mmol), 3-phenylpropylamine (35 mg, 0.261 mmol, 1 equiv), 2,6-lutidine (0.084 mL, 0.783 mmol, 3 equiv), HOAt (43 mg, 0.313 mmol, 1.2 equiv) and EDCI.HCl (60 mg, 0.313 mmol, 1.2 equiv) were employed. Flash chromatography (20% EtOAc/hexanes) gave 119 mg (79%) of MRS-3-27.

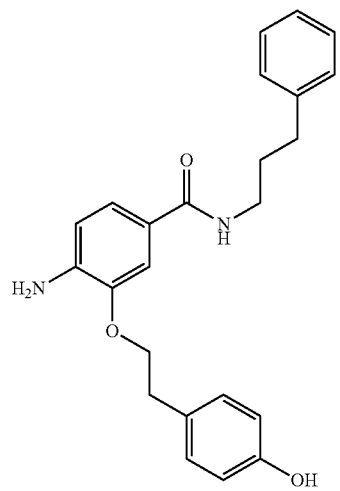 [SMILES: Nc1ccc(C(=O)NCCCc2ccccc2)cc1OCCc1ccc(O)cc1]

(MRS-3-41) The general procedures for TBAF deprotection and Zn nitro reduction were employed: Amide MRS-3-27 (100 mg, 0.173 mmol), TBAF (0.90 mL, 2 equiv, 1 M in THF), Zn nanopowder (124 mg, 1.90 mmol, 10 equiv). Flash chromatography (50% EtOAc/hexanes) produced 39 mg (58%) of MRS-3-41. $^1$H NMR (600 MHz, DMSO-d$_6$) δ 9.25 (s, 1H), 8.05 (d, J=8.1 Hz, 1H), 7.30-7.20 (m, 7H), 7.15 (d, J=6.8 Hz, 2H), 6.70 (d, J=7.4 Hz, 2H), 5.10 (s, 2H), 4.10 (t, J=6.4 Hz, 2H), 3.20-3.15 (m, 2H), 2.90 (t, J=6.7 Hz, 2H), 2.60 (t, J=6.4 Hz, 2H), 1.80-1.70 (m, 2H); MS-ESI (m/z) calcd for [C$_{24}$H$_{26}$N$_2$O$_3$+H]$^+$ 391.2. found: 391.2.

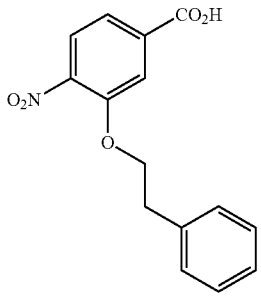 [SMILES: O=C(O)c1ccc([N+](=O)[O-])c(OCCc2ccccc2)c1]

(MRS-3-17) Sodium hydride (60%, 0.150 g, 6.22 mmol) was suspended in THF (10 mL) and 2-phenylethanol (0.317 g, 2.59 mmol) was added drop-wise at 0° C. The mixture was stirred at 0° C. for 15 minutes under an atmosphere of argon before 3-fluoro-4-nitrobenzoic acid (0.400 g, 2.16 mmol) was added. The mixture was stirred at 0° C. for 5 minutes and room temperature for 2 hours, quenched with saturated aqueous NH$_4$Cl, diluted with EtOAc, and extracted with aqueous HCl (0.1 M, ×2). The organic layer was collected, concentrated, and the product purified by flash chromatography (SiO$_2$, 3:2:0.1 hexanes/Et$_2$O/HOAc) to give MRS-3-17 as a solid (0.428 g, 69%).

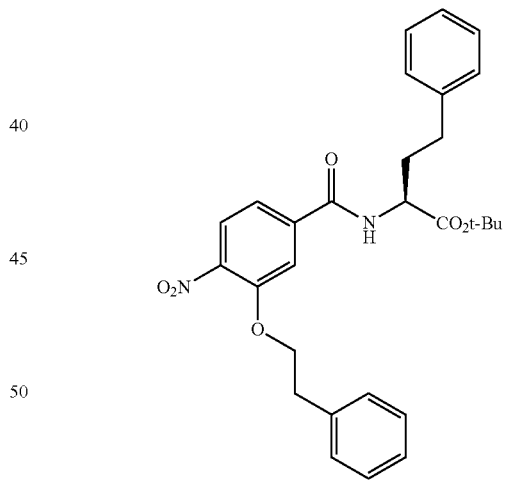

(MRS-3-33) The general procedure for amine coupling was followed: carboxylic acid MRS-3-17 (100 mg, 0.348 mmol), HoPhe-OtBu (82 mg, 0.348 mmol, 1 equiv), 2,6-lutidine (0.120 mL, 1.04 mmol, 3 equiv), HOAt (57 mg, 0.417 mmol, 1.2 equiv) and EDCI.HCl (80 mg, 0.417 mmol, 1.2 equiv) were employed. Flash chromatography (25% EtOAc/hexanes) gave 148 mg (84%) of MRS-3-33. $^1$H NMR (600 MHz, DMSO-d$_6$) δ 7.75 (d, J=7.9 Hz, 1H), 7.50 (s, 1H), 7.40-7.11 (m, 11H), 4.80-4.65 (m, 1H), 4.38 (t, J=7.0 Hz, 2H), 3.10 (t, J=6.7 Hz, 2H), 2.60-2.52 (m, 2H), 2.40-2.30 (m, 1H), 2.20-2.10 (m, 1H), 1.50 (s, 9H); MS-ESI (m/z) calcd for [C$_{29}$H$_{32}$N$_2$O$_6$+H]$^+$ 505.2. found: 505.2.

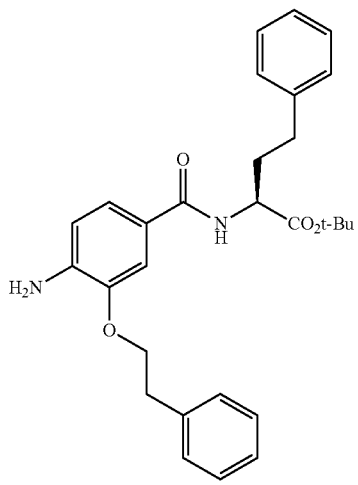 [SMILES: CC(C)(C)OC(=O)[C@H](CCc1ccccc1)NC(=O)c1ccc([N+](=O)[O-])c(OCCc2ccccc2)c1]

(MRS-3-47) The general procedure for zinc-nitro reduction was used: arylnitro MRS-3-33 (80 mg, 0.173 mmol), Zn nanopowder (113 mg, 1.73 mmol, 10 equiv) and acetone/saturated aqueous NH$_4$Cl (5 mL each) were employed. Flash chromatography (25% EtOAC/hexanes) gave 58 mg (71%, 2 steps) of aniline MRS-3-47. $^1$H NMR (600 MHz, DMSO-d$_6$) δ 8.20 (d, J=8.2 Hz, 1H), 7.40-7.15 (m, 12H), 5.20 (s, 2H), 4.25 (q, J=6.0 Hz, 1H), 4.18 (t, J=7.0 Hz, 2H), 3.10 (t, J=6.7 Hz, 2H), 2.70-2.62 (m, 1H), 2.60-2.55 (m, 1H), 2.10-2.00 (m, 2H), 1.45 (s, 9H); MS-ESI (m/z) calcd for [C$_{29}$H$_{34}$N$_2$O$_4$+H]$^+$ 475.2. found: 475.2.

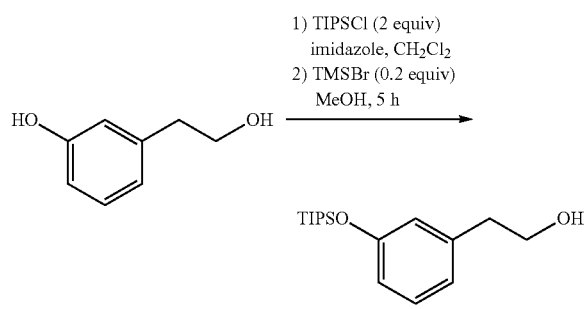

The above two-step synthesis is described in Shah et al., *Org Biomol Chem* 6:2168-2172 (2008).

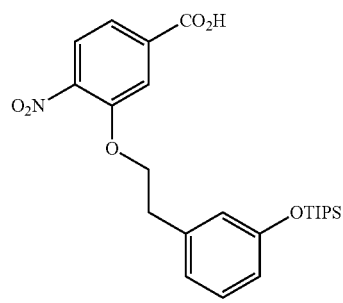

(MRS-3-93) Sodium hydride (60%, 0.124 g, 2.59 mmol) was suspended in THF (5 mL) and 2-(3-(((triisopropylsilyl)oxy)phenyl)ethanol (0.382 g, 1.29 mmol) was added dropwise at 0° C. The mixture was stirred at 0° C. for 15 minutes under an atmosphere of argon before 3-fluoro-4-nitrobenzoic acid (0.200 g, 1.08 mmol) was added. The mixture was stirred at 0° C. for 5 minutes and room temperature for 2 hours, quenched with saturated aqueous NH$_4$Cl, diluted with EtOAc, and extracted with aqueous HCl (0.1 M, ×2). The organic layer was collected, concentrated, and the product purified by flash chromatography (SiO$_2$, 3:1:0.1 hexanes/Et$_2$O/HOAc) to give MRS-3-93 as a solid (0.421 g, 85%).

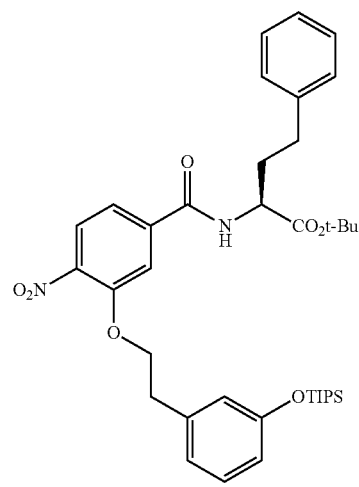

(MRS-3-99) The general procedure for amine coupling was followed: carboxylic acid MRS-3-93 (230 mg, 0.500 mmol), HoPhe-OtBu (114 mg, 0.500 mmol, 1 equiv), 2,6-lutidine (0.170 mL, 1.49 mmol, 3 equiv), HOAt (81 mg, 0.599 mmol, 1.2 equiv) and EDCI.HCl (114 mg, 0.599 mmol, 1.2 equiv) were employed. Flash chromatography (25% EtOAc/hexanes) gave 337 mg (99%) of MRS-3-99. $^1$H NMR (600 MHz, DMSO-d$_6$) δ 7.90 (d, J=8.2 Hz, 1H), 7.55 (s, 1H), 7.40-7.35 (m, 5H), 7.20 (d, J=8.1 Hz, 1H), 6.95 (d, J=7.4 Hz, 1H), 6.90 (s, 1H), 6.85-6.80 (m, 1H), 6.75 (d, J=6.6 Hz, 1H), 4.80 (q, J=6.9 Hz, 1H), 4.40 (t, J=6.9 Hz, 2H), 3.20 (t, J=6.8 Hz, 2H), 2.80-2.70 (m, 2H), 2.45-2.35 (m, 1H), 2.23-2.11 (m, 1H), 1.60 (s, 9H), 1.40-1.24 (m, 3H), 1.15 (d, J=7.0 Hz, 18H); MS-ESI (m/z) calcd for [C$_{38}$H$_{52}$N$_2$O$_7$Si+H]$^+$ 677.3. found: 677.3.

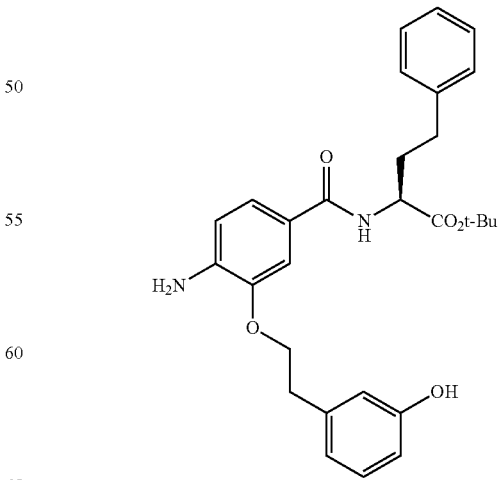

(MRS-3-113) The general procedures for TBAF deprotection and Zn nitro reduction were employed: Amide MRS- 3-99 (200 mg, 0.295 mmol), TBAF (0.590 mL, 2 equiv, 1 M in THF), Zn nanopowder (193 mg, 2.95 mmol, approx 10 equiv). Flash chromatography (50% EtOAc/hexanes) produced 99 mg (68%) of MRS-3-113. $^1$H NMR (600 MHz, DMSO-$d_6$) δ 9.40 (s, 1H), 8.20 (d, J=8.2 Hz, 1H), 7.40-7.20 (m, 7H), 6.75-6.70 (m, 2H), 6.62-6.55 (m, 2H), 5.25 (s, 2H), 4.45 (q, J=6.2 Hz, 1H), 4.20 (t, J=7.2 Hz, 2H), 3.00 (t, J=6.7 Hz, 2H), 2.70-2.60 (m, 1H), 2.55-2.50 (m, 1H), 2.00-1.95 (m, 2H), 1.49 (s, 9H); MS-ESI (m/z) calcd for $[C_{29}H_{34}N_2O_5+H]^+$ 491.2. found: 491.2.

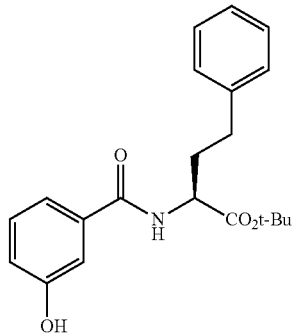 [SMILES: CC(C)(C)OC(=O)[C@H](CCc1ccccc1)NC(=O)c1cccc(O)c1]

(MRS-3-35) The general procedure for amine coupling was followed: 3-hydroxybenzoic acid (47 mg, 0.348 mmol), HoPhe-OtBu (82 mg, 0.348 mmol, 1 equiv), 2,6-lutidine (0.120 mL, 1.04 mmol, 3 equiv), HOAt (57 mg, 0.417 mmol, 1.2 equiv) and EDCl.HCl (80 mg, 0.417 mmol, 1.2 equiv) were employed. Flash chromatography (30% EtOAc/hexanes) gave 100 mg (81%) of phenol MRS-3-35.

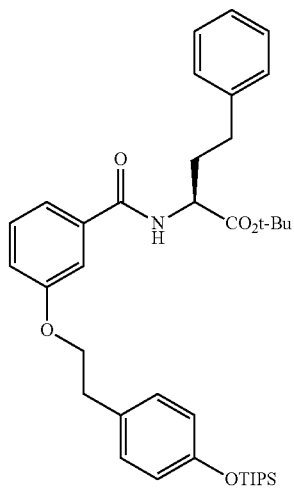

(MRS-3-89) Phenol MRS-3-35 (540 mg, 1.51 mmol) and alkyl bromide MM-1-73 (651 mg, 1.82 mmol, 1.20 equiv) were dissolved in acetone (10 mL) at room temperature. $K_2CO_3$ (628 mg, 4.55 mmol, 3 equiv) was added, and the mixture was heating at reflux for 24 hours. The reaction mixture was cooled to room temperature, filtered, and concentrated. Flash chromatography (25% EtOAc/hexanes) provided 365 mg (38%) of ether MRS-3-89. $^1$H NMR (600 MHz, DMSO-$d_6$) δ 7.40-7.20 (m, 9H), 7.10 (d, J=6.9 Hz, 2H), 6.80 (d, J=6.6 Hz, 2H), 4.70 (q, J=6.4 Hz, 1H), 4.18 (t, J=7.2 Hz, 2H), 3.05 (t, J=6.7 Hz, 2H), 2.80-2.60 (m, 2H), 2.30-2.20 (m, 1H), 2.10-2.00 (m, 1H), 1.50 (s, 9H), 1.30-1.20 (m, 3H), 1.10 (d, J=6.4 Hz, 18H); MS-ESI (m/z) calcd for $[C_{38}H_{53}NO_5Si+H]^+$ 632.2. found: 632.2.

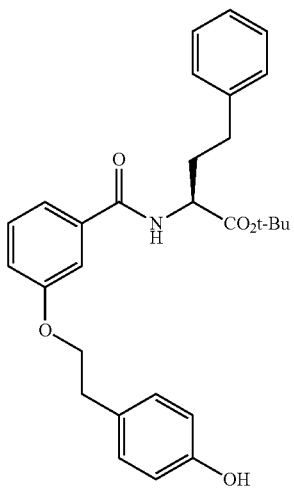 [SMILES: CC(C)(C)OC(=O)[C@H](CCc1ccccc1)NC(=O)c1cccc(OCCc2ccc(O)cc2)c1]

(MRS-3-95) Ether MRS-3-89 (150 mg, 0.237 mmol) was dissolved in THF (1 mL). TBAF (0.474 mL, 2 equiv, 1 M in THF) was added, and the mixture was stirred for 1 hour. After removal of the solvent, flash chromatography (25% EtOAc/hexanes) gave 80 mg (71%) of phenol MRS-3-95. $^1$H NMR (600 MHz, DMSO-$d_6$) δ 7.40-7.10 (m, 11H), 6.68 (d, J=6.4 Hz, 2H), 4.20 (q, J=6.4 Hz, 1H), 4.18 (t, J=6.9 Hz, 2H), 2.90 (t, J=6.9 Hz, 2H), 2.70-2.65 (m, 1H), 2.60-2.55 (m, 1H), 2.10-2.00 (m, 2H), 1.39 (s, 9H); MS-ESI (m/z) calcd for $[C_{29}H_{33}NO_5+H]^+$ 476.2. found: 476.2.

General Procedure for Preparation of 3-halo-(4-((triisopropylsilyl)oxy)phenyl)ethanols

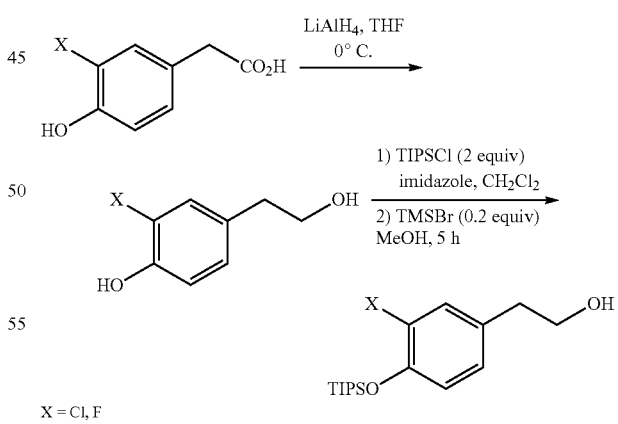

X = Cl, F

The Cl and F substituted phenols were prepared by the above sequence from commercially available benzoic acids. The LAH reduction was as described in Bubert et al., *Chem Med Chem*, 3:1708-1730 (2008). The double TIPS protection/selective mono-deprotection steps are as described in Shah et al., *J. Org. Biomol. Chem.* 6:2168-2172 (2008).

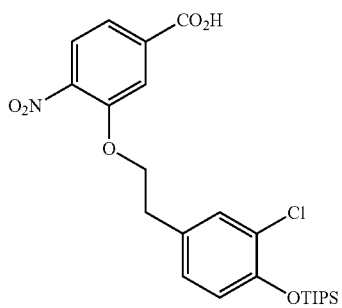

(MRS-3-105) Sodium hydride (60%, 0.109 g, 4.53 mmol) was suspended in THF (5 mL) and 2-(3-chloro-4-(triisopropylsiloxy)phenyl)ethanol (0.747 g, 2.26 mmol) was added drop-wise at 0° C. The mixture was stirred at 0° C. for 15 minutes under an atmosphere of argon before 3-fluoro-4-nitrobenzoic acid (0.350 g, 1.89 mmol) was added. The mixture was stirred at 0° C. for 5 minutes and room temperature for 2 hours, quenched with saturated aqueous NH$_4$Cl, diluted with EtOAc, and extracted with aqueous HCl (0.1 M, ×2). The organic layer was collected, concentrated, and the product purified by flash chromatography (SiO$_2$, 3:1:0.1 EtOAc/hexanes/HOAc) to give MRS-3-105 as a solid (0.747 g, 80%).

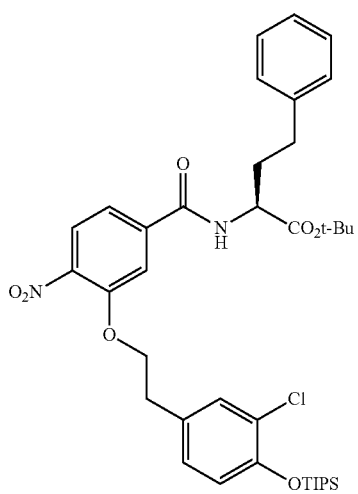

(MRS-3-109) The general procedure for amine coupling was followed: carboxylic acid MRS-3-105 (247 mg, 0.500 mmol), HoPhe-OtBu (117 mg, 0.500 mmol, 1 equiv), 2,6-lutidine (0.170 mL, 1.49 mmol, 3 equiv), HOAt (81 mg, 0.599 mmol, 1.2 equiv) and EDCI.HCl (114 mg, 0.599 mmol, 1.2 equiv) were employed. Flash chromatography (25% EtOAc/hexanes) gave 352 mg (99%) of MRS-3-109. $^1$H NMR (600 MHz, DMSO-d$_6$) δ 8.10 (d, J=6.9 Hz, 1H), 7.50-7.20 (m, 8H), 6.80 (d, J=8.1 Hz, 1H), 6.60 (d, J=7.4 Hz, 1H), 4.80 (q, J=6.9 Hz, 1H), 3.70 (t, J=6.4 Hz, 2H), 2.60 (t, J=6.8 Hz, 2H), 2.55-2.50 (m, 2H), 2.45-2.35 (m, 1H), 2.23-2.11 (m, 1H), 1.50 (s, 9H), 1.40-1.24 (m, 3H), 1.15 (d, J=6.9 Hz, 18H); MS-ESI (m/z) calcd for [C$_{38}$H$_{51}$ClN$_2$O$_7$Si+H]$^+$ 711.2. found: 711.3.

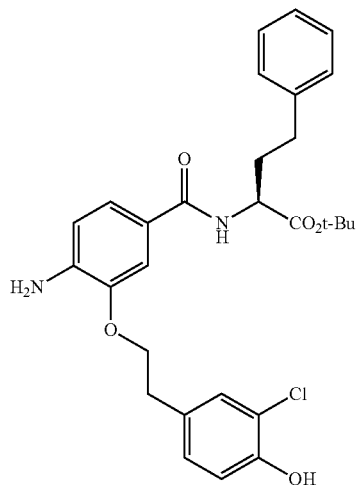

(MRS-3-133) The general procedures for TBAF deprotection and Zn nitro reduction were employed: Amide MRS-3-109 (350 mg, 0.482 mmol), TBAF (1.00 mL, 2 equiv, 1 M in THF), Zn nanopowder (297 mg, 4.54 mmol, approx 10 equiv). Flash chromatography (50% EtOAc/hexanes) produced 200 mg (78%, 2 steps) of MRS-3-105. $^1$H NMR (600 MHz, DMSO-d$_6$) δ 8.30 (d, J=8.2 Hz, 1H), 7.55 (d, J=6.8 Hz, 1H), 7.43 (s, 1H), 7.35-7.25 (m, 6H), 6.75 (d, J=6.2. Hz, 1H), 6.55 (d, J=6.6 Hz, 1H), 5.57 (s, 2H), 4.25 (q, J=6.4 Hz, 1H), 3.60 (t, J=6.7 Hz, 2H), 2.70-2.60 (m, 4H), 2.00-1.95 (m, 2H), 1.49 (s, 9H); MS-ESI (m/z) calcd for [C$_{29}$H$_{33}$ClN$_2$O$_5$+H]$^+$ 525.2. found: 525.2.

(MRS-3-111) Sodium hydride (60%, 0.037 g, 1.55 mmol) was suspended in THF (4 mL) and 2-(3-fluoro-4-(triisopropylsiloxy)phenyl)ethanol (0.243 g, 0.77 mmol) was added dropwise at 0° C. The mixture was stirred at 0° C. for 15 minutes under an atmosphere of argon before 3-fluoro-4-nitrobenzoic acid (0.120 g, 0.65 mmol) was added. The mixture was stirred at 0° C. for 5 minutes and room temperature for 2 hours, quenched with saturated aqueous NH$_4$Cl, diluted with EtOAc, and extracted with aqueous HCl (0.1 M, ×2). The organic layer was collected, concentrated, and the product purified by flash chromatography (SiO$_2$, 3:1:0.1 EtOAc/hexanes/HOAc) to give MRS-3-111 as a solid (0.238 g, 77%).

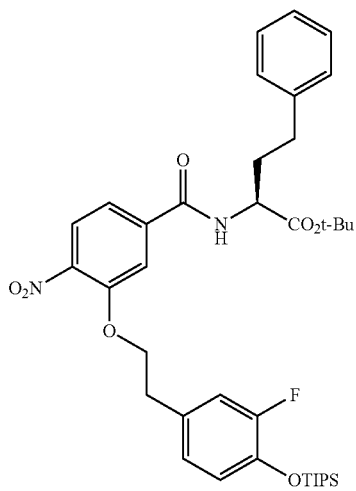

(MRS-3-117) The general procedure for amine coupling was followed: carboxylic acid MRS-3-111 (238 mg, 0.498 mmol), HoPhe-OtBu (117 mg, 0.500 mmol, 1 equiv), 2,6-lutidine (0.170 mL, 1.49 mmol, 3 equiv), HOAt (81 mg, 0.599 mmol, 1.2 equiv) and EDCI.HCl (114 mg, 0.599 mmol, 1.2 equiv) were employed. Flash chromatography (25% EtOAc/hexanes) gave 250 mg (72%) of MRS-3-117. $^1$H NMR (600 MHz, DMSO-$d_6$) δ 7.90 (d, J=8.1 Hz, 1H), 7.60 (s, $^1$H), 7.45-7.20 (m, 7H), 6.90 (d, J=8.2 Hz, 1H), 6.60 (d, J=7.4 Hz, 1H), 4.55 (q, J=6.4 Hz, 1H), 4.45 (t, J=6.3 Hz, 2H), 3.20 (t, J=6.4 Hz, 2H), 2.70-2.60 (m, 2H), 2.40-2.35 (m, 1H), 2.30-2.18 (m, 1H), 1.52 (s, 9H), 1.35-1.25 (m, 3H), 1.10 (d, J=6.2 Hz, 18H); MS-ESI (m/z) calcd for $[C_{38}H_{51}FN_2O_7Si+H]^+$ 694.3. found: 694.3.

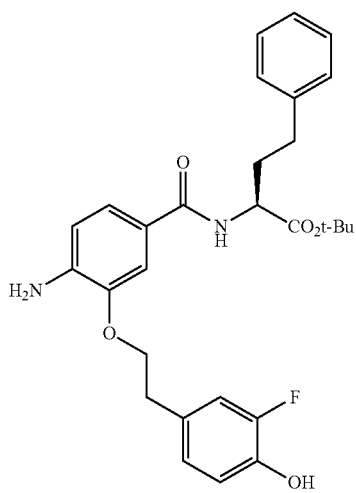

(MRS-3-137) The general procedures for TBAF deprotection and Zn nitro reduction were employed: Amide MRS-3-117 (250 mg, 0.359 mmol), TBAF (0.720 mL, 2 equiv, 1 M in THF), Zn nanopowder (300 mg, 4.58 mmol, approx 13 equiv). Flash chromatography (50% EtOAc/hexanes) produced 132 mg (72%, 2 steps) of aniline MRS-3-137. $^1$H NMR (600 MHz, DMSO-$d_6$) δ 9.55 (s, 1H), 8.25 (d, J=8.1 Hz, 1H), 7.45-7.15 (m, 8H), 6.85 (d, J=6.9. Hz, 1H), 6.65 (d, J=7.1 Hz, 1H), 5.20 (s, 2H), 4.20 (q, J=6.9 Hz, 1H), 4.15 (t, J=6.1 Hz, 2H), 2.90 (t, J=6.7 Hz, 2H), 2.75-2.70 (m, 1H), 2.62-2.58 (m, 1H), 2.00-1.95 (m, 2H), 1.40 (s, 9H); MS-ESI (m/z) calcd for $[C_{29}H_{33}FN_2O_5+H]^+$ 509.2. found: 509.2.

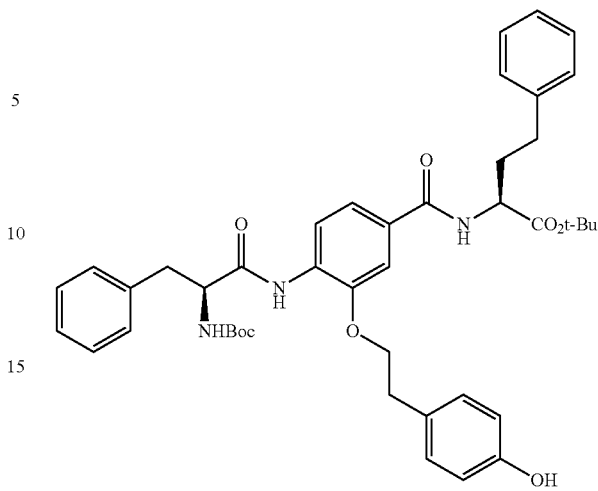

(MM-1-315) TIPS-Neoseptin-4 (200 mg, 0.309 mmol), HOAt (46 mg, 0.340 mmol, 1.1 equiv) and Boc-Phe-OH (82 mg, 0.309 mmol, 1.0 equiv) were dissolved in anhydrous DMF (1.5 mL). 2,6-Lutidine (0.144 mL, 1.24 mmol, 4.0 equiv) was added. Upon dissolution of the reagents, EDCI.HCl (62 mg, 0.325 mmol, 1.05 equiv) was added, and the mixture was stirred 48 hours. After dilution with EtOAc (10 mL), the mixture was washed with 1 N HCl (5 mL), saturated NaHCO$_3$ (5 mL) and brine (5 mL). The organic phase was dried over Na$_2$SO$_4$, decanted and concentrated. The resulting residue was redissolved in anhydrous THF (2 mL) and TBAF (1.0 mL, 3.0 equiv, 1 M in THF) was added drop-wise at room temperature. After 30 minutes, H$_2$O (10 mL) was added, and the mixture was diluted with EtOAc (10 mL). The aqueous phase was extracted once with EtOAc (10 mL), and the combined organic phases were dried over Na$_2$SO$_4$, decanted and concentrated. Flash chromatography (40% EtOAc/hexanes) gave 192 mg (89%) of the amide MM-1-315. $^1$H NMR (600 MHz, DMSO-$d_6$) δ 8.45 (d, J=8.4 Hz, 1H), 7.50 (s, 1H), 7.40-7.20 (m, 11H), 7.10 (d, J=7.2 Hz, 2H), 6.65 (d, J=7.1 Hz, 2H), 4.55 (q, J=6.1 Hz, 1H), 4.50-4.45 (m, 1H), 4.15 (t, J=6.4 Hz, 2H), 3.00 (t, J=6.4 Hz, 2H), 2.70-2.60 (m, 4H), 2.35-2.25 (m, 1H), 2.15-2.00 (m, 1H), 1.50 (s, 9H), 1.45 (s, 9H); MS-ESI (m/z) calcd for $[C_{43}H_{51}N_3O_8+H]^+$ 737.3. found: 738.3.

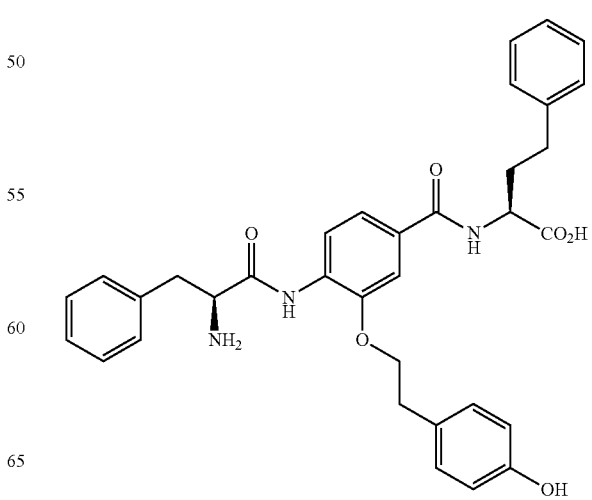

(Neoseptin-1) Compound MM-1-315 (78 mg, 0.112 mmol) was dissolved in 4 N HCl/dioxane (1 mL, 4.00 mmol, approx. 36 equiv). The mixture was stirred for 6 hours, after which the solvent and excess HCl were evaporated under an $N_2$ stream to reveal 65 mg (99%) of Neoseptin-1 as the HCl salt.

Each of the patents, patent applications and articles cited herein is incorporated by reference.

The foregoing description and the examples are intended as illustrative and are not to be taken as limiting. Still other variations within the spirit and scope of this invention are possible and will readily present themselves to those skilled in the art.

The invention claimed is:

1. A compound that corresponds in structure to Formula I, below, or a pharmaceutically acceptable salt thereof

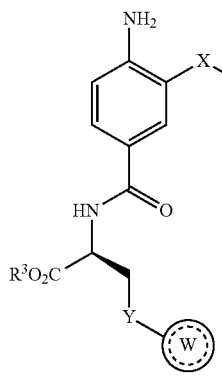

wherein
- X is O, S, $NR^1$, $CH_2$, where $R^1$ is H, or a $C_1$-$C_4$ hydrocarbyl, or X is absent and two atoms link the depicted phenyl rings;
- Y is O, S, $NR^2$, or $CH_2$, wherein $R^2$ is H, or a $C_1$-$C_4$ hydrocarbyl group;
- $R^3$ is a $C_1$-$C_6$ hydrocarbyl group;
- $R^4$ and $R^5$ are hydrido or hydroxyl but only one of $R^4$ and $R^5$ is hydrido, or both of $R^4$ and $R^5$ are hydroxyl;
- W is a single 6-membered hydrocarbyl ring structure said ring structure W optionally containing one or more substituent groups bonded to one or more ring atoms, in which said one or more substituents contain a total of up to 8 atoms, selected from the group consisting of fluorine, chlorine, carbon, nitrogen, oxygen, sulfur, and mixtures thereof; and
- a dotted line (----) represents one or more optional double bonds.

2. The compound according to claim 1, wherein X is absent or O.

3. The compound according to claim 1, wherein Y is $CH_2$.

4. The compound according to claim 1, wherein $R^3$ is a bulky hydrocarbyl group containing 4-6 carbon atoms.

5. The compound according to claim 1, wherein ring structure W contains a substituent selected from the group consisting of azido, fluoro, methyl, methoxy and trifluoromethyl groups, and said substituent is present at the 4-position of a 6-membered ring counting from the position of attachment to the remainder of the molecule.

6. A compound that corresponds in structure to Formula III or Formula IV, below, or pharmaceutically acceptable salts thereof

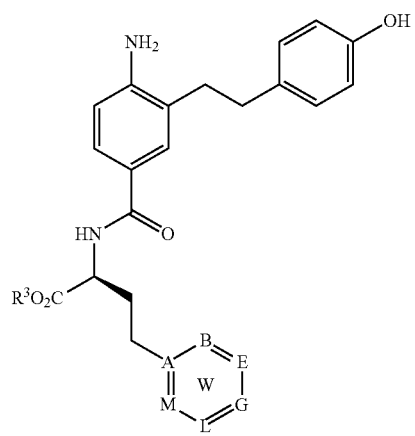

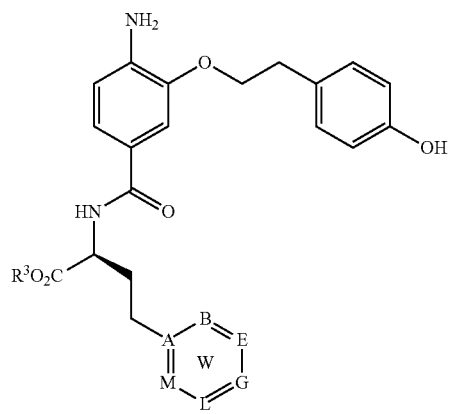

wherein ring W ring is phenyl that optionally contains one or more substituent groups bonded to one or more ring atoms, in which said one or more substituents contain a total of up to 8 atoms, selected from the group consisting of fluorine, chlorine, carbon, nitrogen, oxygen, sulfur, and mixtures thereof, and $R^3$ is a bulky hydrocarbyl group containing 4-6 carbon atoms.

7. The compound according to claim 6, wherein $R^3$ is a tert-butyl group, a neopentyl group, a cyclopentyl group or a cyclohexyl group.

8. A compound corresponding in structure to the structural formula below, or a pharmaceutically acceptable salt thereof

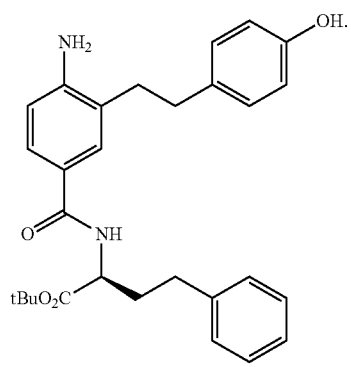 [SMILES: CC(C)(C)OC(=O)[C@H](CCc1ccccc1)NC(=O)c1ccc(N)c(CCc2ccc(O)cc2)c1]

9. A compound corresponding in structure to the structural formula below, or a pharmaceutically acceptable salt thereof

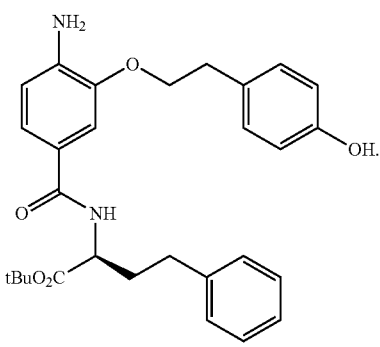 [SMILES: CC(C)(C)OC(=O)[C@H](CCc1ccccc1)NC(=O)c1ccc(N)c(OCCc2ccc(O)cc2)c1]

10. A pharmaceutical composition that comprises an effective amount of a compound of claim 1 or a pharmaceutically acceptable salt thereof dissolved or dispersed in a physiologically acceptable carrier.

11. The pharmaceutical composition according to claim 10 wherein said effective amount is an adjuvant effective amount.

12. The pharmaceutical composition according to claim 10 wherein said effective amount is a TLR4 agonist effective amount.

13. A method of vaccination wherein mammalian cells in need of vaccination are contacted with an immunizing composition that comprises an effective amount of an immunogen and an effective amount of an adjuvant, wherein the adjuvant is a compound or a pharmaceutically acceptable compound salt of Formula I in claim 1.

14. The method according to claim 13, wherein said immunogen and said adjuvant are administered in the same composition.

* * * * *

UNITED STATES PATENT AND TRADEMARK OFFICE
CERTIFICATE OF CORRECTION

| | | |
|---|---|---|
| PATENT NO. | : 9,649,373 B2 | Page 1 of 1 |
| APPLICATION NO. | : 14/770002 | |
| DATED | : May 16, 2017 | |
| INVENTOR(S) | : Beutler et al. | |

It is certified that error appears in the above-identified patent and that said Letters Patent is hereby corrected as shown below:

In the Specification

Column 1, Lines 10-15, the paragraph GOVERNMENTAL SUPPORT should be changed to:
-- STATEMENT OF GOVERNMENT LICENSE RIGHTS
This invention was made with government support under grant number AI082657 awarded by the National Institutes of Health. The government has certain rights in the invention. --

Signed and Sealed this
Fifth Day of May, 2020

Andrei Iancu
*Director of the United States Patent and Trademark Office*